(12) United States Patent
Gu et al.

(10) Patent No.: US 8,927,724 B2
(45) Date of Patent: *Jan. 6, 2015

(54) ISOXAZOLE BETA-LACTAMASE INHIBITORS

(71) Applicant: Cubist Pharmaceuticals, Inc., Lexington, MA (US)

(72) Inventors: Yu Gui Gu, Acton, MA (US); Yong He, Bedford, MA (US); Ning Yin, Lexington, MA (US); Dylan C. Alexander, Watertown, MA (US); Jason B. Cross, Acton, MA (US); Chester A. Metcalf, III, Needham, MA (US); Robert Busch, Wakefield, MA (US); Dongpeng Wan, Lexington, MA (US); Jon Christian Baber, Somerville, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/853,498

(22) Filed: Mar. 29, 2013

(65) Prior Publication Data

US 2013/0345190 A1  Dec. 26, 2013

Related U.S. Application Data

(60) Provisional application No. 61/618,127, filed on Mar. 30, 2012, provisional application No. 61/790,248, filed on Mar. 15, 2013.

(51) Int. Cl.
  *C07D 471/08* (2006.01)
  *A61K 31/546* (2006.01)
  (Continued)

(52) U.S. Cl.
  CPC ........... *A61K 31/397* (2013.01); *A61K 31/4545* (2013.01); *A61K 31/407* (2013.01); *C07D 471/08* (2013.01); *A61K 31/437* (2013.01); *A61K 31/546* (2013.01); *A61K 31/545* (2013.01); *A61K 45/06* (2013.01); *A61K 31/427* (2013.01); *A61K 31/4365* (2013.01); *A61K 31/439* (2013.01)
  USPC ........... 546/183; 546/121; 514/202; 514/203; 514/300; 514/359

(58) Field of Classification Search
  USPC .......................................... 546/183; 514/359
  See application file for complete search history.

(56) References Cited

U.S. PATENT DOCUMENTS

| 7,112,592 B2 | 9/2006 | Lampilas et al. |
| 7,612,087 B2 | 11/2009 | Aszodi et al. |

(Continued)

FOREIGN PATENT DOCUMENTS

| EP | 2135959 A1 | 12/2012 |
| FR | 2 835 186 A | 8/2003 |

(Continued)

OTHER PUBLICATIONS

Crompton, et al: Beta-Lactamase inhibitors, the inhibition of serine beta-lactamases by specific boronic acids; Biochem J., 1988, vol. 251, pp. 453-459.

(Continued)

*Primary Examiner* — John Mabry
*Assistant Examiner* — Daniel Carcanague
(74) *Attorney, Agent, or Firm* — Lathrop & Gage LLP; Brian C. Trinque

(57) ABSTRACT

β-Lactamase inhibitor compounds (BLIs) are disclosed, including compounds that have activity against class A, class C or class D β-lactamases. Methods of manufacturing the BLIs, and uses of the compounds in the preparation of pharmaceutical compositions and antibacterial applications are also disclosed.

39 Claims, 11 Drawing Sheets

(51) Int. Cl.
*A61K 31/439* (2006.01)
*A61K 31/545* (2006.01)
*A61K 31/407* (2006.01)
*A61K 45/06* (2006.01)
*A61K 31/4545* (2006.01)
*A61K 31/397* (2006.01)
*A61K 31/437* (2006.01)
*A61K 31/427* (2006.01)
*A61K 31/4365* (2006.01)

(56) References Cited

U.S. PATENT DOCUMENTS

| | | | |
|---|---|---|---|
| 7,732,610 | B2 | 6/2010 | Lampilas et al. |
| 8,178,554 | B2 | 5/2012 | Lampilas et al. |
| 8,471,025 | B2 | 6/2013 | Dedhiya et al. |
| 8,487,093 | B2 | 7/2013 | Blizzard et al. |
| 2011/0046102 | A1 | 2/2011 | Ledoussal et al. |
| 2012/0053350 | A1 | 3/2012 | Mangion et al. |
| 2012/0165533 | A1 | 6/2012 | Abe et al. |
| 2012/0323010 | A1 | 12/2012 | Ronsheim et al. |
| 2013/0012712 | A1 | 1/2013 | Priour et al. |
| 2013/0059774 | A1 | 3/2013 | Patel et al. |
| 2013/0289012 | A1* | 10/2013 | Gu et al. ............ 514/203 |
| 2013/0296290 | A1* | 11/2013 | Gu et al. ............ 514/202 |
| 2013/0296291 | A1* | 11/2013 | Gu et al. ............ 514/202 |
| 2013/0296292 | A1* | 11/2013 | Gu et al. ............ 514/202 |
| 2013/0296293 | A1* | 11/2013 | Gu et al. ............ 514/202 |
| 2013/0296555 | A1* | 11/2013 | Gu et al. ............ 544/127 |
| 2013/0303504 | A1* | 11/2013 | Gu et al. ............ 514/202 |
| 2013/0345190 | A1 | 12/2013 | Gu et al. |

FOREIGN PATENT DOCUMENTS

| | | |
|---|---|---|
| FR | 2 812 635 A | 2/2008 |
| FR | 2 930 553 A1 | 10/2009 |
| FR | 2 951 171 A | 4/2011 |
| KR | 2010130176 A | 12/2010 |
| WO | WO 02/010172 A1 | 7/2002 |
| WO | WO 03/063864 A2 | 7/2003 |
| WO | WO2007/129176 A2 | 11/2007 |
| WO | WO 2009/091856 A2 | 7/2009 |
| WO | WO2009/133442 A1 | 11/2009 |
| WO | WO 2010-118361 A1 | 1/2010 |
| WO | WO 2010-056827 A1 | 5/2010 |
| WO | WO2010/126820 A1 | 11/2010 |
| WO | WO 2011/042560 A1 | 4/2011 |
| WO | WO2011/101710 A1 | 8/2011 |
| WO | WO2012/086241 A1 | 6/2012 |
| WO | WO2012/172368 A1 | 12/2012 |
| WO | WO 2013/014496 A1 | 1/2013 |
| WO | WO 2013/014497 A1 | 1/2013 |
| WO | WO 2013/030735 A1 | 3/2013 |
| WO | WO 2013/038330 A1 | 3/2013 |

OTHER PUBLICATIONS

International Search Report, PCT/US2013/034562, dated Jul. 30, 2013, 6 pages.
Written Opinion, PCT/US2013/034562, dated Jul. 30, 2013, 5 pages.
Patani, et al: Bioisosterism: A Rational Approach in Drug Design; Chem Rev, 1996, vol. 96, pp. 3147-3176.
International Search Report, PCT/US2013/034589, dated Jul. 29, 2013, 4 pages.
Written Opinion, PCT/US2013/034589, dated Jul. 29, 2013, 5 pages.
Mangion, et al: A Concise of a beta-Lactamase Inhibitor; Organic Letters, Oct. 21, 2011, 13(2), pp. 5480-5483.
Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 2: Synthesis and stucture—activity relationships in the S-3578 series"; Bioorganic and Medicinal Chemistry 2004, vol. 12, pp. 4211-4219.
Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 3: 7b-[2-(5-Amino-1,2,4-thiadiazol-3-yl)-2-ethoxyiminoacetamido] cephalosporins bearing 4-[3-(aminoalkyl)-ureido]-1-pyridinium at C-3'"; Bioorganic and Medicinal Chemistry 2004, vol. 12, pp. 4221-4231.
Yoshizawa, H. et al.; "S-3578, A New Broad Spectrum Parenteral Cephalosporin Exhibiting Potent Activity Against both Methicillin-resistant *Staphylococcus aureus* (MRSA) and *Pseudomonas aeruginosa* Synthesis and Structure—activity Relationships"; The Journal of Antibiotics 2002, vol. 55, No. 11, pp. 975-992.
Ida, T. et al. "CP6679, a new injectable cephalosporin with broad spectrum and potent activities against methicillin-resistant *Staphylococcus aureus* and *Pseudomonas aeruginosa*"; Journal of Infection and Chemotherapy 2002, vol. 8, pp. 138-144.

* cited by examiner

Figure 1A

Table I
Compounds of Formula A-II

| Cmpd. No. | R¹ | R |
|---|---|---|
| 601 | H₂N-CH₂- | -OSO₃H |
| 602 | H₂N-CH₂CH₂- | -OSO₃H |
| 603 | H₂N-C(=NH)-NH-CH₂- (guanidinyl-methyl) | -OSO₃H |
| 604 | H₂N-C(=NH)-NH-CH₂CH₂- (guanidinyl-ethyl) | -OSO₃H |
| 605 | H₂N-CH₂CH₂-NH-C(=O)- | -OSO₃H |
| 606 | 4-piperidinyl (HN in ring) | -OSO₃H |
| 607 | 1-(amidino)-piperidin-4-yl | -OSO₃H |
| 608 | H₂N-C(=NH)-NH-CH₂CH₂-NH-C(=O)- | -OSO₃H |
| 609 | piperidin-4-yl-NH-CH₂CH₂- | -OSO₃H |
| 610 | 1-(amidino)-piperidin-4-yl-NH-CH₂CH₂- | -OSO₃H |

Figure 1B
Table I
Compounds of Formula A-II
| Cmpd. No. | R¹ | R |
|---|---|---|
| 611 | 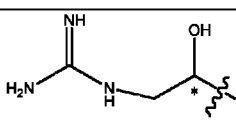 |  |
| 612 | 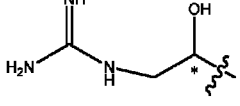 |  |
| 613 | 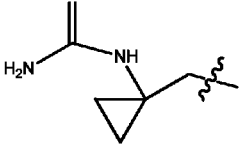 |  |
| 614 | 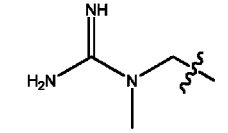 |  |
| 615 | 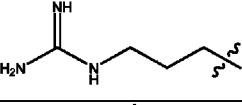 |  |
| 616 | 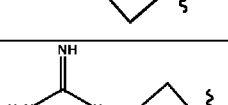 |  |
| 617 | 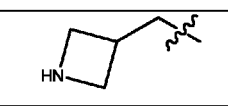 |  |
| 618 |  |  |
| 619 |  |  |

Figure 1C

Table I

Compounds of Formula A-II

| Cmpd. No. | R¹ | R |
|---|---|---|
| 620 | H₂N-CH₂CH₂-NH-CH₂CH₂-⁓ | —OSO₃H |
| 621 | H₂N-C(=NH)-NH-CH₂CH₂-NH-CH₂CH₂-⁓ | —OSO₃H |
| 622 | azetidine-NH-CH₂-⁓ (3-aminoazetidinyl-NH-CH₂) | —OSO₃H |
| 623 | azetidine-NH-CH₂CH₂-⁓ | —OSO₃H |
| 624 | azetidine-O-CH₂-⁓ | —OSO₃H |
| 625 | N-methylpyridinium-⁓ | —OSO₃H |
| 626 | N,N-dimethylpiperidinium-⁓ | —OSO₃H |
| 627 | piperidine-CH₂-⁓ | —OSO₃H |
| 628 | azetidine-⁓ | —OSO₃H |

Figure 1D
Table I
Compounds of Formula A-II
| Cmpd. No. | R¹ | R |
|---|---|---|
| 629 | 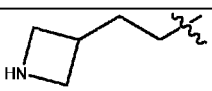 |  |
| 630 | 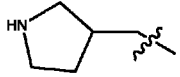 |  |

Figure 2A

Table II Standard BLI Potentiation MIC Assay in Combination with Ceftolozane Against a Panel of Isogenic and Clinical Strains Expressing β-Lactamases.

| Strain # | β-Lactamase | Bkgd | No BLI | CCC | 612 | 611 | 620 | 621 | 614 | 615 | 613 | 618 | 624 | 622 | 623 | 616 | 617 | 626 |
|---|---|---|---|---|---|---|---|---|---|---|---|---|---|---|---|---|---|---|
| Eco.2806 | KPC-2 | isogenic | E | B | B | B | A | A | B | B | B | B | A | B | A | B | A | B |
| Pae.2808 | KPC-2 | clinical | E | C | B | B | C | C | B | B | C | B | B | C | C | B | C | B |
| Kpn.2478 | KPC-3, TEM+ | clinical | E | C | B | B | C | C | B | B | C | B | B | B | C | B | B | C |
| Kpn.2490 | KPC-3, SHV–, TEM1 | clinical | E | B | A | A | B | AA | B | A | A | A | B | B | C | B | A | B |
| Kpn.2783 | CTX-M-15, SHV+, TEM+ | clinical | E | A | B | A | A | B | B | B | B | B | B | B | B | B | B | B |
| Kpn.571 | TEM-26 | clinical | D | AA | A | A | A | A | AA | A | A | AA | A | A | A | A | A | B |
| Pae.2885 | AmpC | clinical | B | A | A | C | A | A | B | A | C | A | A | C | A | A | A | A |
| Cfr.568 | AmpC | clinical | E | C | B | C | C | C | B | C | C | B | C | C | C | B | B | C |
| Ecl.569 | AmpC | clinical | E | B | B | B | A | B | B | A | B | A | B | A | B | A | A | C |
| Kpn.2914 | KPC-2, SHV– | clinical | D | B | B | B | B | C | B | B | B | B | B | B | B | B | B | B |
| Kpn.2913 | KPC-2, SHV– | clinical | D | A | A | A | A | A | A | A | A | A | A | A | A | A | A | B |
| Kpn.2917 | KPC-2, SHV– | clinical | D | A | A | AA | A | A | A | A | A | AA | A | A | A | A | A | A |
| Kpn.2918 | KPC-3, SIIV , THM+ | clinical | E | C | C | B | C | C | B | C | C | B | C | C | C | C | C | C |
| Kpn.2909 | KPC-3, SHV–, TEM1 | clinical | E | B | B | B | B | B | B | B | B | B | B | B | B | B | C | B |
| Eco.2711 | KPC | clinical | D | A | A | A | A | A | A | A | A | A | A | A | A | A | A | A |
| Eco.2781 | KPC-2, TEM+ | clinical | C | AA | A | AA | A | A | AA | A | A | A | A | A | A | A | B | A |
| Kpn.2926 | CTX-M-15, OXA-48 | clinical | E | B | C | C | C | C | B | C | B | B | C | C | C | C | C | D |
| Pae.2757 | AmpC over-expn | clinical | C | B | B | B | B | B | B | B | B | B | B | B | B | B | B | C |
| Pae.2863 | AmpC de-repress | clinical | C | B | B | C | C | B | B | B | B | B | B | C | B | B | B | B |
| Eco.2843 | DHA-1 | isogenic | E | A | A | A | A | A | A | A | A | A | A | A | A | A | A | A |
| Eco.2491 | CMY-2 | clinical | D | B | B | A | A | A | A | A | A | A | A | A | A | A | A | B |
| Eco.2902 | Aba-ADC-33 | isogenic | E | B | B | C | C | D | C | B | C | C | C | C | C | B | C | C |
| Eco.2840 | KPC-4 | isogenic | E | D | D | D | D | D | D | D | D | D | D | D | D | D | D | D |
| Eco.2845 | OXA-15 | isogenic | E | D | D | C | D | C | D | D | D | D | D | D | D | D | D | D |
| MIC90 | | | E | C | B | C | C | C | B | C | C | B | C | C | C | B | C | C |
| MIC50 | | | E | B | B | B | B | B | B | B | B | B | B | B | B | B | B | B |

Table II Standard BLI Potentiation MIC Assay in Combination with Ceftolozane Against a Panel of Isogenic and Clinical Strains Expressing β-Lactamases.

| Strain # | β-Lactamase | Bkgd | No BLI | CCC | 627 | 625 | 619 | 609 | 610 | 601 | 602 | 603 | 604 | 605 | 606 | 607 |
|---|---|---|---|---|---|---|---|---|---|---|---|---|---|---|---|---|
| Eco.2806 | KPC-2 | isogenic | E | B | B | A | A | B | A | B | B | A | A | B | A | B |
| Pae.2808 | KPC-2 | clinical | E | C | C | C | C | C | B | C | C | B | B | C | B | C |
| Kpm.2478 | KPC-3, TEM+ | clinical | E | C | C | C | C | C | C | C | D | B | B | C | B | C |
| Kpm.2490 | KPC-3, SHV1, TEM+ | clinical | E | B | B | B | B | A | A | B | C | A | A | B | B | A |
| Kpm.2783 | CTX-M-15, SHV+, TEM+ | clinical | E | A | B | B | B | B | B | B | C | A | B | B | B | B |
| Kpm.571 | TEM-26 | clinical | D | AA | A | B | A | A | A | A | B | A | A | A | A | A |
| Pae.2885 | AmpC | clinical | B | A | A | A | A | A | A | B | B | B | A | A | A | A |
| Cfr.568 | AmpC | clinical | E | C | C | B | B | C | B | B | C | C | C | C | C | C |
| Ecl.569 | AmpC | clinical | E | B | B | A | B | B | A | B | C | B | A | B | A | A |
| Kpm.2914 | KPC-2, SHV+ | clinical | D | B | B | B | A | B | B | B | C | A | B | B | B | B |
| Kpm.2913 | KPC-2, SHV+ | clinical | E | A | A | B | A | A | A | A | B | A | A | C | A | A |
| Kpm.2917 | KPC-2, SHV1 | clinical | D | A | A | A | AA | A | A | A | B | A | A | B | A | A |
| Kpm.2918 | KPC-3, SHV+, TEM1 | clinical | E | C | C | B | C | C | C | C | D | B | B | C | C | C |
| Kpm.2909 | KPC-3, SHV+, TEM+ | clinical | E | B | C | B | B | B | B | A | C | B | B | C | B | C |
| Eco.2711 | KPC | clinical | D | A | A | B | A | A | A | A | B | A | A | A | B | A |
| Eco.2781 | KPC-2, TEM+ | clinical | C | AA | A | A | AA | A | A | A | A | AA | AA | A | A | A |
| Kpm.2926 | CTX-M-15, OXA-48 | clinical | E | B | B | C | C | C | A | A | E | B | B | C | C | D |
| Pae.2757 | AmpC over-expn | clinical | C | B | B | B | B | B | B | B | B | B | B | B | B | B |
| Pae.2863 | AmpC de-repress | clinical | C | B | B | B | B | B | A | B | C | B | B | B | B | B |
| Eco.2843 | DHA-1 | isogenic | E | A | A | A | A | A | A | A | B | A | A | B | A | A |
| Eco.2491 | CMY-2 | clinical | D | A | A | B | A | A | A | A | B | A | A | A | A | A |
| Eco.2902 | Aba-ADC-33 | isogenic | E | B | C | C | B | B | B | B | D | B | B | B | B | C |
| Eco.2840 | KPC-4 | isogenic | E | D | D | D | D | D | B | C | E | D | D | D | D | D |
| Eco.2845 | OXA-15 | isogenic | E | C | D | D | C | C | C | C | D | C | C | C | C | C |
| MIC90 | | | E | C | C | C | B | B | A | B | D | B | B | C | C | C |
| MIC50 | | | E | B | B | B | B | B | A | B | C | B | B | B | B | B |

Table III: Synergy MIC (sMIC) Against a Panel of Isogenic and Clinical Strains Expressing β-lactamases

| β-Lactamase | Bkgd | Sp | β-Lactam (4 µg/mL) | CCC | 612 | 611 | 620 | 621 | 614 | 615 | 613 | 618 | 624 | 622 | 623 | 616 | 617 | 626 | 627 | 625 |
|---|---|---|---|---|---|---|---|---|---|---|---|---|---|---|---|---|---|---|---|---|
| none | isogenic | Eco | none | D | ND | D | F | F | D | F | F | E | E | F | F | F | F | F | F | F |
| KPC-2 | isogenic | Eco | CXA-101 | B | A | AA | A | A | A | AA | A | AA | A | A | A | A | A | A | A | A |
| OXA-15 | isogenic | Eco | CXA-101 | D | D | C | D | D | C | D | D | C | D | D | D | D | E | A | D | D |
| CTX-M-15 | isogenic | Eco | CXA-101 | A | B | B | C | A | B | D | B | A | B | D | D | B | A | C | B | C |
| SHV-12 | isogenic | Eco | CXA-101 | B | B | B | A | B | B | B | C | B | B | C | C | C | C | C | D | C |
| P99 | isogenic | Eco | CXA-101 | A | AA | A | A | A | AA | A | A | A | A | B | A | A | A | A | B | A |
| KPC-3 | clinical | Kpn | CXA-101 | C | B | B | B | C | B | B | C | B | B | C | C | B | C | C | C | C |
| KPC-2 | clinical | Pae | CXA-101 | B | A | B | B | B | B | B | B | B | B | C | C | B | B | B | C | B |

AA = < 0.25 µg/mL; A = 0.25-0.5 µg/mL; B = 1-2 µg/mL; C = 4-8 µg/mL; D = 16-32 µg/mL; E = 64 µg/mL; F = ≥128 µg/mL

CXA-101 is Ceftolozane

Eco is *Escherichia coli*, Kpn is *Klebsiella pneumoniae*, Pae is *Pseudomonas aeruginosa*

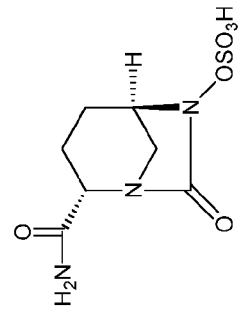

CCC is comparator compound

Figure 3B

Table III: Synergy MIC (sMIC) Against a Panel of Isogenic and Clinical Strains Expressing β-lactamases

| β-Lactamase | Bkgd | Sp | β-Lactam (4 μg/mL) | COMPOUNDS |  |  |  |  |  |  |  |  |  |  |  |
|---|---|---|---|---|---|---|---|---|---|---|---|---|---|---|---|
|  |  |  |  | CCC | 619 | 609 | 610 | 601 | 602 | 603 | 604 | 605 | 606 | 607 | 608 |
| none | isogenic | Eco | none | D | E | F | F | D | E | E | D | F | F | F | F |
| KPC-2 | isogenic | Eco | CXA-101 | B | A | A | A | A | B | A | A | B | A | B | A |
| OXA-15 | isogenic | Eco | CXA-101 | D | D | D | D | D |  | C | C | D |  | D | D |
| CTX-M-15 | isogenic | Eco | CXA-101 | A | B | B | B | B | B | A | B | C | B | B | B |
| SHV-12 | isogenic | Eco | CXA-101 | B | D | C | C | B | B | B | B | B | C | C | B |
| P99 | isogenic | Eco | CXA-101 | A | A | A | A | A | A | A | A | B | B | B | A |
| KPC-3 | clinical | Kpn | CXA-101 | C | D | C | C | C | C | B | B | C | C | C | C |
| KPC-2 | clinical | Pae | CXA-101 | B | C | B | C | C | C | A | B | C | C | C | B |

AA=< 0.25μg/mL; A = 0.25-0.5 μg/mL; B = 1-2 μg/mL; C = 4-8 μg/mL; D = 16-32 μg/mL; E = 64μg/mL; F =≥128μg/mL

CXA-101 is Ceftolozane

Eco is *Escherichia coli*, Kpn is *Klebsiella pneumoniae*, Pae is *Pseudomonas aeruginosa*

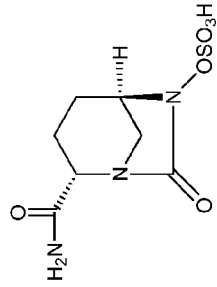

CCC is comparator compound

Table IV: Inhibition Kinetics for the KPC-2 β-lactamase

| | CCC | 612 | 611 | 620 | 621 | 614 | 615 | 613 | 618 | 624 | 622 | 623 | 616 | 617 | 626 | 627 | 625 | 619 | 609 | 610 |
|---|---|---|---|---|---|---|---|---|---|---|---|---|---|---|---|---|---|---|---|---|
| Kinact/K mM$^{-1}$s$^{-1}$ | C | B | B | B | B | B | B | B | B | B | B | B | B | B | B | B | B | B | B | B |

| | CCC | 601 | 602 | 603 | 604 | 605 | 606 | 607 | 608 |
|---|---|---|---|---|---|---|---|---|---|
| Kinact/K mM$^{-1}$s$^{-1}$ | C | B | C | B | A | B | B | B | A |

A = 1000-5000 mM$^{-1}$s$^{-1}$; B = 100-999 mM$^{-1}$s$^{-1}$; C = 1-99 mM$^{-1}$s$^{-1}$

CCC is comparator compound

Figure 5A

Table V: Synergy MIC (sMIC) of Comparator Compounds Against a Panel of Isogenic and Clinical Strains Expressing β-lactamases

| β-Lactamase | Bkgd | Sp | β-Lactam (4 µg/mL) | [pyrazole-diazabicyclo] | [imidazole-diazabicyclo] | [piperidine-oxadiazolone-diazabicyclo] | [oxadiazolone-diazabicyclo] | [methyltriazole-diazabicyclo] |
|---|---|---|---|---|---|---|---|---|
| none | isogenic | Eco | none | D | F | F | F | F |
| KPC-2 | isogenic | Eco | CXA-101 | C | F | C | C | C |
| OXA-15 | isogenic | Eco | CXA-101 | ND | ND | ND | ND | F |
| CTX-M-15 | isogenic | Eco | CXA-101 | C | F | D | B | D |
| SHV-12 | isogenic | Eco | CXA-101 | C | F | D | C | D |
| P99 | isogenic | Eco | CXA-101 | C | F | B | B | C |
| KPC-3 | clinical | Kpn | CXA-101 | D | F | C | D | E |
| KPC-2 | clinical | Pae | CXA-101 | F | F | D | F | D |

AA=<0.25µg/mL; A = 0.25-0.5 µg/mL; B = 1-2 µg/mL; C = 4-8 µg/mL; D = 16-32 µg/mL; E = 64µg/mL; F =≥128µg/mL

CXA-101 is Ceftolozane

Eco is *Escherichia coli*, Kpn is *Klebsiella pneumoniae*, Pae is *Pseudomonas aeruginosa*

Figure 5B

Table V: Synergy MIC (sMIC) of Comparator Compounds Against a Panel of Isogenic and Clinical Strains Expressing β-lactamases

| β-Lactamase | Bkgd | Sp | β-Lactam (4 µg/mL) | 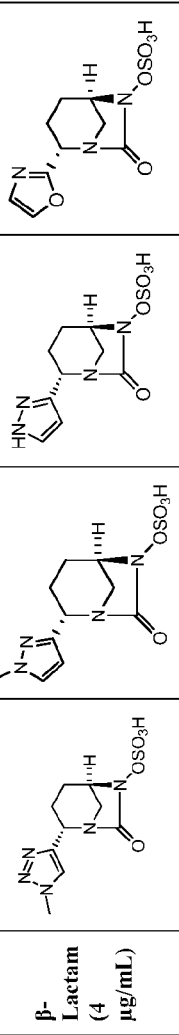 | 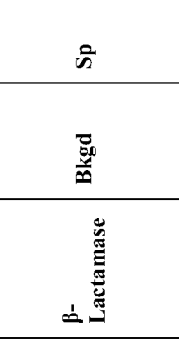 |  | |
|---|---|---|---|---|---|---|---|
| none | isogenic | Eco | none | E | F | F | F |
| KPC-2 | isogenic | Eco | CXA-101 | A | D | C | B |
| OXA-15 | isogenic | Eco | CXA-101 | ND | F | F | D |
| CTX-M-15 | isogenic | Eco | CXA-101 | D | F | D | B |
| SHV-12 | isogenic | Eco | CXA-101 | B | C | C | B |
| P99 | isogenic | Eco | CXA-101 | A | C | B | A |
| KPC-3 | clinical | Kpn | CXA-101 | E | F | F | D |
| KPC-2 | clinical | Pae | CXA-101 | E | F | F | D |

AA= < 0.25µg/mL; A = 0.25-0.5 µg/mL; B = 1-2 µg/mL; C = 4-8 µg/mL; D = 16-32 µg/mL; E = 64µg/mL; F =≥128µg/mL

CXA-101 is Ceftolozane

Eco is *Escherichia coli*, Kpn is *Klebsiella pneumoniae*, Pae is *Pseudomonas aeruginosa*

ISOXAZOLE BETA-LACTAMASE INHIBITORS

RELATED APPLICATIONS

This application claims priority to U.S. Provisional Application No. 61/618,127, filed Mar. 30, 2012, and U.S. Provisional Application No. 61/790,248, filed Mar. 15, 2013. The entire contents of these applications are incorporated herein by reference in their entireties.

TECHNICAL FIELD

This disclosure is directed to β-lactamase inhibitors (BLIs) which are effective as inhibitors of β-lactamases and, when used in combination with β-lactam antibiotics are useful in the treatment of bacterial infections. The compounds when combined with a β-lactam antibiotic are effective in treating infections caused by bacteria that are resistant to β-lactam antibiotics due to the presence of β-lactamases. Pharmaceutical compositions comprising such compounds, methods of using such compounds, and processes for preparing such compounds are also disclosed.

BACKGROUND

Bacterial resistance to β-lactam antibiotics, especially in Gram-negative bacteria, is most commonly mediated by β-lactamases. β-lactamases are enzymes that catalyze the hydrolysis of the β-lactam ring, which inactivates the antibacterial activity of the β-lactam antibiotic and allows the bacteria to become resistant Inhibition of the β-lactamase with a BLI slows or prevents degradation of the β-lactam antibiotic and restores β-lactam antibiotic susceptibility to β-lactamase producing bacteria. Many of these β-lactamases are not effectively inhibited by BLIs currently on the market rendering the β-lactam antibiotics ineffective in treating bacteria that produce these β-lactamases. There is an urgent need for novel BLIs that inhibit β-lactamases that are not effectively inhibited by the current clinical BLIs (e.g. KPC, class C and class D β-lactamases) and that could be used in combination with β-lactam antibiotics to treat infections caused by β-lactam resistant bacteria.

SUMMARY OF INVENTION

The present invention provides, in one aspect, compounds of chemical formula (I), or pharmaceutically-acceptable salts thereof, which are BLIs and are useful in combination with β-lactam antibiotics for the treatment of bacterial infections.

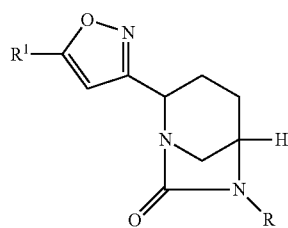

(I)

wherein
R is selected from

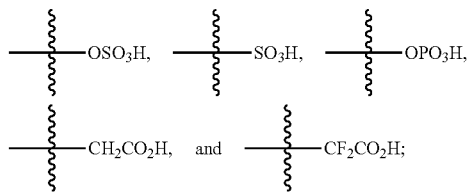

and
$R^1$ is selected from:

a.

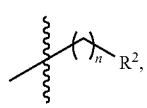

wherein $R^2$ is selected from

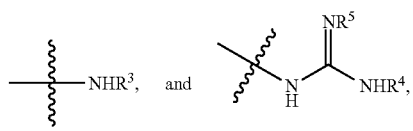

wherein each of $R^3$, $R^4$ and $R^5$ is independently selected from hydrogen, $(C_1\text{-}C_3)$-alkyl, aminoalkyl, aminocycloalkyl, and hydroxyalkyl, and n is selected from 1, 2 and 3;

b.

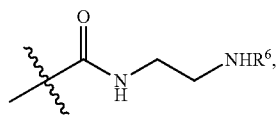

wherein $R^6$ is selected from
H and

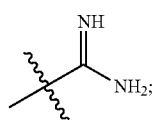

c.

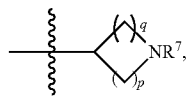

wherein $R^7$ is selected from H, $(C_1\text{-}C_3)$-unsubstituted alkyl, amino-$(C_2\text{-}C_3)$-alkyl, aminocycloalkyl, hydroxyalkyl, and

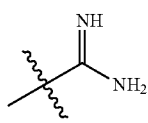

wherein each of p and q is independently selected from 1 and 2.

In another aspect, the invention provides compounds of chemical Formula (A-I) or a pharmaceutically acceptable salt thereof, which are BLIs and are useful in combination with β-lactam antibiotics for the treatment of bacterial infections.

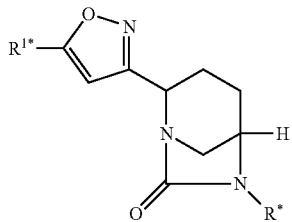

(A-I)

wherein
R* is selected from

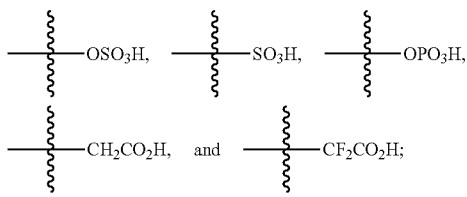

and
$R^{1*}$ is selected from:

a.

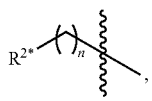

wherein $R^{2*}$ is selected from

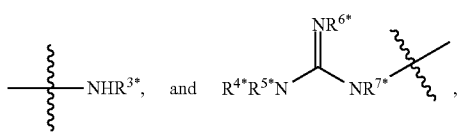

$R^{3*}$ is selected from hydrogen, $(C_1-C_3)$-alkyl, aminoalkyl, aminocycloalkyl, hydroxyalkyl,

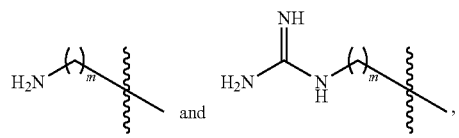

each of $R^{4*}$, $R^{5*}$, $R^{6*}$ and $R^{7*}$ is independently selected from hydrogen, $(C_1-C_6)$-alkyl, aminoalkyl, aminocycloalkyl, and hydroxyalkyl, provided that at least one of $R^{4*}$, $R^{5*}$, $R^{6*}$ and $R^{7*}$ is hydrogen,
n is selected from 1, 2, 3 and 4, and
m is selected from 1, 2 and 3;

b.

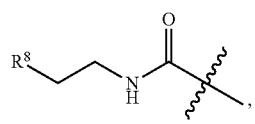

wherein $R^8$ is selected from —$NH(C_1-C_3)$-alkyl and

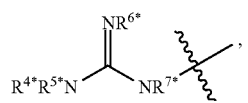

wherein each of $R^{4*}$, $R^{5*}$, $R^{6*}$ and $R^{7*}$ is as described previously;

c.

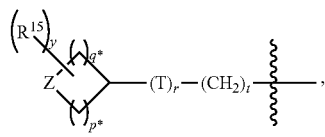

wherein Z is selected from $CR^9R^{10}$ and $NR^{11}$,
each of $R^9$ and $R^{10}$ is independently selected from H, $NH_2$, —$NH(C_1-C_3)$-alkyl and

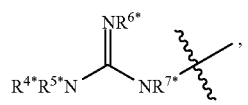

wherein each of $R^{4*}$, $R^{5*}$, $R^{6*}$ and $R^{7*}$ is as described previously,
alternatively, $R^9$ and $R^{10}$ together with the carbon to which they are attached, form a cycloalkyl or heterocyclyl ring containing 4-6 ring members,
$R^{11}$ is selected from H and

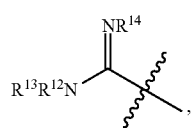

each of $R^{12}$, $R^{13}$ and $R^{14}$ is independently selected from hydrogen, ($C_1$-$C_6$)-alkyl, aminoalkyl, aminocycloalkyl, and hydroxyalkyl, provided that at least one of $R^{12}$, $R^{13}$ and $R^{14}$ is hydrogen, $R^{15}$ is selected from $NH_2$ and

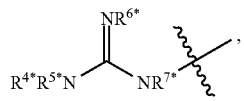

wherein each of $R^{4*}$, $R^{5*}$, $R^{6*}$ and $R^{7*}$ is as described previously, each of p* and q* is independently selected from 0, 1, 2 and 3, T is selected from NH and O, t is selected from 0, 1, 2, 3, and 4, and each of r and y is independently selected from 0 and 1;

d.

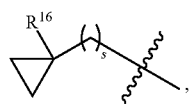

wherein $R^{16}$ is selected from $NH_2$, —$NH(C_1$-$C_3)$-alkyl and

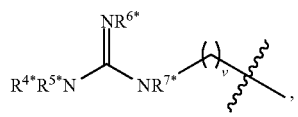

wherein each of $R^{4*}$, $R^{5*}$, $R^{6*}$ and $R^{7*}$ is as described previously, s is selected from 0 and 1, and, v is selected from 0, 1, 2, and 3;

e.

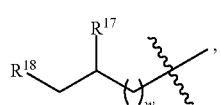

wherein $R^{18}$ is selected from $NH_2$ and

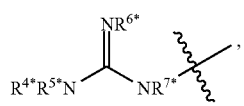

wherein each of $R^{4*}$, $R^{5*}$, $R^{6*}$ and $R^{7*}$ is as described previously, $R^{17}$ is selected from amino and hydroxyl, and w is selected from 0 and 1;

f.

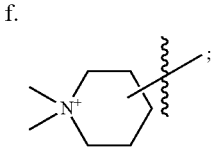

g.

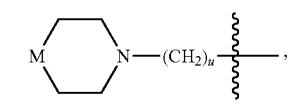

wherein M is selected from $NR^{19}$, $CR^{20}R^{21}$ and O, wherein $R^{19}$ is selected from H and

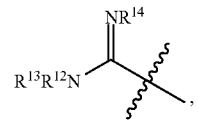

where each of $R^{12}$, $R^{13}$ and $R^{14}$ is as described previously, each of $R^{20}$ and $R^{21}$ is independently selected from H, $NH_2$ and

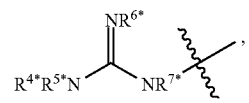

wherein each of $R^{4*}$, $R^{5*}$, $R^{6*}$ and $R^{7*}$ is as described previously, and u is selected from 0, 1 and 2; and h.

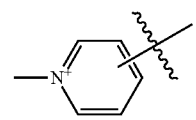

In one embodiment, the invention provides use of a compound of Formula I for inhibiting β-lactamases.

In one embodiment, the invention provides use of a compound of Formula A-I for inhibiting β-lactamases.

In one embodiment, the invention provides compounds of Formula I with high binding affinity for β-lactamase enzymes.

In one embodiment, the invention provides compounds of Formula A-I with high binding affinity for β-lactamase enzymes.

In one embodiment, the present invention also provides antibacterial compositions comprising compounds of Formula I and at least one β-lactam antibiotic.

In one embodiment, the present invention also provides antibacterial compositions comprising compounds of Formula A-I and at least one β-lactam antibiotic.

In one embodiment, the present invention provides pharmaceutical compositions comprising compounds of Formula I and at least one β-lactam antibiotic and methods of use thereof.

In one embodiment, the present invention provides pharmaceutical compositions comprising compounds of Formula A-I and at least one β-lactam antibiotic and methods of use thereof.

In one embodiment, the invention provides methods of use of the compounds of Formula I to treat bacterial infections in a subject.

In one embodiment, the invention provides methods of use of the compounds of Formula A-I to treat bacterial infections in a subject.

BRIEF DESCRIPTION OF THE DRAWINGS

FIGS. 1A-1D show Table I, Representative Compounds of Formula A-II

FIGS. 2A-2B show Table II, Standard BLI potentiation MIC assay against a panel of isogenic and clinical strains expressing β-lactamases.

FIGS. 3A-3B show Table III, the synergy MIC of representative compounds of Formula II-A against a panel of isogenic and clinical strains expressing β-lactamases.

FIGS. 5A-5B show Table V, Synergy MIC of Comparator Compounds Against a Panel of Isogenic and Clinical Strains Expressing β-lactamases

DETAILED DESCRIPTION

Definitions

Figure 4:
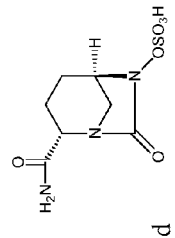
FIG. 4 shows Table IV, an assay to determine inhibition kinetics of representative compounds of Formula II-A for the KPC-2 β-lactamase.

Molecular terms, when used in this application, have their common meaning unless otherwise specified.

The term "alkyl" is defined as a linear or branched, saturated radical having one to about twenty carbon atoms unless otherwise specified. Preferred alkyl radicals are "lower alkyl" radicals having one to about five carbon atoms. Examples of alkyl groups include, without limitation, methyl, ethyl, tert-butyl, isopropyl, and hexyl. A subset of the term alkyl is "$(C_1-C_3)$-unsubstituted alkyl" which is defined as an alkyl group that bears no substituent groups. Examples of $(C_1-C_3)$-unsubstituted alkyl groups include methyl, ethyl, propyl and isopropyl. It is understood that if a $(C_1-C_3)$-alkyl is "substituted" that one or more hydrogen atoms is replaced by a substitutent.

The term amino denotes a $NH_2$ radical.

The term "aminoalkyl" denotes an alkyl in which one or more of the alkyl hydrogen atoms has been replaced by an amino group.

The term "aminocycloalkyl" denotes a cycloalkyl in which one of the cycloalkyl hydrogen atoms has been replaced by an amino group.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to seven ring members. Examples of a cycloalkyl group include, without limitation, cyclopropyl, cyclobutyl, cyclohexyl, and cycloheptyl.

The term "hydroxyalkyl" denotes an alkyl radical in which one or more of the alkyl hydrogen atoms has been replaced by a hydroxyl group.

It will be understood by one of skill in the art that a

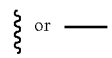

denote the point of attachment of a substituent group where indicated. For example

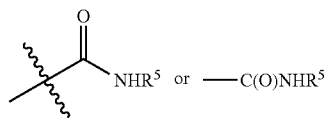

represent that the point of attachment of the amide moiety is at the carbonyl carbon.

The functional classification of β-lactamases and terms "Class A", "Class C", and "Class D" β-lactamases are understood by one of skill in the art and are described in "Updated Functional Classification of β-Lactamases", Bush, K.; Jacoby, G. A.; *Antimicrob. Agents Chemother.* 2010, 54, 969-976, herein incorporated by reference.

The salts of the compounds of the invention include acid addition salts and base addition salts. In a one embodiment, the salt is a pharmaceutically acceptable salt of the compound of Formula I. The term "pharmaceutically acceptable salts" embraces salts commonly used to form alkali metal salts and to form addition salts of free acids or free bases. The nature of the salt is not critical, provided that it is pharmaceutically-acceptable. Suitable pharmaceutically acceptable acid addition salts of the compounds of the invention may be prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention by treating, for example, the compound of the invention with the appropriate acid or base.

The compounds of the invention can possess one or more asymmetric carbon atoms and are thus capable of existing in the form of optical isomers as well as in the form of racemic or non-racemic mixtures thereof. The compounds of the invention can be utilized in the present invention as a single isomer or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from the optically active salts. An alternative process for separation of optical isomers includes the use of a chiral chromatography column optimally chosen to maximize the separation of the enantiomers. Still another available method involves synthesis of covalent diastereoisomeric molecules by treating compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers may be in the form of a free acid, a free base, an ester or a salt.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The invention also embraces isolated compounds. An isolated compound refers to a compound which represents at least 10%, such as at least 20%, such as at least 50% and further such as at least 80% of the compound present in the mixture. In one embodiment, the compound, a pharmaceutically acceptable salt thereof, or a pharmaceutical composition comprising the compound exhibits detectable (i.e. statistically significant) activity when tested in conventional biological assays such as those described herein.

β-Lactamase Inhibitors (BLIs)

In one aspect, the invention provides compounds of Formula I or pharmaceutically-acceptable salts thereof:

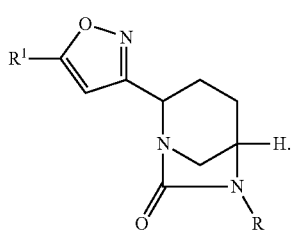

(I)

Substituent R of Formula I is selected from

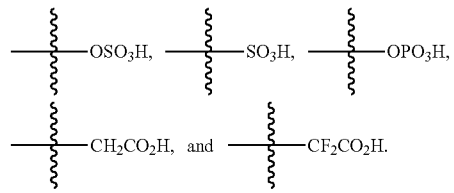

In a preferred embodiment, R is

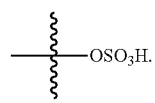

The group $R^1$ of Formula I is selected from:
a.

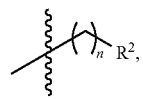

wherein $R^2$ is selected from

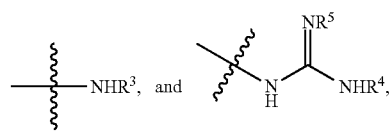

wherein each of $R^3$, $R^4$ and $R^5$ is independently selected from hydrogen, $(C_1-C_3)$-alkyl, aminoalkyl, aminocycloalkyl, and hydroxyalkyl, and n is selected from 1, 2 and 3;

b.

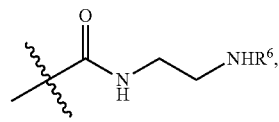

wherein $R^6$ is selected from
H and

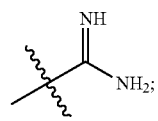

c.

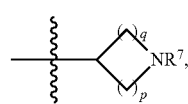

wherein R⁷ is selected from H, (C₁-C₃)-unsubstituted alkyl, amino-(C₂-C₃)-alkyl, aminocycloalkyl, hydroxyalkyl, and

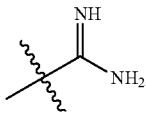

wherein each of p and q is independently selected from 1 and 2.

In one aspect of the invention n is 1. In another aspect of the invention n is 2. In another aspect of the invention n is 3.

In one aspect R¹ is selected from
—CH₂NH₂, —CH₂CH₂NH₂, —CONH(CH₂)₂NH₂,

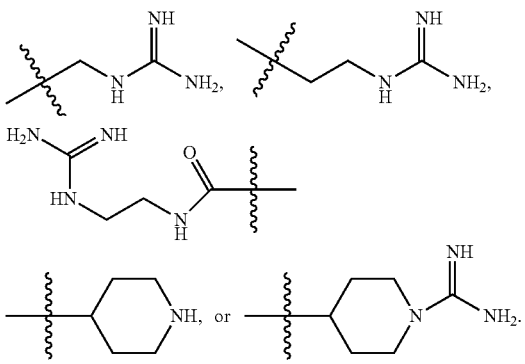

In one embodiment of the invention, R¹ is selected from

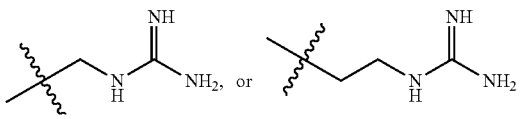 [SMILES: *CNC(=N)N ; *CCNC(=N)N]

In one embodiment of the invention, the compounds of the invention are of the stereochemistry disclosed in Formula II.

(II)

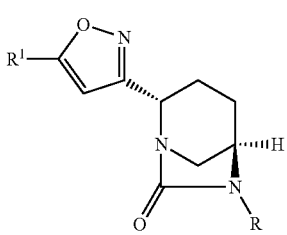

In another embodiment of the invention, the compound is of Formula II and R is —OSO₃H and R¹ is —CH₂NH₂.

In another embodiment of the invention, the compound is of Formula II and R is —OSO₃H and R¹ is —CH₂CH₂NH₂.

In another embodiment of the invention, the compound is of Formula II and R is —OSO₃H and R¹ is —CONH(CH₂)₂NH₂.

In another embodiment of the invention, the compound is of Formula II and R is —OSO₃H and R¹ is

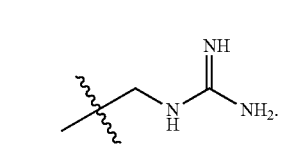 [SMILES: *CNC(=N)N]

In another embodiment of the invention, the compound is of Formula II and R is —OSO₃H and R¹ is

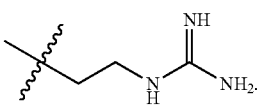 [SMILES: *CCNC(=N)N]

In another embodiment of the invention, the compound is of Formula II and R is —OSO₃H and R¹ is

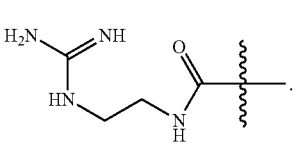 [SMILES: *C(=O)NCCNC(=N)N]

In another embodiment of the invention, the compound is of Formula II and R is —OSO₃H and R¹ is

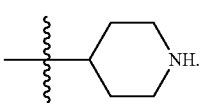

In another embodiment of the invention, the compound is of Formula II and R is —OSO₃H and R¹ is

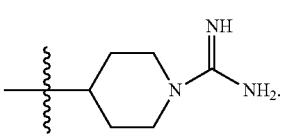 [SMILES: *C1CCN(C(=N)N)CC1]

Preferred compounds of Formula I are the compounds:

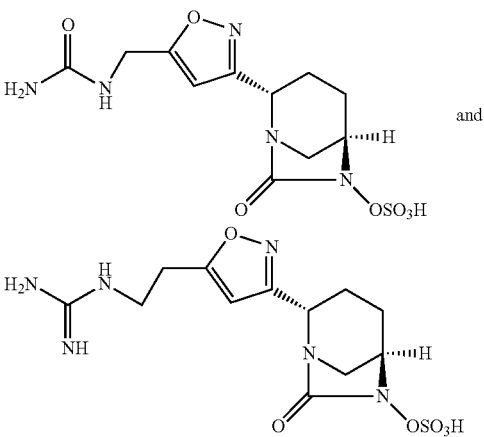

It will be understood by one of skill in the art that depending on the nature of $R^1$ and R, compounds of Formula I may exist in a salt or zwitterionic form.

In one aspect, the invention provides compounds of Formula A-I or pharmaceutically-acceptable salts thereof:

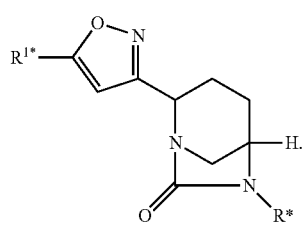
(A-I)

Substituent R* of Formula A-I is selected from

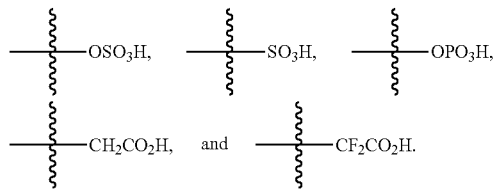

In a preferred embodiment, R* is

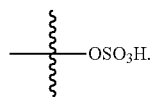

The group $R^{1*}$ is selected from:

a.

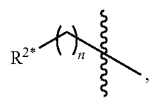

wherein $R^{2*}$ is selected from

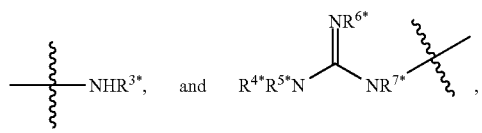

$R^{3*}$ is selected from hydrogen, $(C_1-C_3)$-alkyl, aminoalkyl, aminocycloalkyl, hydroxyalkyl,

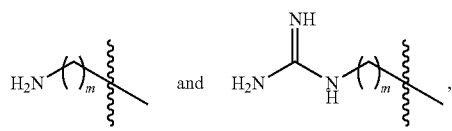

each of $R^{4*}$, $R^{5*}$, $R^{6*}$ and $R^{7*}$ is independently selected from hydrogen, $(C_1-C_6)$-alkyl, aminoalkyl, aminocycloalkyl, and hydroxyalkyl, provided that at least one of $R^{4*}$, $R^{5*}$, $R^{6*}$ and $R^{7*}$ is hydrogen, n is selected from 1, 2, 3 and 4, and m is selected from 1, 2 and 3;

b.

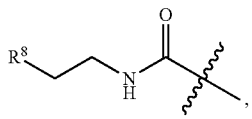

wherein $R^8$ is selected from —$NH(C_1-C_3)$-alkyl and

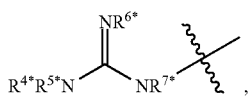

wherein each of $R^{4*}$, $R^{5*}$, $R^{6*}$ and $R^{7*}$ is as described previously;

c.

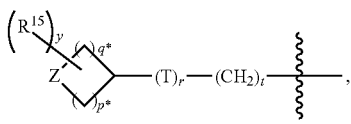

wherein Z is selected from $CR^9R^{10}$ and $NR^{11}$, each of $R^9$ and $R^{10}$ is independently selected from H, $NH_2$, —$NH(C_1-C_3)$-alkyl and

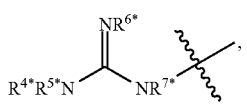

wherein each of $R^{4*}$, $R^{5*}$, $R^{6*}$ and $R^{7*}$ is as described previously, alternatively, $R^9$ and $R^{10}$ together with the carbon to which they are attached, form a cycloalkyl or heterocyclyl ring containing 4-6 ring members, $R^{11}$ is selected from H and

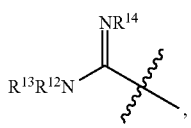

each of $R^{12}$, $R^{13}$ and $R^{14}$ is independently selected from hydrogen, $(C_1-C_6)$-alkyl, aminoalkyl, aminocycloalkyl, and hydroxyalkyl, provided that at least one of $R^{12}$, $R^{13}$ and $R^{14}$ is hydrogen, $R^{15}$ is selected from $NH_2$ and

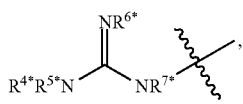

wherein each of $R^{4*}$, $R^{5*}$, $R^{6*}$ and $R^{7*}$ is as described previously,
each of $p^*$ and $q^*$ is independently selected from 0, 1, 2 and 3,
T is selected from NH and O,
t is selected from 0, 1, 2, 3, and 4, and
each of r and y is independently selected from 0 and 1;

d.

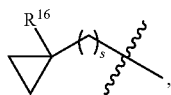

wherein $R^{16}$ is selected from $NH_2$, —$NH(C_1$-$C_3)$-alkyl and

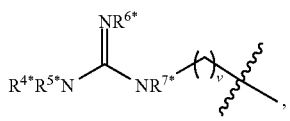

wherein each of $R^{4*}$, $R^{5*}$, $R^{6*}$ and $R^{7*}$ is as described previously,
s is selected from 0 and 1, and,
v is selected from 0, 1, 2, and 3;

e.

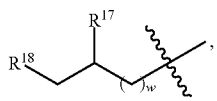

wherein $R^{18}$ is selected from $NH_2$ and

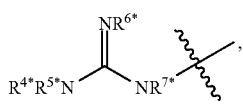

wherein each of $R^{4*}$, $R^{5*}$, $R^{6*}$ and $R^{7*}$ is as described previously,
$R^{17}$ is selected from amino and hydroxyl, and
w is selected from 0 and 1;

f.

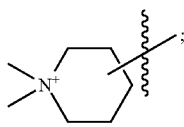

g.

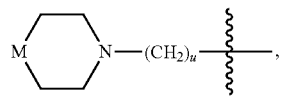

wherein M is selected from $NR^{19}$, $CR^{20}R^{21}$ and O,
wherein $R^{19}$ is selected from H and

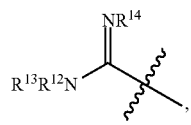

where each of $R^{12}$, $R^{13}$ and $R^{14}$ is as described previously,
each of $R^{20}$ and $R^{21}$ is independently selected from H, $NH_2$ and

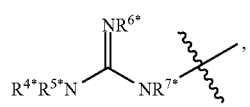

wherein each of $R^{4*}$, $R^{5*}$, $R^{6*}$ and $R^{7*}$ is as described previously, and
u is selected from 0, 1 and 2; and h.

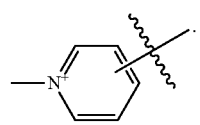

In one aspect of the invention $R^{1*}$ is selected from

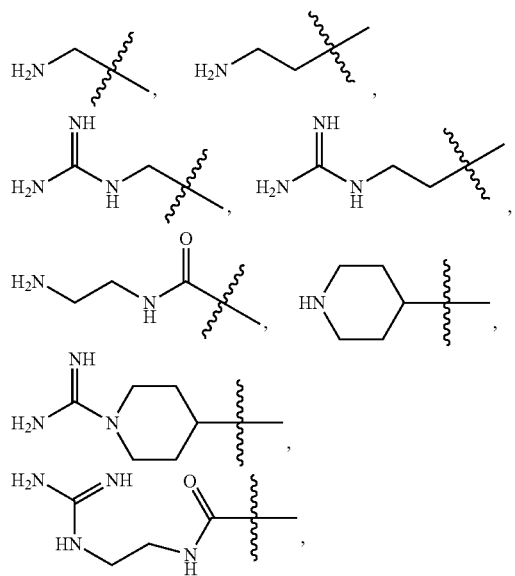

In one embodiment of the invention R$^{1*}$ is selected from

In one embodiment of the invention, the compounds of the invention are of the stereochemistry disclosed in Formula A-II.

(A-II)

In another embodiment of the invention, R* and R$^{1*}$ are chosen from the substituents listed in Table I (See FIG. 1). Preferred compounds of Formula A-I are It will be understood by one of skill in the art that depending on the nature of R$^{1*}$ and R*, compounds of Formula I may exist in a salt or zwitterionic form.

Enzyme Inhibition and Binding Affinity

The compounds of the invention (e.g. compounds of Formula I, compounds of Formula A-I, compounds of Formula II, compounds of Formula A-II) are effective in inhibiting β-lactamase. In one aspect of the invention the compounds of Table I are effective β-lactamase inhibitors. In one aspect the compound

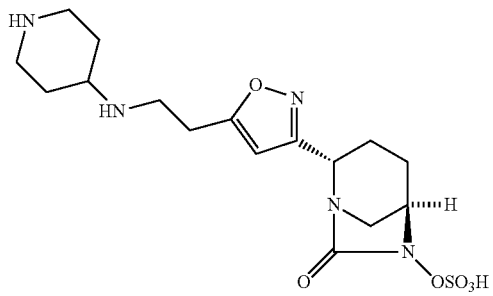

is effective in inhibiting β-lactamase. In one aspect the compound

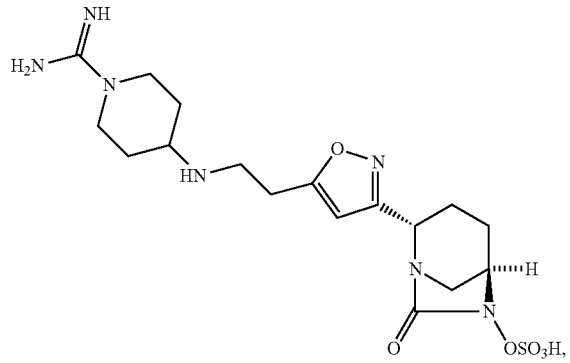

is effective in inhibiting β-lactamase

When used in combination with β-lactam antibiotics, the compounds of the invention (e.g. compounds of Formula I, compounds of Formula A-I, compounds of Formula II, compounds of Formula A-II) potentiate the activity of the β-lactam antibiotic against microorganisms that are normally resistant to β-lactam antibiotics due to the presence of a β-lactamase or multiple β-lactamases.

In one aspect of the invention the compounds of the invention (e.g. compounds of Formula I, compounds of Formula A-I, compounds of Formula II, compounds of Formula A-II) inhibit β-lactamases selected from class A, class C or class D β-lactamases. In one aspect of the invention the compounds of Formula I, inhibit β-lactamases selected from class A, class C or class D β-lactamases. In one aspect of the invention the compounds of Formula A-I inhibit β-lactamases selected from class A, class C or class D β-lactamases. In one aspect of the invention the compounds of Formula II inhibit β-lactamases selected from class A, class C or class D β-lactamases. In one aspect of the invention the compounds of Formula A-II inhibit β-lactamases selected from class A, class C or class D β-lactamases. In one aspect of the invention the compounds of Table I inhibit β-lactamases selected from class A, class C or class D β-lactamases. In one aspect of the invention the compound of Formula

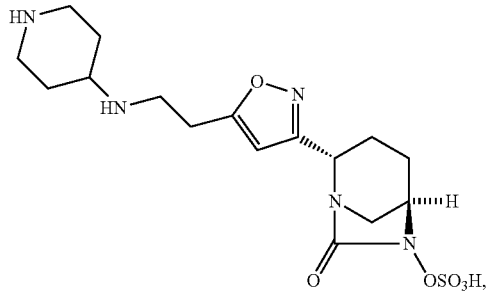

inhibits β-lactamases selected from class A, class C or class D β-lactamases. In one aspect of the invention the compound of Formula

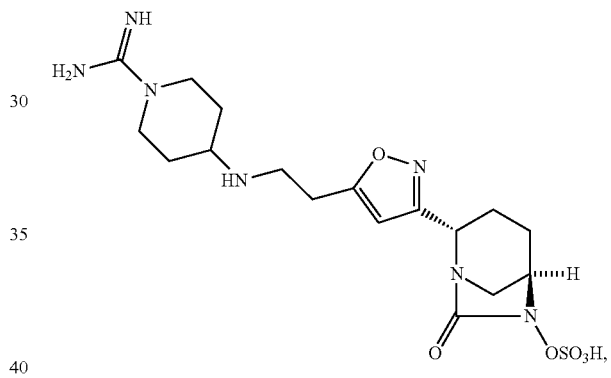

inhibits β-lactamases selected from class A, class C or class D β-lactamases. Class A β-lactamases for example, include, but are not limited to, TEM, SHV, CTX-M, KPC, GES, VEB, SME, and GEX. In a preferred aspect of the invention, the compounds of the invention (e.g. compounds of Formula I, compounds of Formula A-I, compounds of Formula II, compounds of Formula A-II) inhibit KPC β-lactamases. In a preferred aspect of the invention, the compounds of Formula I inhibit KPC β-lactamases. In a preferred aspect of the invention, the compounds of Formula A-I inhibit KPC β-lactamases. In a preferred aspect of the invention, the compounds of Formula II inhibit KPC β-lactamases. In a preferred aspect of the invention, the compounds of Formula A-II inhibit KPC β-lactamases. More preferably the compounds of the invention (e.g. compounds of Formula I, compounds of Formula A-I, compounds of Formula II, compounds of Formula A-II) inhibit KPC-2 or KPC-3 β-lactamases. More preferably the compounds of Formula I inhibit KPC-2 or KPC-3 β-lactamases. More preferably the compounds of Formula A-I inhibit KPC-2 or KPC-3 β-lactamases. More preferably the compounds of Formula II inhibit KPC-2 or KPC-3 β-lactamases. More preferably the compounds of Formula A-II inhibit KPC-2 or KPC-3 β-lactamases. In one aspect of the invention, the compounds of the invention (e.g. compounds of Formula I, compounds of Formula A-I, compounds of Formula II, compounds of Formula A-II) inhibit KPC-2 or KPC-3 β-lactamases in clinical strains (FIG. 2, Table II). In one aspect of the invention, the compounds of Formula I inhibit KPC-2 or KPC-3 β-lactamases in clinical strains (FIG. 2, Table II). In one aspect of the invention, the compounds of Formula A-I inhibit KPC-2 or KPC-3 β-lactamases in clinical strains (FIG. 2, Table II). In one aspect of the invention, the compounds of Formula II inhibit KPC-2 or KPC-3 β-lactamases in clinical strains (FIG. 2, Table II). In one aspect of the invention, the compounds of Formula A-II inhibit KPC-2 or KPC-3 β-lactamases in clinical strains (FIG. 2, Table II). Class C β-lactamases for example, include, but are not limited to chromosomal AmpCs, and plasmid based ACC, DHA, CMY, FOX, ACT, MIR, LAT, MOX β-lactamases. Class D β-lactamase enzymes, for example, include, but are not limited to oxacillinases or OXA β-lactamases. In a preferred aspect of the invention, the compounds of the invention (e.g. compounds of Formula I, compounds of Formula A-I, compounds of Formula II, compounds of Formula A-II) inhibit OXA-15 β-lactamases. In a preferred aspect of the invention, the compounds of Formula I inhibit OXA-15 β-lactamases. In a preferred aspect of the invention, the compounds of Formula A-I inhibit OXA-15 β-lactamases. In a preferred aspect of the invention, the compounds of Formula II inhibit OXA-15 β-lactamases. In a preferred aspect of the invention, the compounds of Formula A-II inhibit OXA-15 β-lactamases.

Unless otherwise indicated, the activity of the BLI compounds can be described by the MIC value obtained from a Synergy MIC assay or a BLI potentiation assay (e.g. as described herein), both of which are run in the presence of a β-lactam. The lower the sMIC or MIC value the more active the BLI, regardless of the mechanism of action of the BLI compound (e.g., including inhibition of β-lactamases by the BLI or any other mechanism of action or combination of mechanisms of action). The sMIC and BLI potentiation assay data supports that the compounds of the invention (e.g. compounds of Formula I, compounds of Formula A-I, compounds of Formula II, compounds of Formula A-II) potentiate (i.e. make more potent) the activity of the β-lactam antibiotic against β-lactamase producing strains by inhibiting the β-lactamase.

In one embodiment, the BLI activity is measured by growth inhibition of a β-lactamase producing bacterial strains in a Synergy MIC (sMIC) assay. Preferably, the sMIC value for the compounds of the invention (e.g. compounds of Formula I, compounds of Formula A-I, compounds of Formula II, compounds of Formula A-II) is 8 µg/mL or less. In a more preferred aspect of the invention, the sMIC value for the compounds of the invention (e.g. compounds of Formula I, compounds of Formula A-I, compounds of Formula II, compounds of Formula A-II) is 4 µg/mL to 8 µg/mL. In an even more preferred aspect of the invention, the sMIC value for the compounds of the invention (e.g. compounds of Formula I, compounds of Formula A-I, compounds of Formula II, compounds of Formula A-II) is 1 to 2 µg/mL. In a still more preferred aspect of the invention, the sMIC value for the compounds of the invention (e.g. compounds of Formula I, compounds of Formula A-I, compounds of Formula II, compounds of Formula A-II) is 0.2 to 0.5 µg/mL. Synergy MICs for representative compounds of the invention are described in Table III (See FIG. 3). It will be understood by one of skill in the art that the growth inhibition of β-lactamase producing strains can also be measured by a checkerboard synergy assay like that disclosed in International Patent Application Number WO 2008/039420 or a standard BLI potentiation assay using a fixed concentration of BLI.

In one embodiment, the BLI activity is measured by growth inhibition of a β-lactamase producing bacterial strains in a standard BLI potentiation assay using a fixed concentration of BLI. Preferably, the MIC value for the compounds of the invention (e.g. compounds of Formula I, compounds of Formula A-I, compounds of Formula II, compounds of Formula A-II) is 8 µg/mL or less. In a more preferred aspect of the invention, the MIC value for the compounds of the invention (e.g. compounds of Formula I, compounds of Formula A-I, compounds of Formula II, compounds of Formula A-II) is 4 to 8 µg/mL. In an even more preferred aspect of the invention, the MIC value for the compounds of the invention (e.g. compounds of Formula I, compounds of Formula A-I, compounds of Formula II, compounds of Formula A-II) is 1 to 2 µg/mL. In a still more preferred aspect of the invention, the MIC value for the compounds of the invention (e.g. compounds of Formula I, compounds of Formula A-I, compounds of Formula II, compounds of Formula A-II) is 0.2 µg/mL to 0.5 µg/mL.

The compounds of the present invention (e.g. compounds of Formula I, compounds of Formula A-I, compounds of Formula II, compounds of Formula A-II) have a broad spectrum of activity across a wide variety of β-lactamase producing bacteria. It was surprisingly found that the compounds of the present invention (e.g. compounds of Formula I, compounds of Formula A-I, compounds of Formula II, compounds of Formula A-II) are active in potentiating activity of β-lactam antibiotics, in particular, Ceftolozane, against strains expressing class D β-lactamase OXA-15 β-lactamase. Currently marketed BLIs inhibit most of the class A β-lactamases, but poorly inhibit class A KPC β-lactamases and class C β-lactamases and have variable success in inhibiting penicillinase and carbapenemase-type class D β-lactamases. The compounds of the present invention (e.g. compounds of Formula I, compounds of Formula A-I, compounds of Formula II, compounds of Formula A-II) are active against a wide variety of bacterial strains that express class A and C β-lactamases and also, surprisingly are active against bacterial strains that express the class D cephalosporinase OXA-15 (Tables II and III). This increased activity against the class D β-lactamase is critical because differential effectiveness against different types of β-lactamase producing bacteria is necessary in order to effectively use β-lactam antibiotics to treat resistant strains of bacteria (vide infra).

In one embodiment, the compounds the invention (e.g. compounds of Formula I, compounds of Formula A-I, compounds of Formula II, compounds of Formula A-II) are unexpectedly more active against bacterial strains that express OXA-15 β-lactamases than the most structurally similar compound, Avibactam (comparator compound CCC). Compounds that are more active than Avibactam against bacterial strains that express the class D cephalosporinase OXA-15 are, for example, compounds 603, 604, 611, 614, 618.

In one embodiment, the compounds of the invention (e.g. compounds of Formula I, compounds of Formula A-I, compounds of Formula II, compounds of Formula A-II) are unexpectedly more active against and/or show broader spectrum of activity against bacterial strains that express KPC β-lactamases than the most structurally similar compound, Avibactam. Compounds that are more active than Avibactam for at least one, bacterial strain that expresses KPC β-lactamase and/or show a better spectrum of activity against bacterial strains that express KPC β-lactamases than Avibactam are, for example, compounds 601, 602, 603, 604, 605, 606, 607, 608, 609, 610, 611, 612, 613, 614, 615, 616, 617, 618, 620, 621, 622, 623, 624, 625, 626, and 627.

In another aspect of the invention, the compounds of the invention (e.g. compounds of Formula I, compounds of Formula A-I, compounds of Formula II, compounds of Formula A-II) have high binding affinity for the β-lactamase enzyme.

Consequently these compounds are better inhibitors of the β-lactamase enzyme. The inhibition kinetics of the compounds of the invention (e.g. compounds of Formula I, compounds of Formula A-I, compounds of Formula II, compounds of Formula A-II) was measured according to the procedure outlined in Example 37. The compounds of the invention (e.g. compounds of Formula I, compounds of Formula A-I, compounds of Formula II, compounds of Formula A-II) have a high binding affinity for the β-lactamase enzyme.

In one embodiment the compounds of the invention (e.g. compounds of Formula I, compounds of Formula A-I, compounds of Formula II, compounds of Formula A-II) have a binding affinity of 1000-5000 $mM^{-1}s^{-1}$. Compounds that have a binding affinity of 1000-5000 $mM^{-1}s^{-1}$ are, for example, compound 604 and 608 (Table IV).

In one embodiment the compounds of the invention (e.g. compounds of Formula

I, compounds of Formula A-I, compounds of Formula II, compounds of Formula A-II) have a binding affinity of 100-999 $mM^{-1}s^{-1}$. Compounds that have a binding affinity of 100-999 $mM^{-1}s^{-1}$ are, for example, compounds 601, 603, 605, 606, 607, 609, 610, 611, 612, 613, 614, 615, 616, 617, 618, 619, 620, 621, 622, 623, 624, 625, 626, and 627 (Table IV).

In one embodiment the compounds of the invention (e.g. compounds of Formula I, compounds of Formula A-I, compounds of Formula II, compounds of Formula A-II) have a binding affinity of 1-99 $mM^-s^{-1}$. Compounds that have a binding affinity of 1-99 $mM^-s^{-1}$ are, for example, 602 (Table IV).

It was surprisingly found that the compounds of the present invention have a higher binding affinity for the β-lactamase enzyme than the closest structural comparator Avibactam (Table IV, See FIG. 4).

The compounds of the invention were also shown to be better BLIs than other comparator compounds as shown in FIG. 5.

Pharmaceutical Compositions Comprising the Compounds of the Invention and Use Thereof Another object of the invention is pharmaceutical compositions or formulations comprising compounds the invention (e.g. compounds of Formula I, compounds of Formula A-I, compounds of Formula II, compounds of Formula A-II), or salts thereof, preferably further comprising a β-lactam antibiotic. In one embodiment of the invention is pharmaceutical compositions or formulations comprising compounds of Formula I, or salts thereof, preferably further comprising a β-lactam antibiotic. In one embodiment of the invention is pharmaceutical compositions or formulations comprising compounds of Formula A-I, or salts thereof, preferably further comprising a β-lactam antibiotic. In one embodiment of the invention is pharmaceutical compositions or formulations comprising compounds of Formula II, or salts thereof, preferably further comprising a β-lactam antibiotic. In one embodiment of the invention is pharmaceutical compositions or formulations comprising compounds of Formula A-II, or salts thereof, preferably further comprising a β-lactam antibiotic. In one embodiment of the invention is pharmaceutical compositions or formulations comprising compounds of Table I. In one embodiment of the invention is pharmaceutical compositions or formulations comprising compounds of Formula

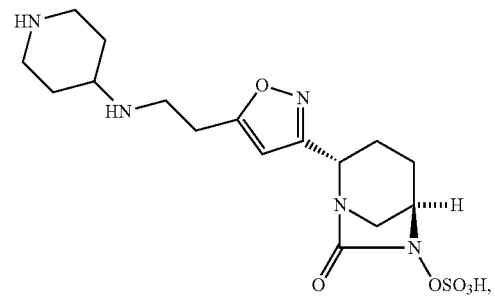

or salts thereof, preferably further comprising a β-lactam antibiotic. In one embodiment of the invention is pharmaceutical compositions or formulations comprising compounds of Formula

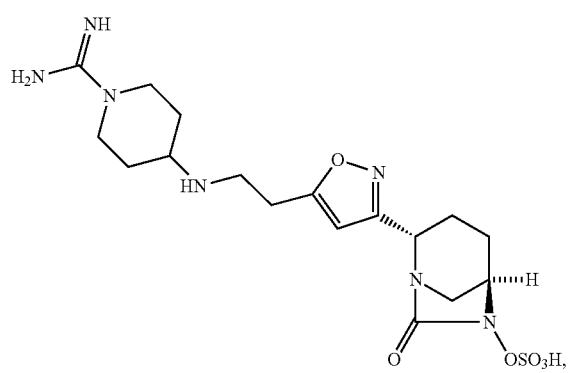

or salts thereof, preferably further comprising a β-lactam antibiotic.

The pharmaceutical compositions can be formulated for oral, intravenous, intramuscular, subcutaneous or parenteral administration for the therapeutic or prophylactic treatment of diseases, such as bacterial infections. Preferably, the pharmaceutical composition is formulated for intravenous administration.

The pharmaceutical preparations disclosed herein may be prepared in accordance with standard procedures and are administered at dosages that are selected to reduce, prevent or eliminate infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the compounds disclosed herein (e.g. one or more compounds of Formula I, compounds of Formula A-I, compounds of Formula II, compounds of Formula A-II), preferably a compound of Formula A-I or Formula A-II, in conjunction with a β-lactam antibiotic, in association with one or more nontoxic, pharmaceutically-acceptable carriers and/or diluents and/or adjuvants and/or excipients. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Non-limiting examples of carriers and excipients include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, compounds of the present invention (e.g. compounds of Formula I, compounds of Formula A-I, compounds of Formula II, compounds of Formula A-II) preferably a compound of Formula A-I or Formula A-II, in conjunction with a β-lactam antibiotic, can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations of the invention may contain conventional additives such as suspending agents, emulsifying agents, non-aqueous agents, preservatives, coloring agents and flavoring agents. Non-limiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition (e.g. compounds of Formula I, compounds of Formula A-I, compounds of Formula II, compounds of Formula A-II) preferably a compound of Formula A-I or Formula A-II, in conjunction with a β-lactam antibiotic, can be dissolved or suspended in any of the commonly used intravenous fluids and administered by infusion. Intravenous fluids include, without limitation, physiological saline or Ringer's solution. Intravenous administration may be accomplished by using, without limitation, syringe, mini-pump or intravenous line.

Pharmaceutical compositions of this invention (e.g. compounds of Formula I, compounds of Formula A-I, compounds of Formula II, compounds of Formula A-II) preferably a compound of Formula A-I or Formula A-II, for parenteral injection comprise pharmaceutically-acceptable aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity can be maintained, for example, by the use of coating materials such as lecithin, by the maintenance of the required particle size in the case of dispersions, and by the use of surfactants. The compositions can include various buffers.

These compositions may also contain adjuvants such as preservatives, wetting agents, emulsifying agents, and dispersing agents. They may also contain taggants or other anti-counterfeiting agents, which are well known in the art. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

Solid dosage forms for oral administration include capsules, tablets, pills, powders, and granules. Such forms may include forms that dissolve or disintegrate quickly in the oral environment. In such solid dosage forms, the active compound preferably a compound of Formula A-I or Formula A-II in conjunction with a β-lactam antibiotic, can be mixed with at least one inert, pharmaceutically-acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropylmethylcellulose, hydroxypropylcellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof; and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, can be prepared with coatings and shells such as functional and aesthetic enteric coatings and other coatings well known in the pharmaceutical formulating art. They may optionally contain opacifying agents and colorants. They may also be in a form capable of controlled or sustained release. Examples of embedding compositions that can be used for such purposes include polymeric substances and waxes.

The pharmaceutical compositions can be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. No. 4,452,775 (issued to Kent), U.S. Pat. No. 5,039,660 (issued to Leonard), and U.S. Pat. No. 3,854,480 (issued to Zaffaroni).

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form.

Alternatively, delayed absorption of a parenterally administered drug form can be accomplished by dissolving or suspending the drug in an oil vehicle.

For intramuscular preparations, a sterile formulation of compounds, preferably a compound of Formula A-I or Formula A-II in conjunction with a β-lactam antibiotic, or suitable soluble salt forms thereof, for example hydrochloride salts, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, or parental formulation of compounds, preferably a compound of Formula A-I or Formula A-II in conjunction with a β-lactam antibiotic, may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less.

An infusion is a dose that is administered at a rate of 30 minutes or greater. In one embodiment, the infusion is one hour or greater. In another embodiment, the infusion is substantially constant.

For topical use the pharmaceutical compositions, preferably a compound of Formula A-I or Formula A-II in conjunction with a β-lactam antibiotic, can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the pharmaceutical composition can be presented in liquid or semi-liquid form formulated in hydrophobic or hydrophilic bases as ointments, creams, lotions, paints or powders.

For rectal administration, the pharmaceutical compositions, preferably a compound of Formula A-I or Formula A-II in conjunction with a β-lactam antibiotic, can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of compounds, preferably a compound of Formula A-I or Formula A-II in conjunction with a β-lactam antibiotic, can be a solution of one or more compounds, or salts thereof, in a suitable diluent, in sterile hermetically sealed ampoules or sterile syringes. The concentration of the compounds, preferably a compound of Formula A-I or Formula A-II in conjunction with a β-lactam antibiotic, in the unit dosage may vary, e.g. from about 1 percent to about 50 percent, depending on the compound used and its solubility and the dose desired by the physician. If the compositions contain dosage units, each dosage unit can contain from 1-500 mg of the active material. For adult human treatment, the dosage employed can range from 5 mg to 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention, preferably in combination with a β-lactam antibiotic for the drugs in the art-recognized protocols.

Exemplary procedures for delivering an antibacterial agent are described in U.S. Pat. Nos. 6,468,967; 6,852,689; and 5,041,567, issued to Rogers and in PCT patent application number EP94/02552 (publication no. WO 95/05384), the disclosures of which are incorporated herein by reference in their entirety. In one embodiment, one or more compounds of the invention, preferably a compound of Formula A-I or Formula A-II in conjunction with a β-lactam antibiotic, or pharmaceutical compositions thereof are administered orally, rectally or via injection (intravenous, intramuscular or subcutaneous). In another embodiment, one or more compounds of the invention, preferably a compound of Formula A-I or Formula A-II in conjunction with a β-lactam antibiotic, or pharmaceutical compositions thereof are administered orally, rectally or via injection (intravenous, intramuscular or subcutaneous) to treat an infection caused by β-lactam resistant bacteria. In another embodiment, one or more compounds of the invention, preferably a compound of Formula A-I or Formula A-II in conjunction with a β-lactam antibiotic, or pharmaceutical compositions thereof are administered orally to treat an infection caused by β-lactamase producing bacteria.

As used herein, the phrases "therapeutically-effective dose" and "therapeutically-effective amount" refer to an amount of a compound that prevents the onset, alleviates the symptoms, stops the progression of a bacterial infection, or results in another desired biological outcome such as, e.g., improved clinical signs or reduced/elevated levels of lymphocytes and/or antibodies.

The term "treating" or "treatment" is defined as administering, to a subject, a therapeutically-effective amount of one or more compounds both to prevent the occurrence of an infection and to control or eliminate an infection. Those in need of treatment may include individuals already having a particular medical disease as well as those at risk for the disease (i.e., those who are likely to ultimately acquire the disorder).

The term "subject," as used herein, refers to a mammal, a plant, a lower animal, or a cell culture. In one embodiment, a subject is a human or other animal patient in need of antibacterial treatment.

The term "administering" or "administration" and the like, refers to providing the compound of the invention (e.g. compounds of Formula I, compounds of Formula A-I, compounds of Formula II, compounds of Formula A-II) to the subject in need of treatment. Preferably the subject is a mammal, more preferably a human. The present invention comprises administering the compound of the invention (e.g. compounds of Formula I, compounds of Formula A-I, compounds of Formula II, compounds of Formula A-II) in conjunction with a β-lactam antibiotic. When a compound of the invention (e.g. compounds of Formula I, compounds of Formula A-I, compounds of Formula II, compounds of Formula A-II) is administered in conjunction with a β-lactam antibiotic, the compound of the invention (e.g. compounds of Formula I, compounds of Formula A-I, compounds of Formula II, compounds of Formula A-II) and the β-lactam antibiotic can be administered at the same time or different times. When the compounds of the invention (e.g. compounds of Formula I, compounds of Formula A-I, compounds of Formula II, compounds of Formula A-II) and the β-lactam antibiotic are administered at the same time, they can be administered as a single composition or pharmaceutical composition or they can be administered separately. It is understood that when a compound of the invention (e.g. compounds of Formula I, compounds of Formula A-I, compounds of Formula II, compounds of Formula A-II) is administered in conjunction with a β-lactam antibiotic, that the active agents can be administered in a single combination or in multiple combinations. For example, when administered by IV, the compound of the invention (e.g. compounds of Formula I, compounds of Formula A-I, compounds of Formula II, compounds of Formula A-II) can be dissolved or suspended in any of the commonly used intravenous fluids and administered by infusion, then a β-lactam antibiotic can be dissolved or suspended in any of the commonly used intravenous fluids and administered by infusion. Conversely the β-lactam antibiotic can be dissolved or suspended in any of the commonly used intravenous fluids and administered by infusion, then a compound of Formula I can be dissolved or suspended in any of the commonly used intravenous fluids and administered by infusion. Alternatively, a pharmaceutical composition comprising a compound of the invention (e.g. compounds of Formula I, compounds of Formula A-I, compounds of Formula II, compounds of Formula A-II) and a β-lactam antibiotic can be dissolved or suspended in any of the commonly used intravenous fluids and administered by infusion.

In one embodiment of the invention, is provided a method of treating or preventing a bacterial infection comprising administering to a subject in need thereof a therapeutically-effective amount of the pharmaceutical composition comprising a compound of the invention (e.g. compounds of Formula I, compounds of Formula A-I, compounds of Formula II, compounds of Formula A-II) and a β-lactam antibiotic. In one embodiment of the invention, is provided a method of treating or preventing a bacterial infection comprising administering to a subject in need thereof a therapeutically-effective amount of the pharmaceutical composition comprising a compound of Formula I, and a β-lactam antibiotic. In one embodiment of the invention, is provided a method of treating or preventing a bacterial infection comprising administering to a subject in need thereof a therapeutically-effective amount of the pharmaceutical composition comprising a compound of Formula A-I, and a β-lactam antibiotic. In one embodiment of the invention, is provided a method of treating or preventing a bacterial infection comprising administering to a subject in need thereof a therapeutically-effective amount of the pharmaceutical composition comprising a compound of Formula II, and a β-lactam antibiotic. In one embodiment of the invention, is provided a method of treating or preventing a bacterial infection comprising administering to a subject in need thereof a therapeutically-effective amount of the pharmaceutical composition comprising a compound of Formula A-II, and a β-lactam antibiotic.

In one embodiment of the invention, is provided a method of treating or preventing a bacterial infection comprising administering to a subject in need thereof, a therapeutically-effective amount of a β-lactam antibiotic in conjunction with a compound of the invention (e.g. compounds of Formula I, compounds of Formula A-I, compounds of Formula II, compounds of Formula A-II). In one embodiment of the invention, is provided a method of treating or preventing a bacterial infection comprising administering to a subject in need thereof, a therapeutically-effective amount of a β-lactam antibiotic in conjunction with a compound of Formula I. In one embodiment of the invention, is provided a method of treating or preventing a bacterial infection comprising administering to a subject in need thereof, a therapeutically-effective amount of a β-lactam antibiotic in conjunction with a compound of Formula A-I. In one embodiment of the invention, is provided a method of treating or preventing a bacterial infection comprising administering to a subject in need thereof, a therapeutically-effective amount of a β-lactam antibiotic in conjunction with a compound of Formula II. In one embodiment of the invention, is provided a method of treating or preventing a bacterial infection comprising administering to a subject in need thereof, a therapeutically-effective amount of a β-lactam antibiotic in conjunction with a compound of Formula A-II. In one embodiment of the invention, is provided a method of treating or preventing a bacterial infection comprising administering to a subject in need thereof, a therapeutically-effective amount of a β-lactam antibiotic in conjunction with a compound of Table I. In one embodiment of the invention, is provided a method of treating or preventing a bacterial infection comprising administering to a subject in need thereof, a therapeutically-effective amount of a β-lactam antibiotic in conjunction with a compound of Formula

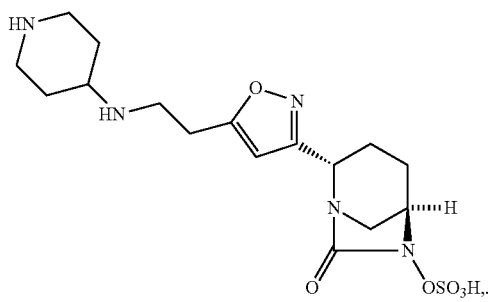

In one embodiment of the invention, is provided a method of treating or preventing a bacterial infection comprising administering to a subject in need thereof, a therapeutically-effective amount of a β-lactam antibiotic in conjunction with a compound of Formula

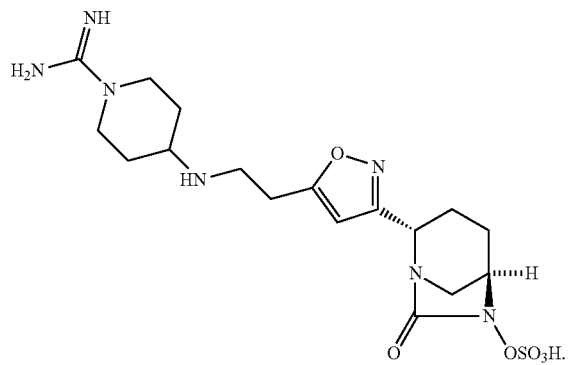

In one embodiment of the invention, is provided a method of treating or preventing a bacterial infection in a subject comprising the steps of
a. administering to the subject a compound of the invention; and
b. administering to the subject a therapeutically-effective amount of a β-lactam antibiotic.

In one embodiment the compound in step a is a compound of Formula I. In one embodiment the compound in step a is a compound of Formula A-I. In one embodiment the compound in step a is a compound of Formula II. In one embodiment the compound in step a is a compound of Formula A-II. In one embodiment the compound in step a is a compound of Table I. In one embodiment the compound in step a is a compound of Formula A-II. In one embodiment the compound in step a is a compound of Formula

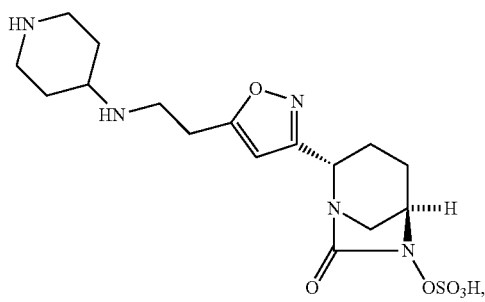

In one embodiment the compound in step a is a compound of Formula

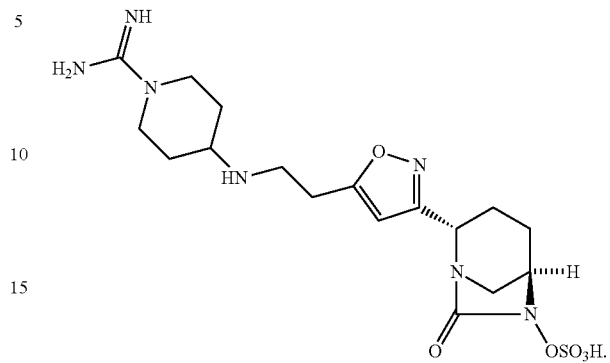

In one embodiment, the β-lactam antibiotic in step b is Ceftolozane or Ceftazidime. In one embodiment the compound in step a is a compound of Formula

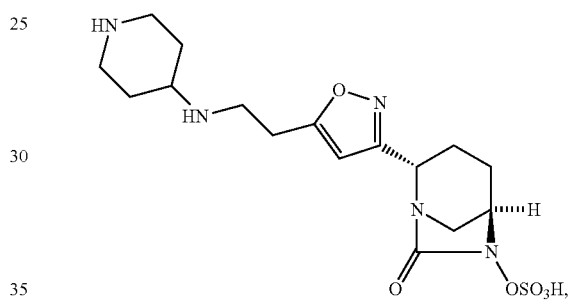

and the β-lactam antibiotic in step b is Ceftolozane. In one embodiment the compound in step a is a compound of Formula

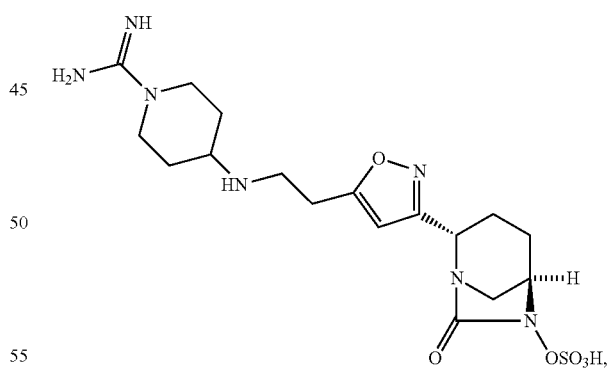

and the β-lactam antibiotic in step b is Ceftolozane.

In one embodiment of the invention, is provided a method of treating or preventing a bacterial infection in a subject comprising the steps of
a. administering to the subject a therapeutically-effective amount of a β-lactam antibiotic; and
b. administering to the subject a compound of the invention.

In one embodiment the compound in step b is a compound of Formula I. In one embodiment the compound in step b is a compound of Formula A-I. In one embodiment the compound in step b is a compound of Formula II. In one embodiment the compound in step b is a compound of Formula A-II. In one embodiment the compound in step b is a compound of Table I. In one embodiment the compound in step b is a compound of Formula

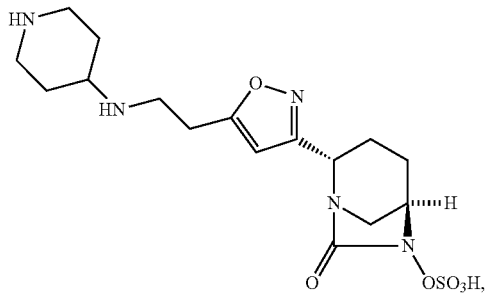

In one embodiment the compound in step b is a compound of Formula

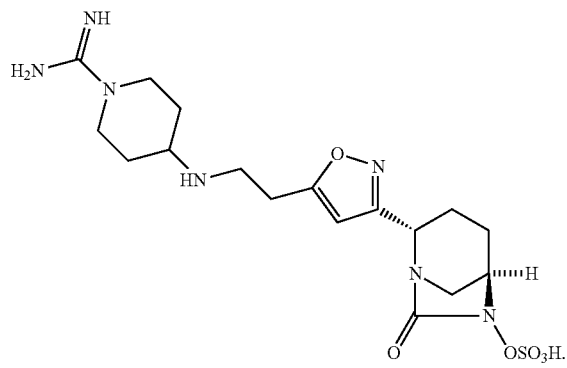

In one embodiment, the β-lactam antibiotic in step a is Ceftolozane or Ceftazidime. In one embodiment the compound in step b is a compound of Formula

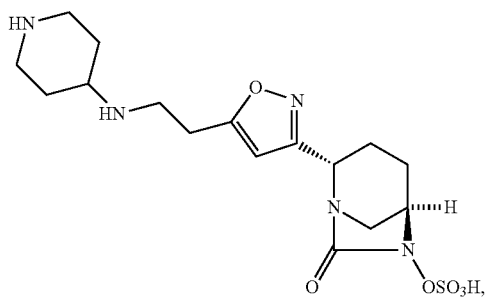

and the β-lactam antibiotic in step a is Ceftolozane. In one embodiment the compound in step a is b compound of Formula

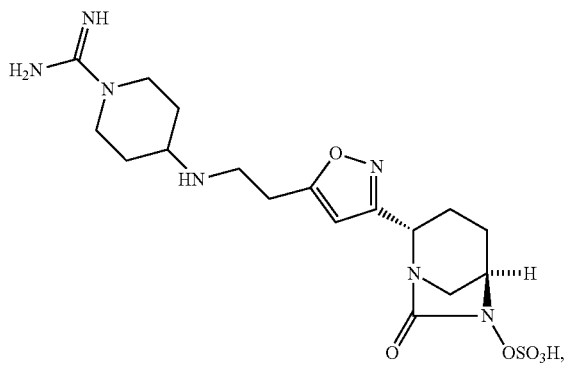

and the β-lactam antibiotic in step a is Ceftolozane. In one embodiment, the invention provides a method for treating an infection in a subject by administering a therapeutically-effective amount of one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, or compositions thereof. In one embodiment, the method comprises administering to a subject in need thereof a pharmaceutical composition comprising at least one of the compounds described herein, preferably a compound of Formula A-I or Formula A-II in conjunction with a β-lactam antibiotic. In one embodiment the compound is of Formula

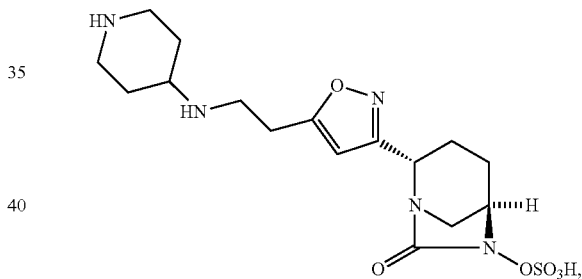

in conjunction with a β-lactam antibiotic, preferably Ceftolozane or Ceftazidime, or compositions thereof. In one embodiment the compound is of Formula

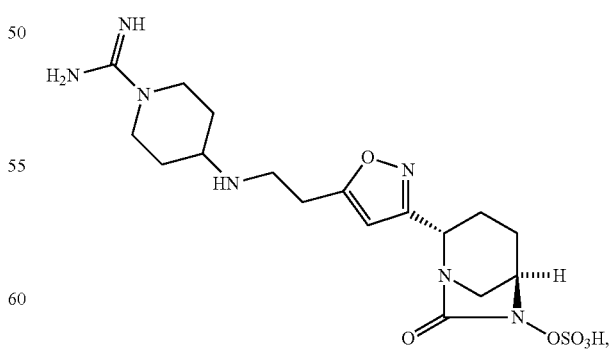

in conjunction with a β-lactam antibiotic, preferably Ceftolozane or Ceftazidime, or compositions thereof. In one embodiment, the pharmaceutical composition can comprise any one of the compounds described herein as the sole active compound or in combination with another compound, composition, or biological material. The compound may be administered orally, parenterally, by inhalation, topically, rectally, nasally, buccally, vaginally, or by an implanted reservoir, external pump or catheter. The compound may be prepared for ophthalmic or aerosolized uses. The compounds of the present invention can be administered as an aerosol for the treatment of pneumonia or other lung-based infections. In one embodiment, the aerosol delivery vehicle is an anhydrous or dry powder inhaler. One or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, or pharmaceutical compositions thereof also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In one embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered intravenously, subcutaneously or orally. In one embodiment for administering one or more compounds according to the invention (e.g. compounds of Formula I, compounds of Formula A-I, compounds of Formula II, compounds of Formula A-II), preferably a compound of Formula A-I or Formula A-II in conjunction with a β-lactam antibiotic to a cell culture, the one or more compounds may be administered in a nutrient medium.

In one embodiment, one or more compounds according to the invention (e.g. compounds of Formula I, compounds of Formula A-I, compounds of Formula II, compounds of Formula A-II), preferably a compound of Formula A-I or A-II in conjunction with a β-lactam antibiotic, may be used to treat a subject having a bacterial infection in which the infection is caused or exacerbated by any type of bacteria, such as Gram-negative bacteria. In one aspect of the invention, the bacterial infection is caused by β-lactam resistant bacteria. In one aspect the bacterial infection is caused by β-lactamase producing bacteria. In another aspect the bacterial infection is caused by class A, class C or class D β-lactamase producing bacteria. In another aspect the bacterial infection is caused by class A β-lactamase producing bacteria. In another aspect the infection is caused by class C β-lactamase producing bacteria. In still another aspect the infection is caused by class D β-lactamase producing bacteria. In still another aspect the infection is caused by KPC β-lactamase producing bacteria. In still another aspect the infection is caused by OXA β-lactamase producing bacteria. In still another aspect, the bacterial infection is caused by a bacteria that produces multiple β-lactamases. Bacteria that produce multiple β-lactamases may produce β-lactamases of the same class or of different classes (e.g. class A and class A or class A and class C or class A and class D etc).

Representative Gram-negative pathogens known to express β-lactamases include, but are not limited to *Acinetobacter* spp. (including *Acinetobacter baumannii*), *Citrobacter* spp., *Escherichia* spp. (including *Escherichia coli*), *Haemophilus influenzae, Morganella morganii, Pseudomonas aeruginosa, Klebsiella* spp. (including *Klebsiella pneumoniae*), *Enterobacter* spp. (including *Enterobacter cloacae* and *Enterobacter aerogenes*), *Pasteurella* spp., *Proteus* spp. (including *Proteus mirabilis*), *Serratia* spp. (including *Serratia marcescens*), and *Providencia* spp. Bacterial infections can be caused or exacerbated by Gram-negative bacteria including strains which express β-lactamases that may confer resistance to penicillins, cephalosporins, monobactams and/or carbapenems. The co-administration of a novel BLI that inhibits these β-lactamases with a β-lactam antibiotic could be used to treat infections caused by β-lactam resistant bacteria.

In one aspect of the invention the infection is caused by a β-lactamase producing bacteria selected from *Acinetobacter* spp, *Citrobacter* spp, *Escherichia coli, Enterobacter cloacae), Haemophilus influenzae, Pseudomonas aeruginosa, Proteus mirabilis, Serratia marcescens*, and *Klebsiella pneumoniae,*

β-Lactam antibiotics that may be administered concurrently with compounds of the invention (e.g. compounds of Formula I, compounds of Formula A-I, compounds of Formula II, compounds of Formula A-II) include, but are not limited to cephalosporin, carbapenem, monobactam, penem and penicillin classes of antibiotics.

In one embodiment of the invention, the β-lactam antibiotic is a cephalosporin. Examples of cephalosporins include, but are not limited to, Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef and Ceftolozane. In one embodiment the cephalosporin is Ceftolozane or Ceftazidime.

In one embodiment of the invention, the β-lactam antibiotic is a carbapenen. Examples of carbapenem antibiotics include, but are not limited to, Imipenem, Imipenem/Cilastatin, Biapenem, Doripenem, Meropenem, Ertapenem and Panipenem. In one embodiment the Carbapenem is Imipenem/Cilastatin or Meropenem.

In one embodiment of the invention, the β-lactam antibiotic is a monobactam. Examples of monobactam antibiotics include, but are not limited to Aztreonam, Tigemonam, Carumonam, BAL30072 and Nocardicin A.

In one embodiment of the invention, the β-lactam antibiotic is a penem. In one embodiment of the invention, the β-lactam antibiotic is a penicillin. Examples of penicillin antibiotics include, but are not limited to Amoxicillin, Ampicillin, Azlocillin, Mezlocillin, Apalcillin, Hetacillin, Becampicillin, Carbenicillin, Sulbenicillin, Ticarcillin, Piperacillin, Azlocillin, Mecillinam, Pivmecillinam, Methicillin, Ciclacillin, Talampicillin, Aspoxicillin, Oxacillin, Cloxacillin, Dicloxacillin, Flucloxacillin, Nafcillin and Pivampicillin.

The pharmaceutical compositions, preferably a compound of the invention (e.g. compounds of Formula I, compounds of Formula A-I, compounds of Formula II, compounds of Formula A-II) in conjunction with a β-lactam antibiotic, can be used to treat a bacterial infection of any organ or tissue in the body caused by β-lactam resistant bacteria, preferably, Gram-negative β-lactam resistant bacteria. These organs or tissue include, without limitation, skeletal muscle, skin, bloodstream, kidneys, heart, lung and bone. For example, a pharmaceutical composition comprising at least one compound of the invention (e.g. compounds of Formula I, compounds of Formula A-I, compounds of Formula II, compounds of Formula A-II), preferably a compound of Formula A-I or Formula A-II in conjunction with a β-lactam antibiotic, can be administered to a subject to treat, without limitation, skin and soft tissue infections (e.g., complex skin infections), bacteremia, intra-abdominal infections and urinary tract infections (e.g., cUTI). In addition, a compound of the invention (e.g. compounds of Formula I, compounds of Formula A-I, compounds of Formula II, compounds of Formula A-II) may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *Pseudomonas aeruginosa*. At least one compound of the invention (e.g. compounds of Formula I, compounds of Formula A-I, compounds of Formula II, compounds of Formula A-II), preferably a compound of Formula A-I or Formula A-II in conjunction with a β-lactam antibiotic, can be administered to a subject to treat mixed infections that comprise different types of Gram-negative bacteria, or which comprise both Gram-positive and Gram-negative bacteria. These types of infections include intra-abdominal infections and obstetrical/gynecological infections. At least one compound of the invention (e.g. compounds of Formula I, compounds of Formula A-I, compounds of Formula II, compounds of Formula A-II), preferably a compound of Formula A-I or Formula A-II in conjunction with a β-lactam antibiotic, may also be administered to a subject to treat an infection including, without limitation, endocarditis, nephritis, septic arthritis, intra-abdominal sepsis, bone and joint infections and osteomyelitis. At least one compound of the invention (e.g. compounds of Formula I, compounds of Formula A-I, compounds of Formula II, compounds of Formula A-II), preferably compound of Formula A-I or Formula A-II in conjunction with a β-lactam antibiotic, or pharmaceutical compositions thereof, may also be directly injected or administered into an abscess, ventricle or joint. Pharmaceutical compositions of the invention (e.g. compounds of Formula I, compounds of Formula A-I, compounds of Formula II, compounds of Formula A-II), preferably compound of Formula A-I or Formula A-II in conjunction with a β-lactam antibiotic, may be administered as an aerosol for the treatment of pneumonia or other lung-based infections. In one embodiment, the aerosol delivery vehicle is an anhydrous, liquid or dry powder inhaler.

Actual dosage levels of active ingredients in the pharmaceutical compositions of one or more compounds according to the invention (e.g. compounds of Formula I, compounds of Formula A-I, compounds of Formula II, compounds of Formula A-II), preferably a compound of Formula A-I or Formula A-II in conjunction with a β-lactam antibiotic, may be varied so as to obtain a therapeutically-effective amount of the active compound(s) to achieve the desired therapeutic response for a particular patient, compositions, and mode of administration. The effective amount can be determined as described herein. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans. It will be understood by one of skill in the art that the when the composition comprises a compound of the invention (e.g. compounds of Formula I, compounds of Formula A-I, compounds of Formula II, compounds of Formula A-II) and a β-lactam antibiotic, both the compound of the invention (e.g. compounds of Formula I, compounds of Formula A-I, compounds of Formula II, compounds of Formula A-II) and the β-lactam antibiotic are active compounds.

The method comprises administering to the subject an effective dose of one or more compounds of the invention (e.g. compounds of Formula I, compounds of Formula A-I, compounds of Formula II, compounds of Formula A-II), preferably in conjunction with a β lactam antibiotic. An effective dose of a compound of the invention (e.g. compounds of Formula I, compounds of Formula A-I, compounds of Formula II, compounds of Formula A-II) is generally between 125 mg/day to 2000 mg/day. In one embodiment, an effective dose is from about 0.1 to about 100 mg/kg of one or more compounds of the invention (e.g. compounds of Formula I, compounds of Formula A-I, compounds of Formula II, compounds of Formula A-II) or pharmaceutically acceptable salts thereof. In one embodiment, the dose is from about 0.1 to about 50 mg/kg of one or more compounds of the invention (e.g. compounds of Formula I, compounds of Formula A-I, compounds of Formula II, compounds of Formula A-II) or pharmaceutically acceptable salts thereof. In another embodiment, the dose is from about 1 to about 25 mg/kg of one or more compounds of the invention (e.g. compounds of Formula I, compounds of Formula A-I, compounds of Formula II, compounds of Formula A-II) or pharmaceutically acceptable salts thereof. In another embodiment, the dose is from about 1 to about 12 mg/kg of one or more compounds of the invention (e.g. compounds of Formula I, compounds of Formula A-I, compounds of Formula II, compounds of Formula A-II). In another embodiment, the dose is about 1, 2, 3, 4, 5, 6, 7, 8, 9, 10, 11, or 12 mg/kg of one or more compounds of the invention (e.g. compounds of Formula I, compounds of Formula A-I, compounds of Formula II, compounds of Formula A-II). In another embodiment, the compounds of the invention (e.g. compounds of Formula I, compounds of Formula A-I, compounds of Formula II, compounds of Formula A-II) are administered to a human at a dose of 100 mg to 1000 mg per dose up to four times per day. In another embodiment, the compounds of the invention (e.g. compounds of Formula I, compounds of Formula A-I, compounds of Formula II, compounds of Formula A-II) are administered to a human at a dose of 125 mg to 750 mg per dose up to four times per day. In another embodiment, the compounds of the invention (e.g. compounds of Formula I, compounds of Formula A-I, compounds of Formula II, compounds of Formula A-II) are administered to a human at a dose of 250 mg to 500 mg per dose up to four times a day. An effective dose for cell culture is usually between about 0.1 and about 1000 µg/mL. In one embodiment, the effect dose for cell culture is between about 0.1 and about 200 µg/mL.

In one embodiment, a β-lactam antibiotic and a compound of the invention (e.g. compounds of Formula I, compounds of Formula A-I, compounds of Formula II, compounds of Formula A-II) are administered in ratio of 1:4 to 8:1 antibiotic:compound of the invention (e.g. compounds of Formula I, compounds of Formula A-I, compounds of Formula II, compounds of Formula A-II). In one embodiment the ratio is 1:4. In another embodiment the ratio is 3:4. In another embodiment the ratio is 5:4. In another embodiment the ratio is 7:4. In another embodiment the ratio is 1:2. In another embodiment the ratio is 3:2. In another embodiment the ratio is 5:2. In another embodiment the ratio is 7:2. In another embodiment the ratio is 1:3. In another embodiment the ratio is 2:3. In another embodiment the ratio is 4:3. In another embodiment the ratio is 5:3. In another embodiment the ratio is 7:3. In another embodiment the ratio is 1:2. In another embodiment the ratio is 3:2. In another embodiment the ratio is 5:2. In another embodiment the ratio is 7:2. In another embodiment the ratio is 1:1. In another embodiment the ratio is 2:1. In another embodiment the ratio is 3:1. In another embodiment the ratio is 4:1. In another embodiment the ratio is 5:1. In another embodiment the ratio is 6:1. In another embodiment the ratio is 7:1. In another embodiment the ratio is 8:1. It will be understood by one of skill in the art that the β-lactam antibiotic and compound of the invention (e.g. compounds of Formula I, compounds of Formula A-I, compounds of Formula II, compounds of Formula A-II) can be administered within the range of ratios provided regardless of the method of drug delivery. It will also be understood by one of skill in the art that the β-lactam antibiotic and compound of the invention (e.g. compounds of Formula I, compounds of Formula A-I, compounds of Formula II, compounds of Formula A-II) can be administered within the range of ratios provided together, for example, in a pharmaceutical composition, or sequentially, i.e. the β-lactam antibiotic is administered, followed by administration of a compound of the invention (e.g. compounds of Formula I, compounds of Formula A-I, compounds of Formula II, compounds of Formula A-II) or vice versa.

One or more compounds of the invention (e.g. compounds of Formula I, compounds of Formula A-I, compounds of Formula II, compounds of Formula A-II) may also be administered in the diet or feed of a patient or animal. If administered as part of a total dietary intake, the amount of compound employed can be less than 1% by weight of the diet, such as no more than 0.5% by weight. The diet for animals can be normal foodstuffs to which the compound can be added or it can be added to a premix.

One or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, can be administered as a single daily dose or in multiple doses per day. In one embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, is administered as a single dose per day. In another embodiment, one or more compounds of the invention (e.g. compounds of Formula I, compounds of Formula A-I, compounds of Formula II, compounds of Formula A-II), preferably a compound of Formula A-I of Formula A-II in conjunction with a β-lactam antibiotic is administered as two equal doses per day. In another embodiment, the compounds of the invention (e.g. compounds of Formula I, compounds of Formula A-I, compounds of Formula II, compounds of Formula A-II), preferably a compound of Formula A-I or Formula A-II in conjunction with a β-lactam antibiotic is administered in three equal doses per day. In another embodiment, the compounds of the invention (e.g. compounds of Formula I, compounds of Formula A-I, compounds of Formula II, compounds of Formula A-II), preferably a compound of Formula A-I or Formula A-II in conjunction with a β-lactam antibiotic is administered in four equal doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound of the invention and the β-lactam antibiotic and the microorganism or microorganisms involved in the infection. The treatment regimen for one type of infection may differ greatly from the treatment regimen of another infection. For example, one type of infection may require administration via intravenous administration once daily, while another infection may require a treatment regimen of multiple dosing orally.

One or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, may be administered according to this method until the bacterial infection is eradicated or reduced. In one embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for a period of time from 3 days to 6 months. In another embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for 7 to 56 days. In another embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for 7 to 28 days. In a further embodiment, one or more compounds of the invention (e.g. compounds of Formula I, compounds of Formula A-I, compounds of Formula II, compounds of Formula A-II), preferably a compound of Formula A-I or Formula A-II in conjunction with a β-lactam antibiotic, are administered for 7 to 14 days. Compounds of the present invention may be administered for a longer or shorter time period if it is so desired.

Other embodiments of the invention include:

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 β-lactam antibiotic or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 cephalosporin antibiotic or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and Ceftolozane or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 carbapenem antibiotic or a pharmaceutically acceptable salt thereof.

A pharmaceutical composition comprising a compound of the invention (e.g. compounds of Formula I, compounds of Formula A-I, compounds of Formula II, compounds of Formula A-II), preferably a compound of Formula A-I or Formula A-II and at least 1 monobactam antibiotic or a pharmaceutically acceptable salt thereof.

The embodiments described herein provide compounds of the invention (e.g. compounds of Formula I, compounds of Formula A-I, compounds of Formula II, compounds of Formula A-II), preferably a compound of Formula A-I or Formula A-II that are novel and active β-lactamase inhibitors. Other embodiments described herein provide novel compounds of the invention (e.g. compounds of Formula I, compounds of Formula A-I, compounds of Formula II, compounds of Formula A-II), preferably a compound of Formula A-I or Formula A-II in conjunction with β-lactam antibiotics for treatment of infections. Further embodiments described herein provide novel compounds of the invention (e.g. compounds of Formula I, compounds of Formula A-I, compounds of Formula II, compounds of Formula A-II), preferably a compound of Formula A-I or Formula A-II that show unexpected activity against β-lactamases that other compounds in the class do not have.

Preparation of Compounds of the Invention

A compound of the invention (e.g. compounds of Formula I, compounds of Formula A-I, compounds of Formula II, compounds of Formula A-II) can be prepared by a variety of synthetic routes, including synthetic schemes described herein. These synthetic routes can be applied to large scale synthesis with appropriate adjustment of reaction sequence, reaction conditions, isolation/purification methods and choice of solvents which are environmentally friendly and cost-effective.

The following abbreviations have the following meanings unless otherwise indicated. Abbreviations not defined below have their generally accepted meaning Bn=benzyl
Boc=tert-butoxycarbonyl
Boc$_2$O=di-tert-butyldicarbonate
Burgess reagent=methyl N-triethylammoniumsulfonyl) carbamate
CDI=carbonyldiimidazole
CFU=colony-forming units
CLSI=Clinical Laboratory Standards Institute
cSSSI=complicated skin and skin structure infections
DBU=1,8-diazabicyclo[5.4.0]undec-7-ene
DCM=dichloromethane
DEAD=diethyl azodicarboxylate
DIAD=diisopropyl azodicarboxylate
DIPEA=diisopropylethylamine
DMF=N,N-dimethylformamide
DMAc=N,N-dimethylacetamide
DMSO=dimethyl sulfoxide
EDCI=1-ethyl-3-(3'-dimethylaminopropyl)carbodiimide
ELSD=evaporative light scattering detector
EtOAc=ethyl acetate
ESI-MS=electrospray ionization mass spectrometry
Fmoc=Fluorenylmethyloxycarbonyl
HAP=Hospital-Acquired Pneumonia
HATU=2-(7-aza-1H-benzotriazole-1-yl)-1,1,3,3-tetramethyluronium hexafluorophosphate
HCl=hydrochloride
HOBt=1-hydroxybenzotrizole
Hrs=hours
HPLC=high performance liquid chromatography
Hunig's base=N,N-Diisopropylethylamine
Lawesson's reagent=2,4-bis(4-methoxyphenyl)-1,3,2,4-dithiadiphosphetane-2,4-disulfide
MIC=minimum inhibitory concentration
mL=milliliter
MS=mass spectrometry
MRSA=methicillin-resistant *Staphylococcus aureus*
NMR=nuclear magnetic resonance
Ns=nitrobenzenesulfonyl
Pa=*Pseudomonas aeruginosa*
Prep=preparative
Ppm=parts per million
Py=pyridine
sat.=saturated
rt=room temperature
TBAF=tetrabutylammonium fluoride
TBS=t-butyldimethylsilyl
TES=triethylsilyl
TEA=triethylamine
TEMPO=2,2,6,6-tetramethyl-1-piperidinyloxy, free radical
THF=tetrahydrofuran
TFA=trifluoroacetic acid
TMS=trimethylsilyl
TLC=thin layer chromatography
VAP=Ventilator-Associated Pneumonia The compounds of Formula (I) can be prepared from intermediate 1, according to the following reaction schemes and examples, or modifications thereof, using readily available starting materials, reagents and conventional synthetic procedures including, for example, procedures described in U.S. Pat. No. 7,112,592 and WO2009/091856. Compound 3 can be synthesized following standard isoxazole ring formation chemistry from the chlorooxime intermediate 2d, which can be prepared from ester intermediate 1 (see, e.g., Abele, E.; Lukevics, E. *Heterocycles* 2000, 53, 2285-2336; Barr, L.; Lincoln, S. F.; Easton, C. J. *Chemistry—A European Journal* 2006, 12, 8571-8580; Walker, D. G.; Brodfuehrer, P. R.; Brundidge, S. P. Shih, K. M.; Sapino, C. Jr. *J. Org. Chem.* 1988, 53, 983-991 and references cited therein).

It may be necessary to protect certain functionalities in the molecule depending on the nature of the $R^1$ group. Protecting these functionalities should be within the expertise of one skilled in the art. See, e.g. P. G. M. Wuts and T. W. Greene, *Protective Groups in Organic Synthesis*, Fourth Edition, John Wiley and Sons, 2006, hereafter Greene.

Scheme 1

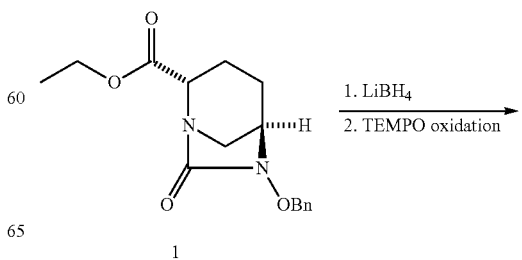

1

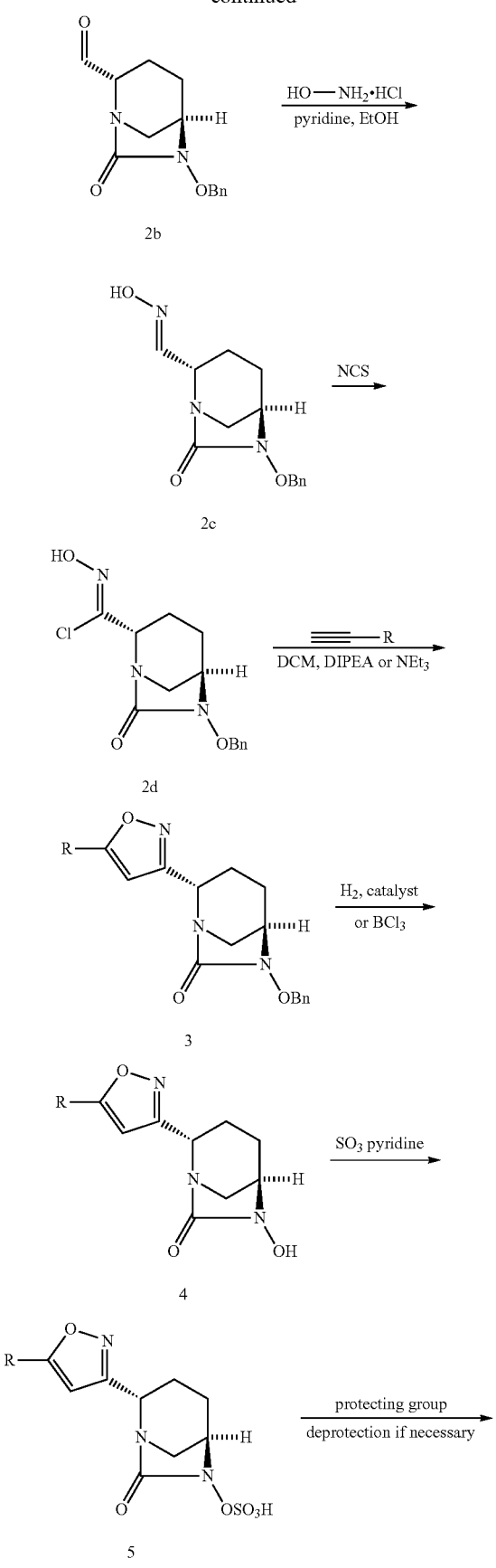

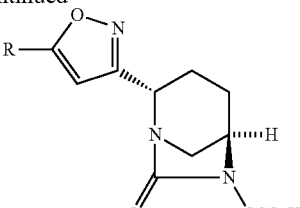

The benzylic ether protecting group in 3 can be removed via standard hydrogenolysis conditions, such as, but not limited to, Pd/H$_2$ in MeOH or THF or by acid-catalysed hydrolysis, such as, but not limited to, BCl$_3$ in DCM to provide the hydroxy-urea intermediate 4, which can be used directly in the next step without further purification. Sulfation of 4 can be achieved by treatment with a sulfating reagent, such a, but not limited to, SO$_3$.pyridine complex, in an appropriate solvent, such as pyridine, DMF or DMAc at a temperature of 0-80° C., preferable at room temperature. Compound 5 can then be isolated and purified via conventional methods. For example, 5 can be purified by standard reverse phase prep-HPLC using an appropriate buffer system, i.e. ammonium formate buffer. In some cases, 5 can be purified by normal phase silica gel chromatography after converting to an appropriate salt form, such as sulfate tetrabutyl ammonium salt. The tetrabutyl ammonium salt can then be converted to a sodium salt by cation exchange. When a protecting group(s) is present in the sidechain (i.e. Boc or Fmoc for amine and guanidine protection, TBS or TES for alcohol protection, etc), a deprotection step is needed to convert 5 to its final product 6, which can be purified by reverse phase prep-HPLC using the conditions mentioned above. For example, for N-Boc deprotection, 5 can be treated with an acid, such as TFA, in an appropriate solvent, such as DCM at a temperature of 0-30° C., preferable at 0° C. to rt to give 6. For an O-TBS, or O-TES deprotection, a fluoride reagent such as HF.pyridine, HF.NEt$_3$, or TBAF can be used. For Fmoc deprotection, amines, such as diethylamine, DBU, piperidine, etc can be used.

EXAMPLES

The specific examples which follow illustrate the synthesis of certain compounds. The methods disclosed may be adopted to variations in order to produce compounds of Formula (I), but not otherwise specifically disclosed. Further, the disclosure includes variations of the methods described herein to produce the compounds of Formula (I) that would be understood by one skilled in the art based on the instant disclosure.

All temperatures are understood to be in Centigrade (C) when not specified. The nuclear magnetic resonance (NMR) spectral characteristics refer to chemical shifts (γ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), singlet (s), multiplet (m), doublet (d), quartet (q), doublet of doublet (dd), doublet of triplet (dt), and doublet of quartet (dq). The solvents employed for taking NMR spectra are DMSO-d6 (perdeuterodimethysulfoxide), D$_2$O (deuterated water), CDCl$_3$ (deuterochloroform) and other conventional deuterated solvents. The prep-HPLC conditions are: Waters SunFire® C18 (30×100 mm, 5 μm OBD) column; flow rate: 30-80 mL/minute, ELSD or Mass-triggered fraction collection; sample loading: Each injection loading varied from 30-300 mg for different crude samples depending on their solubility and purity profiles; Solvent system using ammonium formate buffer: solvent A: water with 20 mM ammonium formate, solvent B: 85% of acetonitrile in water with 20 mM ammonium formate. Solvent system using $NH_4HCO_3$ buffer: solvent A: water with 10 mM $NH_4HCO_3$, solvent B: acetonitrile. Solvent system using $NH_4OH$ buffer: solvent A: water with 0.1% $NH_4OH$, solvent B: acetonitrile with 0.1% $NH_4OH$.

Example 1

Synthesis of (2S,5R)-ethyl 6-(benzyloxy)-7-oxo-1,6-diazabicyclo[3.2.1]octane-2-carboxylate (Intermediate Compound 1)

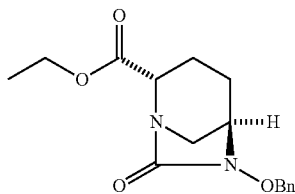

Step 1: Synthesis of (S)-1-tert-butyl 2-ethyl 5-oxopiperidine-1,2-dicarboxylate

Method A:

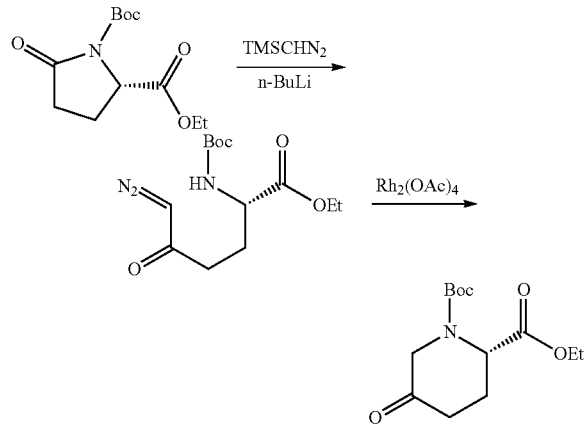

n-BuLi (600 mL, 1.5 mol) was added dropwise to a solution of $TMSCHN_2$ (690 mL, 1.38 mol) in dry THF (3 L) at −78° C., and the mixture was stirred at −78° C. for 30 minutes. The mixture was then transferred to a solution of (S)-1-tert-butyl 2-ethyl 5-oxopyrrolidine-1,2-dicarboxylate (300 g, 1.17 mol) in dry THF (3 L) via cannula, and the mixture was stirred at −78° C. for 30 minutes. The reaction mixture was then quenched with sat. $NH_4Cl$ solution, and extracted with DCM (3×). The combined organic layer was concentrated under reduced pressure and the crude product was purified by silica gel column chromatography (3:1 petroleum ether/EtOAc) to afford (S)-ethyl 2-((tert-butoxycarbonyl)amino)-6-diazo-5-oxohexanoate (262 g, 75%) as a yellow solid.

A solution of (S)-ethyl 2-((tert-butoxycarbonyl)amino)-6-diazo-5-oxohexanoate (350 g, 1.18 mol) in DCM (1500 mL) was added to a 0° C. solution of $Rh_2(OAc)_4$ (3.5 g, 7.9 mmol) in DCM (750 mL). The reaction mixture was then stirred at 20° C. overnight and then concentrated under reduced pressure. The crude sample was purified by silica gel column chromatography (5:1 petroleum ether/EtOAc) to afford (S)-1-tert-butyl 2-ethyl 5-oxopiperidine-1,2-dicarboxylate (175.9 g, 55%) as a yellow oil.

Method B:

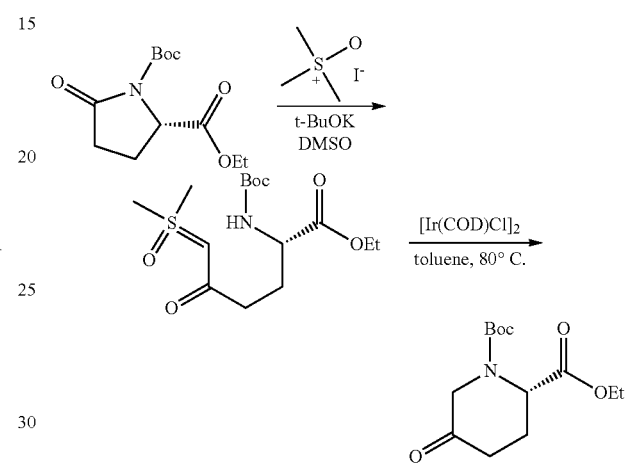

t-BuOK (330 g, 2.9 mol) was added to a solution of trimethylsulfoxonium iodide (750 g, 3.5 mol) in dry DMSO (3 L) and the mixture was stirred at rt for 1 h. (S)-1-tert-Butyl 2-ethyl 5-oxopyrrolidine-1,2-dicarboxylate (900 g, 3.5 mol) was added and the mixture was stirred at rt for 2-3 hrs. Water was added to quench the reaction and the mixture was extracted with EtOAc (5×). The combined organic layer was concentrated under reduced pressure and the crude sample was purified by silica gel column chromatography (1:1 petroleum ether/EtOAc then 1:10 MeOH/DCM) to afford sulfoxonium ylide intermediate (977 g, 80%) as a white solid.

A solution of sulfoxonium ylide intermediate (156 g, 0.446 mol) and $[Ir(COD)Cl]_2$ (3 g, 4.46 mmol) in toluene (4 L) was degassed by bubbling nitrogen through the solution for 10 minutes. The reaction mixture was heated to 80-90° C. for 2-3 hrs and then cooled to 20° C. The toluene was concentrated under reduced pressure and the resulting residue was purified by silica gel column chromatography (10:1 to 3:1 gradient elution petroleum ether/EtOAc) to afford (S)-1-tert-butyl 2-ethyl 5-oxopiperidine-1,2-dicarboxylate (140 g, 57.8%) as a yellow oil.

Step 2: Synthesis of (2S,5S)-1-tert-butyl 2-ethyl 5-hydroxypiperidine-1,2-dicarboxylate

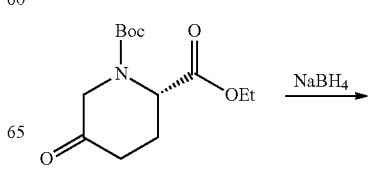

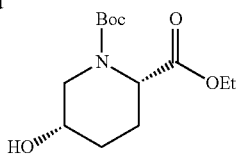

NaBH₄ (36 g, 1.0 mol) was added in portions to a −40° C. solution of (S)-1-tert-butyl 2-ethyl 5-oxopiperidine-1,2-dicarboxylate (250 g, 0.92 mol) in EtOH (1500 mL). The reaction mixture was then stirred at −40° C. for 0.5 hr then quenched with 10% HOAc solution. After diluting with water, the mixture was extracted with DCM (3×). The combined organic layer was concentrated under reduced pressure and purified by silica gel column chromatography (1:1 petroleum ether/EtOAc) to afford (2S,5S)-1-tert-butyl 2-ethyl 5-hydroxypiperidine-1,2-dicarboxylate (205 g, 80%) as a yellow oil.

Step 3: Synthesis of (2S,5R)-1-tert-butyl 2-ethyl 5-(N-(benzyloxy)-2-nitrophenylsulfonamido)piperidine-1,2-dicarboxylate

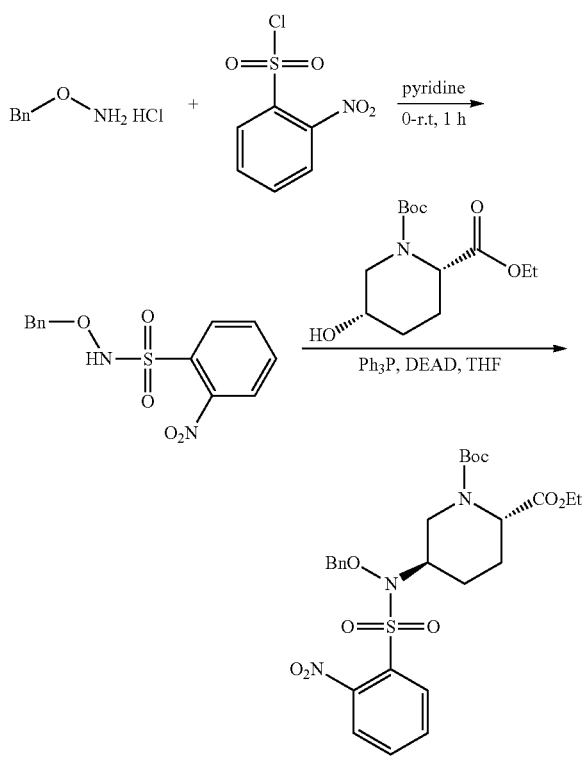

A solution of 2-nitrobenzene-1-sulfonyl chloride (500 g, 2.26 mol) in pyridine (1500 mL) was added dropwise to a 0° C. solution of O-benzylhydroxylamine hydrochloride (400 g, 2.51 mol) in pyridine (1500 mL). The reaction mixture was allowed to warm to room temperature then was stirred at 20° C. overnight. The mixture was concentrated under reduced pressure, diluted with DCM and washed with HCl (10%, 3×). The combined organic layer was concentrated under reduced pressure and re-crystallized with DCM to afford N-(benzyloxy)-2-nitrobenzenesulfonamide (485 g, 62.6%) as a yellow solid.

To a solution of N-(benzyloxy)-2-nitrobenzenesulfonamide (212 g, 0.69 mol) in THF (1000 mL) was added (2S,5S)-1-tert-butyl 2-ethyl 5-hydroxypiperidine-1,2-dicarboxylate (171 g, 0.63 mol) and PPh₃ (275 g, 1.05 mol), followed by dropwise addition of a solution of DEAD (195 g, 1.12 mol) in THF (500 mL). The mixture was then stirred at 20° C. overnight. The reaction mixture was then concentrated under reduced pressure and purified by silica gel column chromatography (3:1 petroleum ether/EtOAc) to afford (2S,5R)-1-tert-butyl 2-ethyl 5-(N-(benzyloxy)-2-nitrophenylsulfonamido)piperidine-1,2-dicarboxylate (283.8 g, 80%) as a yellow oil.

Step 4: Synthesis of (2S,5R)-1-tert-butyl 2-ethyl 5-((benzyloxy)amino)piperidine-1,2-dicarboxylate

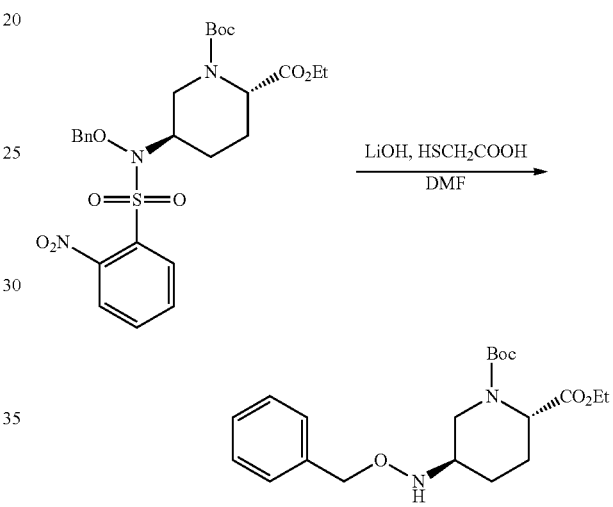

LiOH·H₂O (95 g, 2.3 mol) and 2-mercaptoacetic acid (124 g, 1.3 mol) were added to a solution of (2S,5R)-1-tert-butyl 2-ethyl 5-(N-(benzyloxy)-2-nitrophenylsulfonamido)piperidine-1,2-dicarboxylate (251 g, 0.45 mol) in DMF (1200 mL). The reaction mixture was then stirred at 20° C. overnight. The reaction mixture was diluted with water and extracted with EtOAc (3×). The combined organic layer was washed with saturated sodium chloride (3×), concentrated under reduced pressure and purified by silica gel column chromatography (3:1 petroleum ether/EtOAc) to afford (2S,5R)-1-tert-butyl 2-ethyl 5-((benzyloxy)amino)piperidine-1,2-dicarboxylate (122.9 g, 85%) as a yellow solid.

Step 5: Synthesis of (2S,5R)-ethyl 5-((benzyloxy)amino)piperidine-2-carboxylate

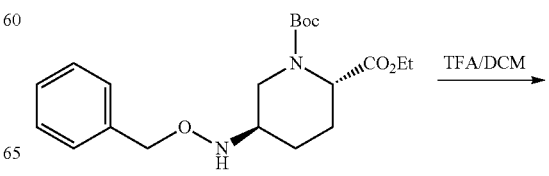

-continued

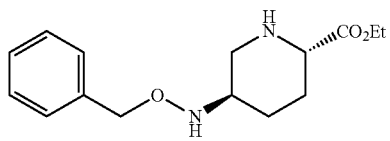

TFA (600 mL) was added to a solution of (2S,5R)-1-tert-butyl 2-ethyl 5-((benzyloxy)amino)piperidine-1,2-dicarboxylate (263 g, 0.7 mol) in DCM (600 mL) at 20° C. The mixture was stirred at rt overnight and then concentrated under reduced pressure. The crude product was adjusted to pH 10 with sat. NaHCO₃ solution then extracted with DCM (3×). The combined organic layer was concentrated under reduced pressure and purified by silica gel column chromatography (20:1 DCM/MeOH) to afford (2S,5R)-ethyl 5-((benzyloxy)amino)piperidine-2-carboxylate (184.9 g, 95%) as a yellow oil.

Step 6: Synthesis of (2S,5R)-ethyl 6-(benzyloxy)-7-oxo-1,6-diazabicyclo[3.2.1]octane-2-carboxylate

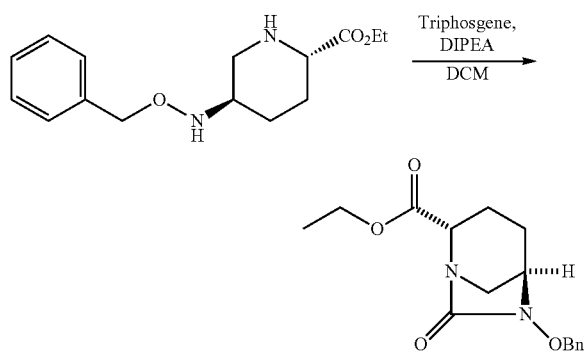

Triphosgene (21.3 g, 72 mmol) was added in portions to a 0° C. solution of (2S,5R)-ethyl 5-((benzyloxy)amino)piperidine-2-carboxylate (50 g, 0.18 mol) and DIPEA (128 mL, 0.72 mol) in DCM (2000 mL). The reaction mixture was allowed to warm to rt. After stirring at rt overnight, the reaction mixture was washed with H₃PO₄ (10%), sat. NaHCO₃ and saturated NaCl. The combined organic layer was concentrated under reduced pressure and purified by silica gel column chromatography (3:1 petroleum ether/EtOAc) to afford (2S,5R)-ethyl 6-(benzyloxy)-7-oxo-1,6-diazabicyclo[3.2.1]octane-2-carboxylate (27.4 g, 50%) as a yellow solid. ¹H NMR (400 Mz, CDCl₃): δ 7.43-7.36 (m, 5H), 5.06 (d, J=11.4 Hz, 1H), 4.90 (d, J=11.4 Hz, 1H), 4.24 (q, J=7.1 Hz, 2H), 4.11-4.08 (m, 1H), 3.32-3.31 (m, 1H), 3.08-3.05 (m, 1H), 2.93 (d, J=11.9 Hz, 1H), 2.14-2.05 (m, 2H), 2.05-2.00 (m, 1H), 1.71-1.63 (m, 1H), 1.29 (t, J=7.1 Hz, 3H).

Example 2

Synthesis of (2S,5R)-6-(benzyloxy)-7-oxo-1,6-diazabicyclo[3.2.1]octane-2-carbaldehyde (Intermediate Compound 2b)

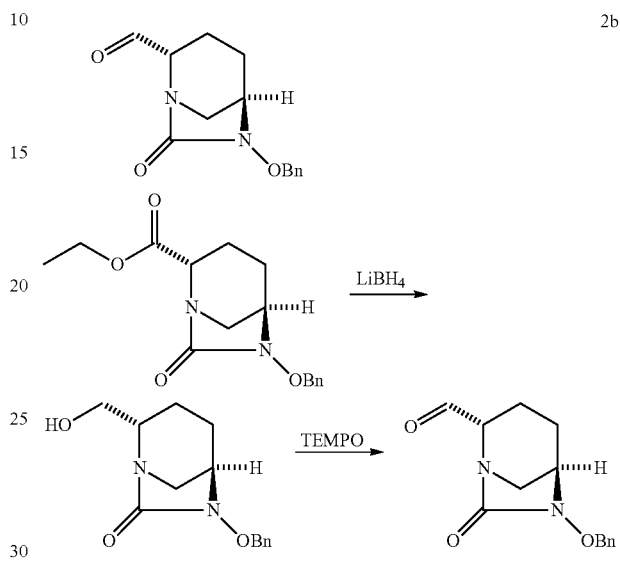

LiBH₄ (0.54 g, 24.67 mmol) was added to a −10° C. solution of (2S,5R)-ethyl 6-(benzyloxy)-7-oxo-1,6-diazabicyclo[3.2.1]octane-2-carboxylate (5 g, 16.44 mmol) in MeOH (50 mL). After 15 minutes another portion of LiBH₄ (0.54 g, 24.67 mmol) was added and the mixture was stirred at −10 to 0° C. for 4-5 h. The reaction mixture was carefully quenched by addition of sat. NaH₂PO₄ (50 mL) at 0° C. The mixture was diluted with water (20 mL) and extracted with DCM (3×). The combined organic layer was concentrated and purified by silica gel column chromatography (gradient elution 0-100% EtOAc/petroleum ether, then 0~2% MeOH/EtOAc) to give (2S,5R)-6-(benzyloxy)-2-(hydroxymethyl)-1,6-diazabicyclo[3.2.1]octan-7-one (3.8 g, 88%) as a white solid. ESI-MS (EI⁺, m/z): 263.1. ¹H NMR (500M, CDCl₃): 7.44-7.35 (m, 5H), 5.05 (d, J=11.5 Hz, 1H), 4.90 (d, J=11.5 Hz, 1H), 3.73-3.69 (m, 1H), 3.61-3.58 (m, 2H), 3.33 (m, 1H), 3.01 (br d, J=12.0 Hz, 1H), 2.91 (m, 1H), 2.03-1.95 (m, 2H), 1.58-1.54 (m, 1H), 1.39-1.24 (m, 1H).

TEMPO (48 mg, 0.3 mmol) was added in portions to a 0° C. solution of (2S,5R)-6-(benzyloxy)-2-(hydroxymethyl)-1,6-diazabicyclo[3.2.1]octan-7-one (7.8 g, 30 mmol) and 1,3,5-trichloro-1,3,5-triazinane-2,4,6-trione (7.0 g, 30 mmol) in DCM (100 mL). The mixture was stirred at 0° C. for 2 h, and filtered through Celite®. The filtrate was dried over Na₂SO₄ and concentrated to afford (2S,5R)-6-(benzyloxy)-7-oxo-1,6-diazabicyclo[3.2.1]octane-2-carbaldehyde (7.0 g, 90%) as a yellow oil. ESI-MS (EI⁺, m/z): 261.1. ¹H NMR (500M, CDCl₃): 9.74 (s, 1H), 7.45-7.36 (m, 5H), 5.07 (d, J=11.5 Hz, 1H), 4.92 (d, J=11.5 Hz, 1H), 3.89 (d, J=8.0 Hz, 1H), 3.27 (m, 1H), 3.21-3.05 (m, 1H), 2.56 (d, J=12.0 Hz, 1H), 2.20-2.15 (m, 1H), 2.05-2.01 (m, 1H), 1.95-1.93 (m, 1H), 1.49-1.46 (m, 1H).

Example 3

Synthesis of (E)-6-(benzyloxy)-7-oxo-1,6-diazabicyclo[3.2.1]octane-2-carbaldehyde oxime (Intermediate Compound 2c)

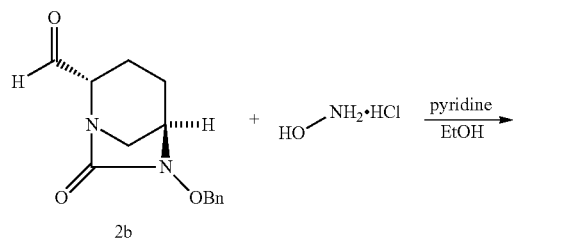

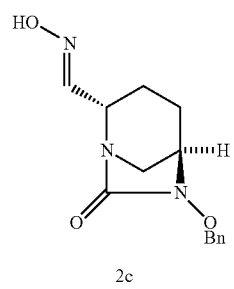

2c

A solution of (2S,5R)-6-(benzyloxy)-7-oxo-1,6-diazabicyclo[3.2.1]octane-2-carbaldehyde (510 mg, 1.96 mmol), hydroxylamine hydrochloride (158 mg, 2.27 mmol) and pyridine (621 mg, 7.85 mmol) in EtOH (15 mL) was stirred at rt for 2 hrs. Then, the reaction mixture was concentrated and the residue was diluted with DCM (25 mL), washed with water (3×), and saturated sodium chloride, dried over Na$_2$SO$_4$ and concentrated. The residue was purified by silica gel column chromatography (3:1 to 3:2 petroleum ether/EtOAC) to afford (E)-6-(benzyloxy)-7-oxo-1,6-diazabicyclo[3.2.1]octane-2-carbaldehyde oxime (228 mg, 42%) as a white solid. ESI-MS (EI$^+$, m/z): 276 [M+H]$^+$.

Example 4

Synthesis of (2S,5R)-2-(5-(aminomethyl)isoxazol-3-yl)-7-oxo-1,6-diazabicyclo[3.2.1]octan-6-yl hydrogen sulfate (Compound 601)

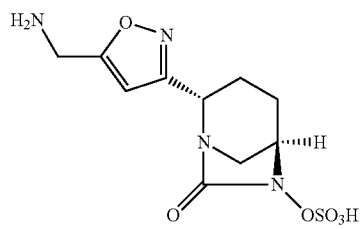

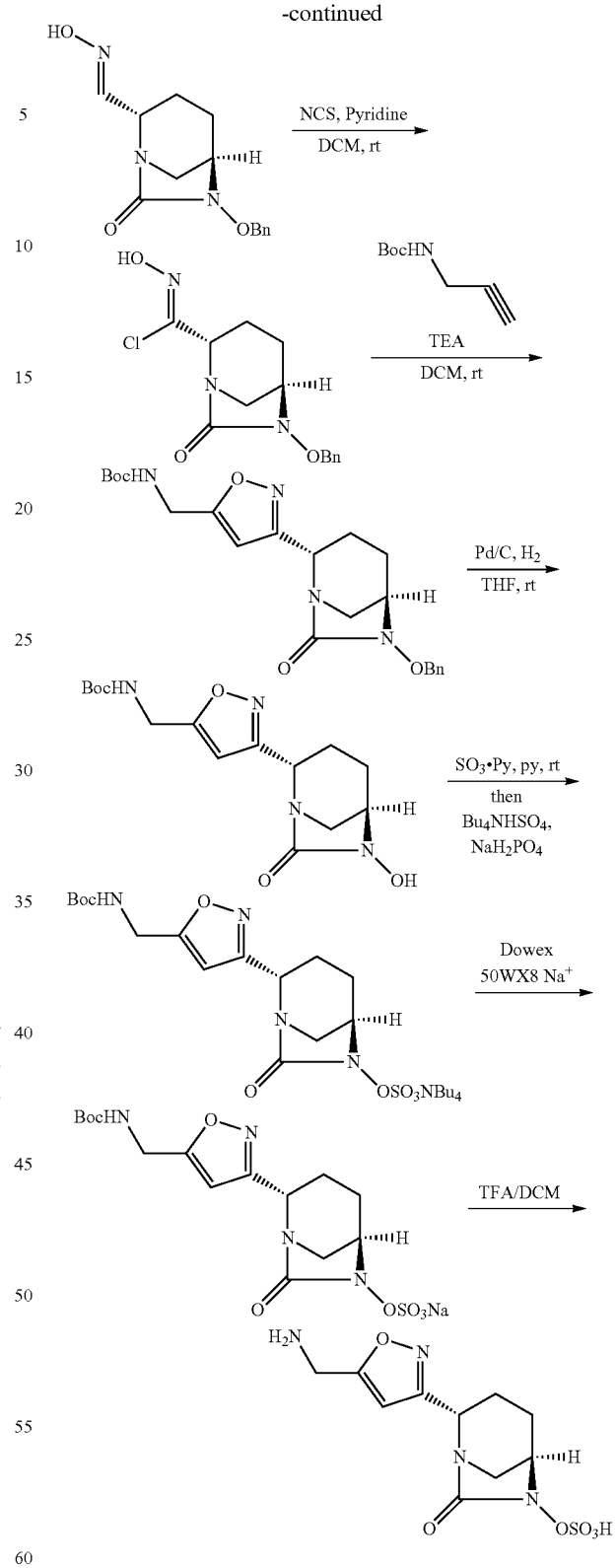

Step 1:

NCS (295 mg, 2.2 mmol) was added to a solution of 6-(benzyloxy)-7-oxo-1,6-diaza-bicyclo[3.2.1]octane-2-carbaldehyde oxime (560 mg, 2.0 mmol) in dry DCM (15 mL) at rt. Pyridine (one drop) was then added, and the reaction mixture was stirred at rt for 18 hrs. The solution was evaporated to afford (2S,5R)-6-(benzyloxy)-N-hydroxy-7-oxo-1,6-diaza-bicyclo[3.2.1]octane-2-carbimidoyl chloride, which was directly used in the next step. ESI-MS (EI$^+$, m/z): 274 [M-Cl]$^+$.

Step 2:

tert-Butyl prop-2-yn-1-ylcarbamate (0.37 g, 2.4 mmol) was added to the solution of (2S,5R)-6-(benzyloxy)-N-hydroxy-7-oxo-1,6-diazabicyclo[3.2.1]octane-2-carbimidoyl chloride (~2.0 mmol) in dry DCM (20 mL), followed by the addition of TEA (0.31 mL, 2.2 mmol) in dry DCM (2.0 mL) over a period of 30 minutes. The reaction mixture was stirred at rt overnight, then the mixture was diluted with EtOAc, washed with water and saturated sodium chloride. The organic layer was dried over Na$_2$SO$_4$, concentrated and purified by silica gel column chromatography (1:2 petroleum ether/EtOAc) to afford tert-butyl((3-((2S,5R)-6-(benzyloxy)-7-oxo-1,6-diazabicyclo[3.2.1]octan-2-yl)isoxazol-5-yl)methyl)carbamate (180 mg, 21% for two steps) as a white solid. ESI-MS (EI$^+$, m/z): 429.1 [M+H]$^+$. $^1$H NMR (500 MHz, CDCl$_3$): δ 7.45-7.35 (m, 5H), 6.24 (s, 1H), 5.09 (d, J=11.5 Hz, 1H), 4.93 (d, J=11.5 Hz, 1H), 4.58 (d, J=7.5 Hz, 1H), 4.43 (m, 2H), 3.32 (s, 1H), 2.86-2.84 (m, 1H), 2.68 (d, J=11.5 Hz, 1H), 2.34-2.30 (m, 1H), 2.23-2.18 (m, 1H), 2.10-2.04 (m, 1H), 1.82-1.78 (m, 1H), 1.45 (s, 9H).

Step 3:

To a solution of tert-butyl (3-((2S,5R)-6-(benzyloxy)-7-oxo-1,6-diazabicyclo[3.2.1]octan-2-yl)isoxazol-5-yl)methylcarbamate (210 mg, 0.5 mmol) in THF (5 mL) was added 10% Pd/C (100 mg). The reaction mixture was then filtered and concentrated to afford tert-butyl((3-((2S,5R)-6-hydroxy-7-oxo-1,6-diazabicyclo[3.2.1]octan-2-yl)isoxazol-5-yl)methyl)carbamate (180 mg, 99%) as a light yellow solid, which was used directly in the next step. ESI-MS (EI$^+$, m/z): 339.1 [M+H]$^+$.

Step 4:

To a solution of tert-butyl (3-((2S,5R)-6-hydroxy-7-oxo-1,6-diazabicyclo[3.2.1]octan-2-yl)isoxazol-5-yl)methylcarbamate (180 mg, 0.5 mmol) in dry pyridine (2.5 mL) was added SO$_3$.Py (480 mg, 3.0 mmol). The mixture was stirred at rt for 3 hrs and then concentrated under reduced pressure. The residue was re-dissolved in aqueous NaH$_2$PO$_4$ (1.5 M, 20 mL) then tetrabutylammonium hydrogensulphate (230 mg, 0.67 mmol) was added. The mixture was stirred at rt for 20 minutes then extracted with EtOAc (4×). The combined organic layer was dried and concentrated and the residue was purified by silica gel column chromatography (gradient elution 10:1 to 3:1 DCM/acetone) to afford tetrabutylammonium (2S,5R)-2-(5-(((tert-butoxycarbonyl)amino)methyl)isoxazol-3-yl)-7-oxo-1,6-diazabicyclo[3.2.1]octan-6-yl sulfate (180 mg, 54%) as a white solid. ESI-MS (EI$^-$, m/z): 417.0 [M-H]$^-$. $^1$H NMR (500 MHz, CDCl$_3$): δ 6.28 (s, 1H), 4.97 (bs, 1H), 4.54 (d, J=7 Hz, 1H), 4.44-4.30 (m, 2H), 4.35 (m, 1H), 3.35-3.28 (m, 8H), 3.19-3.17 (m, 1H), 2.76 (d, J=11.5 Hz, 1H), 2.36-2.32 (m, 1H), 2.27-2.24 (m, 1H), 2.18-2.12 (m, 1H), 1.87-1.81 (m, 1H), 1.71-1.65 (m, 8H), 1.50-1.47 (m, 17H), 1.01 (t, J=7.0 Hz, 12H).

Step 5, Resin Exchange:

Tetrabutylammonium (2S,5R)-2-(5-(tert-butoxycarbonylaminomethyl)-isoxazol-3-yl)-7-oxo-1,6-diaza-bicyclo[3.2.1]octan-6-yl sulfate (180 mg, 0.27 mmol) was dissolved in a minimum amount of HPLC grade water (~10 mL) and passed through a column of 20 g of DOWEX 50WX 8 Na$^+$resin (the resin was pre-washed with >0.5 L of HPLC grade water) and eluted with HPLC grade water to afford sodium (2S,5R)-2-(5-(((tert-butoxycarbonyl)amino)methyl)isoxazol-3-yl)-7-oxo-1,6-diazabicyclo[3.2.1]octan-6-yl sulfate (109 mg, 92%) was obtained after lyophilization as a white solid. ESI-MS (Er, m/z): 417.0 [M-H]$^-$. $^1$H NMR (500 MHz, D$_2$O): δ 6.32 (s, 1H), 4.61 (d, J=6.5 Hz, 1H), 4.32 (s, 2H), 4.13 (m, 1H), 3.10-3.08 (m, 1H), 2.91 (d, J=12.5 Hz, 1H), 2.21-2.17 (m, 1H), 2.09-2.02 (m, 2H), 1.86-1.82 (m, 1H), 1.34 (s, 9H).

Step 6:

TFA (0.40 mL) was added to a 0° C. solution of sodium (2S,5R)-2-(5-(tert-butoxycarbonylaminomethyl)isoxazol-3-yl)-7-oxo-1,6-diaza-bicyclo[3.2.1]octan-6-yl sulfate (54 mg, 0.12 mmol) in dry DCM (1.2 mL). The reaction mixture was stirred at 0° C. for 30 minutes to 1 h and then diluted with diethyl ether. The precipitate was collected via centrifugation, washed with ether (3×) and further dried under high vacuum to provide (2S,5R)-2-(5-(aminomethyl)isoxazol-3-yl)-7-oxo-1,6-diazabicyclo[3.2.1]octan-6-yl hydrogen sulfate as a TFA salt (~30 mg). ESI-MS (EI$^+$, m/z): 319.2. The TFA salt (~30 mg) was further purified by prep-HPLC using ammonium formate buffer to provide (2S,5R)-2-(5-(aminomethyl)isoxazol-3-yl)-7-oxo-1,6-diazabicyclo[3.2.1]octan-6-yl hydrogen sulfate (601, 10 mg, 26%) as a white solid. ESI-MS (EI$^+$, m/z): 319.21. $^1$H NMR (300 MHz, D$_2$O) δ 6.61 (s, 1H), 4.68-4.65 (m, 1H), 4.35 (s, 2H), 4.17-4.14 (m, 1H), 3.14-3.10 (m, 1H), 2.95-2.91 (m, 1H), 2.31-1.80 (m, 4H).

Example 5

Synthesis of (2S,5R)-2-(5-(guanidinomethyl)isoxazol-3-yl)-7-oxo-1,6-diazabicyclo[3.2.1]octan-6-yl hydrogen sulfate (Compound 603)

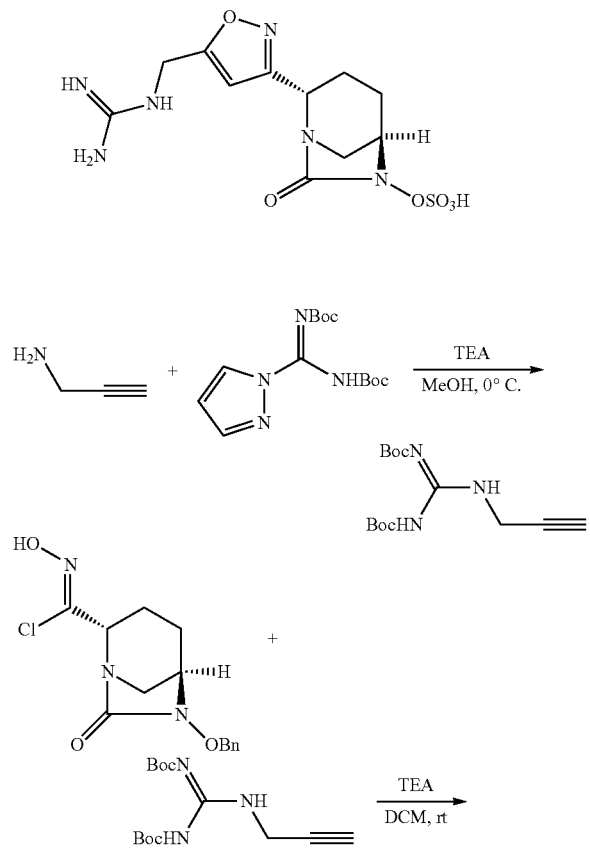

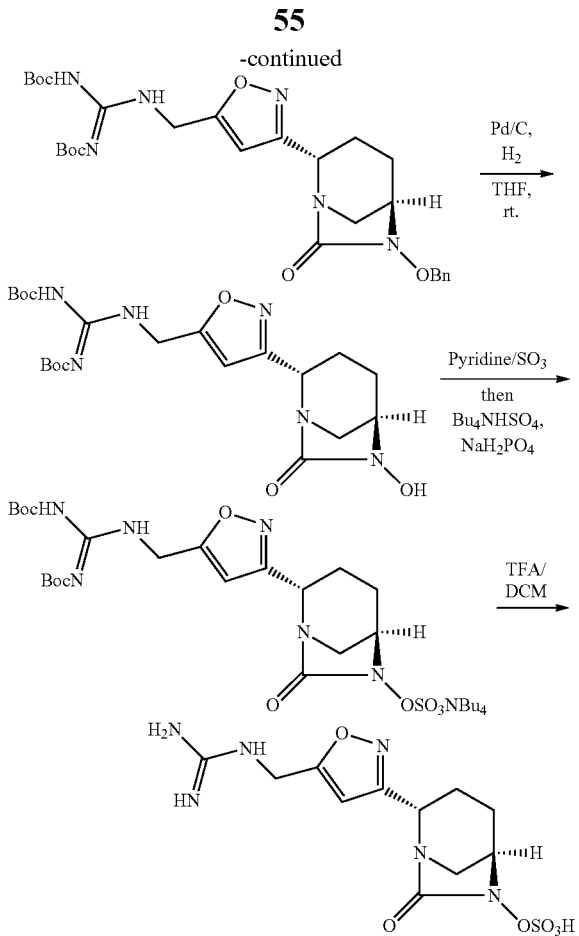

Step 1: Synthesis of 1-(2,3-bis(tert-butoxycarbonyl)guanidino)prop-2-yne

Di-tert-butyl (1H-pyrazol-1-yl)methanediylidenedicarbamate (1.71 g, 5.5 mmol) was added to a 0° C. solution of prop-2-yn-1-amine (275 mg, 5.0 mmol) and TEA (1.5 g, 15 mmol) in MeOH (40 mL). The reaction mixture was stirred at 0° C. for 3 hrs and then concentrated under reduced pressure. The residue was purified by silica gel column chromatography (1:10 EtOAc/Hexanes) to give 1-(2,3-bis(tert-butoxycarbonyl)guanidino) prop-2-yne (1.4 g, 93%) as a white solid. ESI-MS (EI+, m/z): 298.1 [M+H]+.

Step 2: Synthesis of (2S,5R)-6-(benzyloxy)-2-(5-((2,3-bis(tert-butoxycarbonyl)guanidino)methyl)isoxazol-3-yl)-1,6-diaza-bicyclo[3.2.1]octan-7-one 1-(2,3-bis(tert-butoxycarbonyl)guanidino)prop-2-yne (362 mg, 1.22 mmol) was added to the solution of (2S,5R)-6-(benzyloxy)-N-hydroxy-7-oxo-1,6-diaza-bicyclo[3.2.1]octane-2-carbimidoyl chloride (473 mg, 1.53 mmol) in dry DCM (20 mL) at rt, followed by dropwise addition of TEA (0.16 g, 1.53 mmol). The mixture was stirred at rt for 2 hrs and then concentrated. The residue was purified by silica gel column chromatography (gradient elution 1:15 to 1:5 EtOAc/Hexanes) to give (2S,5R)-6-(benzyloxy)-2-(5-((2,3-bis(tert-butoxycarbonyl)guanidino)methyl)isoxazol-3-yl)-1,6-diazabicyclo[3.2.1]octan-7-one (190 mg, 22% for two steps) as a white solid. ESI-MS (EI+, m/z): 571.2 [M+H]+. 1H NMR (500 MHz, CDCl3): δ 11.49 (s, 1H), 8.86 (bs, 1H), 7.47-7.34 (m, 5H), 6.32 (s, 1H), 5.09 (d, J=11.5 Hz, 1H), 4.93 (d, J=12.0 Hz, 1H), 4.87-4.76 (m, 2H), 4.59 (d, J=7.0 Hz, 1H), 3.36 (s, 1H), 2.87-2.85 (m, 1H), 2.70 (d, J=12 Hz, 1H), 2.35-2.30 (m, 1H), 2.24-2.18 (m, 1H), 2.10-2.05 (m, 1H), 1.81-1.78 (m, 1H), 1.50 (s, 18H).

Step 3: Synthesis of (2S,5R)-6-(hydroxy)-2-(5-((2,3-bis(tert-butoxycarbonyl)guanidino)methyl)isoxazol-3-yl)-1,6-diaza-bicyclo[3.2.1]octan-7-one To a solution of (2S,5R)-6-(benzyloxy)-2-(5-((2,3-bis(tert-butoxycarbonyl)guanidino)methyl)isoxazol-3-yl)-1,6-diaza-bicyclo[3.2.1]octan-7-one (240 mg, 0.42 mmol) in THF (20 mL) was added 10% Pd/C (120 mg). The mixture was stirred under H2 atmosphere at rt for 1.5 hrs. The reaction mixture was then filtered and concentrated to afford (2S,5R)-6-(hydroxy)-2-(5-((2,3-bis(tert-butoxycarbonyl)guanidino)methyl)isoxazol-3-yl)-1,6-diaza-bicyclo[3.2.1]octan-7-one (200 mg, 99%) as white solid, which was directly used in the next step. ESI-MS (EI+, m/z): 481.2 [M+H]+.

Step 4: Synthesis of tetrabutylammonium(2S,5R)-2-(5-((2,3-bis(tert-butoxycarbonyl)guanidino)methyl)isoxazol-3-yl)-7-oxo-1,6-diaza-bicyclo[3.2.1]octan-6-yl sulfate To a solution of (2S,5R)-6-(hydroxy)-2-(5-((2,3-bis(tert-butoxycarbonyl)guanidino)methyl)isoxazol-3-yl)-1,6-diaza-bicyclo[3.2.1]octan-7-one (200 mg, 0.42 mmol) in dry pyridine (2.5 mL) was added SO3.Py (400 mg, 2.5 mmol). The mixture was stirred at rt for 3 hrs then concentrated under reduced pressure. The residue was re-dissolved in aqueous NaH2PO4 (1.5 M, 20 mL). Tetrabutylammonium hydrogensulphate (200 mg, 0.58 mmol) was added. The mixture was stirred at rt for 20 minutes then was extracted with EtOAc (4×). The combined organic layer was dried and concentrated and the residue was purified by silica gel column chromatography (gradient elution 10:1 to 5:1 DCM/acetone) to give tetrabutylammonium (2S,5R)-2-(5-((2,3-bis(tert-butoxycarbonyl)guanidino)methyl)isoxazol-3-yl)-7-oxo-1,6-diazabicyclo[3.2.1]octan-6-yl sulfate (220 mg, 66%) as a white solid. ESI-MS (EI−, m/z): 559.0 [M−H]−. 1H NMR (500 MHz, CDCl3): δ 11.48 (s, 1H), 8.78 (bs, 1H), 6.34 (s, 1H), 4.77-4.76 (m, 2H), 4.55 (d, J=7.5 Hz, 1H), 4.35 (m, 1H), 3.38-3.28 (m, 8H), 3.20-3.18 (m, 1H), 2.78 (d, J=11.5 Hz, 1H), 2.37-2.30 (m, 1H), 2.28-2.24 (m, 1H), 2.17-2.11 (m, 1H), 1.88-1.82 (m, 1H), 1.71-1.63 (m, 8H), 1.50-1.44 (m, 26H), 1.01 (t, J=7.0 Hz, 12H).

Step 5:

TFA (2.20 mL) was added to a 0° C. solution of tetrabutylammonium (2S,5R)-2-(5-((2,3-bis(tert-butoxycarbonyl)guanidino)methyl)isoxazol-3-yl)-7-oxo-1,6-diazabicyclo[3.2.1]octan-6-yl sulfate (465 mg, 0.60 mmol) in dry DCM (6.60 mL). The reaction mixture was allowed to warm to rt. The reaction mixture was stirred at rt for 2 hrs and then diluted with ether. The precipitate was collected via centrifugation, washed with diethyl ether (3×) and further dried under high vacuum. The crude TFA salt was purified by prep-HPLC using ammonium formate buffer to provide (2S,5R)-2-(5-(guanidinomethyl)isoxazol-3-yl)-7-oxo-1,6-diazabicyclo[3.2.1]octan-6-yl hydrogen sulfate (603, 60 mg, 20%) as a white solid. ESI-MS (EI+, m/z): 361.2. 1H NMR (300 MHz, D2O/DMSO-d6) δ 6.58 (s, 1H), 4.74-4.71 (m, 1H), 4.67 (s, 2H), 4.23 (br s, 1H), 3.22-3.17 (m, 1H), 2.99 (d, J=12.0 Hz, 1H), 2.36-2.26 (m, 1H), 2.24-2.10 (m, 2H), 2.02-1.91 (m, 1H).

Example 6

Synthesis of (2S,5R)-2-(5-(2-aminoethyl)isoxazol-3-yl)-7-oxo-1,6-diazabicyclo[3.2.1]octan-6-yl hydrogen sulfate (Compound 602)

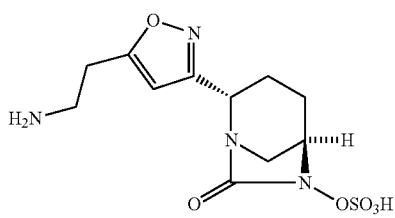

Following Steps 1-6 in Example 4, replacing tert-butyl prop-2-yn-1-ylcarbamate in Step 2 with tert-butyl but-3-yn-1-ylcarbamate; (2S,5R)-2-(5-(2-aminoethyl)-1,3,4-oxadiazol-2-yl)-7-oxo-1,6-diazabicyclo[3.2.1]octan-6-yl hydrogen sulfate TFA salt (602, 8 mg) was obtained as a light yellow solid. ESI-MS (EI$^+$, m/z): 333.2. $^1$H NMR (300 MHz, D$_2$O) δ 6.39 (s, 1H), 4.62 (d, J=6.8 Hz, 1H), 4.16-4.12 (m, 1H), 3.32 (t, J=7.1 Hz, 3H), 3.25-3.04 (m, 4H), 2.97-2.93 (m, 1H), 2.30-1.79 (m, 4H).

Example 7

Synthesis of (2S,5R)-2-(5-(2-guanidinoethyl)isoxazol-3-yl)-7-oxo-1,6-diazabicyclo[3.2.1]octan-6-yl hydrogen sulfate (Compound 604)

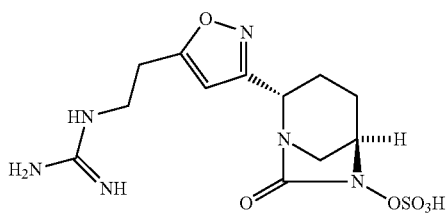

Following Steps 1-5 in Example 5, replacing prop-2-yn-1-amine in Step 1 with but-3-yn-1-amine; (2S,5R)-2-(5-(2-guanidinoethyl)isoxazol-3-yl)-7-oxo-1,6-diazabicyclo[3.2.1]octan-6-yl hydrogen sulfate (604, 48 mg) was obtained as a light yellow solid after prep-HPLC purification using ammonium formate buffer. ESI-MS (EI$^+$, m/z): 375.1. $^1$H NMR (300 MHz, D$_2$O/DMSO-d6) δ 6.33 (s, 1H), 4.62 (d, J=6.6 Hz, 1H), 4.14 (br s, 1H), 3.51 (t, J=6.4 Hz, 2H), 3.15-3.07 (m, 1H), 3.05 (t, J=6.4 Hz, 2H), 2.88 (d, J=6.4 Hz, 1H), 2.26-1.99 (m, 3H), 1.85-1.80 (m, 1H).

Example 8

Synthesis of (2S,5R)-7-oxo-2-(5-(piperidin-4-yl)isoxazol-3-yl)-1,6-diazabicyclo[3.2.1]octan-6-yl hydrogen sulfate (Compound 606)

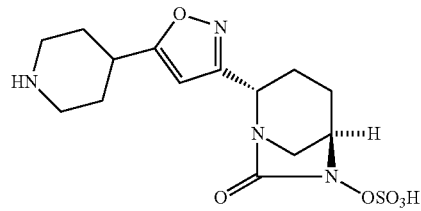

Following Steps 1-6 in Example 4, replacing tert-butyl prop-2-yn-1-ylcarbamate in Step 2 with tert-butyl 4-ethynylpiperidine-1-carboxylate, (2S,5R)-7-oxo-2-(5-(piperidin-4-yl)isoxazol-3-yl)-1,6-diazabicyclo[3.2.1]octan-6-yl hydrogen sulfate (606, 35 mg) was obtained as a white solid after prep-HPLC purification using ammonium formate buffer. ESI-MS (EI$^+$, m/z): 371.3.

Example 9

Synthesis of (2S,5R)-2-(5-(1-carbamimidoylpiperidin-4-yl)isoxazol-3-yl)-7-oxo-1,6-diazabicyclo[3.2.1]octan-6-yl hydrogen sulfate (Compound 607)

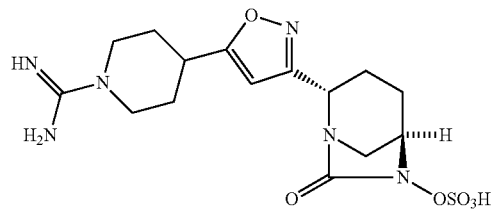

Following Steps 1-5 in Example 5, replacing prop-2-yn-1-amine in Step 1 with 4-ethynylpiperidine; (2S,5R)-2-(5-(1-carbamimidoylpiperidin-4-yl)isoxazol-3-yl)-7-oxo-1,6-diazabicyclo[3.2.1]octan-6-yl hydrogen sulfate TFA salt (607, 32 mg) was obtained. ESI-MS (EI$^+$, m/z): 415.2.

Example 10

Synthesis of (2S,5R)-2-(5-((2-aminoethyl)carbamoyl)isoxazol-3-yl)-7-oxo-1,6-diazabicyclo[3.2.1]octan-6-yl hydrogen sulfate (Compound 605)

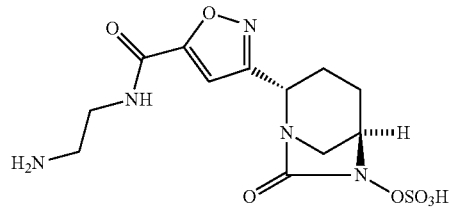

Following Steps 1-6 in Example 4, replacing tert-butyl prop-2-yn-1-ylcarbamate in Step 2 with tert-butyl (2-propiolamidoethyl)carbamate, (2S,5R)-2-(5-((2-aminoethyl)carbamoyl)isoxazol-3-yl)-7-oxo-1,6-diazabicyclo[3.2.1]octan-6-yl hydrogen sulfate TFA salt (605, 20 mg) was obtained as a light yellow solid. ESI-MS (EI$^+$, m/z): 376.1. $^1$H NMR (300 MHz, D$_2$O) δ 7.05 (s, 1H), 4.70 (m, 1H, overlapped with D$_2$O peak) 4.16 (br s, 1H), 3.66 (t, J=5.8 Hz, 2H), 3.19 (t, J=5.8 Hz, 2H), 3.16-3.08 (m, 1H), 2.93 (d, J=12.0 Hz, 1H), 2.31-2.24 (m, 1H), 2.16-2.04 (m, 2H), 1.94-1.85 (m, 1H).

Example 11

Synthesis of (2S,5R)-2-(5-((2-guanidinoethyl)carbamoyl)isoxazol-3-yl)-7-oxo-1,6-diazabicyclo[3.2.1]octan-6-yl hydrogen sulfate (Compound 608)

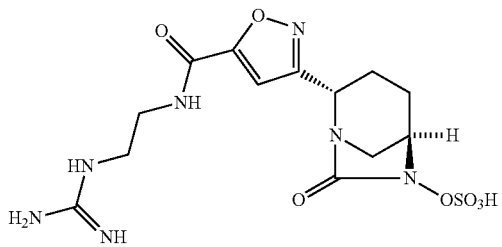

Following Steps 1-5 in Example 5, replacing prop-2-yn-1-amine in Step 1 with N-(2-aminoethyl)propiolamido; (2S,5R)-2-(5-((2-guanidinoethyl)carbamoyl)isoxazol-3-yl)-7-oxo-1,6-diazabicyclo[3.2.1]octan-6-yl hydrogen sulfate (608, 25 mg) was obtained as a white solid after prep-HPLC purification using ammonium formate buffer. ESI-MS (EI$^+$, m/z): 418.12. $^1$H NMR (300 MHz, D$_2$O) δ 4.79-4.76 (m, 1H), 4.16 (br s, 1H), 4.47-4.32 (m, 4H), 4.17-4.11 (m, 2H), 3.19-3.16 (m, 1H), 2.92 (d, J=12.0 Hz, 1H), 2.32-2.22 (m, 1H), 2.20-2.06 (m, 2H), 1.97-1.88 (m, 1H).

Example 12

Synthesis of (2S,5R)-7-oxo-2-(5-(2-(piperidin-4-ylamino)ethyl)isoxazol-3-yl)-1,6-diazabicyclo[3.2.1]octan-6-yl hydrogen sulfate (Compound 609)

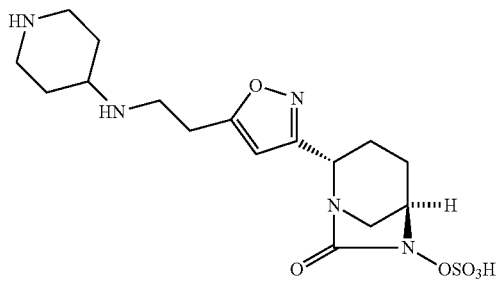

Synthetic Scheme:

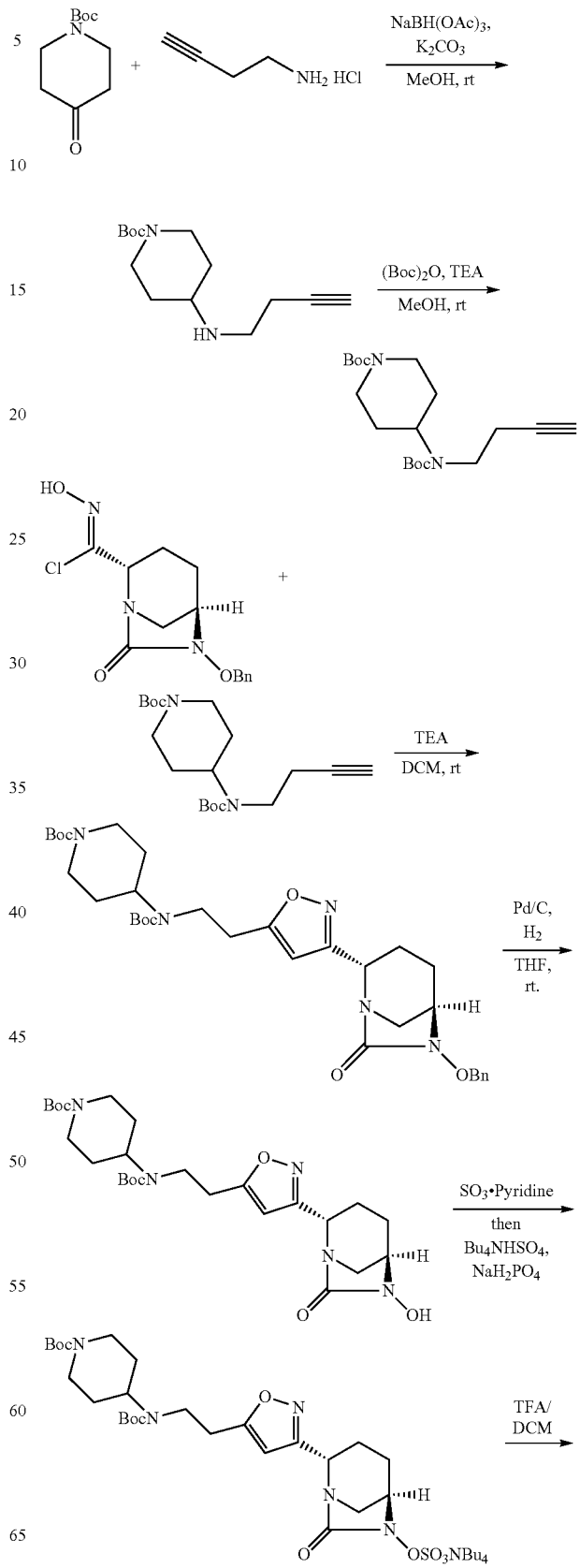

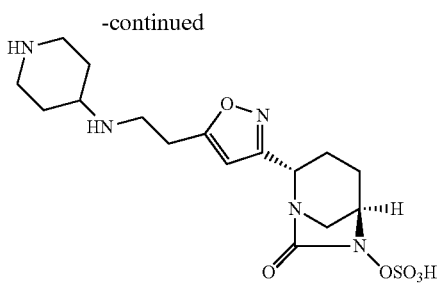

Procedures and Characterization:

Step 1: Synthesis of tert-butyl 4-(but-3-ynylamino)piperidine-1-carboxylate

A mixture of but-3-yn-1-amine hydrochloride (26.4 g, 0.25 mol), K$_2$CO$_3$ (17.4 g, 0.13 mol), and tert-butyl 4-oxopiperidine-1-carboxylate (41.8 g, 0.21 mol) in MeOH (500 mL) was stirred at rt for 5 hrs. Then, NaBH(OAc)$_3$ (133.6 g, 0.63 mol) was added and the suspension was stirred at rt for 17 hrs. The crude reaction mixture was used directly in the next step. ESI-MS (EI$^+$, m/z): 253.2 [M+H]$^+$.

Step 2: Synthesis of tert-butyl 4-(but-3-ynyl(tert-butoxycarbonyl)amino)piperidine-1-carboxylate The reaction mixture in Step 1 was cooled to 0° C. and Et$_3$N (88.0 mL, 0.63 mol) and (Boc)$_2$O (91.6 g, 0.42 mol) were added. The solution was allowed to warm to rt, then was stirred at rt for 17 hrs. The reaction mixture was concentrated, and then EtOAc (800 mL) was added. The organic layer was washed with saturated sodium chloride (3×), dried over Na$_2$SO$_4$, and concentrated. The residue was purified by silica gel column chromatography (gradient elution 0~10% EtOAC/petroleum ether) to afford tert-butyl 4-(but-3-ynyl(tert-butoxycarbonyl)amino)piperidine-1-carboxylate (66.0 g, 90%) as a colorless oil. ESI-MS (EI$^+$, m/z): 353.2 [M+H]$^+$.

Step 3-6:

Following Steps 2-5 in Example 5, replacing 1-(2,3-bis(tert-butoxycarbonyl)guanidino)prop-2-yne in Step 2 with tert-butyl 4-(but-3-yn-1-yl(tert-butoxycarbonyl)amino)piperidine-1-carboxylate; (2S,5R)-7-oxo-2-(5-(2-(piperidin-4-ylamino)ethyl)isoxazol-3-yl)-1,6-diazabicyclo[3.2.1]octan-6-yl hydrogen sulfate (609, 220 mg) was obtained as a white solid after prep-HPLC purification using ammonium formate buffer. ESI-MS (EI$^+$, m/z): 416.4. $^1$H NMR (300 MHz, D$_2$O) δ 6.29 (s, 1H), 4.59 (d, J=6.3 Hz, 1H), 4.12 (s, 1H), 3.39 (d, J=13.3 Hz, 2H), 3.10-2.91 (m, 9H), 2.23-1.95 (m, 5H), 1.87-1.76 (m, 1H), 1.54-1.40 (m, 2H).

Example 13

Synthesis of (2S,5R)-2-(5-(2-((1-carbamimidoylpiperidin-4-yl)amino)ethyl)isoxazol-3-yl)-7-oxo-1,6-diazabicyclo[3.2.1]octan-6-yl hydrogen sulfate (Compound 610)

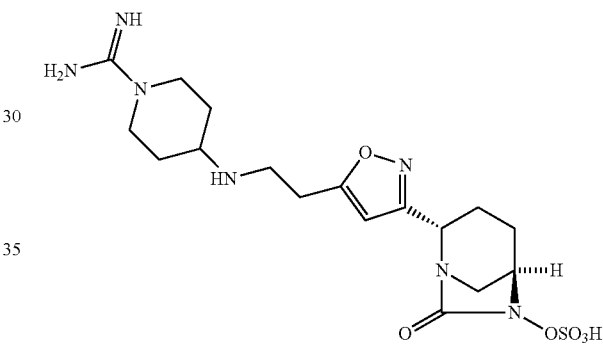

Synthetic Scheme:

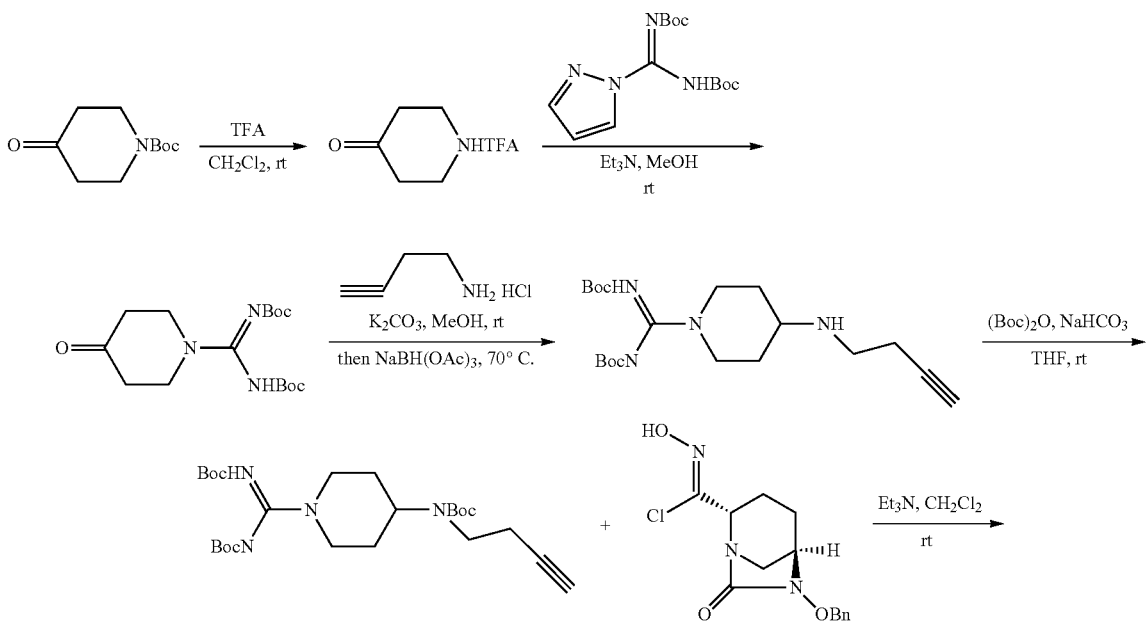

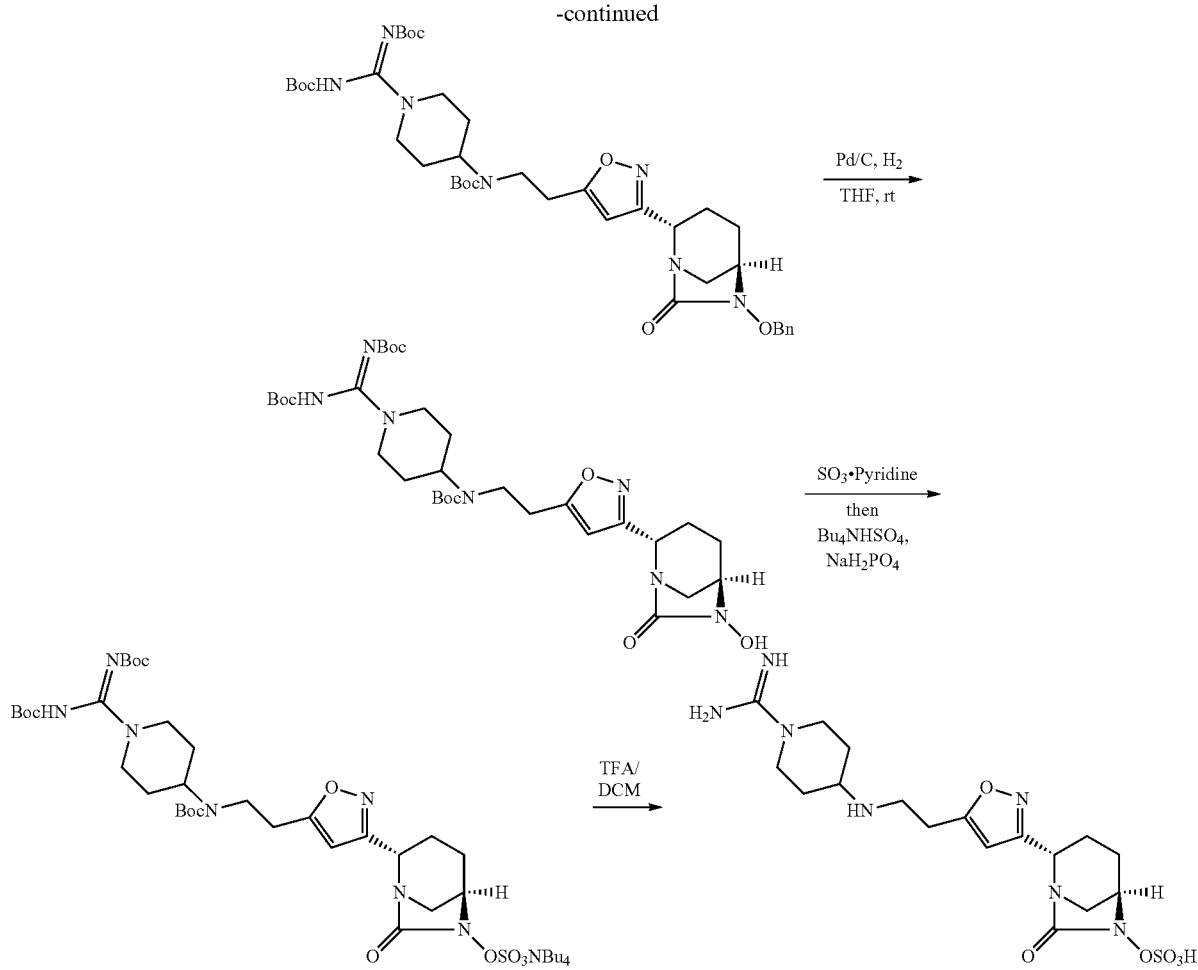

Procedures and Characterization:

Step 1: Synthesis of piperidin-4-one

A mixture of tert-butyl 4-oxopiperidine-1-carboxylate (10.0 g, 50 mmol), TFA (20 mL) and CH$_2$Cl$_2$ (100 mL) was stirred at rt for 1 h. The reaction mixture was then concentrated to afford piperidin-4-one (15.0 g, 100%) as a colorless oil. $^1$H NMR: (500 MHz, DMSO-d$_6$): δ 2.51 (m, 4H), 3.43 (m, 4H), 9.03 (m, 2H).

Step 2: Synthesis of di-tert-butyl (4-oxopiperidin-1-yl)methylenedicarbamate (Z)-di-tert-butyl (1H-imidazol-1-yl)methylenedicarbamate (16.3 g, 52.5 mmol) was add to a 0° C. solution of piperidin-4-one (15 g, 50 mmol) and Et$_3$N (25.4 g, 251 mmol) in MeOH (200 mL). The reaction mixture was allowed to warm to rt then was stirred at rt for 17 hrs. The reaction mixture was concentrated, and then EtOAc (300 mL) was added. The organic layer was washed with saturated sodium chloride (3×), dried over Na$_2$SO$_4$, and concentrated. The residue was purified by silica gel column chromatography (gradient elution 0~20% EtOAc/petroleum ether) to afford di-tert-butyl (4-oxopiperidin-1-yl)methylenedicarbamate (12.8 g, 75%) as a white solid. ESI-MS (EI$^+$, m/z): 342.1 [M+H]$^+$.

Step 3: Synthesis of di-tert-butyl(4-(but-3-ynylamino)piperidin-1-yl)methanediylidenedicarbamate A mixture of but-3-yn-1-amine hydrochloride (3.0 g, 28.4 mmol), K$_2$CO$_3$ (2.0 g, 14.2 mmol), MeOH (150 mL), di-tert-butyl (4-oxopiperidin-1-yl)methylene-dicarbamate (8.1 g, 23.7 mmol) and 4 Å molecular sieve (6.0 g) was stirred at rt for 3 hrs. Then, NaBH(OAc)$_3$ (15.1 g, 71.1 mmol) was added, and the suspension was stirred at 70° C. for 1 h. The reaction mixture was filtered and concentrated to afford di-tert-butyl (4-(but-3-ynylamino)piperidin-1-yl)methanediylidenedicarbamate as a yellow oil (~15.0 g), which was used directly in the next step.

Step 4: Synthesis of di-tert-butyl (4-(but-3-ynyl(tert-butylcarbamate))piperidin-1-yl)methanedi-ylidenedicarbamate A mixture of di-tert-butyl(4-(but-3-ynylamino)piperidin-1-yl) methanediylidenedicarbamate (~15.0 g), di-tert-butyl dicarbonate (10.3 g, 47.4 mmol), aq. NaHCO$_3$ (60 mL) in THF (120 mL) was stirred at rt for 2 hrs. The reaction mixture was then concentrated and extracted with EtOAc (3×). The combined organics were dried (Na$_2$SO$_4$) and concentrated. The residue was purified by silica gel column chromatography (gradient elution 0~20% EtOAc/petroleum ether) to afford di-tert-butyl(4-(but-3-ynyl(tert-butylcarbamate))piperidin-1-yl)methanedi-ylidenedicarbamate as a colorless oil (7.1 g, 60%). ESI-MS (EI+, m/z): 495.3 [M+H]+.

Step 5-8:

Following Steps 2-5 in Example 5, replacing 1-(2,3-bis(tert-butoxycarbonyl)guanidino)prop-2-yne in Step 2 with tert-butyl (1-(N,N'-bis(tert-butoxycarbonyl)carbamimidoyl)piperidin-4-yl)(but-3-yn-1-yl)carbamate; (2S,5R)-2-(5-(2-((1-carbamimidoylpiperidin-4-yl)amino)ethyl)isoxazol-3-yl)-7-oxo-1,6-diazabicyclo[3.2.1]octan-6-yl hydrogen sulfate (610, 502 mg) was obtained as a white solid after prep-HPLC purification using ammonium formate buffer. ESI-MS (EI+, m/z): 458.0. $^1$H NMR (300 MHz, D$_2$O) δ 6.35 (s, 1H), 4.59 (d, J=7.0 Hz, 1H), 4.12 (s, 1H), 3.85 (d, J=14.5 Hz, 2H), 3.40-3.30 (m, 3H), 3.20-2.90 (m, 6H), 2.20-1.75 (m, 6H), 1.62-1.46 (m, 2H).

The Compounds Described in Examples 14-33 were Prepared as Described in the Reaction Schemes Following Similar Procedures of Examples 1-13

Example 14

Synthesis of (2S,5R)-2-(5-((R*)-2-guanidino-1-hydroxyethyl)isoxazol-3-yl)-7-oxo-1,6-diazabicyclo[3.2.1]octan-6-yl hydrogen sulfate (Compound 611)

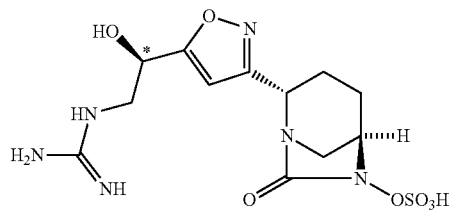

Synthetic Scheme:

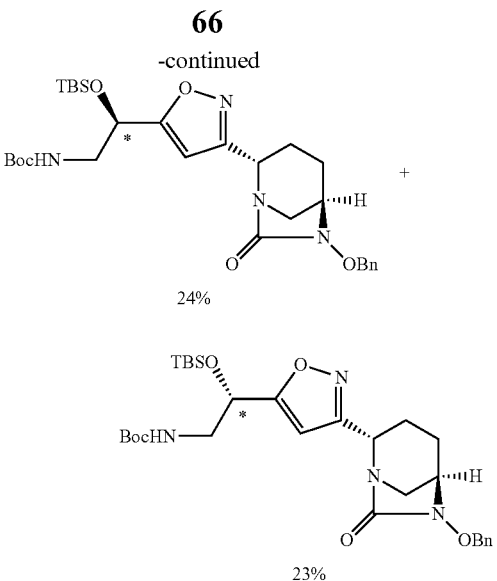

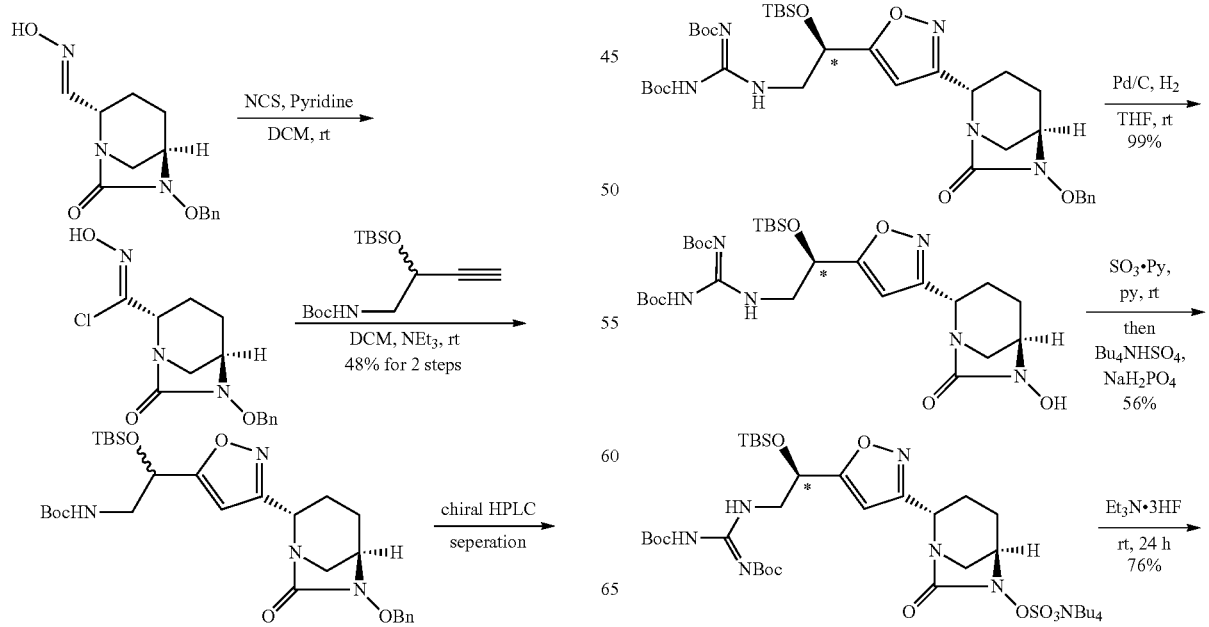

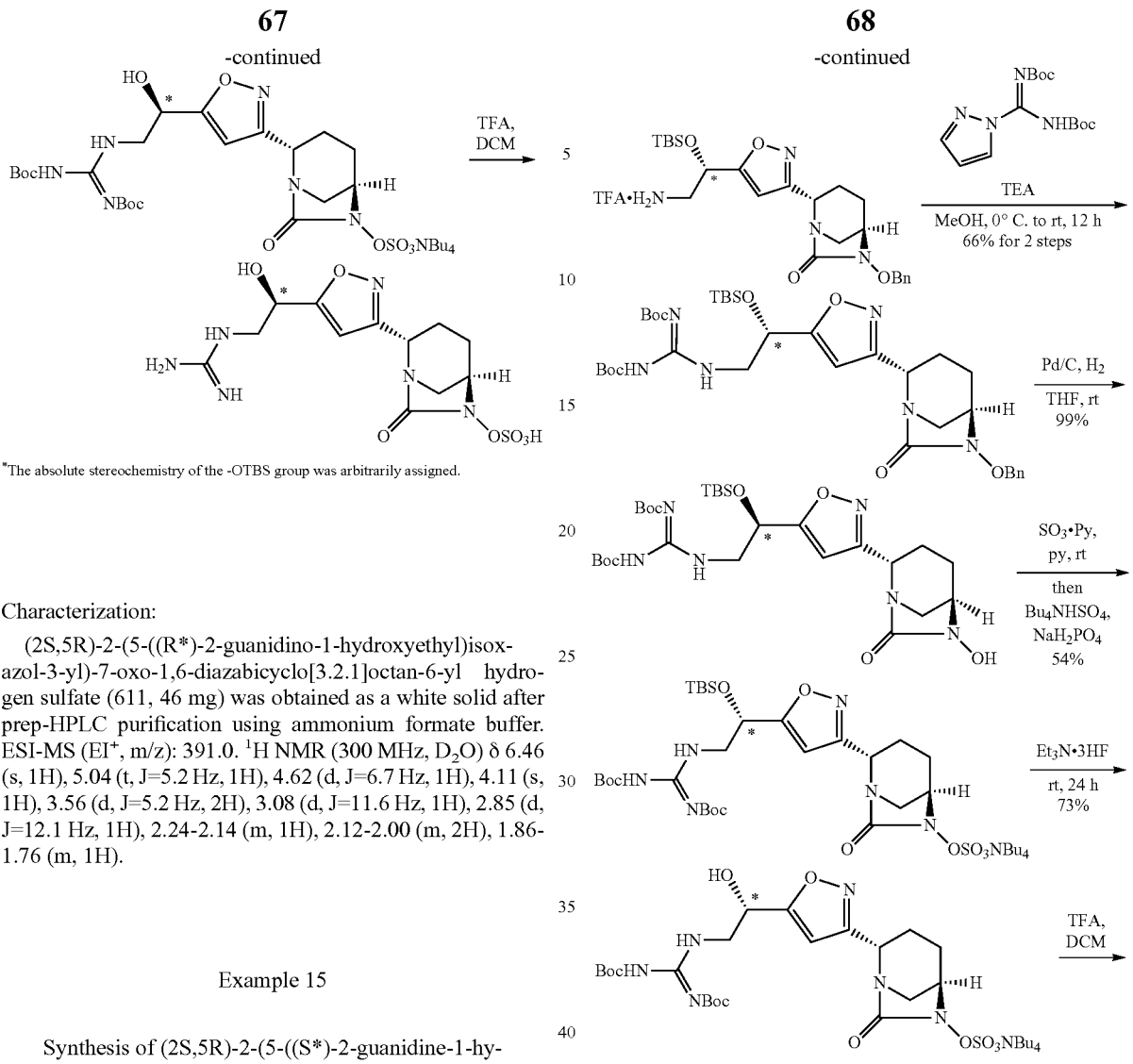

*The absolute stereochemistry of the -OTBS group was arbitrarily assigned.

Characterization:

(2S,5R)-2-(5-((R*)-2-guanidino-1-hydroxyethyl)isoxazol-3-yl)-7-oxo-1,6-diazabicyclo[3.2.1]octan-6-yl hydrogen sulfate (611, 46 mg) was obtained as a white solid after prep-HPLC purification using ammonium formate buffer. ESI-MS (EI+, m/z): 391.0. $^1$H NMR (300 MHz, D$_2$O) δ 6.46 (s, 1H), 5.04 (t, J=5.2 Hz, 1H), 4.62 (d, J=6.7 Hz, 1H), 4.11 (s, 1H), 3.56 (d, J=5.2 Hz, 2H), 3.08 (d, J=11.6 Hz, 1H), 2.85 (d, J=12.1 Hz, 1H), 2.24-2.14 (m, 1H), 2.12-2.00 (m, 2H), 1.86-1.76 (m, 1H).

Example 15

Synthesis of (2S,5R)-2-(5-((S*)-2-guanidine-1-hydroxyethyl)isoxazol-3-yl)-7-oxo-1,6-diazabicyclo[3.2.1]octan-6-yl hydrogen sulfate (Compound 612)

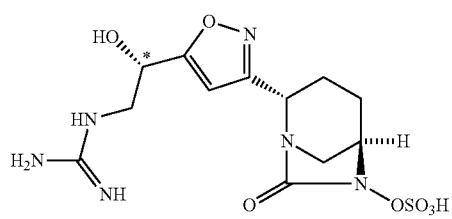

Synthetic Scheme:

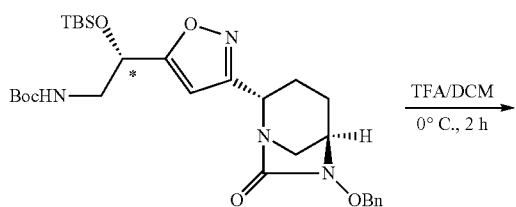

Characterization:

(2S,5R)-2-(5-((S*)-2-guanidino-1-hydroxyethyl)isoxazol-3-yl)-7-oxo-1,6-diazabicyclo[3.2.1]octan-6-yl hydrogen sulfate (612, 72 mg) was obtained as a white solid after prep-HPLC purification using ammonium formate buffer. ESI-MS (EI+, m/z): 391.0. $^1$H NMR (300 MHz, D$_2$O) δ 6.47 (s, 1H), 5.04 (t, J=5.4 Hz, 1H), 4.63 (d, J=6.2 Hz, 1H), 4.12 (s, 1H), 3.65-3.49 (m, 2H), 3.09 (br d, J=12.7 Hz, 1H), 2.87 (d, J=12.2 Hz, 1H), 2.20-1.98 (m, 3H), 1.86-1.78 (m, 1H).

Example 16

Synthesis of (2S,5R)-2-(5-O-guanidinocyclopropyl)methyl)isoxazol-3-yl)-7-oxo-1,6-diazabicyclo[3.2.1]octan-6-yl hydrogen sulfate (Compound 613)

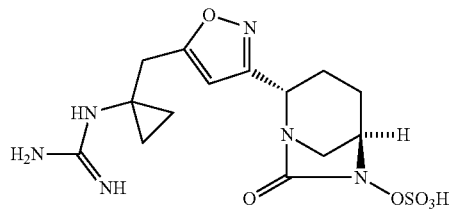

Synthetic Scheme:

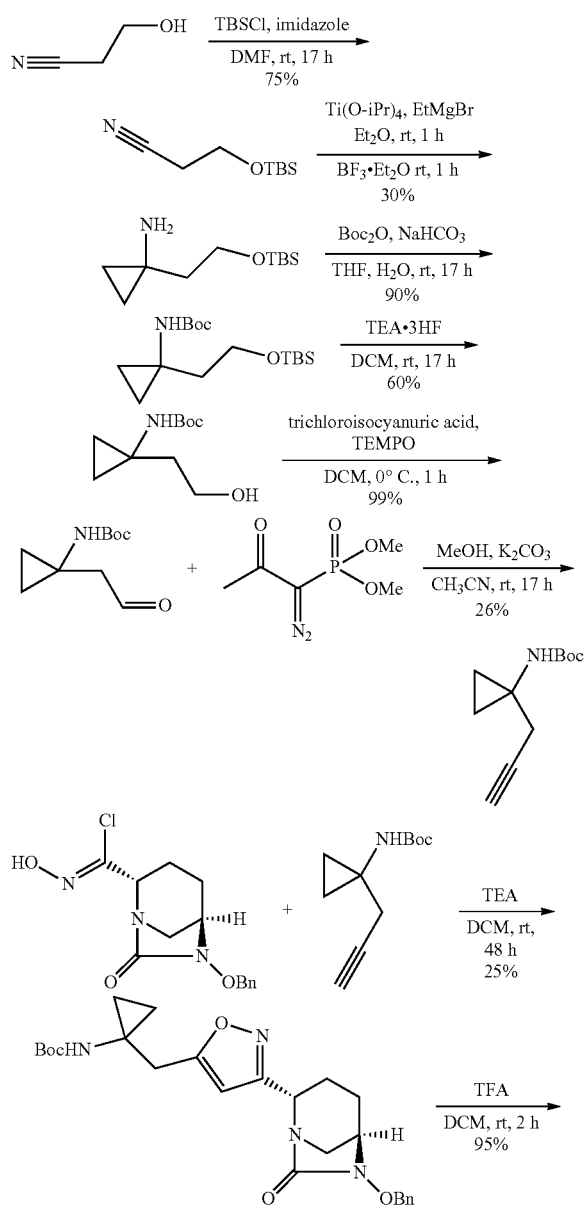

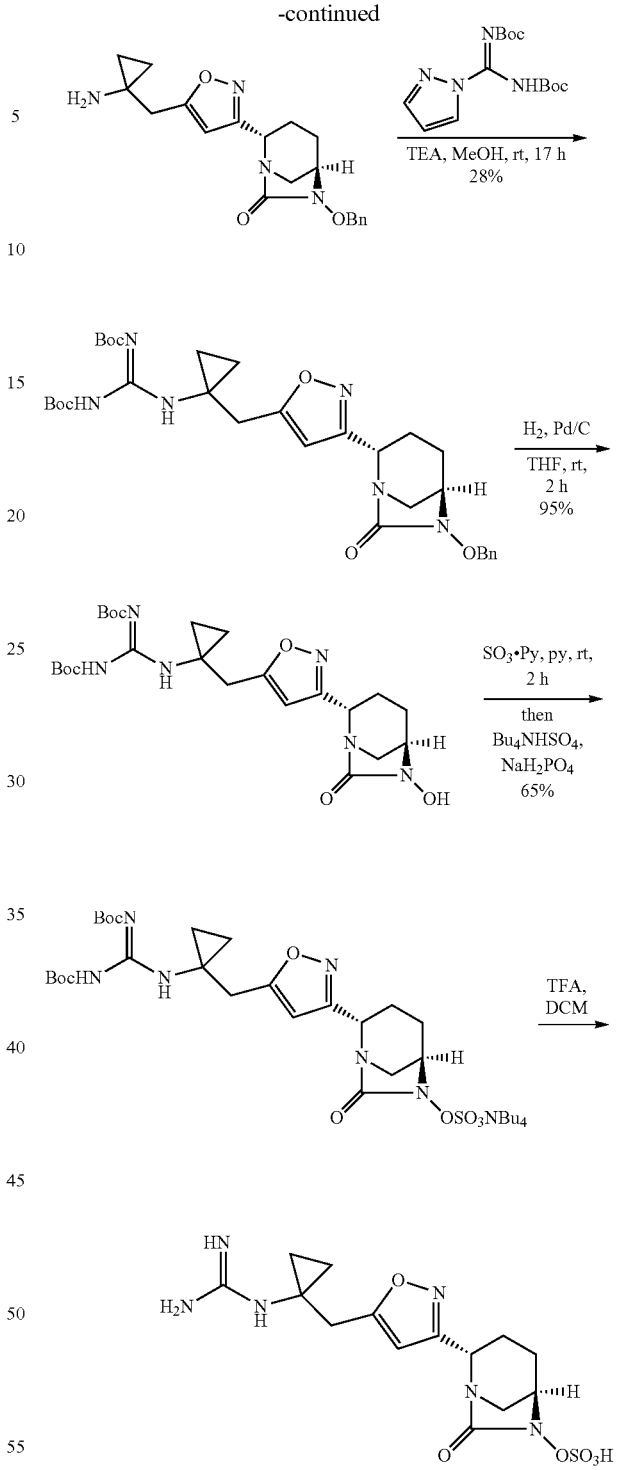

Characterization:

(2S,5R)-2-(5-((1-guanidinocyclopropyl)methyl)isoxazol-3-yl)-7-oxo-1,6-diazabicyclo[3.2.1]octan-6-yl hydrogen sulfate (613, 28 mg) was obtained as a white solid after prep-HPLC purification using ammonium formate buffer. ESI-MS (EI$^+$, m/z): 401.3. $^1$H NMR (300 MHz, D$_2$O) δ 6.35 (s, 1H), 4.61 (d, J=6.6 Hz, 1H), 4.12 (br s, 1H), 3.11-3.09 (m, 1H), 3.08-2.98 (m, 2H), 2.89 (d, J=12.0 Hz, 1H), 2.20-2.00 (m, 3H), 1.89-1.78 (m, 1H), 0.97-0.95 (m, 4H).

Example 17

Synthesis of (2S,5R)-2-(5-O-methylguanidino)methyl)isoxazol-3-yl)-7-oxo-1,6-diazabicyclo[3.2.1]octan-6-yl hydrogen sulfate (Compound 614)

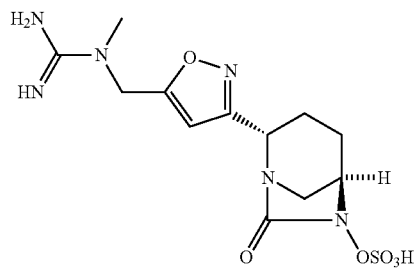

Synthetic Scheme:

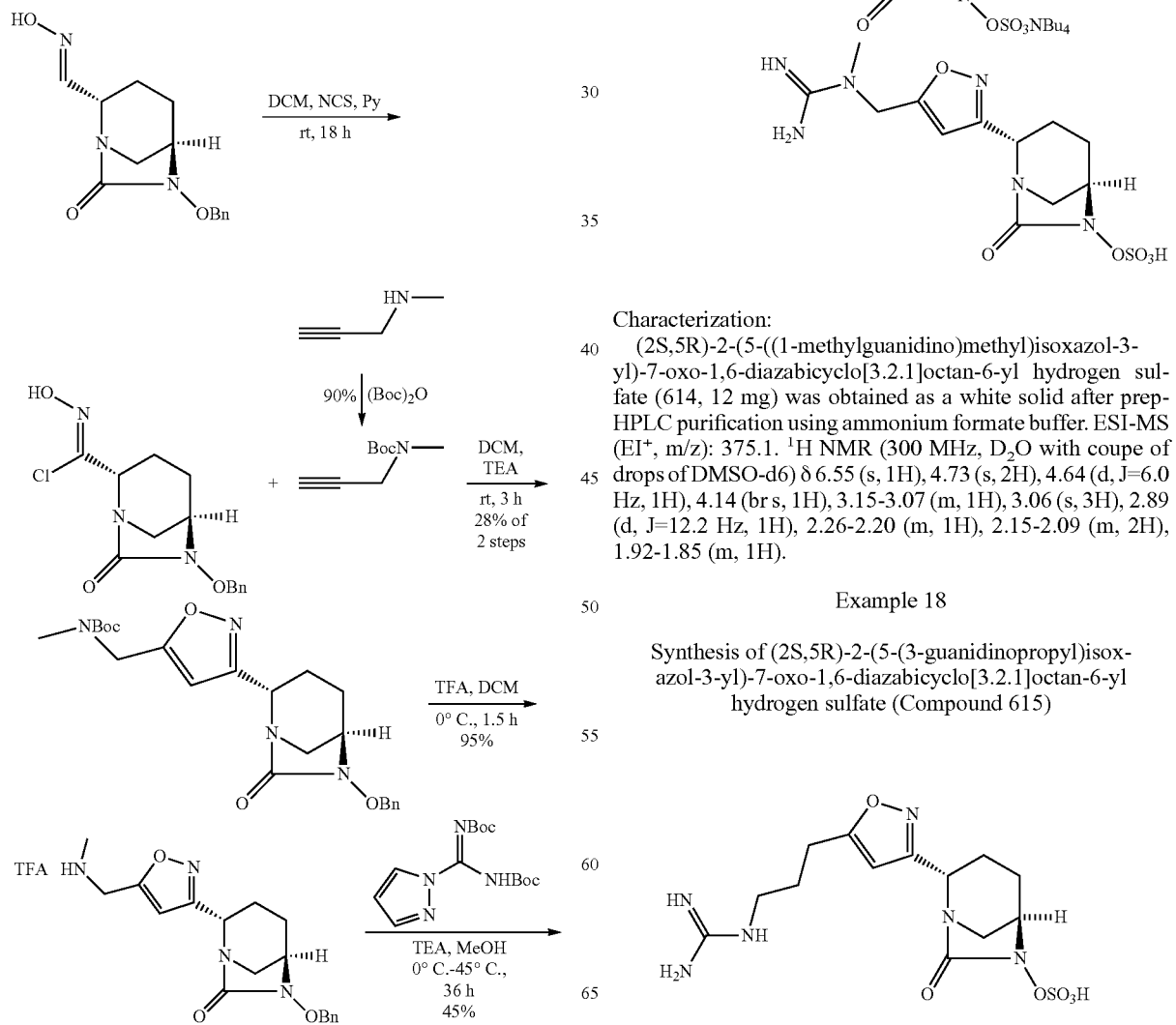

Characterization:

(2S,5R)-2-(5-((1-methylguanidino)methyl)isoxazol-3-yl)-7-oxo-1,6-diazabicyclo[3.2.1]octan-6-yl hydrogen sulfate (614, 12 mg) was obtained as a white solid after prep-HPLC purification using ammonium formate buffer. ESI-MS (EI+, m/z): 375.1. $^1$H NMR (300 MHz, D$_2$O with coupe of drops of DMSO-d6) δ 6.55 (s, 1H), 4.73 (s, 2H), 4.64 (d, J=6.0 Hz, 1H), 4.14 (br s, 1H), 3.15-3.07 (m, 1H), 3.06 (s, 3H), 2.89 (d, J=12.2 Hz, 1H), 2.26-2.20 (m, 1H), 2.15-2.09 (m, 2H), 1.92-1.85 (m, 1H).

Example 18

Synthesis of (2S,5R)-2-(5-(3-guanidinopropyl)isoxazol-3-yl)-7-oxo-1,6-diazabicyclo[3.2.1]octan-6-yl hydrogen sulfate (Compound 615)

Synthetic Scheme:

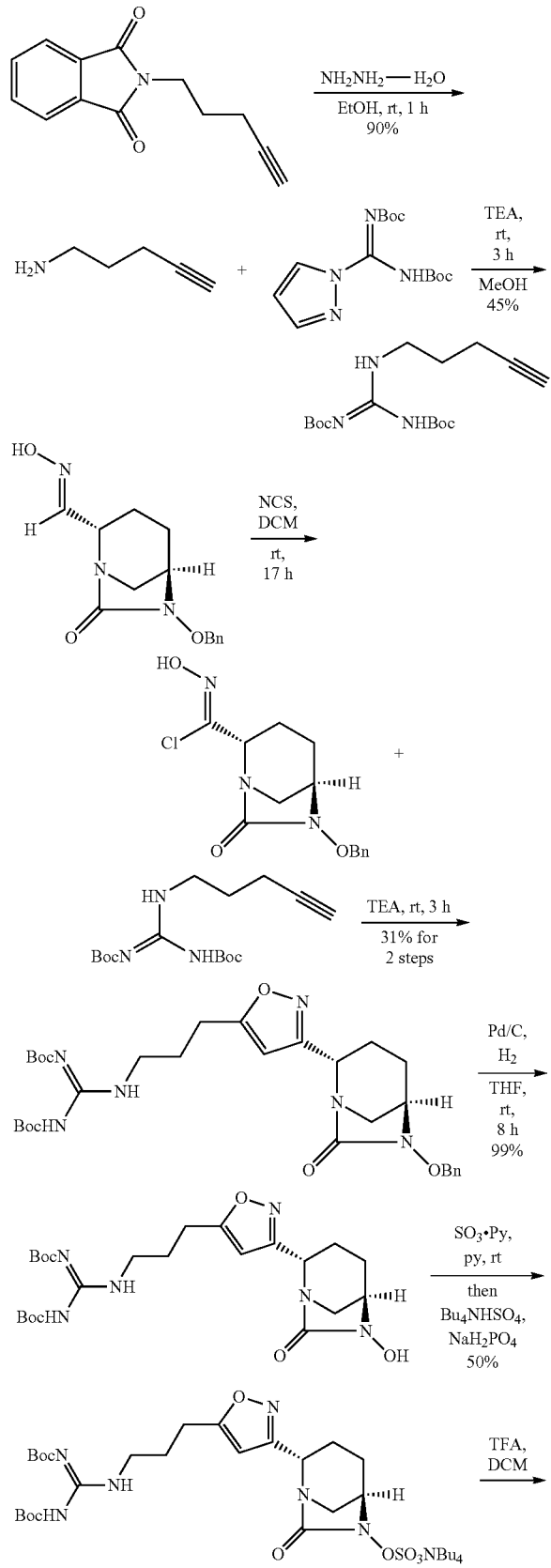

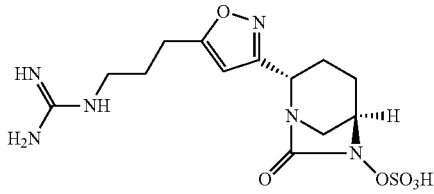

Characterization:

(2S,5R)-2-(5-(3-guanidinopropyl)isoxazol-3-yl)-7-oxo-1,6-diazabicyclo[3.2.1]octan-6-yl hydrogen sulfate (615, 18 mg) was obtained as a white solid after prep-HPLC purification using ammonium formate buffer. ESI-MS (EI+, m/z): 389.1. $^1$H NMR (300 MHz, D$_2$O with couple of drops of DMSO-d6) δ 6.28 (s, 1H), 4.57 (d, J=6.5 Hz, 1H), 4.11 (s, 1H), 3.17 (t, J=6.7 Hz, 2H), 3.07 (br d, J=11.5 Hz, 1H), 2.88 (d, J=12.4 Hz, 1H), 2.83 (t, J=6.7 Hz, 2H), 2.22-1.75 (m, 6H).

Example 19

Synthesis of (2S,5R)-2-(5-((1s,3R)-3-aminocyclobutyl)isoxazol-3-yl)-7-oxo-1,6-diazabicyclo[3.2.1]octan-6-yl hydrogen sulfate (Compound 616)

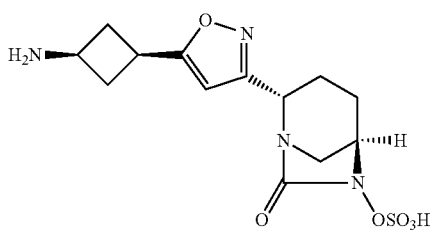

Synthetic Scheme:

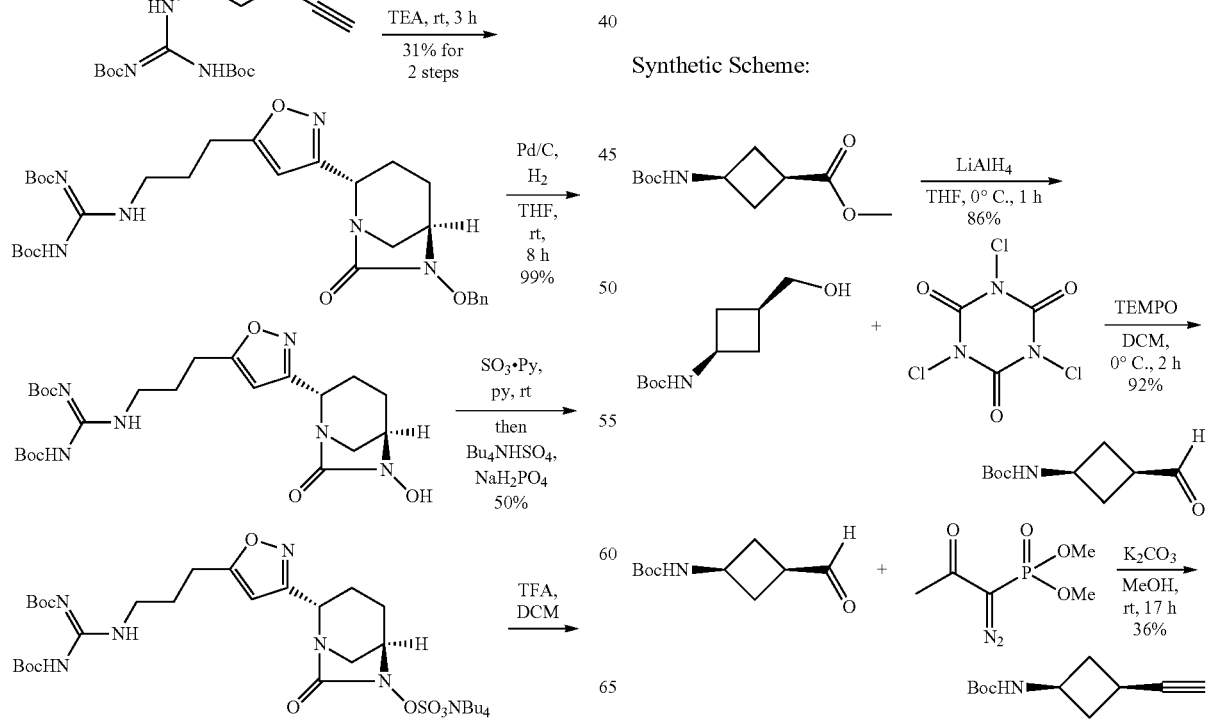

75
-continued

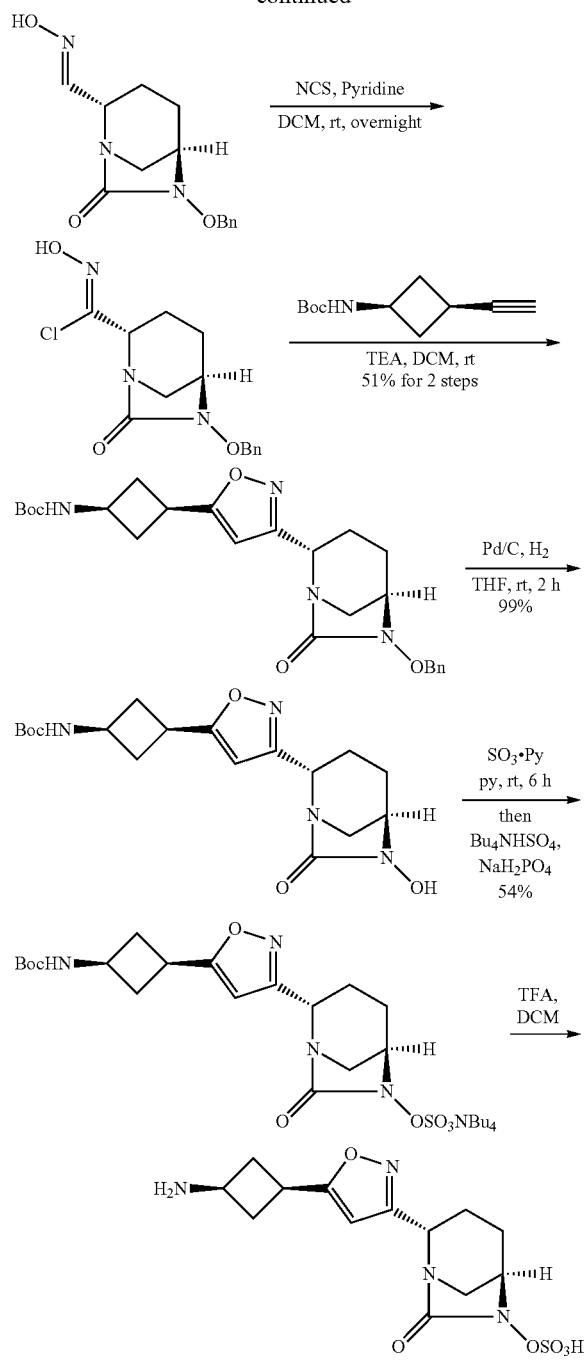

Characterization:

(2S,5R)-2-(5-((1s,3R)-3-aminocyclobutyl)isoxazol-3-yl)-7-oxo-1,6-diazabicyclo[3.2.1]octan-6-yl hydrogen sulfate (616, 7 mg) was obtained as a white solid after prep-HPLC purification using ammonium formate buffer. ESI-MS (EI+, m/z): 359.0. $^1$H NMR (300 MHz, DMSO) δ 6.43 (s, 1H), 4.46 (d, J=6.1 Hz, 1H), 4.02 (br s, 1H), 3.75-3.68 (m, 1H), 3.51-3.45 (m, 1H), 2.94-2.85 (m, 1H), 2.72-2.60 (m, 3H), 2.36-2.30 (m, 2H), 2.15-1.95 (m, 1H), 1.99-1.90 (m, 2H), 1.78-1.72 (m, 1H).

76

Example 20

Synthesis of (2S,5R)-2-(5-((1s,3R)-3-guanidinocyclobutyl)isoxazol-3-yl)-7-oxo-1,6-diazabicyclo[3.2.1]octan-6-yl hydrogen sulfate (Compound 617)

Synthetic Scheme:

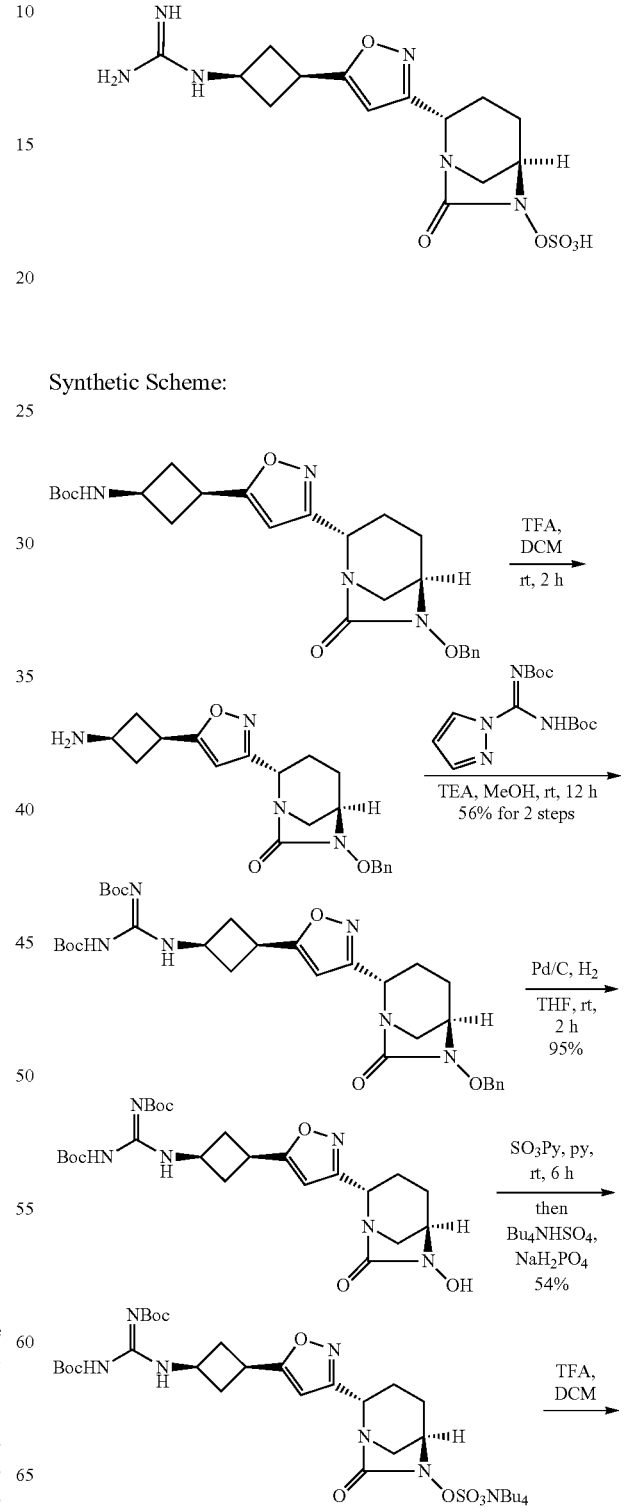

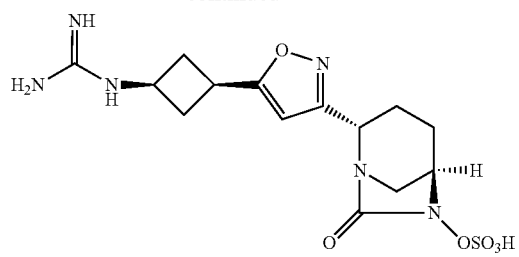

Characterization:

(2S,5R)-2-(5-((1s,3R)-3-guanidinocyclobutyl)isoxazol-3-yl)-7-oxo-1,6-diazabicyclo[3.2.1]octan-6-yl hydrogen sulfate (617, 37 mg) was obtained as a white solid after prep-HPLC purification using ammonium formate buffer. ESI-MS (EI+, m/z): 401.0. $^1$H NMR (300 MHz, DMSO) δ 8.11 (br s, 1H), 7.14 (brs, 4H), 6.41 (s, 1H), 4.45 (d, J=6.3 Hz, 1H), 4.02 (br s, 2H), 3.40-3.30 (m, 1H), 2.91 (br d, J=10.3 Hz, 1H), 2.80-2.63 (m, 3H), 2.30-2.10 (m, 3H), 2.00-1.85 (m, 2H), 1.82-1.66 (m, 1H).

Example 21

Synthesis of (2S,5R)-2-(5-(azetidin-3-ylmethyl)isoxazol-3-yl)-7-oxo-1,6-diazabicyclo[3.2.1]octan-6-yl hydrogen sulfate (Compound 618)

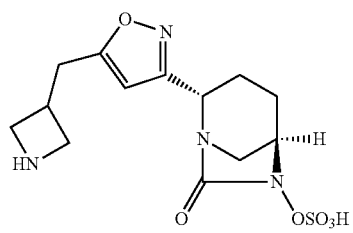

Synthetic Scheme:

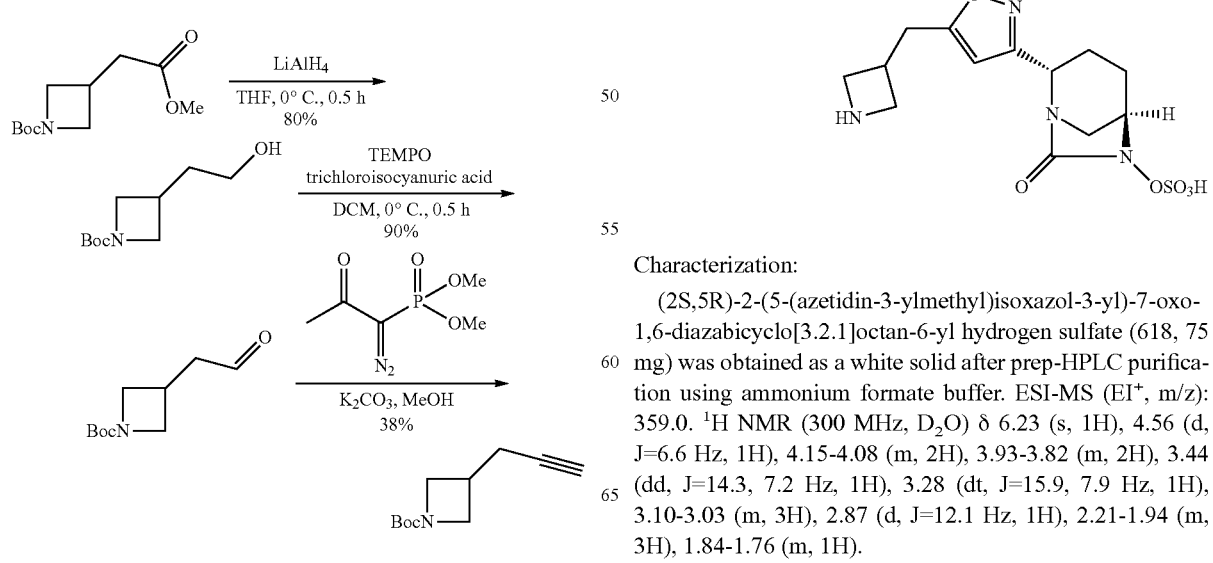

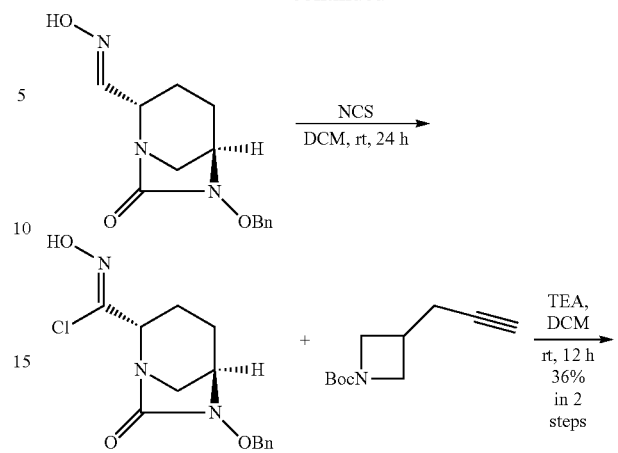

Characterization:

(2S,5R)-2-(5-(azetidin-3-ylmethyl)isoxazol-3-yl)-7-oxo-1,6-diazabicyclo[3.2.1]octan-6-yl hydrogen sulfate (618, 75 mg) was obtained as a white solid after prep-HPLC purification using ammonium formate buffer. ESI-MS (EI+, m/z): 359.0. $^1$H NMR (300 MHz, D$_2$O) δ 6.23 (s, 1H), 4.56 (d, J=6.6 Hz, 1H), 4.15-4.08 (m, 2H), 3.93-3.82 (m, 2H), 3.44 (dd, J=14.3, 7.2 Hz, 1H), 3.28 (dt, J=15.9, 7.9 Hz, 1H), 3.10-3.03 (m, 3H), 2.87 (d, J=12.1 Hz, 1H), 2.21-1.94 (m, 3H), 1.84-1.76 (m, 1H).

Example 22

Synthesis of (2S,5R)-2-(5-O-carbamimidoylazetidin-3-yl)methyl)isoxazol-3-yl)-7-oxo-1,6-diazabicyclo[3.2.1]octan-6-yl hydrogen sulfate (Compound 619,)

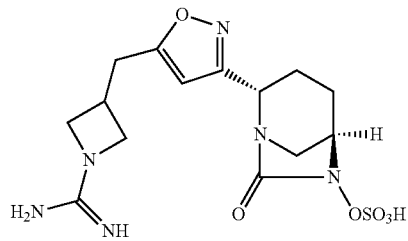

Synthetic Scheme:

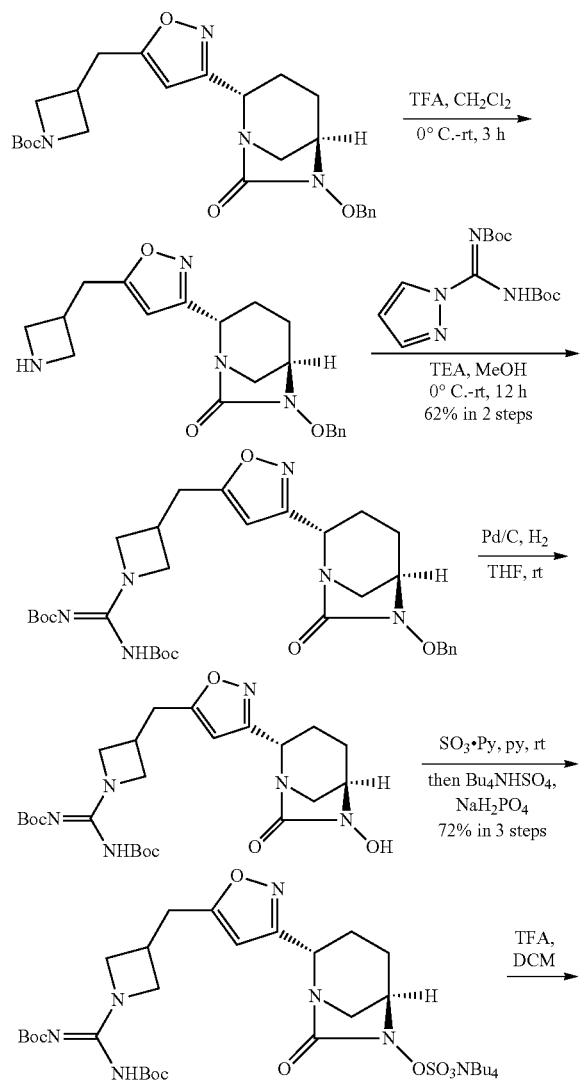

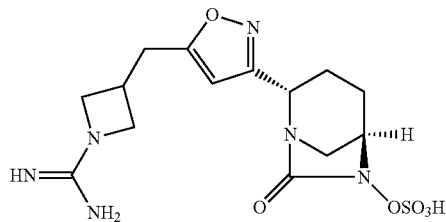

Characterization:

(2S,5R)-2-(5-((1-carbamimidoylazetidin-3-yl)methyl) isoxazol-3-yl)-7-oxo-1,6-diazabicyclo[3.2.1]octan-6-yl hydrogen sulfate (619, 45 mg) was obtained as a white solid after prep-HPLC purification using ammonium formate buffer. ESI-MS (EI$^+$, m/z): 401.0. $^1$H NMR (300 MHz, DMSO) δ 7.28 (br s, 4H), 6.36 (s, 1H), 4.45 (d, J=6.8 Hz, 1H), 4.18 (t, J=8.4 Hz, 2H), 4.02 (br s, 1H), 3.86-3.71 (m, 2H), 3.16 (d, J=7.0 Hz, 2H), 3.09-3.04 (m, 1H), 2.90 (br d, J=8.7 Hz, 1H), 2.67 (d, J=11.8 Hz, 1H), 2.16-2.09 (m, 1H), 2.00-1.90 (m, 2H), 1.80-1.72 (m, 1H).

Example 23

Synthesis of (2S,5R)-2-(5-(2-((2-aminoethyl)amino) ethyl)isoxazol-3-yl)-7-oxo-1,6-diazabicyclo[3.2.1] octan-6-yl hydrogen sulfate (Compound 620)

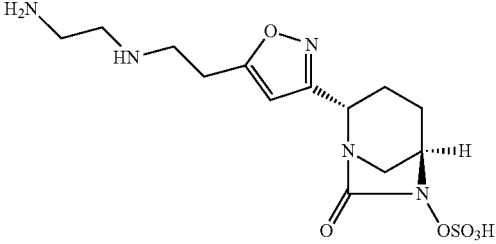

Synthetic Scheme:

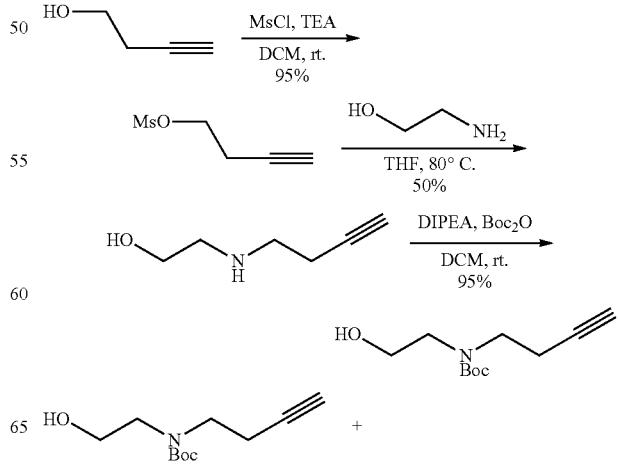

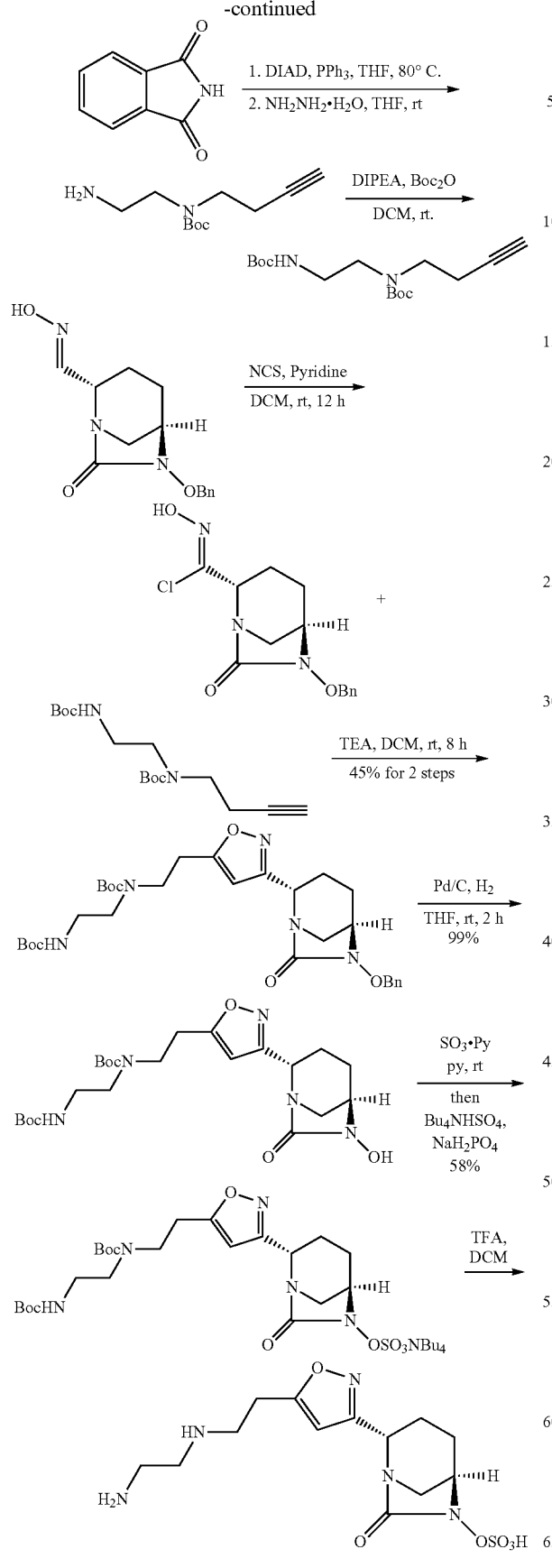

Characterization:
(2S,5R)-2-(5-(2-((2-aminoethyl)amino)ethyl)isoxazol-3-yl)-7-oxo-1,6-diazabicyclo[3.2.1]octan-6-yl hydrogen sulfate (620, 20 mg, as formate salt) was obtained as a white solid after prep-HPLC purification using ammonium formate buffer. ESI-MS (EI$^+$, m/z): 376.3. $^1$H NMR (300 MHz, D$_2$O) δ 8.32 (s, 1H), 6.35 (s, 1H), 4.59 (d, J=6.5 Hz, 1H), 4.11 (br s, 1H), 3.34 (t, J=6.8 Hz, 2H), 3.30-3.13 (m, 6H), 3.11-3.03 (m, 1H), 2.91 (d, J=12.2 Hz, 1H), 2.21-1.98 (m, 3H), 1.88-1.78 (m, 1H).

Example 24

Synthesis of (2S,5R)-2-(5-(2-((2-guanidinoethyl)amino)ethyl)isoxazol-3-yl)-7-oxo-1,6-diazabicyclo[3.2.1]octan-6-yl hydrogen sulfate (Compound 621)

Synthetic Scheme:

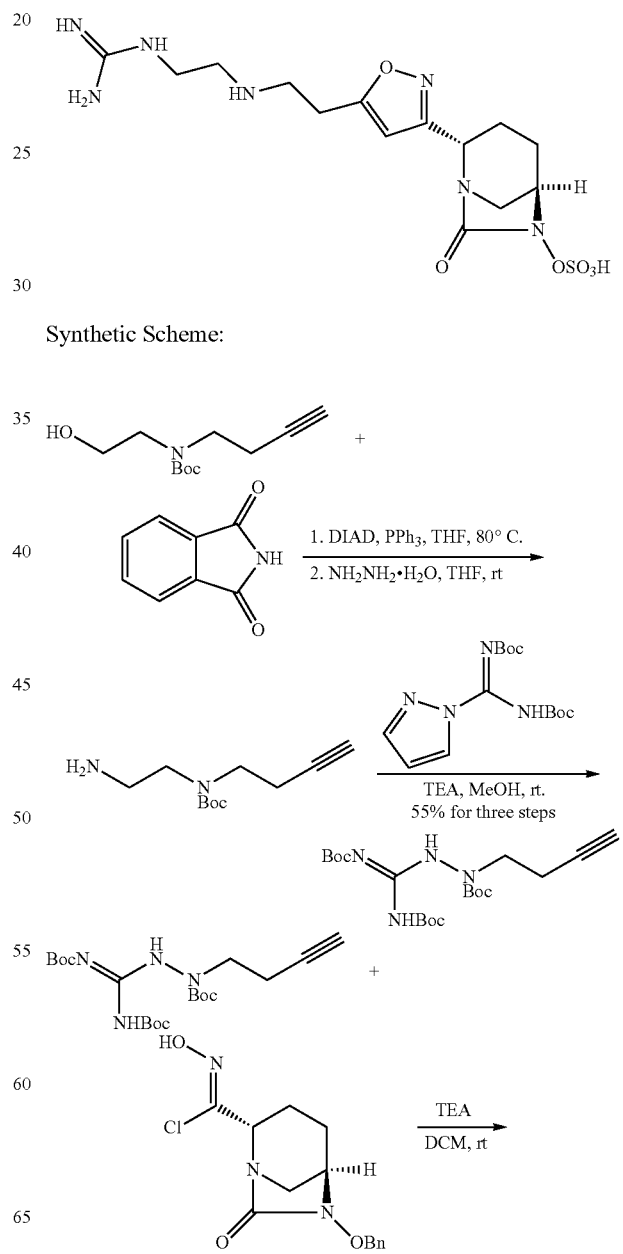

83
-continued

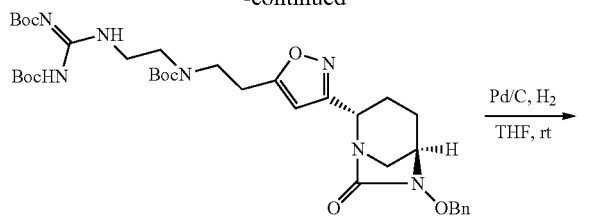

Pd/C, H₂
THF, rt

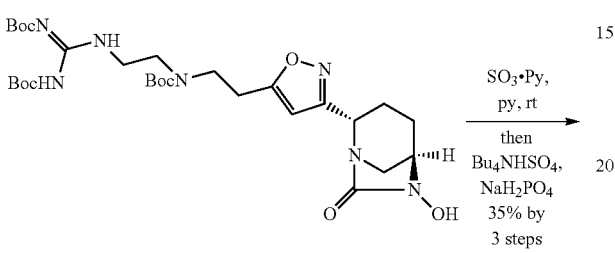

SO₃•Py,
py, rt
then
Bu₄NHSO₄,
NaH₂PO₄
35% by
3 steps

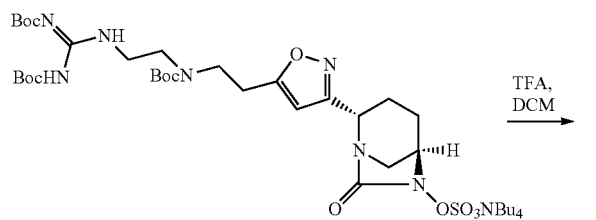

TFA,
DCM

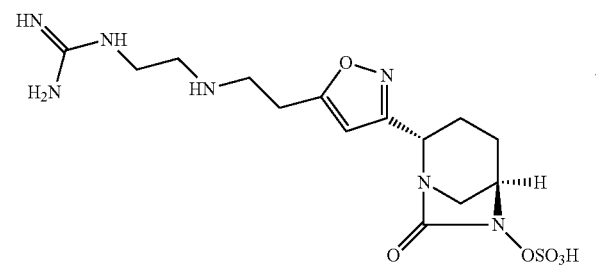

Characterization:

(2S,5R)-2-(5-(2-((2-guanidinoethyl)amino)ethyl)isoxazol-3-yl)-7-oxo-1,6-diazabicyclo[3.2.1]octan-6-yl hydrogen sulfate (612, 15 mg, as formate salt) was obtained as a white solid after prep-HPLC purification using ammonium formate buffer. ESI-MS (EI⁺, m/z): 418.0. ¹H NMR (300 MHz, D₂O) δ 8.28 (s, 1H), 6.30 (s, 1H), 4.55 (d, J=5.9 Hz, 1H), 4.07 (br s, 1H), 3.40 (t, J=5.9 Hz, 2H), 3.25 (t, J=6.1 Hz, 2H), 3.14-3.01 (m, 5H), 2.87 (d, J=12.1 Hz, 1H), 2.16-2.09 (m, 1H), 2.07-1.92 (m, 2H), 1.83-1.74 (m, 1H).

84
Example 25

Synthesis of (2S,5R)-2-(5-((azetidin-3-ylamino)methyl)isoxazol-3-yl)-7-oxo-1,6-diazabicyclo[3.2.1]octan-6-yl hydrogen sulfate (Compound 622)

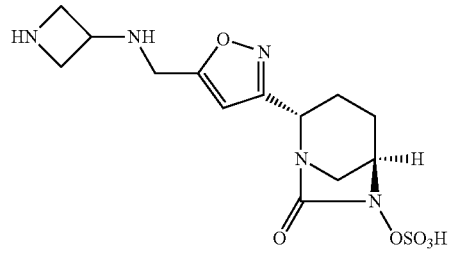

Synthetic Scheme:

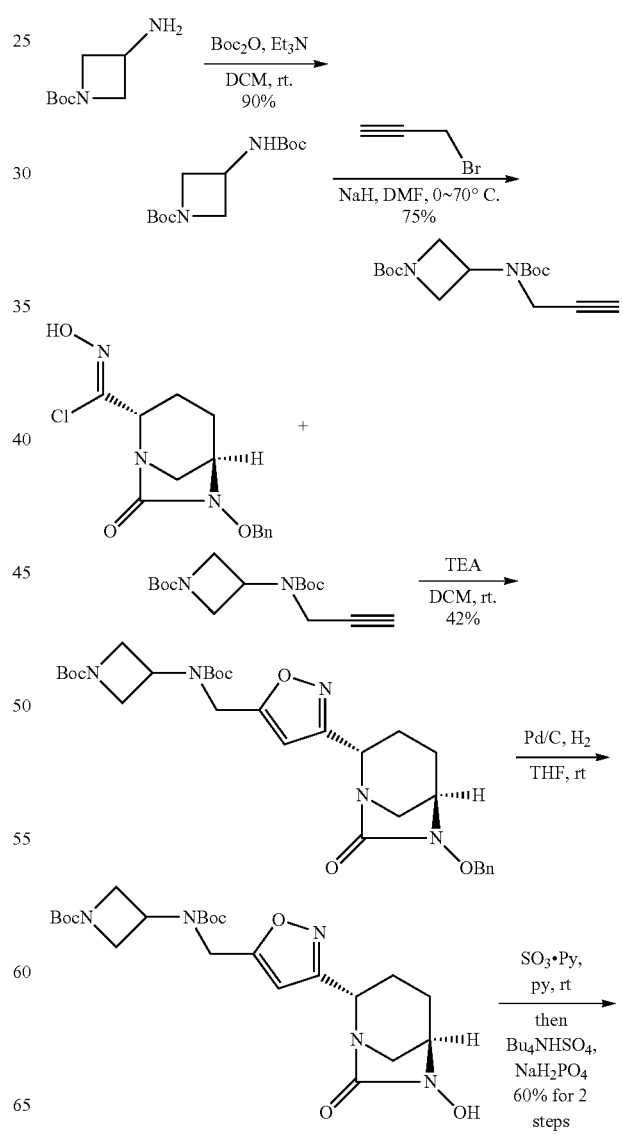

85

-continued

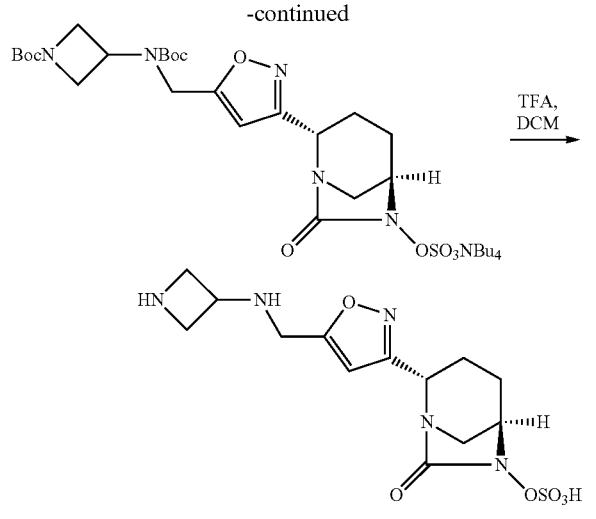

Characterization:

(2S,5R)-2-(5-((azetidin-3-ylamino)methyl)isoxazol-3-yl)-7-oxo-1,6-diazabicyclo[3.2.1]octan-6-yl hydrogen sulfate (622, 267 mg) was obtained as a white solid after prep-HPLC purification using ammonium formate buffer. ESI-MS (EI$^+$, m/z): 374.0. $^1$H NMR (400 MHz, D$_2$O) δ 6.55 (s, 1H), 4.66 (d, J=6.6 Hz, 1H), 4.29-4.10 (m, 5H), 4.10-3.98 (m, 2H), 3.12 (d, J=12.0 Hz, 1H), 2.91 (d, J=12.1 Hz, 1H), 2.30-2.18 (m, 1H), 2.18-1.99 (m, 2H), 1.97-1.78 (m, 1H).

Example 26

Synthesis of (2S,5R)-2-(5-(2-(azetidin-3-ylamino)ethyl)isoxazol-3-yl)-7-oxo-1,6-diazabicyclo[3.2.1]octan-6-yl hydrogen sulfate (Compound 623)

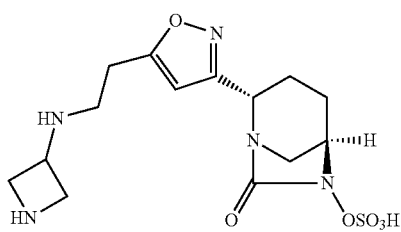

Synthetic Scheme:

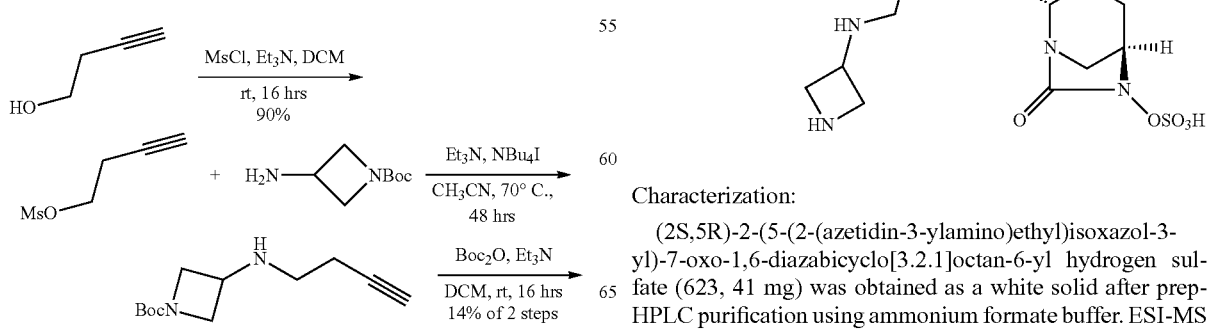

86

-continued

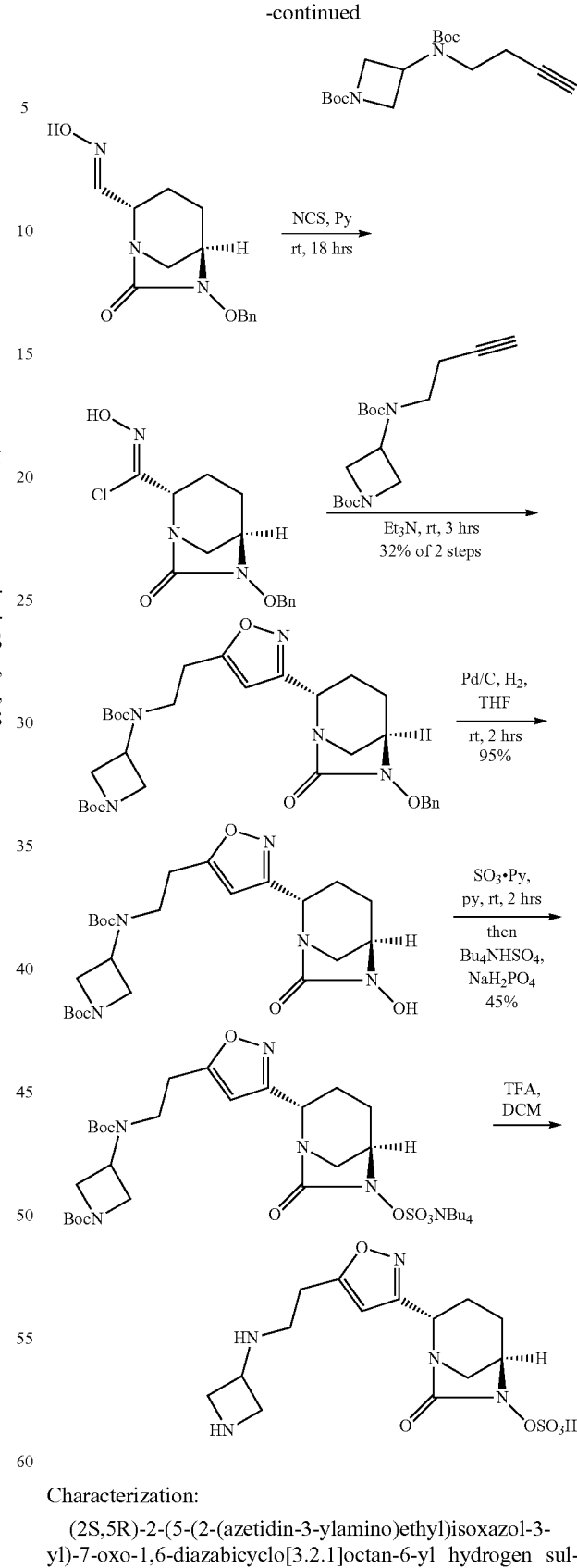

Characterization:

(2S,5R)-2-(5-(2-(azetidin-3-ylamino)ethyl)isoxazol-3-yl)-7-oxo-1,6-diazabicyclo[3.2.1]octan-6-yl hydrogen sulfate (623, 41 mg) was obtained as a white solid after prep-HPLC purification using ammonium formate buffer. ESI-MS (EI$^+$, m/z): 388.0.

Example 27

Synthesis of (2S,5R)-2-(5-((azetidin-3-yloxy)methyl)isoxazol-3-yl)-7-oxo-1,6-diazabicyclo[3.2.1]octan-6-yl hydrogen sulfate (Compound 624)

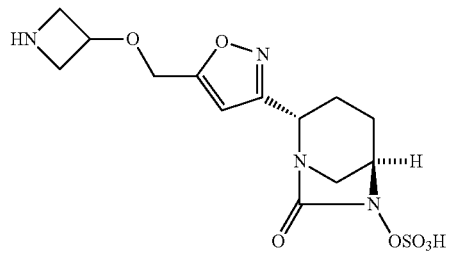

Synthetic Scheme:

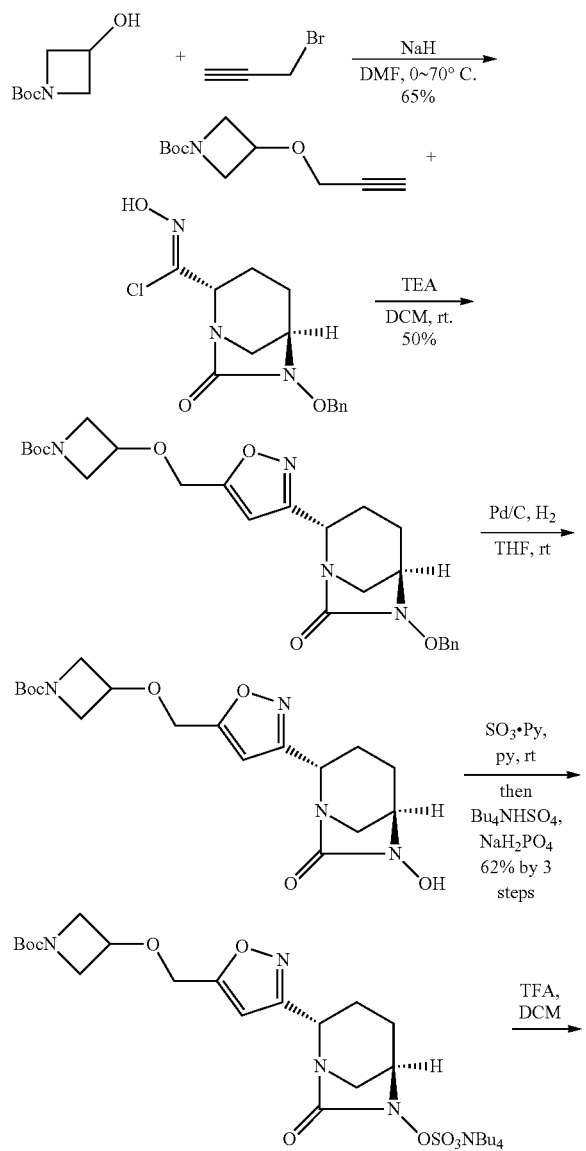

-continued

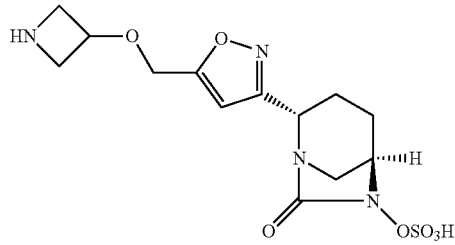

Characterization:

(2S,5R)-2-(5-((azetidin-3-yloxy)methyl)isoxazol-3-yl)-7-oxo-1,6-diazabicyclo[3.2.1]octan-6-yl hydrogen sulfate (624, 349 mg) was obtained as a white solid after prep-HPLC purification using ammonium formate buffer. ESI-MS (EI$^+$, m/z): 375.2. $^1$H NMR (300 MHz, D$_2$O) δ 6.51 (s, 1H), 4.64 (s, 2H), 4.62 (d, J=7.2 Hz, 1H), 4.56-4.52 (m, 1H), 4.20 (dd, J=12.5, 6.7 Hz, 2H), 4.11 (br s, 1H), 3.93 (dd, J=12.3, 5.2 Hz, 2H), 3.08 (br d, J=12.4 Hz, 1H), 2.87 (d, J=12.2 Hz, 1H), 2.22-2.14 (m, 1H), 2.12-2.00 (m, 2H), 187-1.78 (m, 1H).

Example 28

Synthesis of (2S,5R)-2-(5-(1-methylpyridin-1-ium-4-yl)isoxazol-3-yl)-7-oxo-1,6-diazabicyclo[3.2.1]octan-6-yl sulfate (Compound 625)

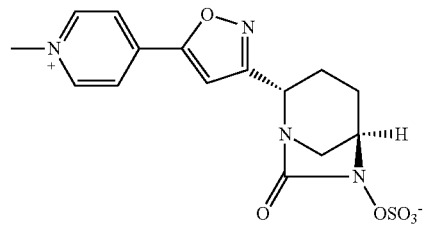

Synthetic Scheme:

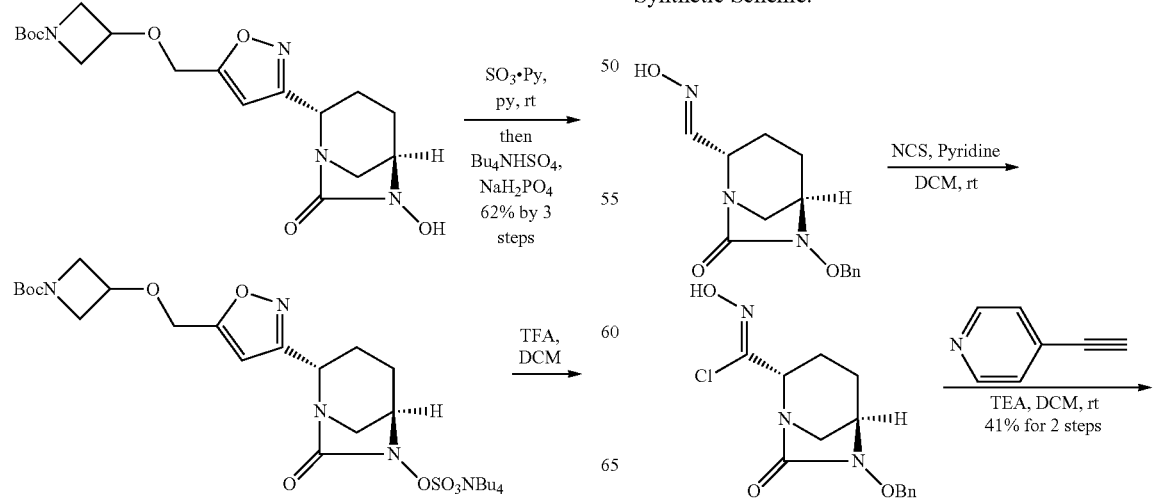

-continued
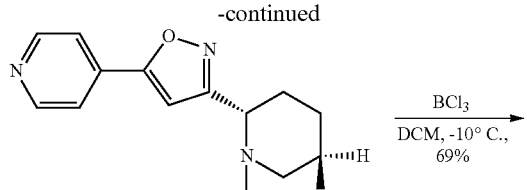
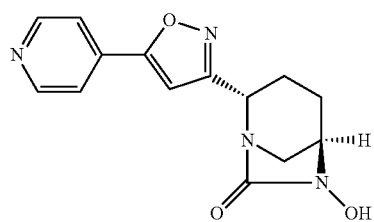
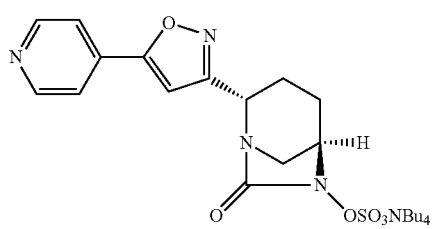
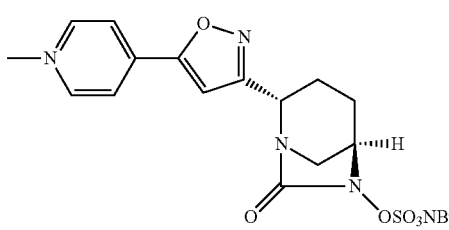
Characterization:
(2S,5R)-2-(5-(1-methylpyridin-1-ium-4-yl)isoxazol-3-yl)-7-oxo-1,6-diazabicyclo[3.2.1]octan-6-yl sulfate (625, 20 mg) was obtained as a white solid. ESI-MS (Er, m/z): 379.0. $^1$H NMR (400 MHz, d6-DMSO) δ 9.15 (d, J=5.2 Hz, 2H), 8.60 (d, J=5.2 Hz, 2H), 7.86 (s, 1H), 4.66 (d, J=5.6 Hz, 1H), 4.36 (s, 3H), 4.07 (br s, 1H), 3.00-2.98 (m, 1H), 2.79 (d, J=12.2 Hz, 1H), 2.24-2.20 (m, 1H), 2.10-2.00 (m, 2H), 1.82-1.78 (m, 1H).
Example 29
Synthesis of (2S,5R)-2-(5-(1,1-dimethylpiperidin-1-ium-4-yl)isoxazol-3-yl)-7-oxo-1,6-diazabicyclo[3.2.1]octan-6-yl sulfate (Compound 626)
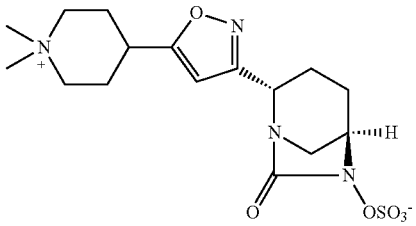
Synthetic Scheme:
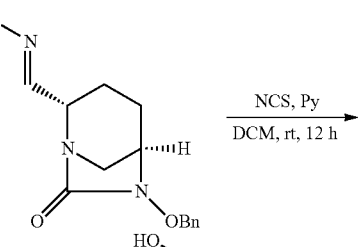
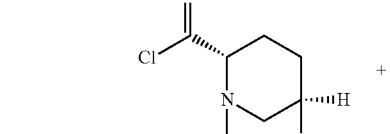
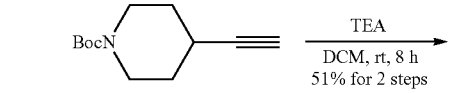
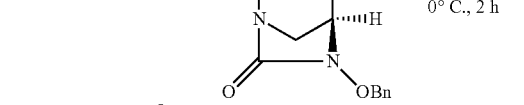
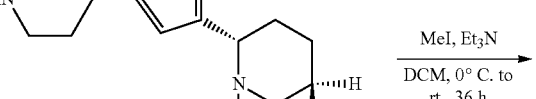
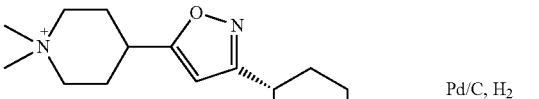
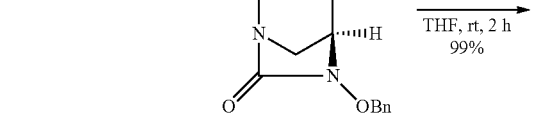

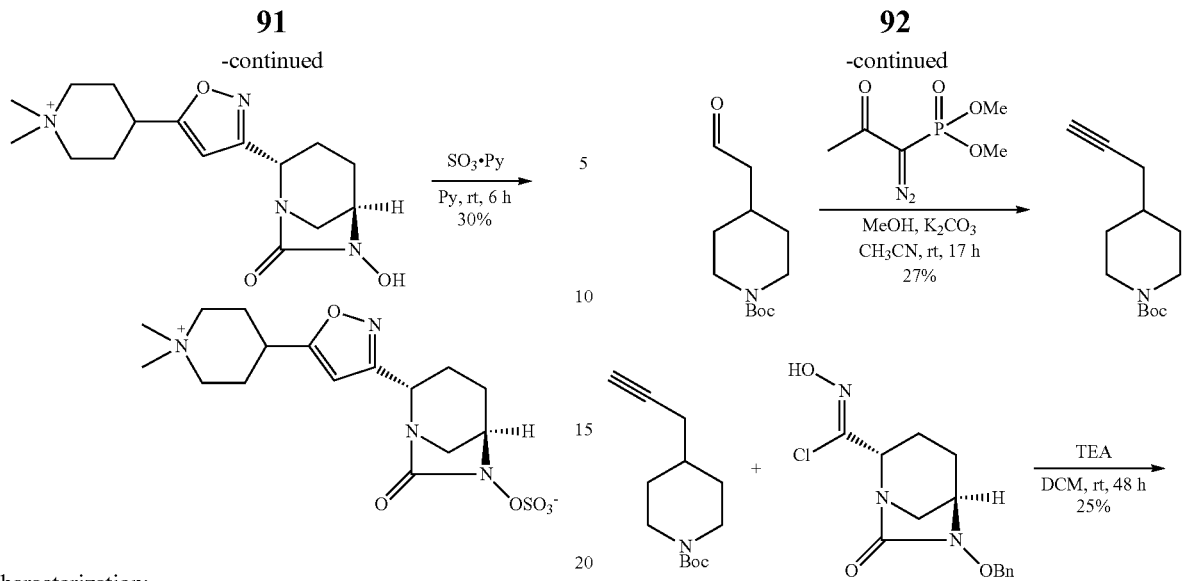

Characterization:

(2S,5R)-2-(5-(1,1-dimethylpiperidin-1-ium-4-yl)isoxazol-3-yl)-7-oxo-1,6-diazabicyclo[3.2.1]octan-6-yl sulfate (626, 86 mg) was obtained as a white solid after prep-HPLC purification using ammonium formate buffer. ESI-MS (EI−, m/z): 399.2. $^1$H NMR (400 MHz, CF$_3$COOD): δ 7.24 (s, 1H), 6.03 (d, J=6.8 Hz, 1H), 5.44 (br s, 1H), 4.76-4.72 (m, 1H), 4.51 (d, J=12.2 Hz, 1H), 4.26-4.12 (m, 4H), 3.99-3.92 (m, 1H), 3.85 (s, 3H), 3.82 (s, 3H), 3.26-3.22 (m, 1H), 3.21-2.85 (m, 7H).

Example 30

Synthesis of (2S,5R)-7-oxo-2-(5-(piperidin-4-ylmethyl)isoxazol-3-yl)-1,6-diazabicyclo[3.2.1]octan-6-yl hydrogen sulfate (Compound 627)

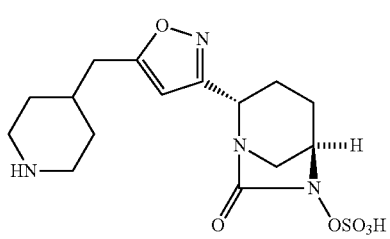

Synthetic Scheme:

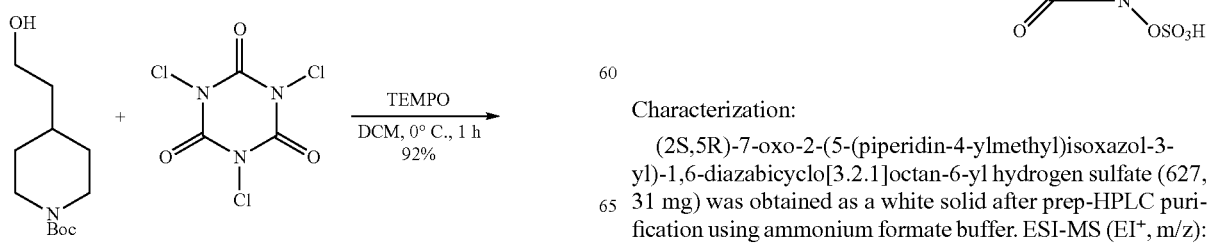

Characterization:

(2S,5R)-7-oxo-2-(5-(piperidin-4-ylmethyl)isoxazol-3-yl)-1,6-diazabicyclo[3.2.1]octan-6-yl hydrogen sulfate (627, 31 mg) was obtained as a white solid after prep-HPLC purification using ammonium formate buffer. ESI-MS (EI+, m/z): 387.0.

Example 31

Synthesis of (2S,5R)-2-(5-(azetidin-3-yl)isoxazol-3-yl)-7-oxo-1,6-diazabicyclo[3.2.1]octan-6-yl hydrogen sulfate (Compound 628)

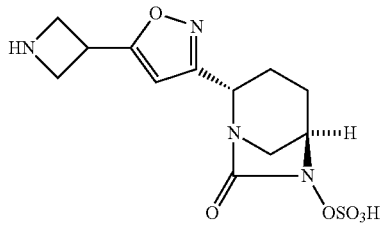

Characterization:

(2S,5R)-2-(5-(azetidin-3-yl)isoxazol-3-yl)-7-oxo-1,6-diazabicyclo[3.2.1]octan-6-yl hydrogen sulfate (628, 15 mg) was obtained as a white solid after prep-HPLC purification using ammonium formate buffer. ESI-MS (EI⁺, m/z): 345.0. $^1$H NMR (300 MHz, $D_2O$) δ 6.48 (s, 1H), 4.62 (d, J=5.2 Hz, 1H), 4.47-4.22 (m, 5H), 4.15-4.12 (m, 1H), 3.17-3.03 (m, 1H), 2.91 (d, J=12.0 Hz, 1H), 2.24-2.17 (m, 1H), 2.12-2.00 (m, 2H), 1.90-1.80 (m, 1H). CB-606,122.

Example 32

Synthesis of (2S,5R)-2-(5-(2-(azetidin-3-yl)ethyl)isoxazol-3-yl)-7-oxo-1,6-diazabicyclo[3.2.1]octan-6-yl hydrogen sulfate (Compound 629)

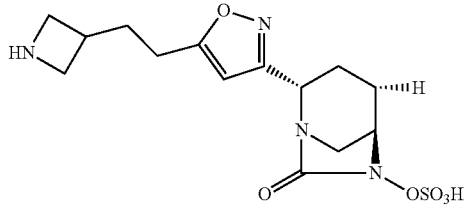

Synthetic Scheme:

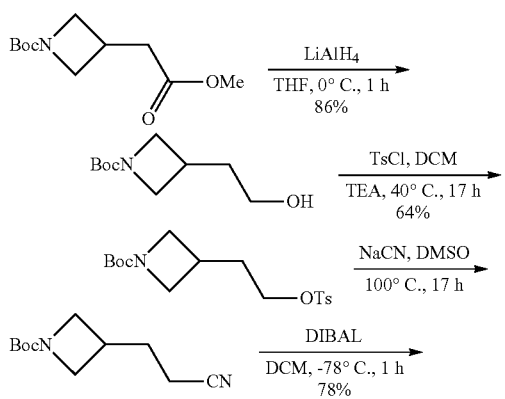

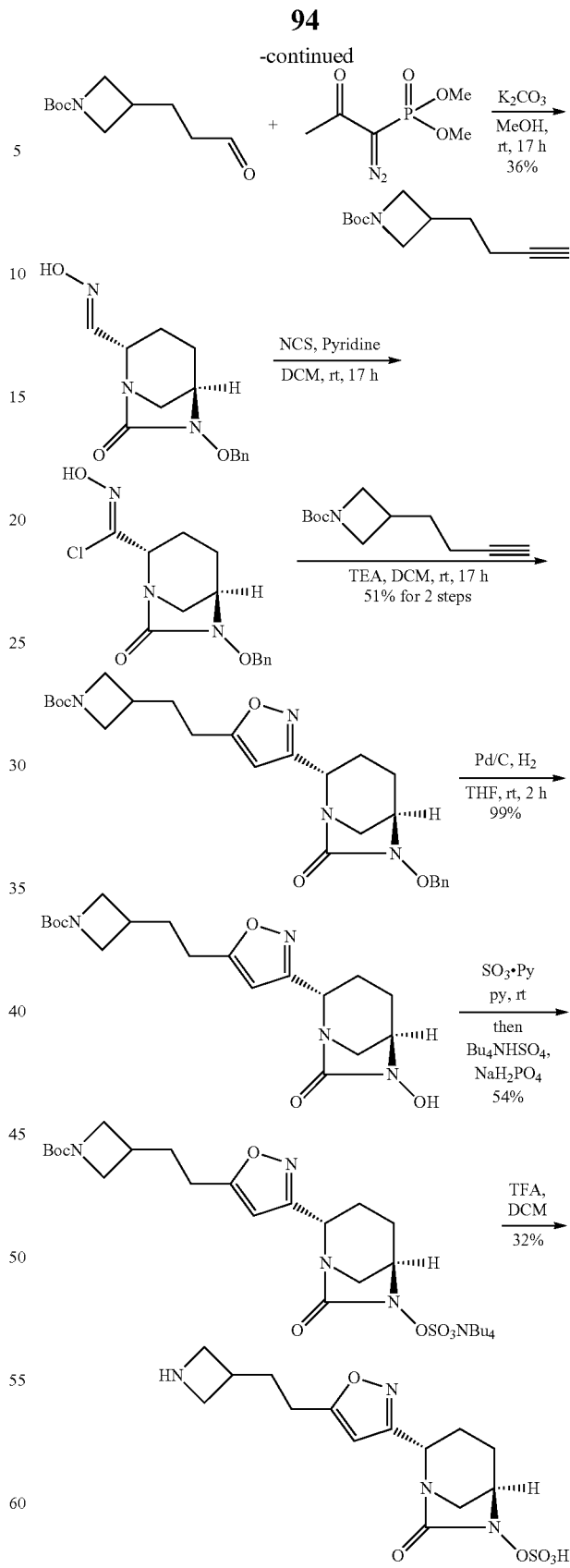

Characterization:

(2S,5R)-2-(5-(2-(azetidin-3-yl)ethyl)isoxazol-3-yl)-7-oxo-1,6-diazabicyclo[3.2.1]octan-6-yl hydrogen sulfate (629, 34 mg) was obtained as a white solid after prep-HPLC purification using ammonium formate buffer. ESI-MS (EI+, m/z): 373.0. $^1$H NMR (300 MHz, DMSO) δ 8.33 (br s, 2H), 6.33 (s, 1H), 4.45 (d, J=6.4 Hz, 1H), 4.01 (br s, 1H), 3.92 (t, J=9.0 Hz, 2H), 3.61 (t, J=9.0 Hz, 2H), 3.40-3.26 (m, 1H), 2.94-2.88 (m, 1H), 2.85-2.70 (m, 4H), 2.16-2.08 (m, 1H), 2.06-1.87 (m, 3H), 1.84-1.67 (m, 1H).

Example 33

Synthesis of (2S,5R)-7-oxo-2-(5-(pyrrolidin-3-ylmethyl)isoxazol-3-yl)-1,6-diazabicyclo[3.2.1]octan-6-yl hydrogen sulfate (Compound 630)

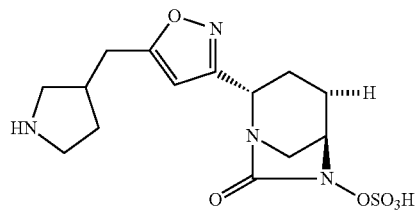

Synthetic Scheme:

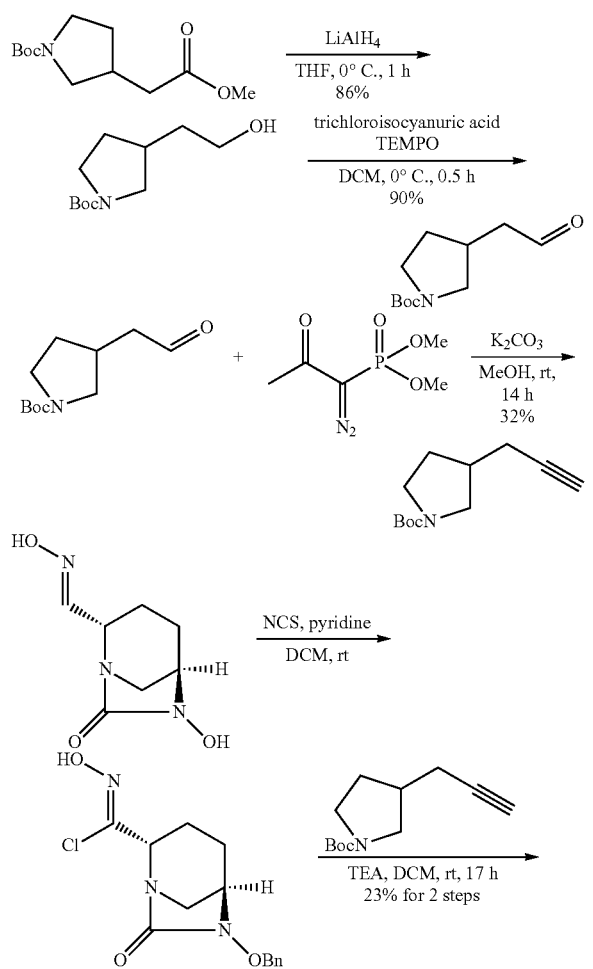

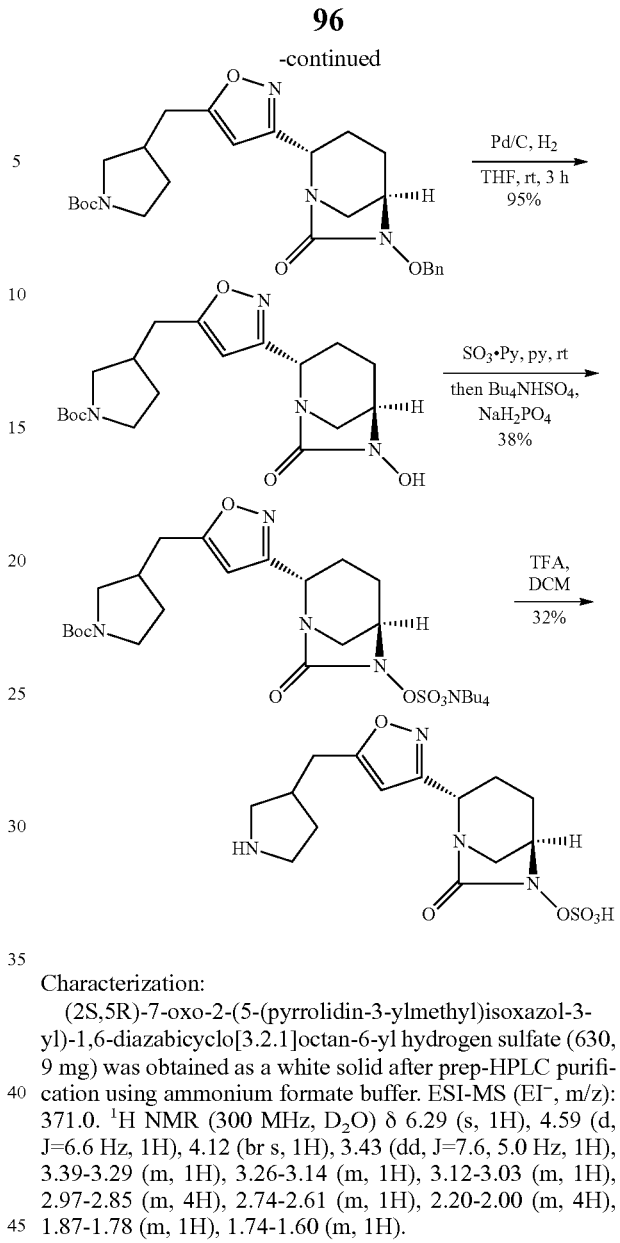

Characterization:

(2S,5R)-7-oxo-2-(5-(pyrrolidin-3-ylmethyl)isoxazol-3-yl)-1,6-diazabicyclo[3.2.1]octan-6-yl hydrogen sulfate (630, 9 mg) was obtained as a white solid after prep-HPLC purification using ammonium formate buffer. ESI-MS (EI−, m/z): 371.0. $^1$H NMR (300 MHz, D$_2$O) δ 6.29 (s, 1H), 4.59 (d, J=6.6 Hz, 1H), 4.12 (br s, 1H), 3.43 (dd, J=7.6, 5.0 Hz, 1H), 3.39-3.29 (m, 1H), 3.26-3.14 (m, 1H), 3.12-3.03 (m, 1H), 2.97-2.85 (m, 4H), 2.74-2.61 (m, 1H), 2.20-2.00 (m, 4H), 1.87-1.78 (m, 1H), 1.74-1.60 (m, 1H).

Example 34

Construction of Isogenic β-Lactamase Strains

A set of β-lactamase expressing isogenic *E. coli* strains was constructed by cloning a β-lactamase gene into a customized derivative of pBR322 (GenBank Accession Number J01749) and transforming the engineered plasmids into *E. coli*. The NdeI restriction site within the plasmid backbone of pBR322 was removed to generate pBR322 ΔNdeI. The pBR322 ΔNdeI vector itself, minus the blaTEM-1 gene, was amplified using two primers: (1) pBR-Pbla 5'-cg catatgactcttccttttcaatattattg-3, SEQ ID 1, a primer with an engineered NdeI restriction site at the 3' end of the blaTEM-1 promoter and (2) pBR-vec-1 5'-gc ggatccctgtcagaccaagtttactc-3', SEQ ID 2, a primer with an engineered BamHI restriction site at the 3' end of the blaTEM-1 open reading frame. The chloramphenicol resistance gene, cat, was generated by PCR amplification from pKD3 (GenBank Accession Number AY048742) using primers with an engineered NdeI restriction site at the 5' end (Pbla-cat 5'-gc<u>catatg</u>atggagaaaaaaatcactgg-3', SEQ ID 3) and an engineered BamHI restriction site at the 3' end (Vec-1-cat 5'-cg<u>ggatcc</u>ctagagaataggaacttcgg-3', SEQ ID 4) of the resistance gene. The two PCR products, pBR322 ΔNdeI and cat were ligated together generating pBR-CBST (pBR322 ΔNdeI ΔTEM-1::cat Seq. ID 5) which retains both the pBR322 tetracycline resistance cassette, tetA, and the plasmid origin of replication but the blaTEM-1 gene was replaced by the cat gene.

Using this engineering strategy a number of plasmids producing β-lactamase genes from different classes (see below) were generated using synthetic genes with an engineered NdeI restriction site at the 5' end and BamHI restriction site at the 3' end of each gene (GenScript). Both the synthetic β-lactamase genes and cat gene were ligated into the NdeI/BamHI sites of the pBR322 ΔNdeI PCR product and transformed into electrocompetent E. coli ElectroMax DH10B (Invitrogen/Life Technologies). E. coli DH10B harboring the recombinant plasmids were selected on LB agar (supplemented with 25 µg/mL tetracycline) and single isolated colonies were then inoculated into 5 mL LB media (supplemented with 25 µg/mL tetracycline), and incubated at 37° C. with aeration (250 rpm) for 18 hrs. The cultures were frozen back at −80° C. in 20% glycerol. The DNA sequence of the cloned β-lactamase genes was confirmed. The β-lactamase gene expression in the recombinant E. coli strains was driven by the blaTEM-1 promoter in the pBR-CBST plasmid and was characterized by MIC profiling of the E. coli recombinant strains against comparator β-lactam/BLI combinations in broth microdilution assay.

| β-Lactamase Expressing Strain | Name & SEQ. ID of plasmids producing β-Lactamase | β-Lactamase Class | Species Origin of β-Lactamase Gene | GenBank Accession Number of β-Lactamase Gene Sequence |
|---|---|---|---|---|
| KPC-2 | pBR-CBST-KPC-2 SEQ ID 6 | A | K. pneumoniae | EU784136 |
| CTX-M-15 | pBR-CBST-CTX-M-15 SEQ ID 7 | A | K. pneumoniae | JF775516 |
| SHV-12 | pBR-CBST-SHV-12 SEQ ID 8 | A | K. pneumoniae | AY008838 |
| P99 AmpC | pBR-CBST-P99 AMPC SEQ ID 9 | C | E. cloacea | XO7274 |
| OXA-15 | pBR-CBST-OXA-15 SEQ ID 10 | D | P. aeruginosa | PAU63835 |
| KPC-4 | pBR-CBST-KPC-4 SEQ ID 11 | A | K. pneumoniae | EU447304 |
| DHA-1 | pBR-CBST-DHA-1 SEQ ID 12 | C | K. pneumoniae | AY585202 |
| ADC-33 | pBR-CBST-ADC-33 SEQ ID 13 | C | A. baumannii | EU687478 |

Nucleotide Sequences of pBR-CBST Plasmids (Containing β-Lactamase or cat Genes)
Used in the E. coli Isogenic Strains (relevant restriction sites are underlined; β-lactamase sequences in all caps, tetA sequence is in italics)

```
pBR-CBST-cat
                                                                      SEQ ID 5
ttcttgaagacgaaagggcctcgtgatacgcctatttttataggttaatgtcatgataataatggtttcttagacgtcaggtggcacttt tcggggaaatgtgcgcggaacccctatttgtttattttctaaatacattcaaatatgtatccgctcatgagacaataaccctgataaat gcttcaataatattgaaaaaggaagagtcatATGGAGAAAAAAATCACTGGATATACCACCGTT

GATATATCCCAATGGCATCGTAAAGAACATTTTGAGGCATTTCAGTCAGTTGC

TCAATGTACCTATAACCAGACCGTTCAGCTGGATATTACGGCCTTTTTAAAGA

CCGTAAAGAAAAATAAGCACAAGTTTTATCCGGCCTTTATTCACATTCTTGCC

CGCCTGATGAATGCTCATACGGAATTTCGTATGGCAATGAAAGACGGTGAGC

TGGTGATATGGGATAGTGTTCACCCTTGTTACACCGTTTTCCATGAGCAAACT

GAAACGTTTTCATCGCTCTGGAGTGAATACCACGACGATTTCCGGCAGTTTCT

ACACATATATTCGCAAGATGTGGCGTGTTACGGTGAAAACCTGGCCTATTTCC

CTAAAGGGTTTATTGAGAATATGTTTTTCGTCTCAGCCAATCCCTGGGTGAGT

TTCACCAGTTTTGATTTAAACGTGGCCAATATGGACAACTTCTTCGCCCCCGT

TTTCACTATGGGCAAATATTATACGCAAGGCGACAAGGTGCTGATGCCGCTG

GCGATTCAGGTTCATCATGCCGTCTGTGATGGCTTCCATGTCGGCAGAATGCT

TAATGAATTACAACAGTACTGCGATGAGTGGCAGGGCGGGGCGTAAGTGGCA

GGGCGGGGCGTAAGGCGCGCCATTTAAATGAAGTTCCTATTCCGAAGTTCCT
```

-continued

ATTCTCTAGggatccctgtcagaccaagtttactcatatatactttagattgatttaaaacttcattttaatttaaaaggatcta ggtgaagatcctttttgataatctcatgaccaaaatcccttaacgtgagttttcgttccactgagcgtcagaccccgtagaaaagatc aaaggatcttcttgagatcctttttttctgcgcgtaatctgctgcttgcaaacaaaaaaaccaccgctaccagcggtggtttgtttgcc ggatcaagagctaccaactctttttccgaaggtaactggcttcagcagagcgcagataccaaatactgtccttctagtgtagccgt agttaggccaccacttcaagaactctgtagcaccgcctacatacctcgctctgctaatcctgttaccagtggctgctgccagtggc gataagtcgtgtcttaccgggttggactcaagacgatagttaccggataaggcgcagcggtcgggctgaacggggggttcgtg cacacagcccagcttggagcgaacgacctacaccgaactgagatacctacagcgtgagctatgagaaagcgccacgcttccc gaagggagaaaggcggacaggtatccggtaagcggcagggtcggaacaggagagcgcacgagggagcttccaggggga aacgcctggtatctttatagtcctgtcgggtttcgccacctctgacttgagcgtcgatttttgtgatgctcgtcaggggggcggagc ctatggaaaaacgccagcaacgcggcctttttacggttcctggccttttgctggccttttgctcacatgttctttcctgcgttatcccct gattctgtggataaccgtattaccgcctttgagtgagctgataccgctcgccgcagccaacgaccgagcgcagcgagtcagtg agcgaggaagcggaagagcgcctgatgcggtattttctccttacgcatctgtgcggtatttcacaccgcatttggtgcactctcagt acaatctgctctgatgccgcatagttaagccagtatacactccgctatcgctacgtgactgggtcatggctgcgccccgacaccc gccaacacccgctgacgcgccctgacgggcttgtctgctcccggcatccgcttacagacaagctgtgaccgtctccgggagct gcatgtgtcagaggttttcaccgtcatcaccgaaacgcgcgaggcagctgcggtaaagctcatcagcgtggtcgtgaagcgatt cacagatgtctgcctgttcatccgcgtccagctcgttgagtttctccagaagcgttaatgtctggcttctgataaagcgggccatgtt aagggcggttttttcctgtttggtcactgatgcctccgtgtaaggggatttctgttcatgggggtaatgataccgatgaaacgaga gaggatgctcacgatacgggttactgatgatgaacatgcccggttactggaacgttgtgagggtaaacaactggcggtatggat gcggcgggaccagagaaaaatcactcagggtcaatgccagcgcttcgttaatacagatgtaggtgttccacagggtagccagc agcatcctgcgatgcagatccggaacataatggtgcagggcgctgacttccgcgtttccagactttacgaaacacggaaaccga agaccattcatgttgttgctcaggtcgcagacgttttgcagcagcagtcgcttcacgttcgctcgcgtatcggtgattcattctgcta accagtaaggcaaccccgccagcctagccgggtcctcaacgacaggagcacgatcatgcgcacccgtggccaggacccaac gctgcccgagatgcgccgcgtgcggctgctggagatggcggacgcgatggatatgttctgccaagggttggtttgcgcattcac agttctccgcaagaattgattggctccaattcttggagtggtgaatccgttagcgaggtgccgccggcttccattcaggtcgaggt

*ggcccggctccatgcaccgcgacgcaacgcggggaggcagacaaggtataggcggcgcctacaatccatgccaccc*

*gttccatgtgctcgccgaggcggcataaatcgccgtgacgatcagcggtccagtgatcgaagttaggctggtaagagccgc*

*gagcgatccttgaagctgtccctgatggtcgtcatctacctgcctggacagcatggcctgcaacgcgggcatcccgatgccg*

*ccggaagcgagaagaatcataatggggaaggccatccagcctcgcgtcgcgaacgccagcaagacgtagcccagcgc*

*gtcggccgccatgccggcgataatggcctgcttctcgccgaaacgtttggtggcgggaccagtgacgaaggcttgagcgag*

*ggcgtgcaagattccgaataccgcaagcgacaggccgatcatcgtcgcgctccagcgaaagcggtcctcgccgaaaatg*

*acccagagcgctgccggcacctgtcctacgagttgcatgataaagaagacagtcataagtgcggcgacgatagtcatgcc*

*ccgcgcccaccggaaggagctgactgggttgaaggctctcaagggcatcggtcgacgctctcccttatgcgactcctgcatt*

*aggaagcagcccagtagtaggttgaggccgttgagcaccgccgccgcaaggaatggtgcatgcaaggagatggcgccc*

*aacagtccccggccacggggcctgccaccataccacgccgaaacaagcgctcatgagcccgaagtggcgagcccga*

*tcttccccatcggtgatgtcggcgatataggcgccagcaaccgcacctgtggcgccggtgatgccggccacgatgcgtccg*

*gcgtagaggattcacaggacgggtgtggtcgccatgatcgcgtagtcgatagtggctccaagtagcgaagcgagcaggac*

*tgggcggcggccaaagcggtcggacagtgctccgagaacgggtgcgcatagaaattgcatcaacgcatatagcgctagc*

*agcacgccatagtgactggcgatgctgtcggaatggacgatatcccgcaagaggcccggcagtaccggcataaccaagc*

*ctatgcctacagcatccagggtgacggtgccgaggatgacgatgagcgcattgttagatttcatacacggtgcctgactgcgt*

*tagcaatttaactgtgataaactaccgcattaaagcttatcgatgataagagtcaaacatgagaa* pBR-CBST-KPC-2

SEQ ID 6 ttcttgaagacgaaagggcctcgtgatacgcctattttataggttaatgtcatgataataatggtttcttagacgtcaggtggcacttt tcggggaaatgtgcgcggaaccccctatttgtttattttctaaatacattcaaatatgtatccgctcatgagacaataaccctgataaat gcttcaataatattgaaaaaggaagagt<u>catATG</u>TCACTGTATCGCCGTCTAGTTCTGCTGTCTTG

TCTCTCATGGCCGCTGGCTGGCTTTTCTGCCACCGCGCTGACCAACCTCGTCG

CGGAACCATTCGCTAAACTCGAACAGGACTTTGGCGGCTCCATCGGTGTGTA

CGCGATGGATACCGGCTCAGGCGCAACTGTAAGTTACCGCGCTGAGGAGCGC

TTCCCACTGTGCAGCTCATTCAAGGGCTTTCTTGCTGCCGCTGTGCTGGCTCG

CAGCCAGCAGCAGGCCGGCTTGCTGGACACACCCATCCGTTACGGCAAAAAT

GCGCTGGTTCCGTGGTCACCCATCTCGGAAAAATATCTGACAACAGGCATGA

CGGTGGCGGAGCTGTCCGCGGCCGCCGTGCAATACAGTGATAACGCCGCCGC

CAATTTGTTGCTGAAGGAGTTGGGCGGCCCGGCCGGGCTGACGGCCTTCATG

CGCTCTATCGGCGATACCACGTTCCGTCTGGACCGCTGGGAGCTGGAGCTGA

ACTCCGCCATCCCAGGCGATGCGCGCGATACCTCATCGCCGCGCGCCGTGAC

GGAAAGCTTACAAAAACTGACACTGGGCTCTGCACTGGCTGCGCCGCAGCGG

CAGCAGTTTGTTGATTGGCTAAAGGGAAACACGACCGGCAACCACCGCATCC

GCGCGGCGGTGCCGGCAGACTGGGCAGTCGGAGACAAAACCGGAACCTGCG

GAGTGTATGGCACGGCAAATGACTATGCCGTCGTCTGGCCCACTGGGCGCGC

ACCTATTGTGTTGGCCGTCTACACCCGGGCGCCTAACAAGGATGACAAGCAC

AGCGAGGCCGTCATCGCCGCTGCGGCTAGACTCGCGCTCGAGGGATTGGGCG

TCAACGGGCAGTAA<u>ggatcc</u>ctgtcagaccaagtttactcatatatactttagattgatttaaaacttcattttaatttaa aaggatctaggtgaagatcctttttgataatctcatgaccaaaatcccttaacgtgagttttcgttccactgagcgtcagaccccgta gaaaagatcaaaggatcttcttgagatccttttttttctgcgcgtaatctgctgcttgcaaacaaaaaaaccaccgctaccagcggtg gtttgtttgccggatcaagagctaccaactctttttccgaaggtaactggatcagcagagcgcagataccaaatactgtccttctag tgtagccgtagttaggccaccacttcaagaactagtagcaccgcctacatacctcgctagctaatcctgttaccagtggctgctg ccagtggcgataagtcgtgtcttaccgggttggactcaagacgatagttaccggataaggcgcagcggtcgggctgaacgggg ggttcgtgcacacagcccagcttggagcgaacgacctacaccgaactgagatacctacagcgtgagctatgagaaagcgcca cgcttcccgaagggagaaaggcggacaggtatccggtaagcggcagggtcggaacaggagagcgcacgagggagcttcca gggggaaacgcctggtatattatagtcctgtcgggtttcgccacctctgacttgagcgtcgatttttgtgatgctcgtcaggggg cggagcctatggaaaaacgccagcaacgcggcctttatacggttcctggccttttgctggccttttgctcacatgttattcctgcgtt atccctgattctgtggataaccgtattaccgcctttgagtgagctgataccgctcgccgcagccgaacgaccgagcgcagcga gtcagtgagcgaggaagcggaagagcgcctgatgcggtattttctccttacgcatctgtgcggtatttcacaccgcatttggtgca ctctcagtacaatctgactgatgccgcatagttaagccagtatacactccgctatcgctacgtgactgggtcatggctgcgcccc gacacccgccaacacccgctgacgcgccctgacgggcttgtagctcccggcatccgcttacagacaagagtgaccgtacc gggagagcatgtgtcagaggttttcaccgtcatcaccgaaacgcgcgaggcagagcggtaaagctcatcagcgtggtcgtg aagcgattcacagatgtagcctgttcatccgcgtccagctcgttgagtttaccagaagcgttaatgtaggcttctgataaagcgg gccatgttaagggcggttttttcctgtttggtcactgatgcctccgtgtaagggggatttctgttcatgggggtaatgataccgatga aacgagagaggatgctcacgatacgggttactgatgatgaacatgcccggttactggaacgttgtgagggtaaacaactggcg gtatggatgcggcgggaccagagaaaaatcactcagggtcaatgccagcgcttcgttaatacagatgtaggtgttccacagggt agccagcagcatcctgcgatgcagatccggaacataatggtgcagggcgctgacttccgcgtttccagactttacgaaacacgg -continued aaaccgaagaccattcatgttgttgctcaggtcgcagacgtatgcagcagcagtcgcttcacgttcgctcgcgtatcggtgattca ttctgctaaccagtaaggcaacccgccagcctagccgggtcctcaacgacaggagcacgatcatgcgcacccgtggccagg acccaacgctgcccgagatgcgccgcgtgcggctgctggagatggcggacgcgatggatatgttctgccaagggttggtttgc gcattcacagttaccgcaagaattgattggctccaattcttggagtggtgaatccgttagcgaggtgccgccggcttccat*tcag*

*gtcgaggtggcccggctccatgcaccgcgacgcaacgcggggaggcagacaaggtatagggcggcgcctacaatccat*

*gccaacccgttccatgtgctcgccgaggcggcataaatcgccgtgacgatcagcggtccagtgatcgaagttaggctggta*

*agagccgcgagcgatccttgaagctgtccctgatggtcgtcatctacctgcctggacagcatggcctgcaacgcgggcatcc*

*cgatgccgccggaagcgagaagaatcataatggggaaggccatccagcctcgcgtcgcgaacgccagcaagacgtagc*

*ccagcgcgtcggccgccatgccggcgataatggcctgcttctcgccgaaacgtttggtggcgggaccagtgacgaaggctt*

*gagcgagggcgtgcaagattccgaataccgcaagcgacaggccgatcatcgtcgcgctccagcgaaagcggtcctcgcc*

*gaaaatgacccagagcgctgccggcacctgtcctacgagttgcatgataaagaagacagtcataagtgcggcgacgata*

*gtcatgccccgcgccaccggaaggagctgactgggttgaaggctctcaagggcatcggtcgacgctctcccttatgcgact*

*cctgcattaggaagcagcccagtagtaggttgaggccgttgagcaccgccgccaaggaatggtgcatgcaaggagat*

*ggcgcccaacagtcccccggccacggggcctgccaccatacccacgccgaaacaagcgctcatgagcccgaagtggcg*

*agcccgatcttccccatcggtgatgtcggcgatataggcgccagcaaccgcacctgtggcgccggtgatgccggccacgat*

*gcgtccggcgtagaggattcacaggacgggtgtggtcgccatgatcgcgtagtcgatagtggctccaagtagcgaagcga*

*gcaggactgggcggcggccaaagcggtcggacagtgctccgagaacgggtgcgcatagaaattgcatcaacgcatatag*

*cgctagcagcacgccatagtgactggcgatgctgtcggaatggacgatatcccgcaagaggcccggcagtaccggcata*

*accaagcctatgcctacagcatccaggggtgacggtgccgaggatgacgatgagcgcattgttagatttcatacacggtgcct* gactgcgttagcaatttaactgtgataaactaccgcattaaagcttatcgatgataagagtcaaacatgagaa pBR-CBST-CTX-M-15

SEQ ID 7 ttcttgaagacgaaagggcctcgtgatacgcctatttttataggttaatgtcatgataataatggtttcttagacgtcaggtggcactttt tcggggaaatgtgcgcggaaccccctatttgatattttttctaaatacattcaaatatgtatccgctcatgagacaataaccctgataaat gcttcaataatattgaaaaggaagagt<u>catATG</u>GAATCTGTTAAATCAGCGAGTTGAGATCAA

AAAATCTGACCTTGTTAACTATAATCCGATTGCGGAAAAGCACGTCAATGGG

ACGATGTCACTGGCTGAGCTTAGCGCGGCCGCGCTACAGTACAGCGATAACG

TGGCGATGAATAAGCTGATTGCTCACGTTGGCGGCCCGGCTAGCGTCACCGC

GTTCGCCCGACAGCTGGGAGACGAAACGTTCCGTCTCGACCGTACCGAGCCG

ACGTTAAACACCGCCATTCCGGGCGATCCGCGTGATACCACTTCACCTCGGG

CAATGGCGCAAACTCTGCGGAATCTGACGCTGGGTAAAGCATTGGGCGACAG

CCAACGGGCGCAGCTGGTGACATGGATGAAAGGCAATACCACCGGTGCAGC

GAGCATTCAGGCTGGACTGCCTGCTTCCTGGGTTGTGGGGGATAAAACCGGC

AGCGGTGGCTATGGCACCACCAACGATATCGCGGTGATCTGGCCAAAAGATC

GTGCGCCGCTGATTCTGGTCACTTACTTCACCCAGCCTCAACCTAAGGCAGAA

AGCCGTCGCGATGTATTAGCGTCGGCGGCTAAAATCGTCACCGACGGTTTGT

AA<u>ggatcc</u>ctgtcagaccaagtttactcatatatactttagattgatttaaaacttcattataatttaaaaggatctaggtgaagatcc tttttgataatctcatgaccaaaatcccttaacgtgagttttcgttccactgagcgtcagaccccgtagaaaagatcaaaggatatct tgagatcctttttttctgcgcgtaatctgctgcttgcaaacaaaaaaaccaccgctaccagcggtggtttgtttgccggatcaagag ctaccaactctttttccgaaggtaactggcttcagcagagcgcagataccaaatactgtccttctagtgtagccgtagttaggccac cacttcaagaactagtagcaccgcctacatacctcgctagctaatcctgttaccagtggctgctgccagtggcgataagtcgtgt cttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaa ggcggacaggtatccggtaagcggcagggtcggaacaggagagcgcacgagggagcttccagggggaaacgcctggtatc tttatagtcctgtcgggtttcgccacctctgacttgagcgtcgattttgtgatgctcgtcaggggggcggagcctatggaaaaacg ccagcaacgcggcctttttacggttcctggccttttgctggccttttgctcacatgttctttcctgcgttatcccctgattctgtggataa ccgtattaccgcctttgagtgagctgataccgctcgccgcagccgaacgaccgagcgcagcgagtcagtgagcgaggaagcg gaagagcgcctgatgcggtattttctccttacgcatctgtgcggtatttcacaccgcatttggtgcactctcagtacaatctgctctga tgccgcatagttaagccagtatacactccgctatcgctacgtgactgggtcatggctgcgccccgacacccgccaacacccgct gacgcgccctgacgggcttgtctgctcccggcatccgcttacagacaagctgtgaccgtctccgggagctgcatgtgtcagagg ttttcaccgtcatcaccgaaacgcgcgaggcagctgcggtaaagctcatcagcgtggtcgtgaagcgattcacagatgtctgcct gttcatccgcgtccagctcgttgagtttctccagaagcgttaatgtctggcttctgataaagcgggccatgttaagggcggttttttc ctgtttggtcactgatgcctccgtgtaagggggatttctgttcatgggggtaatgataccgatgaaacgagagaggatgctcacga tacgggttactgatgatgaacatgcccggttactggaacgttgtgagggtaaacaactggcggtatggatgcggcgggaccaga gaaaaatcactcagggtcaatgccagcgcttcgttaatacagatgtaggtgttccacagggtagccagcagcatcctgcgatgca gatccggaacataatggtgcagggcgctgacttccgcgtttccagactttacgaaacacggaaaccgaagaccattcatgttgtt gctcaggtcgcagacgttttgcagcagcagtcgcttcacgttcgctcgcgtatcggtgattcattctgctaaccagtaaggcaacc ccgcagcctagccgggtcctcaacgacaggagcacgatcatgcgcacccgtggccaggacccaacgctgcccgagatgcg ccgcgtgcggctgctggagatggcggacgcgatggatatgttctgccaagggttggtttgcgcattcacagttctccgcaagaat tgattggctccaattcttggagtggtgaatccgttagcgaggtgccgccggcttccatt *tcaggtcgaggtggcccggctccatgc*

*accgcgacgcaacgcggggaggcagacaaggtatagggcggcgcctacaatccatgccaacccgttccatgtgctcgcc*

*gaggcggcataaatcgccgtgacgatcagcggtccagtgatcgaagttaggctggtaagagccgcgagcgatccttgaag*

*ctgtccctgatggtcgtcatctacctgcctggacagcatggcctgcaacgcgggcatcccgatgccgccggaagcgagaag*

*aatcataatggggaaggccatccagcctcgcgtcgcgaacgccagcaagacgtagcccagcgcgtcggccgccatgccg*

*gcgataatggcctgcttctcgccgaaacgtttggtggcgggaccagtgacgaaggcttgagcgagggcgtgcaagattccg*

*aataccgcaagcgacaggccgatcatcgtcgcgctccagcgaaagcggtcctcgccgaaaatgacccagagcgctgccg*

*gcacctgtcctacgagttgcatgataaagaagacagtcataagtgcggcgacgtagtcatgccccgcgcccaccggaag*

*gagctgactgggttgaaggctctcaagggcatcggtcgacgctctcccttatgcgactcctgcattaggaagcagcccagta*

*gtaggttgaggccgttgagcaccgccgccgcaaggaatggtgcatgcaaggagatggcgcccaacagtcccccggccac*

*ggggcctgccaccatacccacgccgaaacaagcgctcatgagcccgaagtggcgagcccgatcttccccatcggtgatgt*

*cggcgatataggcgccagcaaccgcacctgtggcgccggtgatgccggccacgatgcgtccggcgtagaggattcacag*

*gacgggtgtggtcgccatgatcgcgtagtcgatagtggctccaagtagcgaagcgagcaggactgggcggcggccaaag*

*cggtcggacagtgctccgaacgggtgcgcatagaaattgcatcaacgcatatagcgctagcagcacgccatagtgact*

*ggcgatgctgtcggaatggacgatatcccgcaagaggcccggcagtaccggcataaccaagcctatgcctacagcatcca*

*gggtgacggtgccgaggatgacgatgagcgcattgttagatttcatacacggtgcctgactgcgttagcaatttaactgtgataa* actaccgcattaaagcttatcgatgataagctgtcaaacatgagaa pBR-CBST-SHV-12

SEQ ID 8 ttcttgaagacgaaagggcctcgtgatacgcctatttttataggttaatgtcatgataataatggtttcttagacgtcaggtggcacttt tcggggaaatgtgcgcggaaccccctatttgtttatttttctaaatacattcaaatatgtatccgctcatgagacaataaccctgataaat gcttcaataatattgaaaaaggaagagt<u>catATG</u>CGTTATATTCGCCTGTGTATTATCTCCCTGTT

AGCCACCCTGCCGCTGGCGGTACACGCCAGCCCGCAGCCGCTTGAGCAAATT

AAACAAAGCGAAAGCCAGCTGTCGGGCCGCGTAGGCATGATAGAAATGGAT

-continued

CTGGCCAGCGGCCGCACGCTGACCGCCTGGCGCGCCGATGAACGCTTTCCCA

TGATGAGCACCTTTAAAGTAGTGCTCTGCGGCGCAGTGCTGGCGCGGGTGGA

TGCCGGTGACGAACAGCTGGAGCGAAAGATCCACTATCGCCAGCAGGATCTG

GTGGACTACTCGCCGGTCAGCGAAAAACACCTTGCCGACGGCATGACGGTCG

GCGAACTCTGCGCCGCCGCCATTACCATGAGCGATAACAGCGCCGCCAATCT

GCTGCTGGCCACCGTCGGCGGCCCCGCAGGATTGACTGCCTTTTTGCGCCAG

ATCGGCGACAACGTCACCCGCCTTGACCGCTGGGAAACGGAACTGAATGAGG

CGCTTCCCGGCGACGCCCGCGACACCACTACCCCGGCCAGCATGGCCGCGAC

CCTGCGCAAGCTGCTGACCAGCCAGCGTCTGAGCGCCCGTTCGCAACGGCAG

CTGCTGCAGTGGATGGTGGACGATCGGGTCGCCGGACCGTTGATCCGCTCCG

TGCTGCCGGCGGGCTGGTTTATCGCCGATAAGACCGGAGCTAGCAAGCGGGG

TGCGCGCGGGATTGTCGCCCTGCTTGGCCCGAATAACAAAGCAGAGCGCATT

GTGGTGATTTATCTGCGGGATACCCCGGCGAGCATGGCCGAGCGAAATCAGC

AAATCGCCGGGATCGGCGCGGCGCTGATCGAGCACTGGCAACGCTAAggatccct gtcagaccaagtttactcatatatactttagattgatttaaaacttcattataatttaaaaggatctaggtgaagatcattttgataatct catgaccaaaatcccttaacgtgagttttcgttccactgagcgtcagaccccgtagaaaagatcaaaggatatatgagatcctttt tttctgcgcgtaatctgctgcttgcaaacaaaaaaaccaccgctaccagcggtggtttgtttgccggatcaagagctaccaactctt tttccgaaggtaactggcttcagcagagcgcagataccaaatactgtccttctagtgtagccgtagttaggccaccacttcaagaa ctagtagcaccgcctacatacctcgctagctaatcctgttaccagtggctgctgccagtggcgataagtcgtgtcttaccgggtt ggactcaagacgatagttaccggataaggcgcagcggtcgggctgaacggggggttcgtgcacacagcccagcttggagcg aacgacctacaccgaactgagatacctacagcgtgagctatgagaaagcgccacgcttcccgaagggagaaaggcggacag gtatccggtaagcggcagggtcggaacaggagagcgcacgagggagcttccaggggaaacgcctggtatctttatagtcct gtcgggtttcgccacctctgacttgagcgtcgatttttgtgatgctcgtcaggggcggagcctatggaaaaacgccagcaacg cggcctttttacggttcctggc-
cttttgctggcttttgctcacatgttctttcctgcgttatccctgattctgtggataaccgtattacc gcctttgagtgagctgataccgctcgccgcagccgaacgaccgagcgcagcgagtcagtgagcgaggaagcggaagagcg cctgatgcggtattttctccttacgcatctgtgcggtatttcacaccgcatttggtgcactctcagtacaatctgactgatgccgcata gttaagccagtatacactccgctatcgctacgtgactgggtcatggctgcgccccgacacccgccaacacccgctgacgcgcc ctgacgggcttgtagctcccggcatccgcttacagacaagctgtgaccgtctccgggagctgcatgtgtcagaggttttcaccgt catcaccgaaacgcgcgaggcagctgcggtaaagctcatcagcgtggtcgtgaagcgattcacgatgtagcctgttcatccg cgtccagctcgttgagtttaccagaagcgttaatgtctggcttctgataaagcgggccatgttaagggcggttttttcctgtttggtc actgatgcctccgtgtaagggggatttctgttcatgggggtaatgataccgatgaaacgagagaggatgctcacgatacgggtta ctgatgatgaacatgcccggttactggaacgttgtgagggtaaacaactggcggtatggatgcggcgggaccagagaaaaatc actcagggtcaatgccagcgcttcgttaatacagatgtaggtgttccacagggtagccagcagcatcctgcgatgcagatccgg aacataatggtgcagggcgctgacttccgcgtttccagactttacgaaacacggaaaccgaagaccattcatgttgttgctcaggt cgcagacgttttgcagcagcagtcgcttcacgttcgctcgcgtatcggtgattcattctgctaaccagtaaggcaacccccgccag cctagccgggtcctcaacgacaggagcacgatcatgcgcacccgtggccaggacccaacgctgcccgagatgcgccgcgtg cggctgctggagatggcggacgcgatggatatgttctgccaagggttggtttgcgcattcacagttctccgcaagaattgattggc tccaattcttggagtggtgaatccgttagcgaggtgccgccggcttccatt*caggtcgaggtggcccggctccatgcaccgcga*

*cgcaacgcggggaggcagacaaggtatagggcggcgcctacaatccatgccaacccgttccatgtgctcgccgaggcgg*

*cataaatcgccgtgacgatcagcggtccagtgatcgaagttaggctggtaagagccgcgagcgatccttgaagctgtccct*

-continued gatggtcgtcatctacctgcctggacagcatggcctgcaacgcgggcatcccgatgccgccggaagcgagaagaatcata atggggaaggccatccagcctcgcgtcgcgaacgccagcaagacgtagcccagcgcgtcggccgccatgccggcgata atggcctgcttctcgccgaaacgtttggtggcgggaccagtgacgaaggcttgagcgagggcgtgcaagattccgaatacc gcaagcgacaggccgatcatcgtcgcgctccagcgaaagcggtcctcgccgaaaatgacccagagcgctgccggcacct gtcctacgagttgcatgataaagaagacagtcataagtgcggcgacgatagtcatgccccgcgcccaccggaaggagctg actgggttgaaggctctcaagggcatcggtcgacgctctcccttatgcgactcctgcattaggaagcagcccagtagtaggtt gaggccgttgagcaccgccgccgcaaggaatggtgcatgcaaggagatggcgcccaacagtcccccggccacggggcc tgccaccatacccacgccgaaacaagcgctcatgagcccgaagtggcgagcccgatcttccccatcggtgatgtcggcgat ataggcgccagcaaccgcacctgtggcgccggtgatgccggccacgatgcgtccggcgtagaggattcacaggacgggt gtggtcgccatgatcgcgtagtcgatagtggctccaagtagcgaagcgagcaggactgggcggcggccaaagcggtcgg acagtgctccgagaacgggtgcgcatagaaattgcatcaacgcatatagcgctagcagcacgccatagtgactggcgatg ctgtcggaatggacgatatcccgcaagaggcccggcagtaccggcataaccaagcctatgcctacagcatccagggtgac ggtgccgaggatgacgatgagcgcattgttagatttcatacacggtgcctgactgcgttagcaatttaactgtgataaactaccg cattaaagcttatcgatgataagctgtcaaacatgagaa pBR-CBST-P99
SEQ ID 9
ttcttgaagacgaaagggcctcgtgatacgcctatttttataggttaatgtcatgataataatggtttcttagacgtcaggtggcactt tcggggaaatgtgcgcggaaccccatttgtttattttctaaatacattcaaatatgtatccgctcatgagacaataaccctgataaat gcttcaataatattgaaaaaggaagagtcatATGATGAGAAAATCCCTTTGCTGCGCCCTGCTGC

TCGGCATCTCTTGCTCTGCTCTCGCCACGCCAGTGTCAGAAAAACAGCTGGCG

GAGGTGGTCGCGAATACGATTACCCCGCTGATGAAAGCCCAGTCTGTTCCAG

GCATGGCGGTGGCCGTTATTTATCAGGGAAAACCGCACTATTACACATTTGG

CAAGGCCGATATCGCGGCGAATAAACCCGTTACGCCTCAGACCCTGTTCGAG

CTGGGTTCTATAAGTAAAACCTTCACCGGCGTTTTAGGTGGGGATGCCATTGC

TCGCGGTGAAATTTCGCTGGACGATGCGGTGACCAGATACTGGCCACAGCTG

ACGGGCAAGCAGTGGCAGGGTATTCGTATGCTGGATCTCGCCACCTACACCG

CTGGCGGCCTGCCGCTACAGGTACCGGATGAGGTCACGGATAACGCCTCCCT

GCTGCGCTTTTATCAAAACTGGCAGCCGCAGTGGAAGCCTGGCACAACGCGT

CTTTACGCCAACGCCAGCATCGGTCTTTTTGGTGCGCTGGCGGTCAAACCTTC

TGGCATGCCCTATGAGCAGGCCATGACGACGCGGGTCCTTAAGCCGCTCAAG

CTGGACCATACCTGGATTAACGTGCCGAAAGCGGAAGAGGCGCATTACGCCT

GGGGCTATCGTGACGGTAAAGCGGTGCGCGTTTCGCCGGGTATGCTGGATGC

ACAAGCCTATGGCGTGAAAACCAACGTGCAGGATATGGCGAACTGGGTCATG

GCAAACATGGCGCCGGAGAACGTTGCTGATGCCTCACTTAAGCAGGGCATCG

CGCTGGCGCAGTCGCGCTACTGGCGTATCGGGTCAATGTATCAGGGTCTGGG

CTGGGAGATGCTCAACTGGCCCGTGGAGGCCAACACGGTGGTCGAGGGCAG

CGACAGTAAGGTAGCACTGGCGCCGTTGCCCGTGGCAGAAGTGAATCCACCG

GCTCCCCCGGTCAAAGCGTCCTGGGTCCATAAAACGGGCTCTACTGGCGGGT

TTGGCAGCTACGTGGCCTTTATTCCTGAAAAGCAGATCGGTATTGTGATGCTC

GCGAATACAAGCTATCCGAACCCGGCACGCGTTGAGGCGGCATACCATATCC

TCGAGGCGCTACAGTAAggatccctgtcagaccaagtttactcatatatactttagattgatttaaaacttcatttttaa tttaaaaggatctaggtgaagatcctttttgataatctcatgaccaaaatcccttaacgtgagttttcgttccactgagcgtcagaccc -continued

```
cgtagaaaagatcaaaggatcttcttgagatcctttttttctgcgcgtaatctgctgcttgcaaacaaaaaaaccaccgctaccagc
ggtggtttgtttgccggatcaagagctaccaactcttttttccgaaggtaactggcttcagcagagcgcagataccaaatactgtcct
tctagtgtagccgtagttaggccaccacttcaagaactctgtagcaccgcctacatacctcgctctgctaatcctgttaccagtggc
tgctgccagtggcgataagtcgtgtcttaccgggttggactcaagacgatagttaccggataaggcgcagcggtcgggctgaac
gggggttcgtgcacacagcccagcttggagcgaacgacctacaccgaactgagatacctacagcgtgagctatgagaaagc
gccacgcttcccgaagggagaaaggcggacaggtatccgtaagcggcagggtcggaacaggagagcgcacgagggagc
ttccaggggaaacgcctggtatctttatagtcctgtcgggtttcgccacctctgacttgagcgtcgattttttgtgatgctcgtcagg
ggggcggagcctatggaaaaacgccagcaacgcggcctttttacggttcctggccttttgctggcctttgctcacatgttctttcct
gcgttatcccctgattctgtggataaccgtattaccgcctttgagtgagctgataccgctcgccgcagccgaacgaccgagcgca
gcgagtcagtgagcgaggaagcggaagagcgcctgatgcggtattttctccttacgcatctgtgcggtatttcacaccgcatttg
gtgcactctcagtacaatctgctctgatgccgcatagttaagccagtatacactccgctatcgctacgtgactgggtcatggctgcg
ccccgacacccgccaacacccgctgacgcgccctgacgggcttgtctgctcccggcatccgcttacagacaagctgtgaccgt
ctccgggagctcatgtgtcagaggttttcaccgtcatcaccgaaacgcgcgaggcagctgcggtaaagctcatcagcgtggtc
gtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggattctgttcatgggggtaatgataccga
tgaaacgagagaggatgctcacgatacgggttactgatgatgaacatgcccggttactggaacgttgtgagggtaaacaactgg
cggtatggatgcggcgggaccagagaaaaatcactcagggtcaatgccagcgcttcgttaatacagatgtaggtgttccacagg
gtagccagcagcatcctgcgatgcagatccggaacataatggtgcagggcgctgacttccgcgtttccagactttacgaaacac
ggaaaccgaagaccattcatgttgttgctcaggtcgcagacgtatgcagcagcagtcgcttcacgttcgctcgcgtatcggtgatt
cattctgctaaccagtaaggcaaccccgccagcctagccgggtcctcaacgacaggagcacgatcatgcgcacccgtggcca
ggacccaacgctgcccgagatgcgccgcgtgcggctgctggagatggcggacgcgatggatatgttctgccaagggttggttt
gcgcattcacagttaccgcaagaattgattggctccaattcttggagtggtgaatccgttagcgaggtgccgccggcttccattca
ggtcgaggtggcccggctccatgcaccgcgacgcaacgcggggaggcagacaagtatagggcggcgcctacaatcca
tgccaacccgttccatgtgctcgccgaggcggcataaatcgccgtgacgatcagcggtccagtgatcgaagttaggctggta
agagccgcgagcgatccttgaagctgtccctgatggtcgtcatctacctgcctggacagcatggcctgcaacgcgggcatcc
cgatgccgccggaagcgagaagaatcataatgggaaggccatccagcctcgcgtcgcgaacgccagcaagacgtagc
ccagcgcgtcggccgccatgccggcgataatggcctgcttctcgccgaaacgtttggtggcgggaccagtgacgaaggctt
gagcgagggcgtgcaagattccgaataccgcaagcgacaggccgatcatcgtcgcgctccagcgaaagcggtcctcgcc
gaaaatgacccagagcgctgccggcacctgtcctacgagttgcatgataaagaagacagtcataagtgcggcgacgata
gtcatgccccgcgccaccggaaggagctgactgggttgaaggctctcaagggcatcggtcgacgctctcccttatgcgact
cctgcattaggaagcagcccagtagtaggttgaggccgttgagcaccgccgccaaggaatggtgcatgcaaggagat
ggcgcccaacagtcccccggccacggggcctgccaccatacccacgccgaaacaagcgctcatgagcccgaagtggcg
agcccgatcttcccccatcggtgatgtcggcgatataggcgccagcaaccgcacctgtggcgccggtgatgccggccacgat
gcgtccggcgtagaggattcacaggacgggtgtggtcgccatgatcgcgtagtcgatagtggctccaagtagcgaagcga
gcaggactgggcggcggccaaagcggtcggacagtgctccgagaacgggtgcgcatagaaattgcatcaacgcatatag
cgctagcagcacgccatagtgactggcgatgctgtcggaatggacgatatcccgcaagaggcccggcagtaccggcata
accaagcctatgcctacagcatccagggtgacggtgccgaggatgacgatgagcgcattgttagatttcatacacggtgcct
gactgcgttagcaatttaactgtgataaactaccgcattaaagcttatcgatgataagagtcaaacatgagaa
``` pBR-CBST-OXA-15

SEQ ID 10 ttcttgaagacgaaagggcctcgtgatacgcctattttttataggttaatgtcatgataataatggtttcttagacgtcaggtggcactttt
cggggaaatgtgcgcggaaccccctatttgatattttttctaaatacattcaaatatgtatccgctcatgagacaataaccctgataaat
gcttcaataatattgaaaaaggaagagt<ins>catAT</ins>GGCAATCCGAATCTTCGCGATACTTTTCTCCA
TTTTTTCTCTTGCCACTTTCGCGCATGCGCAAGAAGGCACGCTAGAACGTTCT
GACTGGAGGAAGTTTTTCAGCGAATTTCAAGCCAAAGGCACGATAGTTGTGG
CAGACGAACGCCAAGCGGATCGTGCCATGTTGGTTTTTGATCCTGTGCGATCG
AAGAAACGCTACTCGCCTGCATCGACATTCAAGATACCTCATACACTTTTTGC
ACTTGATGCAGGCGCTGTTCGTGATGAGTTCCAGATTTTTCGATGGGACGGCG
TTAACAGGGGCTTTGCAGGCCACAATCAAGACCAAGATTTGCGATCAGCAAT
GCGGAATTCTACTGTTTGGGTGTATGAGCTATTTGCAAAGGAAATTGGTGATG
ACAAAGCTCGGCGCTATTTGAAGAAAATCGACTATGGCAACGCCGGTCCTTC
GACAAGTAATGGCGATTACTGGATAGAAGGCAGCCTTGCAATCTCGGCGCAG
GAGCAAATTGCATTTCTCAGGAAGCTCTATCGTAACGAGCTGCCCTTTCGGGT
AGAACATCAGCGCTTGGTCAAGGATCTCATGATTGTGGAAGCCGGTCGCAAC
TGGATACTGCGTGCAAAGACGGGCTGGGAAGGCCGTATGGGTTGGTGGGTAG
GATGGGTTGAGTGGCCGACTGGCTCCGTATTCTTCGCACTGAATATTGATACG
CCAAACAGAATGGATGATCTTTTCAAGAGGGAGGCAATCGTGCGGGCAATCC
TTCGCTCTATTGAAGCGTTACCGCCCAACCCGGCAGTCAACTCGGACGCTGC
GCGATAA<ins>ggatccc</ins>tgtcagaccaagtttactcatatatactttagattgatttaaaacttcattataatttaaaaggatctaggt
gaagatcctttttgataatctcatgaccaaaatcccttaacgtgagttttcgttccactgagcgtcagaccccgtagaaaagatcaaa
ggatcttcttgagatcctttttttctgcgcgtaatctgctgcttgcaaacaaaaaaaccaccgctaccagcggtggtttgtttgccgga
tcaagagctaccaactctttttccgaaggtaactggcttcagcagagcgcagataccaaatactgtccttctagtgtagccgtagtt
aggccaccacttcaagaactctgtagcaccgcctacatacctcgctctgctaatcctgttaccagtggctgctgccagtggcgata
agtcgtgtcttaccgggttggactcaagacgatagttaccggataaggcgcagcggtcgggctgaacggggggttcgtgcaca
cagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccaggggggaaacg
cctggtatctttatagtcctgtcgggtttcgccacctctgacttgagcgtcgatttttgtgatgctcgtcaggggggcggagcctatg
gaaaaacgccagcaacgcggcctttttacggttcctggccttttgctggccttttgctcacatgttctttcctgcgttatcccctgattc
tgtggataaccgtattaccgcctttgagtgagctgataccgctcgccgcagccgaacgaccgagcgcagcgagtcagtgagcg
aggaagcggaagagcgcctgatgcggtattttctccttacgcatctgtgcggtatttcacaccgcatttggtgcactctcagtacaa
tctgctctgatgccgcatagttaagccagtatacactccgctatcgctacgtgactgggtcatggctgcgccccgacacccgcca
acacccgctgacgcgccctgacgggcttgtctgctcccggcatccgcttacagacaagctgtgaccgtctccgggagctgcatg
tgtcagaggttttcaccgtcatcaccgaaacgcgcgaggcagctgcggtaaagctcatcagcgtggtcgtgaagcgattcacag
atgtctgcctgttcatccgcgtccagctcgttgagtttctccagaagcgttaatgtctggcttctgataaagcgggccatgttaaggg
cggttttttcctgtttggtcactgatgcctccgtgtaaggggggatttctgttcatgggggtaatgataccgatgaaacgagagaggat
gctcacgatacgggttactgatgatgaacatgcccggttactggaacgttgtgagggtaaacaactggcggtatggatgcggcg
ggaccagagaaaaatcactcagggtcaatgccagcgcttcgttaatacagatgtaggtgttccacagggtagccagcagcatcc
tgcgatgcagatccggaacataatggtgcagggcgctgacttccgcgtttccagactttacgaaacacggaaaccgaagaccat
tcatgttgttgctcaggtcgcagacgttttgcagcagcagtcgcttcacgttcgctcgcgtatcggtgattcattctgctaaccagta -continued

```
aggcaaccccgccagcctagccgggtcctcaacgacaggagcacgatcatgcgcacccgtggccaggacccaacgctgcc cgagatgcgccgcgtgcggctgctggagatggcggacgcgatggatatgttctgccaagggttggtttgcgcattcacagttctc cgcaagaattgattggctccaattcttggagtggtgaatccgttagcgaggtgccgccggcttccattcaggtcgaggtggcccg gctccatgcaccgcgacgcaacgcggggaggcagacaaggtatagggcggcgcctacaatccatgccaacccgttccat gtgctcgccgaggcggcataaatcgccgtgacgatcagcggtccagtgatcgaagttaggctggtaagagccgcgagcga tccttgaagctgtccctgatggtcgtcatctacctgcctggacagcatggcctgcaacgcgggcatcccgatgccgccggaa gcgagaagaatcataatggggaaggccatccagcctcgcgtcgcgaacgccagcaagacgtagcccagcgcgtcggcc gccatgccggcgataatggcctgcttctcgccgaaacgtttggtggcgggaccagtgacgaaggcttgagcgagggcgtgc aagattccgaataccgcaagcgacaggccgatcatcgtcgcgctccagcgaaagcggtcctcgccgaaaatgacccaga gcgctgccggcacctgtcctacgagttgcatgataaagaagacagtcataagtgcggcgacgatagtcatgccccgcgccc accggaaggagctgactgggttgaaggctctcaagggcatcggtcgacgctctcccttatgcgactcctgcattaggaagca gcccagtagtaggttgaggccgttgagcaccgccgccgcaaggaatggtgcatgcaaggagatggcgcccaacagtccc ccggccacggggcctgccaccatacccacgccgaaacaagcgctcatgagcccgaagtggcgagcccgatcttccccat cggtgatgtcggcgatataggcgccagcaaccgcacctgtggcgccggtgatgccggccacgatgcgtccggcgtagagg attcacaggacgggtgtggtcgccatgatcgcgtagtcgatagtggctccaagtagcgaagcgagcaggactgggcggcg gccaaagcggtcggacagtgctccgagaacgggtgcgcatagaaattgcatcaacgcatatagcgctagcagcacgcca tagtgactggcgatgctgtcggaatggacgatatcccgcaagaggcccggcagtaccggcataaccaagcctatgccta agcatccagggtgacggtgccgaggatgacgatgagcgcattgttagatttcatacacggtgcctgactgcgttagcaattta actgtgataaactaccgcattaaagcttatcgatgataagctgtcaaacatgagaa
``` pBR-CBST-KPC-4

SEQ ID 11

```
ttcttgaagacgaaagggcctcgtgatacgcctatttttataggttaatgtcatgataataatggtttcttagacgtcaggtggcacttt tcggggaaatgtgcgcggaacccctatttgtttatttttctaaatacattcaaatatgtatccgctcatgagacaataaccctgataaat gcttcaataatattgaaaaaggaagagtcatATGTCACTGTATCGCCGTCTAGTTCTGCTGTCTTG

TCTCTCATGGCCGCTGGCTGGCTTTTCTGCCACCGCGCTGACCAACCTCGTCG

CGGAACCATTCGCTAAACTCGAACAGGACTTTGGCGGCTCCATCGGTGTGTA

CGCGATGGATACCGGCTCAGGCGCAACTGTAAGTTACCGCGCTGAGGAGCGC

TTCCCACTGTGCAGCTCATTCAAGGGCTTTCTTGCTGCCGCTGTGCTGGCTCG

CAGCCAGCAGCAGGCCGGCTTGCTGGACACACCCATCCGTTACGGCAAAAAT

GCGCTGGTTCGGTGGTCACCCATCTCGGAAAAATATCTGACAACAGGCATGA

CGGTGGCGGAGCTGTCCGCGGCCGCCGTGCAATACAGTGATAACGCCGCCGC

CAATTTGTTGCTGAAGGAGTTGGGCGGCCCGGCCGGGCTGACGGCCTTCATG

CGCTCTATCGGCGATACCACGTTCCGTCTGGACCGCTGGGAGCTGGAGCTGA

ACTCCGCCATCCCAGGCGATGCGCGCGATACCTCATCGCCGCGCGCCGTGAC

GGAAAGCTTACAAAAACTGACACTGGGCTCTGCACTGGCTGCGCCGCAGCGG

CAGCAGTTTGTTGATTGGCTAAAGGGAAACACGACCGGCAACCACCGCATCC

GCGCGGCGGTGCCGGCAGACTGGGCAGTCGGAGACAAAACCGGAACCTGCG

GAGGGTATGGCACGGCAAATGACTATGCCGTCGTCTGGCCCACTGGGCGCGC

ACCTATTGTGTTGGCCGTCTACACCCGGGCGCCTAACAAGGATGACAAGCAC

AGCGAGGCCGTCATCGCCGCTGCGGCTAGACTCGCGCTCGAGGGATTGGGCG

TCAACGGGCAGTAAggatccctgtcagaccaagtttactcatatatactttagattgatttaaaacttcatttttaatttaa aaggatctaggtgaagatcctttttgataatctcatgaccaaaatcccttaacgtgagttttcgttccactgagcgtcagaccccgta
```

-continued gaaaagatcaaaggatcttcttgagatcctttttttctgcgcgtaatctgctgcttgcaaacaaaaaaaccaccgctaccagcggtg gtttgtttgccggatcaagagctaccaactctttttccgaaggtaactggcttcagcagagcgcagataccaaatactgtccttctag tgtagccgtagttaggccaccacttcaagaactctgtagcaccgcctacatacctcgctctgctaatcctgttaccagtggctgctg ccagtggcgataagtcgtgtcttaccgggttggactcaagacgatagttaccggataaggcgcagcggtcgggctgaacgggg ggttcgtgcacacagcccagcttggagcgaacgacctacaccgaactgagatacctacagcgtgagctatgagaaagcgcca cgcttcccgaagggagaaaggcggacaggtatccggtaagcggcagggtcggaacaggagagcgcacgagggagcttcca gggggaaacgcctggtatctttatagtcctgtcgggtttcgccacctctgacttgagcgtcgattttgtgatgctcgtcagggggg cggagcctatggaaaaacgccagcaacgcggccttttacggttcctggccttttgctggccttttgctcacatgttctttcctgcgtt atccctgattctgtggataaccgtattaccgcctttgagtgagctgataccgctcgccgcagccgaacgaccgagcgcagcga gtcagtgagcgaggaagcggaagagcgcctgatgcggtattttctccttacgcatctgtgcggtatttcacaccgcatttggtgca ctctcagtacaatctgctctgatgccgcatagttaagccagtatacactccgctatcgctacgtgactgggtcatggctgcgcccc gacacccgccaacacccgctgacgcgccctgacgggcttgtctgctcccggcatccgcttacagacaagctgtgaccgtctcc gggagctgcatgtgtcagaggttttcaccgtcatcaccgaaacgcgcgaggcagctgcggtaaagctcatcagcgtggtcgtg aagcgattcacagatgtctgcctgttcatccgcgtccagctcgttgagtttctccagaagcgttaatgtctggcttctgataaagcgg gccatgttaagggcggttttttcctgtttggtcactgatgcctccgtgtaaggggattttctgttcatgggggtaatgataccgatga aacgagagaggatgctcacgatacgggttactgatgatgaacatgcccggttactggaacgttgtgagggtaaacaactggcg gtatggatgcggcgggaccagagaaaaatcactcagggtcaatgccagcgcttcgttaatacagatgtaggtgttccacagggt agccagcagcatcctgcgatgcagatccggaacataatggtgcagggcgctgacttccgcgtttccagactttacgaaacacgg aaaccgaagaccattcatgttgttgctcaggtcgcagacgttttgcagcagcagtcgcttcacgttcgctcgcgtatcggtgattca ttctgctaaccagtaaggcaacccgccagcctagccgggtcctcaacgacaggagcacgatcatgcgcacccgtggccagg acccaacgctgcccgagatgcgccgcgtgcggctgctggagatggcggacgcgatggatatgttctgccaagggttggtttgc gcattcacagttctccgcaagaattgattggctccaattcttggagtggtgaatccgttagcgaggtgccgccggcttccatt*tcag*

*gtcgaggtggcccggctccatgcaccgcgacgcaacgcggggaggcagacaaggtatagggcggcgcctacaatccat*

*gccaacccgttccatgtgctcgccgaggcggcataaatcgccgtgacgatcagcggtccagtgatcgaagttaggctggta*

*agagccgcgagcgatccttgaagctgtccctgatggtcgtcatctacctgcctggacagcatggcctgcaacgcgggcatcc*

*cgatgccgccggaagcgagaagaatcataatggggaaggccatccagcctcgcgtcgcgaacgccagcaagacgtagc*

*ccagcgcgtcggccgccatgccggcgataatggcctgcttctcgccgaaacgtttggtggcgggaccagtgacgaaggctt*

*gagcgagggcgtgcaagattccgaataccgcaagcgacaggccgatcatcgtcgcgctccagcgaaagcggtcctcgcc*

*gaaaatgacccagagcgctgccggcacctgtcctacgagttgcatgataaagaagacagtcataagtgcggcgacgata*

*gtcatgccccgcgccaccggaaggagctgactgggttgaaggctctcaagggcatcggtcgacgctctcccttatgcgact*

*cctgcattaggaagcagcccagtagtaggttgaggccgttgagcaccgccgccaaggaatggtgcatgcaaggagat*

*ggcgcccaacagtcccccggccacggggcctgccaccatacccacgccgaaacaagcgctcatgagcccgaagtggcg*

*agcccgatcttcccatcggtgatgtcggcgatataggcgccagcaaccgcacctgtggcgccggtgatgccggccacgat*

*gcgtccggcgtagaggattcacaggacgggtgtggtcgccatgatcgcgtagtcgatagtggctccaagtagcgaagcga*

*gcaggactgggcggcggccaaagcggtcggacagtgctccgagaacgggtgcgcatagaaattgcatcaacgcatatag*

*cgctagcagcacgccatagtgactggcgatgctgtcggaatggacgatatcccgcaagaggcccggcagtaccggcata*

*accaagcctatgcctacagcatccagggtgacggtgccgaggatgacgatgagcgcattgttagatttcatacacggtgcct*

*gactgcgttagcaatttaactgtgataaactaccgcattaaagcttatcgatgataagctgtcaaacatgagaa* pBR-CBST-DHA-1

SEQ ID 12 ttcttgaagacgaaagggcctcgtgatacgcctattttataggttaatgtcatgataataatggtttcttagacgtcaggtggcactttt
tcggggaaatgtgcgcggaacccctatttgtttattttttctaaatacattcaaatatgtatccgctcatgagacaataaccctgataaat
gcttcaataatattgaaaaaggaagagt<u>catATG</u>AAAAAATCGTTATCTGCAACACTGATTTCCG
CTCTGCTGGCGTTTTCCGCCCCGGGGTTTTCTGCCGCTGATAATGTCGCGGCG
GTGGTGGACAGCACCATTAAACCGCTGATGGCACAGCAGGATATTCCCGGGA
TGGCGGTTGCCGTCTCCGTAAAGGGTAAGCCCTATTATTTCAATTATGGTTTT
GCCGATATTCAGGCAAAACAGCCGGTCACTGAAAATACACTATTTGAGCTCG
GATCTGTAAGTAAAACTTTCACAGGTGTGCTGGGTGCGGTTTCTGTGGCGAA
AAAAGAGATGGCGCTGAATGATCCGGCGGCAAAATACCAGCCGGAGCTGGC
TCTGCCGCAGTGGAAGGGGATCACATTGCTGGATCTGGCTACCTATACCGCA
GGCGGACTGCCGTTACAGGTGCCGGATGCGGTAAAAAGCCGTGCGGATCTGC
TGAATTTCTATCAGCAGTGGCAGCCGTCCCGGAAACCGGGCGATATGCGTCT
GTATGCAAACAGCAGTATCGGCCTGTTTGGTGCTCTGACCGCAAACGCGGCG
GGGATGCCGTATGAGCAGTTGCTGACTGCACGCATCCTGGCACCGCTGGGGT
TATCTCACACCTTTATTACTGTGCCGGAAAGTGCGCAAAGCCAGTATGCGTAC
GGTTATAAAACAAAAAACCGGTCCGCGTGTCGCCGGGACAGCTTGATGCGG
AATCTTACGGCGTGAAATCCGCCTCAAAAGATATGCTGCGCTGGGCGGAAAT
GAATATGGAGCCGTCACGGGCCGGTAATGCGGATCTGGAAATGGCAATGTAT
CTCGCCCAGACCCGCTACTATAAAACCGCCGCGATTAACCAGGGGCTGGGCT
GGGAAATGTATGACTGGCCGCAGCAGAAAGATATGATCATTAACGGTGTGAC
CAACGAGGTCGCATTGCAGCCGCATCCGGTAACAGACAACCAGGTTCAGCCG
TATAACCGTGCTTCCTGGGTGCATAAAACGGGCGCAACAACTGGTTTCGGCG
CCTATGTCGCCTTTATTCCGGAAAAACAGGTGGCGATTGTGATTCTGGCGAAT
AAAAACTACCCGAATACCGAAAGAGTCAAAGCTGCACAGGCTATTTTGAGTG
CACTGGAATAA<u>ggatcc</u>ctgtcagaccaagtttactcatatatactttagattgatttaaaacttcattttttaatttaaaagga
tctaggtgaagatcctttttgataatctcatgaccaaaatcccttaacgtgagttttcgttccactgagcgtcagacccgtagaaaa
gatcaaaggatcttcttgagatcctttttttctgcgcgtaatctgctgcttgcaaacaaaaaaaccaccgctaccagcggtggtttgtt
tgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagt
ggcgataagtcgtgtcttaccgggttggactcaagacgatagttaccggataagcgcagcggtcgggctgaacggggggttc
gtgcacacagcccagcttggagcgaacgacctacaccgaactgagatacctacagcgtgagctatgagaaagcgccacgctt
cccgaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggcgg
agcctatggaaaaacgccagcaacgcggcctttttacggttcctggccttttgctggccttttgctcacatgttctttcctgcgttatc
ccctgattctgtggataaccgtattaccgcctttgagtgagctgataccgctcgccgcagccgaacgaccgagcgcagcgagtc
agtgagcgaggaagcggaagagcgcctgatgcggtattttctccttacgcatctgtgcggtatttcacaccgcatttggtcactc
tcagtacaatctgctctgatgccgcatagttaagccagtatacactccgctatcgctacgtgactgggtcatggctgcgccccgac
acccgccaacacccgctgacgcgccctgacgggcttgtctgctcccggcatccgcttacagacaagctgtgaccgtctccggg
agctgcatgtgtcagaggttttcaccgtcatcaccgaaacgcgcgaggcagctgcggtaaagctcatcagcgtggtcgtgaagc -continued gattcacagatgtctgcctgttcatccgcgtccagctcgttgagtttctccagaagcgttaatgtctggcttctgataaagcgggcca
tgttaagggcggttttttcctgtttggtcactgatgcctccgtgtaaggggggatttctgttcatgggggtaatgataccgatgaaacg
agagaggatgctcacgatacgggttactgatgatgaacatgcccggttactggaacgttgtgagggtaaacaactggcggtatg
gatgcggcgggaccagagaaaaatcactcagggtcaatgccagcgcttcgttaatacagatgtaggtgttccacagggtagcc
agcagcatcctgcgatgcagatccggaacataatggtgcagggcgctgacttccgcgtttccagactttacgaaacacggaaac
cgaagaccattcatgttgttgctcaggtcgcagacgttttgcagcagcagtcgcttcacgttcgctcgcgtatcggtgattcattctg
ctaaccagtaaggcaaccccgccagcctagccgggtcctcaacgacaggagcacgatcatgcgcacccgtggccaggaccc
aacgctgcccgagatgcgccgcgtgcggctgctggagatggcggacgcgatggatatgttctgccaagggttggtttgcgcatt
cacagttctccgcaagaattgattggctccaattcttggagtggtgaatccgttagcgaggtgccgccggcttccat*tcaggtcga*
*ggtggcccggctccatgcaccgcgacgcaacgcggggaggcagacaaggtataggggcggcgcctacaatccatgccaa*
*cccgttccatgtgctcgccgaggcggcataaatcgccgtgacgatcagcggtccagtgatcgaagttaggctggtaagagc*
*cgcgagcgatccttgaagctgtccctgatggtcgtcatctacctgcctggacagcatggcctgcaacgcgggcatcccgatg*
*ccgccggaagcgagaagaatcataatggggaaggccatccagcctcgcgtcgcgaacgccagcaagacgtagcccag*
*cgcgtcggccgccatgccggcgataatggcctgcttctcgccgaaacgtttggtggcgggaccagtgacgaaggcttgagc*
*gagggcgtgcaagattccgaataccgcaagcgacaggccgatcatcgtcgcgctccagcgaaagcggtcctcgccgaaa*
*atgacccagagcgctgccggcacctgtcctacgagttgcatgataaagaagacagtcataagtgcggcgacgatagtcat*
*gccccgcgccaccggaaggagctgactgggttgaaggctctcaagggcatcggtcgacgctctcccttatgcgactcctg*
*cattaggaagcagcccagtagtaggttgaggccgttgagcaccgccgccgcaaggaatggtgcatgcaaggagatggcg*
*cccaacagtcccccggccacgggcctgccaccatacccacgccgaaacaagcgctcatgagcccgaagtggcgagcc*
*cgatcttccccatcggtgatgtcggcgatataggcgccagcaaccgcacctgtggcgccggtgatgccggccacgatgcgt*
*ccggcgtagaggattcacaggacgggtgtggtcgccatgatcgcgtagtcgatagtggctccaagtagcgaagcgagcag*
*gactgggcggcggccaaagcggtcggacagtgctccgagaacgggtgcgcatagaaattgcatcaacgcatatagcgct*
*agcagcacgccatagtgactggcgatgctgtcggaatggacgatatcccgcaagaggcccggcagtaccggcataacca*
*agcctatgcctacagcatccagggtgacggtgccgaggatgacgatgagcgcattgttagatttcatacacggtgcctgactg*
*cgttagcaatttaactgtgataaactaccgcattaaagcttatcgatgataagctgtcaaacatgagaa* pBR-CBST-ADC-33

SEQ ID 13 ttcttgaagacgaaagggcctcgtgatacgcctatttttataggttaatgtcatgataataatggtttcttagacgtcaggtggcactttt
tcggggaaatgtgcgcggaaccctatttgtttatttttctaaatacattcaaatatgtatccgctcatgagacaataaccctgataaat
gcttcaataatattgaaaaaggaagagt<u>catATG</u>CGATTTAAAAAAATTTCTTGTCTACTTTTATC
CCCGCTTTTTATTTTTAGTACCTCAATTTATGCGGGCAATACACCAAAAGACC
AAGAAATTAAAAAACTGGTAGATCAAAACTTTAAACCGTTATTAGAAAAATA
TGATGTGCCAGGTATGGCTGTGGGTGTTATTCAAAATAATAAAAAGTATGAA
ATGTATTATGGTCTTCAATCTGTTCAAGATAAAAAAGCCGTAAATAGCAGTA
CCATTTTTGAGCTAGGTTCTGTCAGTAAATTATTTACCGCGACAGCAGGTGGA
TATGCAAAAAATAAAGGAAAAATCTCTTTTGACGATACGCCTGGTAAATATT
GGAAAGAACTAAAAAACACACCGATTGACCAAGTTAACTTACTTCAACTCGC
GACGTATACAAGTGGTAACCTTGCCTTGCAGTTTCCAGATGAAGTAAAAACA
GACCAACAAGTTTTAACTTTTTTCAAAGACTGGAAACCTAAAAACTCAATCG
GTGAATACAGACAATATTCAAATCCAAGTATTGGCCTATTTGGAAAGGTTGT
GGCTTTGTCTATGAATAAACCTTTCGACCAAGTCTTAGAAAAAACAATTTTTC
CGGCCCTTGGCTTAAAACATAGCTATGTAAATGTACCTAAGACCCAGATGCA -continued

AAACTATGCATTTGGTTATAACCAAGAAAATCAGCCGATTCGAGTTAACCGC

GGCCCACTCGATGCCGCCCCTGCGTATGGCGTCAAATCGACACTACCCGACA

TGTTGAGTTTTATTCATGCCAACCTTAACCCACAGAAATATCCGGCTGATATT

CAACGGGCAATTAATGAAACACATCAAGGGCGCTATCAAGTAAATACCATGT

ATCAGGCACTCGGTTGGGAAGAGTTTTCTTATCCGGCAACGTTACAAACTTTA

TTAGACAGTAATTCAGAACAGATTGTGATGAAACCTAATAAAGTGACTGCTA

TTTCAAAGGAACCTTCAGTTAAGATGTACCATAAAACTGGCTCAACCAACGG

TTTCGGAACGTATGTAGTGTTTATTCCTAAAGAAAATATTGGCTTAGTCATGT

TAACCAATAAACGTATTCCAAATGAAGAGCGCATTAAGGCAGCTTATGCTGT

GCTGAATGCAATAAAGAAATAAggatccctgtcagaccaagtttactcatatatactttagattgatttaaaac ttcattttaatttaaaaggatctaggtgaagatcctttttgataatctcatgaccaaaatcccttaacgtgagttttcgttccactgagc gtcagaccccgtagaaaagatcaaaggatcttcttgagatcctttttttctgcgcgtaatctgctgcttgcaaacaaaaaaaccacc gctaccagcggtggtttgtttgccggatcaagagctaccaactctttttccgaaggtaactggcttcagcagagcgcagataccaa atactgtccttctagtgtagccgtagttaggccaccacttcaagaactctgtagcaccgcctacatacctcgctctgctaatcctgtt accagtggctgctgccagtggcgataagtcgtgtcttaccgggttggactcaagacgatagttaccggataaggcgcagcggtc gggctgaacggggggttcgtgcacacagcccagcttggagcgaacgacctacaccgaactgagatacctacagcgtgagcta tgagaaagcgccacgcttcccgaagggagaaaggcggacaggtatccggtaagcggcagggtcggaacaggagagcgca cgagggagcttccaggggaaacgcctggtatctttatagtcctgtcgggtttcgccacctctgacttgagcgtcgatttttgtgat gctcgtcaggggggcggagcctatggaaaaacgccagcaacgcggcctttttacggttcctggccttttgctggccttttgctcac atgttctttcctgcgttatcccctgattctgtggataaccgtattaccgcctttgagtgagctgataccgctcgccgcagccgaacga ccgagcgcagcgagtcagtgagcgaggaagcggaagagcgcctgatgcggtattttctccttacgcatctgtgcggtatttcac accgcatttggtgcactctcagtacaatctgctctgatgccgcatagttaagccagtatacactccgctatcgctacgtgactgggt catggctgcgccccgacacccgccaacacccgctgacgcgccctgacgggcttgtctgctcccggcatccgcttacagacaa gctgtgaccgtctccgggagctgcatgtgtcagaggttttcaccgtcatcaccgaaacgcgcgaggcagctgcggtaaagctca tcagcgtggtcgtgaagcgattcacagatgtctgcctgttcatccgcgtccagctcgttgagtttctccagaagcgttaatgtctgg cttctgataaagcgggccatgttaagggcggttttttcctgtttggtcactgatgcctccgtgtaagggggatttctgttcatgggggt aatgataccgatgaaacgagagaggatgctcacgatacgggttactgatgatgaacatgcccggttactggaacgttgtgaggg taaacaactggcggtatggatgcggcgggaccagagaaaaatcactcagggtcaatgccagcgcttcgttaatacagatgtag gtgttccacagggtagccagcagcatcctgcgatgcagatccggaacataatggtgcagggcgctgacttccgcgtttccagac tttacgaaacacggaaaccgaagaccattcatgttgttgctcaggtcgcagacgttttgcagcagcagtcgcttcacgttcgctcg cgtatcggtgattcattctgctaaccagtaaggcaacccccgccagcctagccgggtcctcaacgacaggagcacgatcatgcgc acccgtggccaggacccaacgctgcccgagatgcgccgcgtgcggctgctggagatggcggacgcgatggatatgttctgcc aagggttggtttgcgcattcacagttctccgcaagaattgattggctccaattcttggagtggtgaatccgttagcgaggtgccgcc ggcttccattcaggtcgaggtggcccggctccatgcaccgcgacgcaacgcggggaggcagacaaggtatagggcggcg cctacaatccatgccaacccgttccatgtgctcgccgaggcggcataaatcgccgtgacgatcagcggtccagtgatcgaa gttaggctggtaagagccgcgagcgatccttgaagctgtccctgatggtcgtcatctacctgcctggacagcatggcctgcaa cgcgggcatcccgatgccgccggaagcgagaagaatcataatggggaaggccatccagcctcgcgtcgcgaacgccag caagacgtagcccagcgcgtcggccgccatgccggcgataatggcctgcttctcgccgaaacgtttggtggcgggaccagt gacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtg -continued

```
cggcgacgatagtcatgccccgcgccaccggaaggagctgactgggttgaaggctctcaagggcatcggtcgacgctct cccttatgcgactcctgcattaggaagcagcccagtagtaggttgaggccgttgagcaccgccgccgcaaggaatggtgca tgcaaggagatggcgcccaacagtcccccggccacggggcctgccaccatacccacgccgaaacaagcgctcatgagc ccgaagtggcgagcccgatcttccccatcggtgatgtcggcgatataggcgccagcaaccgcacctgtggcgccggtgatg ccggccacgatgcgtccggcgtagaggattcacaggacgggtgtggtcgccatgatcgcgtagtcgatagtggctccaagt agcgaagcgagcaggactgggcggcggccaaagcggtcggacagtgctccgagaacgggtgcgcatagaaattgcatc aacgcatatagcgctagcagcacgccatagtgactggcgatgctgtcggaatggacgatatcccgcaagaggcccggca gtaccggcataaccaagcctatgcctacagcatccagggtgacggtgccgaggatgacgatgagcgcattgttagatttcat acacggtgcctgactgcgttagcaatttaactgtgataaactaccgcattaaagcttatcgatgataagctgtcaaacatgagaa
```

Example 35

Standard BLI Potentiation MIC Assay

The ability of compounds to potentiate the activity of β-lactams was demonstrated by determining the minimum inhibitory concentrations (MIC) of β-lactam and BLI compound combinations against various β-lactamase producing bacterial strains using the broth microdilution method. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition").

To prepare for MIC testing, frozen glycerol stocks of clinical isolates (*Klebsiella pneumoniae, Eschericia coli, Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 µg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with 25 µg/mL tetracycline) in 14 mL culture tubes. All strains were incubated at 37° C. with aeration (200 rpm) for ~2 hrs until the optical density at 600 nm ($OD_{600}$) was >0.1.

The two compound components of the assay were each diluted in CAMHB and added to the 96-well broth microdilution assay plates. 50 µL of the β-lactam was added to each well of the assay plate in 2-fold dilutions with final concentrations ranging from 128 to 0.13 µg/mL. 25 µL of the BLI compound was added to all wells in the broth microdilution plates at a final concentration of 4 µg/mL. Inoculum cultures were prepared by standardizing the primary cultures to OD600=0.1 and then adding 20 µL of the adjusted primary culture per 1 mL CAMHB for clinical strains or CAMHB (supplemented with tetracycline at 100 µg/mL) for engineered strains, so that the final inoculum density was ~$10^5$ colony forming units per milliliter. Diluted inoculum cultures were used to inoculate 25 µl, per well in 96-well broth microdilution assay plates. The final volume of each well was 100 µL and contained a β-lactam at different concentrations, a BLI compound at 4 µg/mL concentration, the bacterial culture at an OD600 of approximately 0.001 and when necessary tetracycline at 25 µg/mL.

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. MIC values were defined as the lowest concentration producing no visible turbidity.

MIC values of representative compounds are shown in Table II.

Example 36

Synergy MIC (sMIC) Assay

The synergy MIC (sMIC) assay determines the concentration of the BLI required to potentiate the activity of a fixed concentration of a β-lactam antibiotic against β-lactamase producing bacterial strains. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition"). The assay is set-up by serially diluting the BLI across 11 of the 12 wells in each row of a 96-well broth microdilution assay plate, adding the β-lactam at a fixed concentration to all wells in the assay plate, inoculating the assay plate with bacterial strains, and determining the lowest concentration of BLI required to inhibit overnight bacterial growth. Bacterial growth in the $12^{th}$ well of the assay plate, which contains the β-lactam at a fixed concentration but does not contain any BLI, demonstrates that the bacterial strains are resistant to the β-lactam antibiotic (e.g. ceftolozane) at the fixed concentration of 4 µg/mL.

To prepare for MIC testing, frozen glycerol stocks of clinical isolates (*Klebsiella pneumoniae, Eschericia coli, Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 μg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with tetracycline at 25 μg/mL) in 14 mL culture tubes. All strains were incubated at 37° C. with aeration (200 rpm) for ~2 hrs until the OD600 was >0.1.

The two compound components of the assay were each prepared in CAMHB and added to the 96-well broth microdilution assay plates. 50 μL of the BLI was added to each well of the assay plate in 2-fold dilutions with final concentrations ranging from 128 to 0.13 μg/mL. 25 μL of the β-lactam was added to all wells in the broth microdilution plates at a final concentration of 4 μg/mL. Inoculum cultures were prepared by standardizing the primary cultures to OD600=0.1 and then adding 20 μL of the adjusted primary culture per 1 mL CAMHB for clinical strains or CAMHB (supplemented with tetracycline at 100 μg/mL) for isogenic strains, so that the final inoculum density was ~$10^5$ colony forming units per milliliter. Diluted inoculum cultures were used to inoculate 25 μL per well in 96-well broth microdilution assay plates. The final volume of each well was 100 μL and contained a BLI at different concentrations, a β-lactam at 4 μg/mL concentration, the bacterial culture at an OD600 of approximately 0.001 and when necessary tetracycline at 25 ug/mL.

Interpreting the sMIC Data:

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. sMIC values were defined as the lowest concentration producing no visible turbidity.

The sMIC values represent the amount of BLI required to potentiate the activity of 4 μg/ml of CXA-101 (Ceftolozane) or ceftazidime to inhibit the growth of the β-lactamase producing bacteria.

sMIC values of representative compounds are shown in Table III.

Example 37

Inhibition Kinetics

Inhibition or inactivation of KPC-2 by test inhibitors was assessed using 100 μM nitrocefin (NCF) as a reporter substrate. Assays were performed in 1×PBS pH 7.4, 0.1 mg/ml BSA, in 96-well half area plates, 50 μl reaction volume. NCF was dissolved in DMSO and diluted in assay buffer. Test inhibitors were dissolved in water or DMSO and serially diluted in the assay with final concentrations between 2000-0.195 The enzyme activity in the presence of varying concentrations of test inhibitor was determined by monitoring the hydrolysis of NCF spectrophotometrically at 486 nm, for 5 minutes, 25° C., using a SpectraMax Plus384 microplate reader with SoftMax Pro software (Molecular Devices). Data analysis was performed using GraphPad Prism (GraphPad Software, Inc.).

Progress curves were fit to a first-order rate decay equation (Eq. 1) to determine $k_{observed}$ ($k_{obs}$).

$k_{obs}$ vs. inhibitor concentration [I] curves were then fit to Eq.2 to determine the inhibitor dissociation constant (K) and the first order rate constant of enzyme inactivation at infinite inhibitor concentration ($k_{inact}$). Table IV shows kinetics results from representative test compounds. A larger $k_{inact}$/K ratio indicates a more effective enzyme inactivator.

$$Y_t = V_0 * (1 - e^{(-k_{obs}*t)})/k_{obs} \qquad \text{Eq. 1}$$

Where Y is the absorbance at time t, $V_o$ is the uninhibited enzyme velocity, $k_{obs}$ is the observed rate constant of the enzyme inactivation.

$$k_{obs} = k_{inact} * [I]/([I] + K(1 + S/K_m)) \qquad \text{Eq. 2}$$

Where S is the NCF concentration, $K_m$ is the KPC-2 $K_m$ for NCF

We claim:

1. A compound of Formula (A-I) or a pharmaceutically acceptable salt thereof:

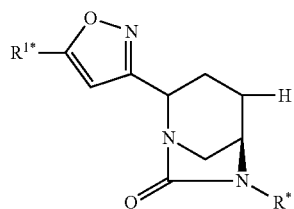

(A-I)

wherein
R* is selected from

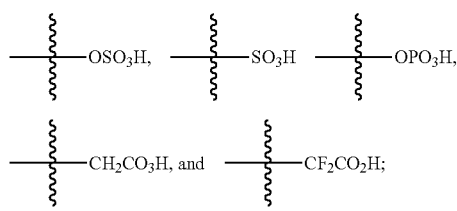

and
R¹* is selected from:

a.

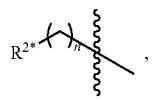

wherein R²* is selected from

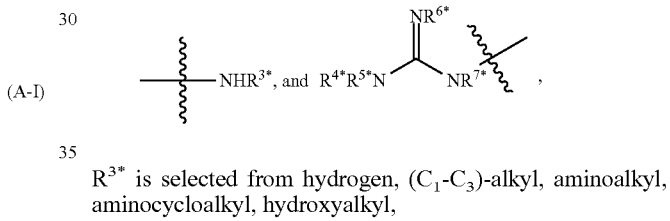

R³* is selected from hydrogen, $(C_1-C_3)$-alkyl, aminoalkyl, aminocycloalkyl, hydroxyalkyl,

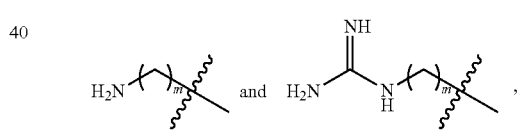

each of R⁴*, R⁵*, R⁶* and R⁷* is independently selected from hydrogen, $(C_1-C_6)$-alkyl, aminoalkyl, aminocycloalkyl, and hydroxyalkyl, provided that at least one of R⁴*, R⁵*, R⁶* and R⁷* is hydrogen,
n is selected from 1, 2, 3 and 4, and
m is selected from 1, 2 and 3;

b.

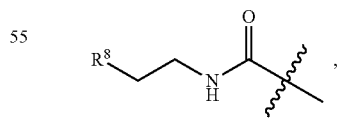

wherein R⁸ is selected from —NH$(C_1-C_3)$-alkyl and

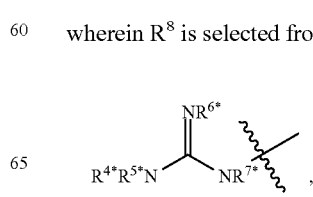

wherein each of $R^{4*}$, $R^{5*}$, $R^{6*}$ and $R^{7*}$ is as described previously;

c.

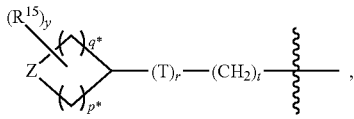

wherein Z is selected from $CR^9R^{10}$ and $NR^{11}$, each of $R^9$ and $R^{10}$ is independently selected from H, $NH_2$, —$NH(C_1$-$C_3)$-alkyl and

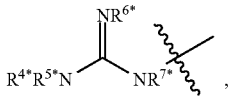

wherein each of $R^{4*}$, $R^{5*}$, $R^{6*}$ and $R^{7*}$ is as described previously, alternatively, $R^9$ and $R^{10}$ together with the carbon to which they are attached, form a cycloalkyl or heterocyclyl ring containing 4-6 ring members, $R^{11}$ is selected from H and

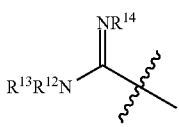

each of $R^{12}$, $R^{13}$ and $R^{14}$ is independently selected from hydrogen, $(C_1$-$C_6)$-alkyl, amino alkyl, aminocycloalkyl, and hydroxyalkyl, provided that at least one of $R^{12}$, $R^{13}$ and $R^{14}$ is hydrogen, $R^{15}$ is selected from $NH_2$ and

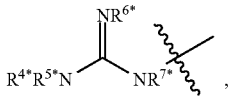

wherein each of $R^{4*}$, $R^{5*}$, $R^{6*}$ and $R^{7*}$ is as described previously, each of p* and q* is independently selected from 0, 1, 2 and 3, T is selected from NH and O, t is selected from 0, 1, 2, 3, and 4, and each of r and y is independently selected from 0 and 1;

d.

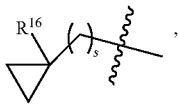

wherein $R^{16}$ is selected from $NH_2$, —$NH(C_1$-$C_3)$-alkyl and

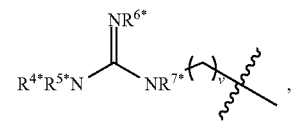

wherein each of $R^{4*}$, $R^{5*}$, $R^{6*}$ and $R^{7*}$ is as described previously, s is selected from 0 and 1, and, v is selected from 0, 1, 2, and 3;

e.

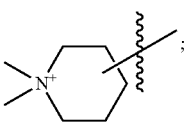

wherein $R^{18}$ is selected from $NH_2$ and

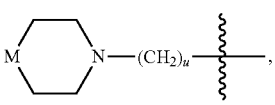

wherein each of $R^{4*}$, $R^{5*}$, $R^{6*}$ and $R^{7*}$ is as described previously, $R^{17}$ is selected from amino and hydroxyl, and w is selected from 0 and 1;

f.

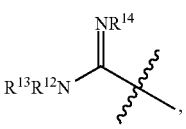

wherein M is selected from $NR^{19}$, $CR^{20}R^{21}$ and O, wherein $R^{19}$ is selected from H and

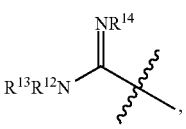

where each of $R^{12}$, $R^{13}$ and $R^{14}$ is as described previously, each of $R^{20}$ and $R^{21}$ is independently selected from H, $NH_2$ and

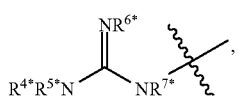

wherein each of R⁴*, R⁵*, R⁶* and R⁷* is as described previously, and u is selected from 0, 1 and 2; and g.

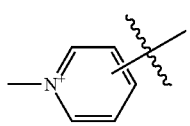

2. A pharmaceutical composition comprising a compound of claim 1 and at least 1 β-lactam antibiotic or a pharmaceutically acceptable salt thereof.

3. The pharmaceutical composition of claim 2 wherein the β-lactam antibiotic is a cephalosporin.

4. The pharmaceutical composition of claim 3 wherein the cephalosporin is Ceftolozane.

5. The compound of claim 1, wherein the compound of Formula A-I has the stereochemistry specified in Formula A-II

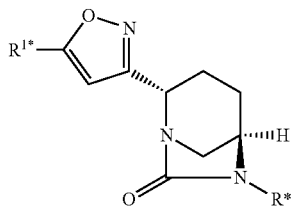

or a pharmaceutically acceptable salt thereof.

6. The compound of claim 5, or a pharmaceutically acceptable salt thereof selected from

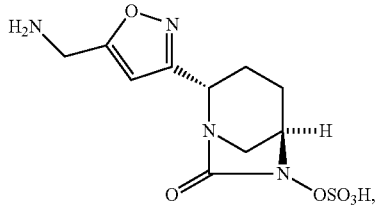

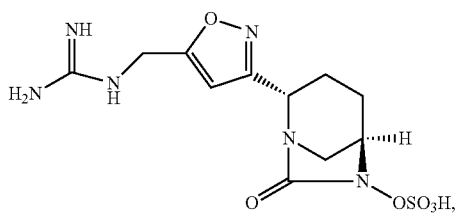

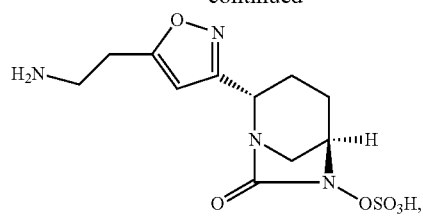

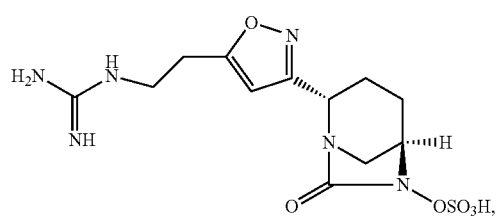

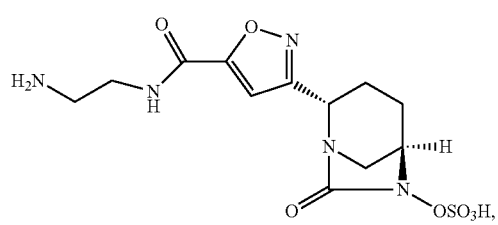

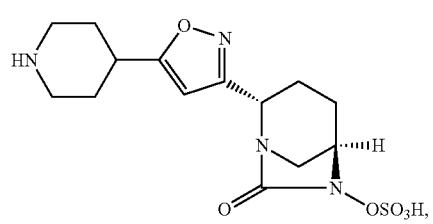

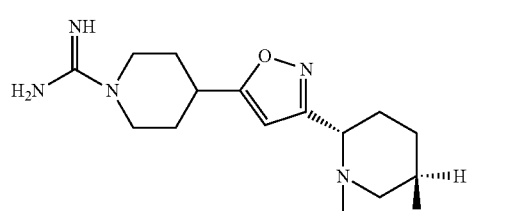

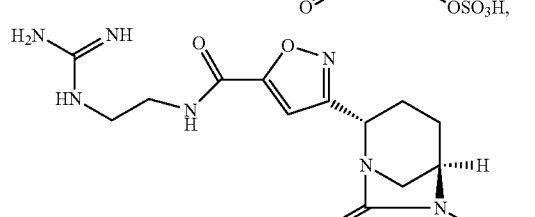

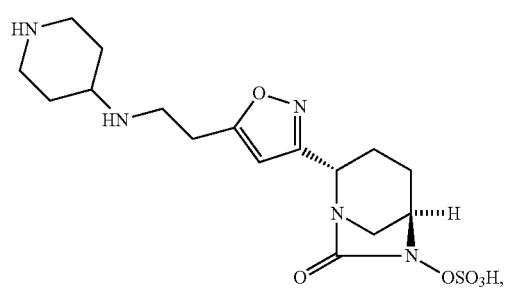

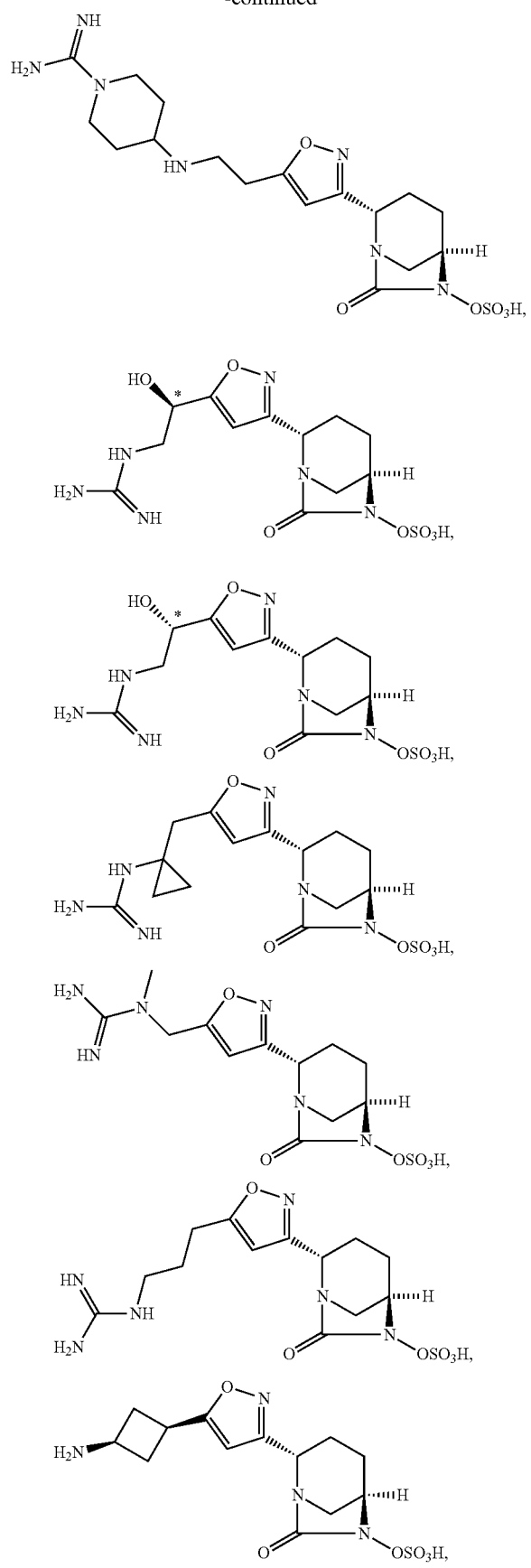
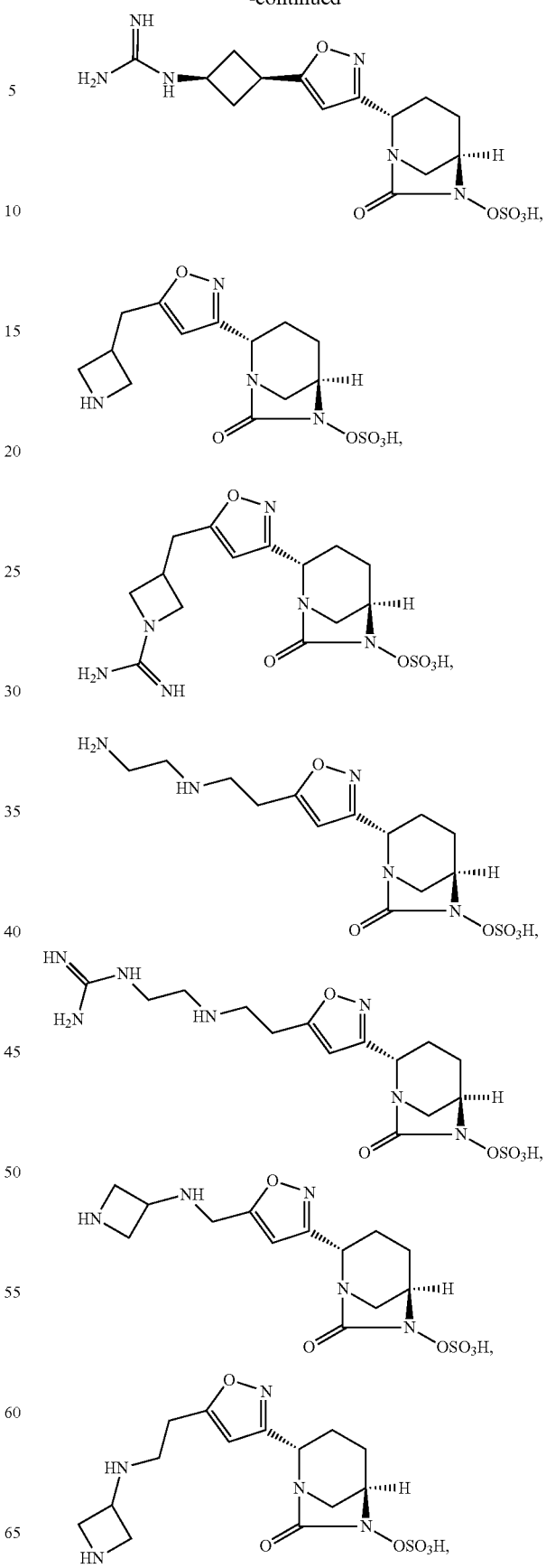

173
-continued
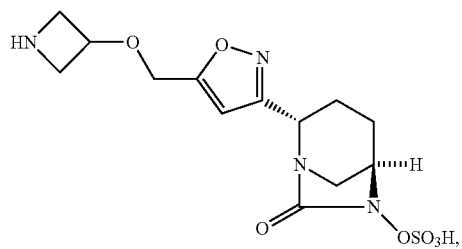
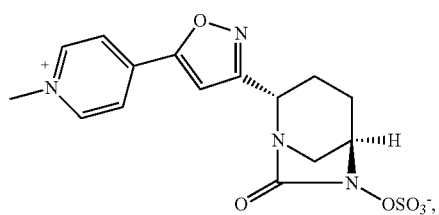
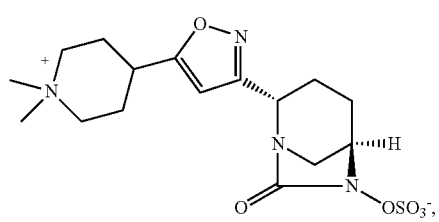
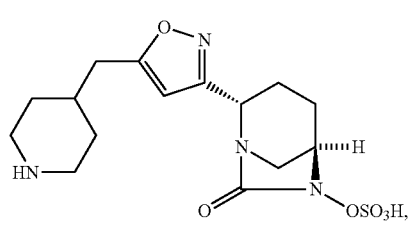
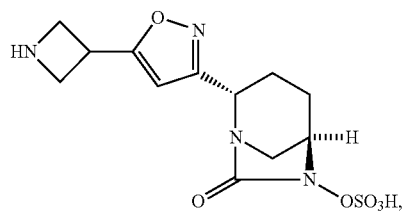
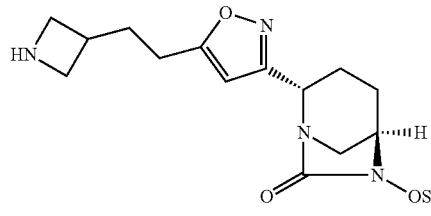
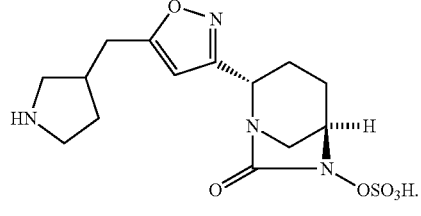
7. The compound according to claim 1 wherein R$^{1*}$ is selected from
174
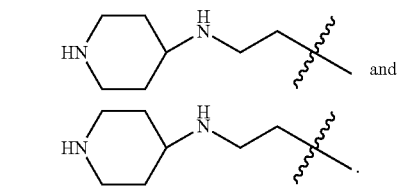
and
8. The compound according to claim 6 selected from
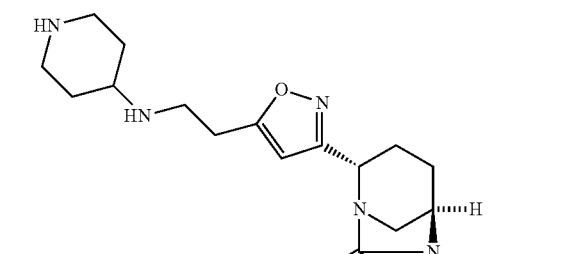
and
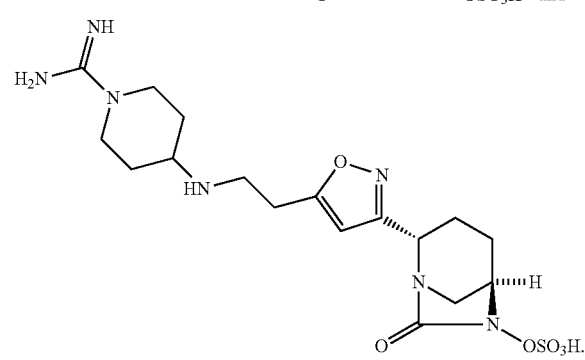
9. The compound according to claim 8 or a pharmaceutically-acceptable salt thereof of the Formula
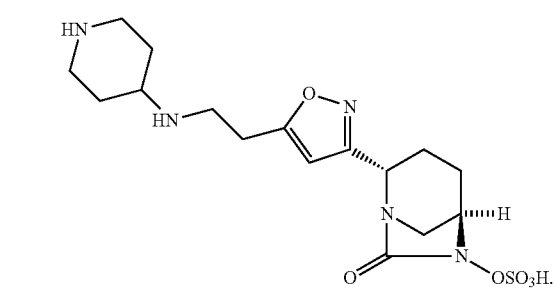
10. The compound according to claim 8 or a pharmaceutically-acceptable salt thereof of the Formula

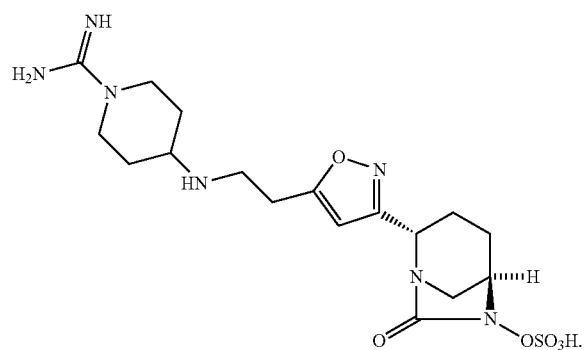

11. A pharmaceutical composition comprising a compound of claim 9 and Ceftolozane.

12. A pharmaceutical composition comprising a compound of claim 10 and Ceftolozane.

13. The compound according to claim 1 of the Formula

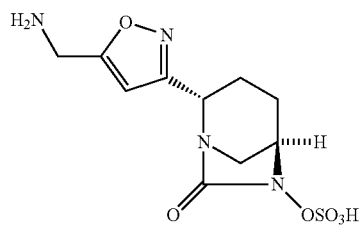

or a pharmaceutically-acceptable salt thereof.

14. The compound according to claim 1 of the Formula

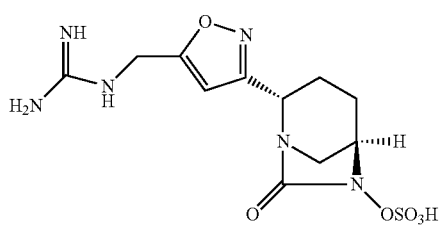

or a pharmaceutically-acceptable salt thereof.

15. The compound according to claim 1 of the Formula

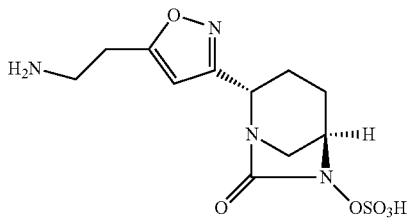

or a pharmaceutically-acceptable salt thereof.

16. The compound according to claim 1 of the Formula

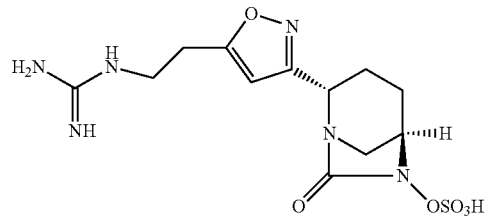

or a pharmaceutically-acceptable salt thereof.

17. The compound according to claim 1 of the Formula

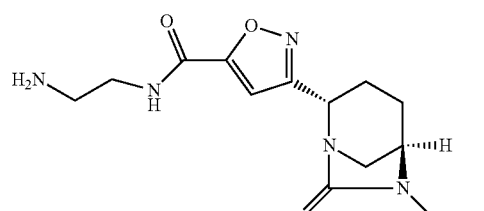

or a pharmaceutically-acceptable salt thereof.

18. The compound according to claim 1 of the Formula

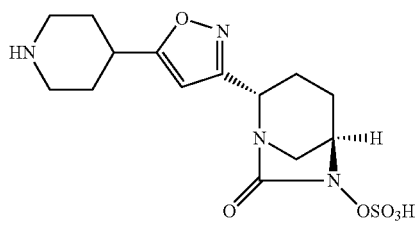

or a pharmaceutically-acceptable salt thereof.

19. The compound according to claim 1 of the Formula

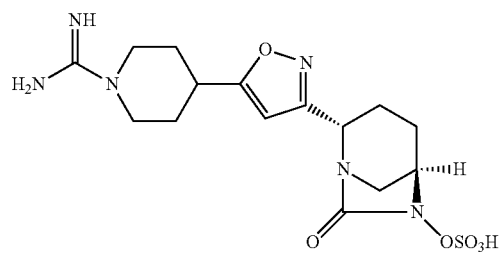

or a pharmaceutically-acceptable salt thereof.

20. The compound according to claim 1 or a pharmaceutically-acceptable salt thereof of the Formula

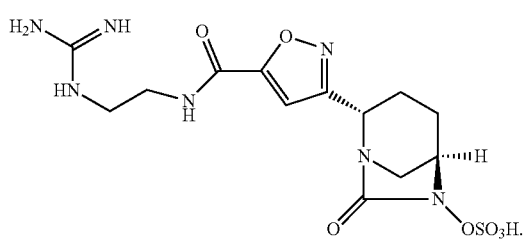

21. The compound according to claim 1 of the Formula

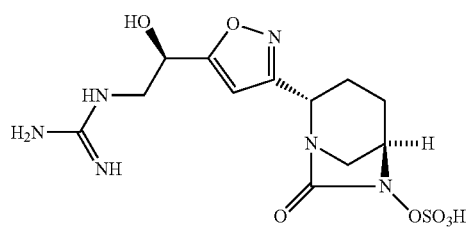

or a pharmaceutically-acceptable salt thereof.

22. The compound according to claim 1 of the Formula

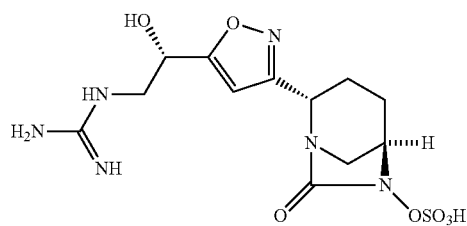

or a pharmaceutically-acceptable salt thereof.

23. The compound according to claim 1 of the Formula

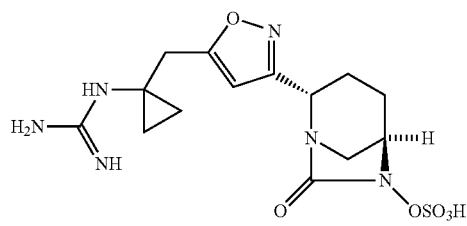

or a pharmaceutically-acceptable salt thereof.

24. The compound according to claim 1 of the Formula

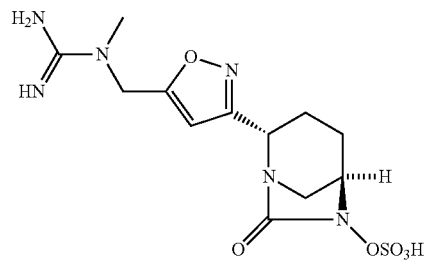

or a pharmaceutically-acceptable salt thereof.

25. The compound according to claim 1 of the Formula

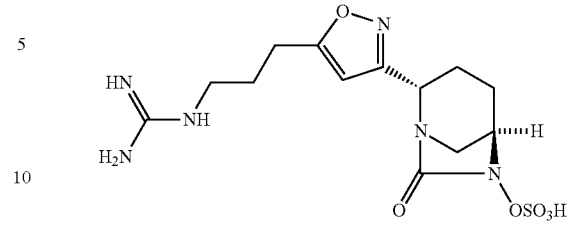

or a pharmaceutically-acceptable salt thereof.

26. The compound according to claim 1 of the Formula

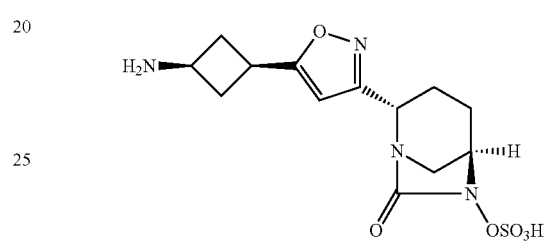

or a pharmaceutically-acceptable salt thereof.

27. The compound according to claim 1 of the Formula

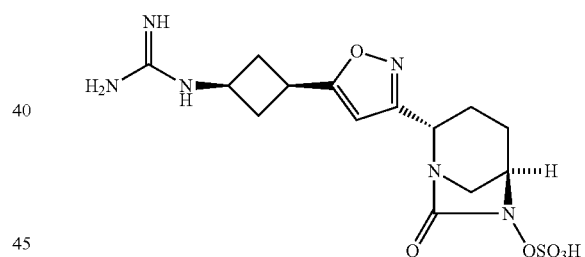

or a pharmaceutically-acceptable salt thereof.

28. The compound according to claim 1 of the Formula

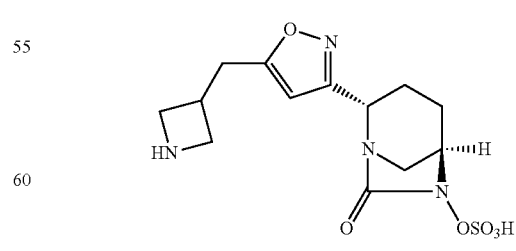

or a pharmaceutically-acceptable salt thereof.

29. The compound according to claim 1 of the Formula

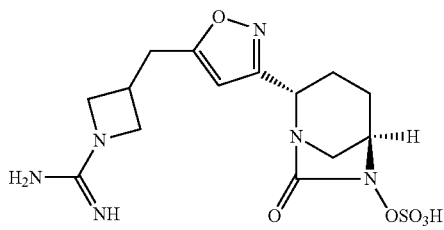

or a pharmaceutically-acceptable salt thereof.

30. The compound according to claim 1 of the Formula

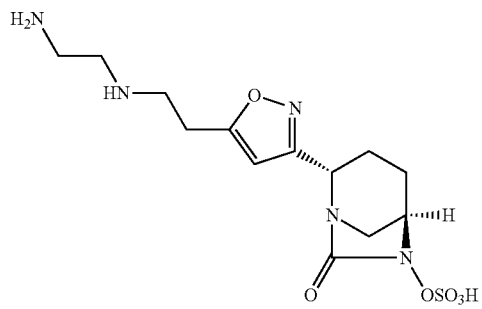

or a pharmaceutically-acceptable salt thereof.

31. The compound according to claim 1 of the Formula

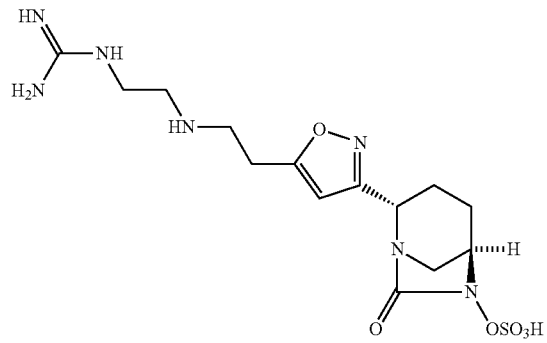

or a pharmaceutically-acceptable salt thereof.

32. The compound according to claim 1 of the Formula

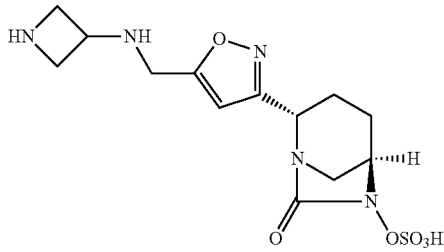

or a pharmaceutically-acceptable salt thereof.

33. The compound according to claim 1 of the Formula

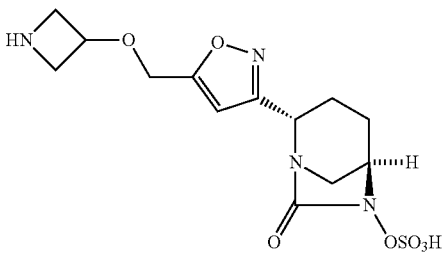

or a pharmaceutically-acceptable salt thereof.

34. The compound according to claim 1 of the Formula

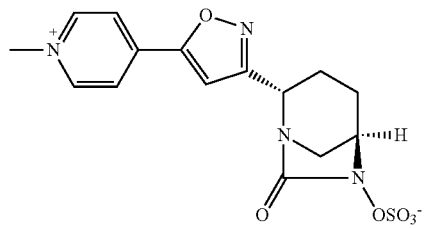

or a pharmaceutically-acceptable salt thereof.

35. The compound according to claim 1 of the Formula

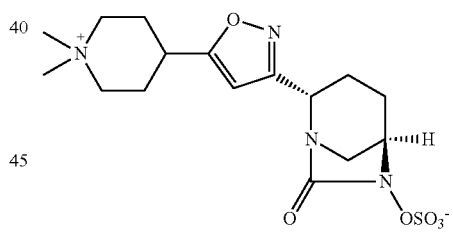

or a pharmaceutically-acceptable salt thereof.

36. The compound according to claim 1 of the Formula

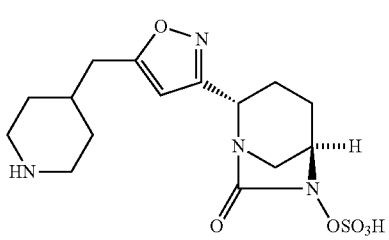

or a pharmaceutically-acceptable salt thereof.

37. The compound according to claim 1 of the Formula
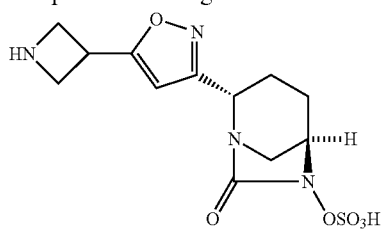
or a pharmaceutically-acceptable salt thereof.
38. The compound according to claim 1 of the Formula
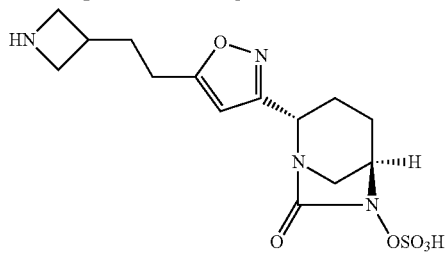
or a pharmaceutically-acceptable salt thereof.
39. The compound according to claim 1 of the Formula
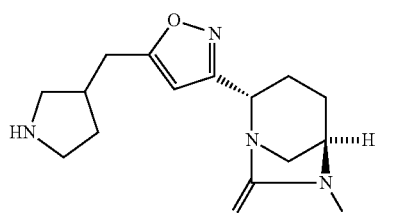
or a pharmaceutically-acceptable salt thereof.
* * * * *

SEQUENCE LISTING

<160> NUMBER OF SEQ ID NOS: 13

<210> SEQ ID NO 1
<211> LENGTH: 32
<212> TYPE: DNA
<213> ORGANISM: Artificial Sequence
<220> FEATURE:
<223> OTHER INFORMATION: Sythetic primer: pBR-Pbla

<400> SEQUENCE: 1
cgcatatgac tcttcctttt tcaatattat tg                32

<210> SEQ ID NO 2
<211> LENGTH: 28
<212> TYPE: DNA
<213> ORGANISM: Artificial Sequence
<220> FEATURE:
<223> OTHER INFORMATION: Sythetic primer: pBR-vec-1

<400> SEQUENCE: 2
gcggatccct gtcagaccaa gtttactc                    28

<210> SEQ ID NO 3
<211> LENGTH: 28
<212> TYPE: DNA
<213> ORGANISM: Artificial Sequence
<220> FEATURE:
<223> OTHER INFORMATION: Sythetic primer: Pbla-cat

<400> SEQUENCE: 3
gccatatgat ggagaaaaaa atcactgg                                          28

<210> SEQ ID NO 4
<211> LENGTH: 28
<212> TYPE: DNA
<213> ORGANISM: Artificial Sequence
<220> FEATURE:
<223> OTHER INFORMATION: Sythetic primer: Vec-1-cat

<400> SEQUENCE: 4 cgggatcccct agagaatagg aacttcgg                                         28

<210> SEQ ID NO 5
<211> LENGTH: 4236
<212> TYPE: DNA
<213> ORGANISM: Artificial Sequence
<220> FEATURE:
<223> OTHER INFORMATION: Synthetic construct: pBR-CBST-cat

<400> SEQUENCE: 5

```
ttcttgaaga cgaaagggcc tcgtgatacg cctatttttta taggttaatg tcatgataat      60
aatggtttct tagacgtcag gtggcacttt tcggggaaat gtgcgcggaa cccctatttg      120
tttattttc taaatacatt caaatatgta tccgctcatg agacaataac cctgataaat      180
gcttcaataa tattgaaaaa ggaagagtca tatggagaaa aaaatcactg gatataccac      240
cgttgatata tcccaatggc atcgtaaaga acattttgag gcatttcagt cagttgctca      300
atgtacctat aaccagaccg ttcagctgga tattacggcc ttttttaaaga ccgtaaagaa      360
aaataagcac aagttttatc cggcctttat tcacattctt gcccgcctga tgaatgctca      420
tacggaattt cgtatggcaa tgaaagacgg tgagctggtg atatgggata gtgttcaccc      480
ttgttacacc gttttccatg agcaaactga acgttttca tcgctctgga gtgaatacca      540
cgacgatttc cggcagtttc tacacatata ttcgcaagat gtggcgtgtt acggtgaaaa      600
cctggcctat ttccctaaag ggtttattga gaatatgttt ttcgtctcag ccaatccctg      660
ggtgagtttc accagttttg atttaaacgt ggccaatatg gacaacttct tcgcccccgt      720
tttcactatg ggcaaatatt atacgcaagg cgacaaggtg ctgatgccgc tggcgattca      780
ggttcatcat gccgtctgtg atggcttcca tgtcggcaga atgcttaatg aattacaaca      840
gtactgcgat gagtggcagg gcggggcgta agtggcaggg cggggcgtaa ggcgcgccat      900
ttaaatgaag ttcctattcc gaagttccta ttctctaggg atccctgtca gaccaagttt      960
actcatatat actttagatt gatttaaaac ttcatttta atttaaaagg atctaggtga     1020
agatcctttt tgataatctc atgaccaaaa tcccttaacg tgagttttcg ttccactgag     1080
cgtcagaccc cgtagaaaag atcaaaggat cttcttgaga tcctttttt ctgcgcgtaa     1140
tctgctgctt gcaaacaaaa aaaccaccgc taccagcggt ggtttgtttg ccggatcaag     1200
agctaccaac tctttttccg aaggtaactg gcttcagcag agcgcagata ccaaatactg     1260
tccttctagt gtagccgtag ttaggccacc acttcaagaa ctctgtagca ccgcctacat     1320
acctcgctct gctaatcctg ttaccagtgg ctgctgccag tggcgataag tcgtgtctta     1380
```

```
ccgggttgga ctcaagacga tagttaccgg ataaggcgca gcggtcgggc tgaacggggg    1440
gttcgtgcac acagcccagc ttggagcgaa cgacctacac cgaactgaga tacctacagc    1500
gtgagctatg agaaagcgcc acgcttcccg aagggagaaa ggcggacagg tatccggtaa    1560
gcggcagggt cggaacagga gagcgcacga gggagcttcc aggggggaaac gcctggtatc    1620 tttatagtcc tgtcgggttt cgccacctct gacttgagcg tcgatttttg tgatgctcgt    1680
caggggggcg gagcctatgg aaaaacgcca gcaacgcggc ctttttacgg ttcctggcct    1740
tttgctggcc ttttgctcac atgttctttc ctgcgttatc ccctgattct gtggataacc    1800
gtattaccgc ctttgagtga gctgataccg ctcgccgcag ccgaacgacc gagcgcagcg    1860
agtcagtgag cgaggaagcg gaagagcgcc tgatgcggta ttttctcctt acgcatctgt    1920
gcggtatttc acaccgcatt tggtgcactc tcagtacaat ctgctctgat gccgcatagt    1980
taagccagta tacactccgc tatcgctacg tgactgggtc atggctgcgc cccgacaccc    2040
gccaacaccc gctgacgcgc cctgacgggc ttgtctgctc ccggcatccg cttacagaca    2100
agctgtgacc gtctccggga gctgcatgtg tcagaggttt tcaccgtcat caccgaaacg    2160
cgcgaggcag ctgcggtaaa gctcatcagc gtggtcgtga agcgattcac agatgtctgc    2220
ctgttcatcc gcgtccagct cgttgagttt ctccagaagc gttaatgtct ggcttctgat    2280
aaagcgggcc atgttaaggg cggttttttc ctgtttggtc actgatgcct ccgtgtaagg    2340
gggatttctg ttcatggggg taatgatacc gatgaaacga gagaggatgc tcacgatacg    2400
ggttactgat gatgaacatg cccggttact ggaacgttgt gagggtaaac aactggcggt    2460
atggatgcgg cgggaccaga gaaaaatcac tcagggtcaa tgccagcgct tcgttaatac    2520
agatgtaggt gttccacagg gtagccagca gcatcctgcg atgcagatcc ggaacataat    2580
ggtgcagggc gctgacttcc gcgtttccag actttacgaa acacggaaac cgaagaccat    2640
tcatgttgtt gctcaggtcg cagacgtttt gcagcagcag tcgcttcacg ttcgctcgcg    2700
tatcggtgat tcattctgct aaccagtaag gcaacccgc cagcctagcc gggtcctcaa    2760
cgacaggagc acgatcatgc gcacccgtgg ccaggaccca acgctgcccg agatgcgccg    2820
cgtgcggctg ctggagatgg cggacgcgat ggatatgttc tgccaagggt tggtttgcgc    2880
attcacagtt ctccgcaaga attgattggc tccaattctt ggagtggtga atccgttagc    2940
gaggtgccgc cggcttccat tcaggtcgag gtggcccggc tccatgcacc gcgacgcaac    3000
gcggggaggc agacaaggta tagggcggcg cctacaatcc atgccaaccc gttccatgtg    3060
ctcgccgagg cggcataaat cgccgtgacg atcagcggtc cagtgatcga agttaggctg    3120
gtaagagccg cgagcgatcc ttgaagctgt ccctgatggt cgtcatctac ctgcctggac    3180
agcatggcct gcaacgcggg catcccgatg ccgccgaag cgagaagaat cataatgggg    3240
aaggccatcc agcctcgcgt cgcgaacgcc agcaagacgt agcccagcgc gtcggccgcc    3300
atgccggcga taatgcctg cttctcgccg aaacgtttgg tggcgggacc agtgacgaag    3360
gcttgagcga gggcgtgcaa gattccgaat accgcaagcg acaggccgat catcgtcgcg    3420
ctccagcgaa agcggtcctc gccgaaaatg acccagagcg ctgccggcac ctgtcctacg    3480
agttgcatga taaagaagac agtcataagt gcggcgacga tagtcatgcc ccgcgcccac    3540
cggaaggagc tgactgggtt gaaggctctc aagggcatcg tcgacgctc tcccttatgc    3600 gactcctgca ttaggaagca gcccagtagt aggttgaggc cgttgagcac cgccgccgca    3660
aggaatggtg catgcaagga gatggcgccc aacagtcccc cggccacggg gcctgccacc    3720
```

| | |
|---|---|
| atacccacgc cgaaacaagc gctcatgagc ccgaagtggc gagcccgatc ttccccatcg | 3780 |
| gtgatgtcgg cgatataggc gccagcaacc gcacctgtgg cgccggtgat gccggccacg | 3840 |
| atgcgtccgg cgtagaggat tcacaggacg ggtgtggtcg ccatgatcgc gtagtcgata | 3900 |
| gtggctccaa gtagcgaagc gagcaggact gggcggcggc caaagcggtc ggacagtgct | 3960 |
| ccgagaacgg gtgcgcatag aaattgcatc aacgcatata gcgctagcag cacgccatag | 4020 |
| tgactggcga tgctgtcgga atggacgata tcccgcaaga ggcccggcag taccggcata | 4080 |
| accaagccta tgcctacagc atccagggtg acggtgccga ggatgacgat gagcgcattg | 4140 |
| ttagatttca tacacggtgc ctgactgcgt tagcaattta actgtgataa actaccgcat | 4200 |
| taaagcttat cgatgataag ctgtcaaaca tgagaa | 4236 |

<210> SEQ ID NO 6
<211> LENGTH: 4391
<212> TYPE: DNA
<213> ORGANISM: Artificial Sequence
<220> FEATURE:
<223> OTHER INFORMATION: Synthetic construct: pBR-CBST-KPC-2

<400> SEQUENCE: 6

| | |
|---|---|
| ttcttgaaga cgaaagggcc tcgtgatacg cctatttttta taggttaatg tcatgataat | 60 |
| aatggtttct tagacgtcag gtggcacttt tcggggaaat gtgcgcggaa cccctatttg | 120 |
| tttatttttc taaatacatt caaatatgta tccgctcatg agacaataac cctgataaat | 180 |
| gcttcaataa tattgaaaaa ggaagagtca tatgtcactg tatcgccgtc tagttctgct | 240 |
| gtcttgtctc tcatggccgc tggctggctt ttctgccacc gcgctgacca acctcgtcgc | 300 |
| ggaaccattc gctaaactcg aacaggactt tggcggctcc atcggtgtgt acgcgatgga | 360 |
| taccggctca ggcgcaactg taagttaccg cgctgaggag cgcttcccac tgtgcagctc | 420 |
| attcaagggc tttcttgctg ccgctgtgct ggctcgcagc cagcagcagg ccggcttgct | 480 |
| ggacacaccc atccgttacg gcaaaaatgc gctggttccg tggtcaccca tctcggaaaa | 540 |
| atatctgaca acaggcatga cggtggcgga gctgtccgcg gccgccgtgc aatacagtga | 600 |
| taacgccgcc gccaatttgt tgctgaagga gttgggcggc ccggccgggc tgacggcctt | 660 |
| catgcgctct atcggcgata ccacgttccg tctggaccgc tgggagctgg agctgaactc | 720 |
| cgccatccca ggcgatgcgc gcgataccct catcgccgcg ccgtgacgg aaagcttaca | 780 |
| aaaactgaca ctgggctctg cactggctgc gccgcagcgg cagcagtttg ttgattggct | 840 |
| aaagggaaac acgaccggca accaccgcat ccgcgcggcg gtgccggcag actgggcagt | 900 |
| cggagacaaa accggaacct gcggagtgta tggcacggca aatgactatg ccgtcgtctg | 960 |
| gcccactggg cgcgcaccta tgtgttggc cgtctacacc cgggcgccta caaggatga | 1020 |
| caagcacagc gaggccgtca tcgccgctgc ggctagactc gcgctcgagg gattgggcgt | 1080 |
| caacgggcag taaggatccc tgtcagacca agtttactca tatatacttt agattgattt | 1140 |
| aaaacttcat ttttaattta aaaggatcta ggtgaagatc cttttttgata atctcatgac | 1200 |
| caaaatccct aacgtgagt tttcgttcca ctgagcgtca gaccccgtag aaaagatcaa | 1260 |
| aggatcttct tgagatcctt ttttctgcg cgtaatctgc tgcttgcaaa caaaaaaacc | 1320 |
| accgctacca gcggtggttt gtttgccgga tcaagagcta ccaactcttt ttccgaaggt | 1380 |
| aactggcttc agcagagcgc agataccaaa tactgtcctt ctagtgtagc cgtagttagg | 1440 |
| ccaccacttc aagaactctg tagcaccgcc tacatacctc gctctgctaa tcctgttacc | 1500 |
| agtggctgct gccagtggcg ataagtcgtg tcttaccggg ttggactcaa gacgatagtt | 1560 |

```
accggataag gcgcagcggt cgggctgaac ggggggttcg tgcacacagc ccagcttgga      1620
gcgaacgacc tacaccgaac tgagatacct acagcgtgag ctatgagaaa gcgccacgct      1680
tcccgaaggg agaaaggcgg acaggtatcc ggtaagcggc agggtcggaa caggagagcg      1740
cacgagggag cttccagggg gaaacgcctg gtatctttat agtcctgtcg ggtttcgcca      1800
cctctgactt gagcgtcgat ttttgtgatg ctcgtcaggg gggcggagcc tatggaaaaa      1860
cgccagcaac gcggccttt tacggttcct ggccttttgc tggccttttg ctcacatgtt      1920
ctttcctgcg ttatcccctg attctgtgga taaccgtatt accgcctttg agtgagctga      1980
taccgctcgc cgcagccgaa cgaccgagcg cagcgagtca gtgagcgagg aagcggaaga      2040
gcgcctgatg cggtattttc tccttacgca tctgtgcggt atttcacacc gcatttggtg      2100
cactctcagt acaatctgct ctgatgccgc atagttaagc cagtatacac tccgctatcg      2160
ctacgtgact gggtcatggc tgcgccccga cacccgccaa cacccgctga cgcgccctga      2220
cgggcttgtc tgctcccggc atccgcttac agacaagctg tgaccgtctc cgggagctgc      2280
atgtgtcaga ggttttcacc gtcatcaccg aaacgcgcga ggcagctgcg gtaaagctca      2340
tcagcgtggt cgtgaagcga ttcacagatg tctgcctgtt catccgcgtc cagctcgttg      2400
agtttctcca gaagcgttaa tgtctggctt ctgataaagc gggccatgtt aagggcggtt      2460
ttttcctgtt tggtcactga tgcctccgtg taagggggat ttctgttcat gggggtaatg      2520
ataccgatga acgagagag gatgctcacg atacgggtta ctgatgatga acatgcccgg      2580
ttactggaac gttgtgaggg taaacaactg gcggtatgga tgcggcggga ccagagaaaa      2640
atcactcagg gtcaatgcca gcgcttcgtt aatacagatg taggtgttcc acagggtagc      2700
cagcagcatc ctgcgatgca gatccggaac ataatggtgc agggcgctga cttccgcgtt      2760
tccagacttt acgaaacacg gaaaccgaag accattcatg ttgttgctca ggtcgcagac      2820
gttttgcagc agcagtcgct tcacgttcgc tcgcgtatcg gtgattcatt ctgctaacca      2880
gtaaggcaac cccgccagcc tagccgggtc ctcaacgaca ggagcacgat catgcgcacc      2940
cgtggccagg acccaacgct gcccgagatg cgccgcgtgc ggctgctgga gatgcggac      3000 gcgatggata tgttctgcca agggttggtt tgcgcattca cagttctccg caagaattga      3060
ttggctccaa ttcttggagt ggtgaatccg ttagcgaggt gccgccggct tccattcagg      3120
tcgaggtggc ccggctccat gcaccgcgac gcaacgcggg gaggcagaca aggtataggg      3180
cggcgcctac aatccatgcc aacccgttcc atgtgctcgc cgaggcggca taaatcgccg      3240
tgacgatcag cggtccagtg atcgaagtta ggctggtaag agccgcgagc gatccttgaa      3300
gctgtccctg atggtcgtca tctacctgcc tggacagcat ggcctgcaac gcgggcatcc      3360
cgatgccgcc ggaagcgaga agaatcataa tggggaaggc catccagcct cgcgtcgcga      3420
acgccagcaa gacgtagccc agcgcgtcgg ccgccatgcc ggcgataatg gcctgcttct      3480
cgccgaaacg tttggtggcg ggaccagtga cgaaggcttg agcgagggcg tgcaagattc      3540
cgaataccgc aagcgacagg ccgatcatcg tcgcgctcca gcgaaagcgg tcctcgccga      3600
aaatgaccca gagcgctgcc ggcacctgtc ctacgagttg catgataaag aagacagtca      3660
taagtgcggc gacgatagtc atgccccgcg cccaccggaa ggagctgact gggttgaagg      3720
ctctcaaggg catcggtcga cgctctccct tatgcgactc ctgcattagg aagcagccca      3780
gtagtaggtt gaggccgttg agcaccgccg ccgcaaggaa tggtgcatgc aaggagatgg      3840
cgcccaacag tcccccggcc acggggcctg ccaccatacc cacgccgaaa caagcgctca      3900
```

| | |
|---|---|
| tgagcccgaa gtggcgagcc cgatcttccc catcggtgat gtcggcgata taggcgccag | 3960 |
| caaccgcacc tgtggcgccg gtgatgccgg ccacgatgcg tccggcgtag aggattcaca | 4020 |
| ggacgggtgt ggtcgccatg atcgcgtagt cgatagtggc tccaagtagc gaagcgagca | 4080 |
| ggactgggcg gcggccaaag cggtcggaca gtgctccgag aacgggtgcg catagaaatt | 4140 |
| gcatcaacgc atatagcgct agcagcacgc catagtgact ggcgatgctg tcggaatgga | 4200 |
| cgatatcccg caagaggccc ggcagtaccg gcataaccaa gcctatgcct acagcatcca | 4260 |
| gggtgacggt gccgaggatg acgatgagcg cattgttaga tttcatacac ggtgcctgac | 4320 |
| tgcgttagca atttaactgt gataaactac cgcattaaag cttatcgatg ataagctgtc | 4380 |
| aaacatgaga a | 4391 |

<210> SEQ ID NO 7
<211> LENGTH: 4116
<212> TYPE: DNA
<213> ORGANISM: Artificial Sequence
<220> FEATURE:
<223> OTHER INFORMATION: Synthetic construct: pBR-CBST-CTX-M-15

<400> SEQUENCE: 7

| | |
|---|---|
| ttcttgaaga cgaaagggcc tcgtgatacg cctattttta taggttaatg tcatgataat | 60 |
| aatggtttct tagacgtcag gtggcacttt tcggggaaat gtgcgcggaa cccctatttg | 120 |
| tttatttttc taaatacatt caaatatgta tccgctcatg agacaataac cctgataaat | 180 |
| gcttcaataa tattgaaaaa ggaagagtca tatggaatct gttaaatcag cgagttgaga | 240 |
| tcaaaaaatc tgaccttgtt aactataatc gattgcgga aaagcacgtc aatgggacga | 300 |
| tgtcactggc tgagcttagc gcggccgcgc tacagtacag cgataacgtg gcgatgaata | 360 |
| agctgattgc tcacgttggc ggcccggcta gcgtcaccgc gttcgcccga cagctgggag | 420 |
| acgaaacgtt ccgtctcgac cgtaccgagc cgacgttaaa caccgccatt ccgggcgatc | 480 |
| cgcgtgatac cacttcacct cgggcaatgg cgcaaactct gcggaatctg acgctgggta | 540 |
| aagcattggg cgacagccaa cgggcgcagc tggtgacatg gatgaaaggc aataccaccg | 600 |
| gtgcagcgag cattcaggct ggactgcctg cttcctgggt tgtggggat aaaaccggca | 660 |
| gcggtggcta tggcaccacc aacgatatcg cggtgatctg gccaaaagat cgtgcgccgc | 720 |
| tgattctggt cacttacttc acccagcctc aacctaaggc agaaagccgt cgcgatgtat | 780 |
| tagcgtcggc ggctaaaatc gtcaccgacg gtttgtaagg atccctgtca gaccaagttt | 840 |
| actcatatat actttagatt gatttaaaac ttcattttta atttaaaagg atctaggtga | 900 |
| agatcctttt tgataatctc atgaccaaaa tcccttaacg tgagttttcg ttccactgag | 960 |
| cgtcagaccc cgtagaaaag atcaaaggat cttcttgaga tcctttttt ctgcgcgtaa | 1020 |
| tctgctgctt gcaaacaaaa aaaccaccgc taccagcggt ggtttgtttg ccggatcaag | 1080 |
| agctaccaac tctttttccg aaggtaactg gcttcagcag agcgcagata ccaaatactg | 1140 |
| tccttctagt gtagccgtag ttaggccacc acttcaagaa ctctgtagca ccgcctacat | 1200 |
| acctcgctct gctaatcctg ttaccagtgg ctgctgccag tggcgataag tcgtgtctta | 1260 |
| ccgggttgga ctcaagacga tagttaccgg ataaggcgca gcggtcgggc tgaacggggg | 1320 |
| gttcgtgcac acagcccagc ttggagcgaa cgacctacac cgaactgaga tacctacagc | 1380 |
| gtgagctatg agaaagcgcc acgcttcccg aagggagaaa ggcggacagg tatccggtaa | 1440 |
| gcggcagggt cggaacagga gagcgcacga gggagcttcc agggggaaac gcctggtatc | 1500 |
| tttatagtcc tgtcgggttt cgccacctct gacttgagcg tcgatttttg tgatgctcgt | 1560 |

```
caggggggcg gagcctatgg aaaaacgcca gcaacgcggc cttttttacgg ttcctggcct    1620 tttgctggcc ttttgctcac atgttctttc ctgcgttatc ccctgattct gtggataacc    1680
gtattaccgc ctttgagtga gctgataccg ctcgccgcag ccgaacgacc gagcgcagcg    1740
agtcagtgag cgaggaagcg gaagagcgcc tgatgcggta ttttctcctt acgcatctgt    1800
gcggtatttc acaccgcatt tggtgcactc tcagtacaat ctgctctgat gccgcatagt    1860
taagccagta tacactccgc tatcgctacg tgactgggtc atggctgcgc ccgacaccc     1920 gccaacaccc gctgacgcgc cctgacgggc ttgtctgctc ccggcatccg cttacagaca    1980
agctgtgacc gtctccggga gctgcatgtg tcagaggttt tcaccgtcat caccgaaacg    2040
cgcgaggcag ctgcggtaaa gctcatcagc gtggtcgtga agcgattcac agatgtctgc    2100
ctgttcatcc gcgtccagct cgttgagttt ctccagaagc gttaatgtct ggcttctgat    2160
aaagcgggcc atgttaaggg cggttttttc ctgtttggtc actgatgcct ccgtgtaagg    2220
gggatttctg ttcatggggg taatgatacc gatgaaacga gagaggatgc tcacgatacg    2280
ggttactgat gatgaacatg cccggttact ggaacgttgt gagggtaaac aactggcggt    2340
atggatgcgg cgggaccaga gaaaaatcac tcagggtcaa tgccagcgct tcgttaatac    2400
agatgtaggt gttccacagg gtagccagca gcatcctgcg atgcagatcc ggaacataat    2460
ggtgcagggc gctgacttcc gcgtttccag actttacgaa acacggaaac cgaagaccat    2520
tcatgttgtt gctcaggtcg cagacgtttt gcagcagcag tcgcttcacg ttcgctcgcg    2580
tatcggtgat tcattctgct aaccagtaag gcaaccccgc cagcctagcc gggtcctcaa    2640
cgacaggagc acgatcatgc gcacccgtgg ccaggaccca acgctgcccg agatgcgccg    2700
cgtgcggctg ctggagatgg cggacgcgat ggatatgttc tgccaagggt tggtttgcgc    2760
attcacagtt ctccgcaaga attgattggc tccaattctt ggagtggtga atccgttagc    2820
gaggtgccgc cggcttccat tcaggtcgag gtggcccggc tccatgcacc gcgacgcaac    2880
gcggggaggc agacaaggta tagggcggcg cctacaatcc atgccaaccc gttccatgtg    2940
ctcgccgagg cggcataaat cgccgtgacg atcagcggtc cagtgatcga agttaggctg    3000
gtaagagccg cgagcgatcc ttgaagctgt ccctgatggt cgtcatctac ctgcctggac    3060
agcatggcct gcaacgcggg catcccgatg ccgccggaag cgagaagaat cataatgggg    3120
aaggccatcc agcctcgcgt cgcgaacgcc agcaagacgt agcccagcgc gtcggccgcc    3180
atgccggcga taatggcctg cttctcgccg aaacgtttgg tggcgggacc agtgacgaag    3240
gcttgagcga gggcgtgcaa gattccgaat accgcaagcg acaggccgat catcgtcgcg    3300
ctccagcgaa agcggtcctc gccgaaaatg acccagagcg ctgccggcac ctgtcctacg    3360
agttgcatga taaagaagac agtcataagt cggcgacga tagtcatgcc ccgcgcccac    3420
cggaaggagc tgactgggtt gaaggctctc aagggcatcg gtcgacgctc tcccttatgc    3480
gactcctgca ttaggaagca gcccagtagt aggttgaggc cgttgagcac cgccgccgca    3540
aggaatggtg catgcaagga gatggcgccc aacagtcccc cggccacggg gcctgccacc    3600
atacccacgc cgaaacaagc gctcatgagc ccgaagtggc gagcccgatc ttccccatcg    3660
gtgatgtcgg cgatataggc gccagcaacc gcacctgtgg cgccggtgat gccggccacg    3720
atgcgtccgg cgtagaggat tcacaggacg ggtgtggtcg ccatgatcgc gtagtcgata    3780
gtggctccaa gtagcgaagc gagcaggact gggcggcggc caaagcggtc ggacagtgct    3840
ccgagaacgg gtgcgcatag aaattgcatc aacgcatata gcgctagcag cacgccatag    3900
```

```
tgactggcga tgctgtcgga atggacgata tcccgcaaga ggcccggcag taccggcata    3960
accaagccta tgcctacagc atccagggtg acggtgccga ggatgacgat gagcgcattg    4020
ttagatttca tacacggtgc ctgactgcgt tagcaattta actgtgataa actaccgcat    4080
taaagcttat cgatgataag ctgtcaaaca tgagaa                              4116

<210> SEQ ID NO 8
<211> LENGTH: 4370
<212> TYPE: DNA
<213> ORGANISM: Artificial Sequence
<220> FEATURE:
<223> OTHER INFORMATION: Synthetic construct: pBR-CBST-SHV-12

<400> SEQUENCE: 8
ttcttgaaga cgaaagggcc tcgtgatacg cctattttta taggttaatg tcatgataat      60
aatggtttct tagacgtcag gtggcacttt tcggggaaat gtgcgcggaa cccctatttg     120 tttattttc taaatacatt caaatatgta tccgctcatg agacaataac cctgataaat     180
gcttcaataa tattgaaaaa ggaagagtca tatgcgttat attcgcctgt gtattatctc     240
cctgttagcc accctgccgc tggcggtaca cgccagcccg cagccgcttg agcaaattaa     300
acaaagcgaa agccagctgt cgggccgcgt aggcatgata gaaatggatc tggccagcgg     360
ccgcacgctg accgcctggc gcgccgatga acgctttccc atgatgagca cctttaaagt     420
agtgctctgc ggcgcagtgc tggcgcgggt ggatgccggt gacgaacagc tggagcgaaa     480
gatccactat cgccagcagg atctggtgga ctactcgccg gtcagcgaaa acaccttgc     540 cgacggcatg acgtcggcg aactctgcgc cgccgccatt accatgagcg ataacagcgc     600
cgccaatctg ctgctggcca ccgtcggcgg ccccgcagga ttgactgcct ttttgcgcca     660
gatcggcgac aacgtcaccc gccttgaccg ctgggaaacg gaactgaatg aggcgcttcc     720
cggcgacgcc cgcgacacca ctaccccggc cagcatggcc gcgaccctgc gcaagctgct     780
gaccagccag cgtctgagcg cccgttcgca acggcagctg ctgcagtgga tggtggacga     840
tcgggtcgcc ggaccgttga tccgctccgt gctgccggcg ggctggttta tcgccgataa     900
gaccggagct agcaagcggg gtgcgcgcgg gattgtcgcc ctgcttggcc cgaataacaa     960
agcagagcgc attgtggtga tttatctgcg ggatacccccg gcgagcatgg ccgagcgaaa    1020
tcagcaaatc gccgggatcg gcgcggcgct gatcgagcac tggcaacgct aaggatccct    1080
gtcagaccaa gtttactcat atatacttta gattgattta aaacttcatt tttaatttaa    1140
aaggatctag gtgaagatcc ttttgataa tctcatgacc aaaatccctt aacgtgagtt    1200
ttcgttccac tgagcgtcag accccgtaga aagatcaaa ggatcttctt gagatcctt     1260 ttttctgcgc gtaatctgct gcttgcaaac aaaaaaacca ccgctaccag cggtggtttg    1320
tttgccggat caagagctac caactctttt tccgaaggta actggcttca gcagagcgca    1380
gataccaaat actgtccttc tagtgtagcc gtagttaggc caccacttca gaactctgt     1440 agcaccgcct acatacctcg ctctgctaat cctgttacca gtggctgctg ccagtggcga    1500
taagtcgtgt cttaccgggt tggactcaag acgatagtta ccggataagg cgcagcggtc    1560
gggctgaacg gggggttcgt gcacacagcc cagcttggag cgaacgacct acaccgaact    1620
gagataccta cagcgtgagc tatgagaaag cgccacgctt cccgaaggga aaaggcgga    1680 caggtatccg gtaagcggca gggtcggaac aggagagcgc acgagggagc ttccagggg    1740 aaacgcctgg tatctttata gtcctgtcgg gtttcgccac ctctgacttg agcgtcgatt    1800
tttgtgatgc tcgtcagggg ggcggagcct atggaaaaac gccagcaacg cggcctttt    1860
```

```
acggttcctg gccttttgct ggccttttgc tcacatgttc tttcctgcgt tatccctga    1920 ttctgtggat aaccgtatta ccgcctttga gtgagctgat accgctcgcc gcagccgaac    1980
gaccgagcgc agcgagtcag tgagcgagga agcggaagag cgcctgatgc ggtattttct    2040
ccttacgcat ctgtgcggta tttcacaccg catttggtgc actctcagta caatctgctc    2100
tgatgccgca tagttaagcc agtatacact ccgctatcgc tacgtgactg ggtcatggct    2160
gcgccccgac acccgccaac acccgctgac gcgccctgac gggcttgtct gctcccggca    2220
tccgcttaca gacaagctgt gaccgtctcc gggagctgca tgtgtcagag gttttcaccg    2280
tcatcaccga aacgcgcgag gcagctgcgg taaagctcat cagcgtggtc gtgaagcgat    2340
tcacagatgt ctgcctgttc atccgcgtcc agctcgttga gtttctccag aagcgttaat    2400
gtctggcttc tgataaagcg ggccatgtta agggcggttt tttcctgttt ggtcactgat    2460
gcctccgtgt aagggggatt tctgttcatg ggggtaatga taccgatgaa acgagagagg    2520
atgctcacga tacgggttac tgatgatgaa catgcccggt tactggaacg ttgtgagggt    2580
aaacaactgg cggtatggat gcggcgggac cagagaaaaa tcactcaggg tcaatgccag    2640
cgcttcgtta atacagatgt aggtgttcca cagggtagcc agcagcatcc tgcgatgcag    2700
atccggaaca taatggtgca gggcgctgac ttccgcgttt ccagacttta cgaaacacgg    2760
aaaccgaaga ccattcatgt tgttgctcag gtcgcagacg ttttgcagca gcagtcgctt    2820
cacgttcgct cgcgtatcgg tgattcattc tgctaaccag taaggcaacc ccgccagcct    2880
agccgggtcc tcaacgacag gagcacgatc atgcgcaccc gtggccagga cccaacgctg    2940
cccgagatgc gccgcgtgcg gctgctggag atggcggacg cgatggatat gttctgccaa    3000
gggttggttt gcgcattcac agttctccgc aagaattgat tggctccaat tcttggagtg    3060
gtgaatccgt tagcgaggtg ccgccggctt ccattcaggt cgaggtggcc cggctccatg    3120
caccgcgacg caacgcgggg aggcagacaa ggtatagggc ggcgcctaca atccatgcca    3180
acccgttcca tgtgctcgcc gaggcggcat aaatcgccgt gacgatcagc ggtccagtga    3240
tcgaagttag gctggtaaga gccgcgagcg atccttgaag ctgtccctga tggtcgtcat    3300
ctacctgcct ggacagcatg gcctgcaacg cgggcatccc gatgccgccg aagcgagaaa    3360
gaatcataat ggggaaggcc atccagcctc gcgtcgcgaa cgccagcaag acgtagccca    3420
gcgcgtcggc cgccatgccg gcgataatgg cctgcttctc gccgaaacgt ttggtggcgg    3480
gaccagtgac gaaggcttga gcgagggcgt gcaagattcc gaataccgca agcgacaggc    3540
cgatcatcgt cgcgctccag cgaaagcggt cctcgccgaa aatgacccag agcgctgccg    3600
gcacctgtcc tacgagttgc atgataaaga agacagtcat aagtgcggcg acgatagtca    3660
tgccccgcgc ccaccggaag gagctgactg ggttgaaggc tctcaagggc atcggtcgac    3720
gctctccctt atgcgactcc tgcattagga gcagcccag tagtaggttg aggccgttga    3780
gcaccgccgc cgcaaggaat ggtgcatgca aggagatggc gcccaacagt cccccggcca    3840
cggggcctgc caccataccc acgccgaaac aagcgctcat gagcccgaag tggcgagccc    3900
gatcttcccc atcggtgatg tcggcgatat aggcgccagc aaccgcacct gtggcgccgg    3960
tgatgccggc cacgatgcgt ccggcgtaga ggattcacag gacgggtgtg gtcgccatga    4020
tcgcgtagtc gatagtggct ccaagtagcg aagcgagcag gactgggcgg cggccaaagc    4080
ggtcggacag tgctccgaga acgggtgcgc atagaaattg catcaacgca tatagcgcta    4140
gcagcacgcc atagtgactg gcgatgctgt cggaatggac gatatcccgc aagaggcccg    4200
```

```
gcagtaccgg cataaccaag cctatgccta cagcatccag ggtgacggtg ccgaggatga      4260
cgatgagcgc attgttagat ttcatacacg gtgcctgact gcgttagcaa tttaactgtg      4320
ataaactacc gcattaaagc ttatcgatga taagctgtca acatgagaa                  4370

<210> SEQ ID NO 9
<211> LENGTH: 4655
<212> TYPE: DNA
<213> ORGANISM: Artificial Sequence
<220> FEATURE:
<223> OTHER INFORMATION: Synthetic construct: pBR-CBST-P99

<400> SEQUENCE: 9
ttcttgaaga cgaaagggcc tcgtgatacg cctatttttta taggttaatg tcatgataat      60
aatggtttct tagacgtcag gtggcacttt tcggggaaat gtgcgcggaa ccccctatttg    120 tttatttttc taaatacatt caaatatgta tccgctcatg agacaataac cctgataaat     180
gcttcaataa tattgaaaaa ggaagagtca tatgatgaga aatcccttt gctgcgccct     240 gctgctcggc atctcttgct ctgctctcgc cacgccagtc tcagaaaaac agctggcgga     300
ggtggtcgcg aatacgatta ccccgctgat gaaagcccag tctgttccag gcatggcggt     360
ggccgttatt tatcagggaa accgcacta ttacacattt gcaaggccg atatcgcggc      420 gaataaaccc gttacgcctc agaccctgtt cgagctgggt tctataagta aaaccttcac     480
cggcgtttta ggtggggatg ccattgctcg cggtgaaatt tcgctggacg atgcggtgac     540
cagatactgg ccacagctga cgggcaagca gtggcagggt attcgtatgc tggatctcgc     600
cacctacacc gctggcggcc tgccgctaca ggtaccggat gaggtcacgg ataacgcctc     660
cctgctgcgc ttttatcaaa actggcagcc gcagtggaag cctggcacaa cgcgtcttta     720
cgccaacgcc agcatcggtc ttttggtgc gctggcggtc aaaccttctg gcatgcccta     780
tgagcaggcc atgacgacgc gggtccttaa gccgctcaag ctggaccata cctggattaa     840
cgtgccgaaa gcgaagagg cgcattacgc ctggggctat cgtgacggta aagcggtgcg     900
cgtttcgccg gtatgctgg atgcacaagc ctatggcgtg aaaaccaacg tgcaggatat     960
ggcgaactgg gtcatggcaa acatggcgc ggagaacgtt gctgatgcct cacttaagca    1020
gggcatcgcg ctggcgcagt cgcgctactg gcgtatcggg tcaatgtatc agggtctggg    1080
ctgggagatg tcaactggcc gtggaggc aacacggtg tcgagggca gcgacagtaa      1140 ggtagcactg gcgccgttgc ccgtggcaga agtgaatcca ccggctcccc cggtcaaagc    1200
gtcctgggtc cataaaacgg ctctactgg cgggtttggc agctacgtgg cctttattcc    1260
tgaaaagcag atcggtattg tgatgctcgc gaatacaagc tatccgaacc cggcacgcgt    1320
tgaggcggca taccatatcc tcgaggcgct acagtaagga tccctgtcag accaagttta    1380
ctcatatata ctttagattg atttaaaact tcattttta tttaaaagga tctaggtgaa    1440
gatccttttt gataatctca tgaccaaaat cccttaacgt gagttttcgt tccactgagc    1500
gtcagacccc gtagaaaaga tcaaaggatc ttcttgagat cctttttttc tgcgcgtaat    1560
ctgctgcttg caaacaaaaa aaccaccgct accagcggtg gtttgtttgc cggatcaaga    1620
gctaccaact cttttccga aggtaactgg cttcagcaga gcgcagatac caaatactgt    1680
ccttctagtg tagccgtagt taggccacca cttcaagaac tctgtagcac cgcctacata    1740
cctcgctctg ctaatcctgt taccagtggc tgctgccagt ggcgataagt cgtgtcttac    1800
cgggttggac tcaagacgat agttaccgga taaggcgcag cggtcgggct gaacggggggg    1860 ttcgtgcaca cagcccagct tggagcgaac gacctacacc gaactgagat acctacagcg    1920
```

```
tgagctatga gaaagcgcca cgcttcccga agggagaaag gcggacaggt atccggtaag    1980
cggcagggtc ggaacaggag agcgcacgag ggagcttcca gggggaaacg cctggtatct    2040
ttatagtcct gtcgggtttc gccacctctg acttgagcgt cgattttttgt gatgctcgtc   2100
agggggggcga agcctatgga aaaacgccag caacgcggcc ttttttacggt tcctggcctt   2160
ttgctggcct tttgctcaca tgttctttcc tgcgttatcc cctgattctg tggataaccg    2220
tattaccgcc tttgagtgag ctgataccgc tcgccgcagc cgaacgaccg agcgcagcga    2280
gtcagtgagc gaggaagcgg aagagcgcct gatgcggtat tttctcctta cgcatctgtg    2340
cggtatttca caccgcattt ggtgcactct cagtacaatc tgctctgatg ccgcatagtt    2400
aagccagtat acactccgct atcgctacgt gactgggtca tggctgcgcc ccgacacccg    2460
ccaacacccg ctgacgcgcc ctgacgggct tgtctgctcc cggcatccgc ttacagacaa    2520
gctgtgaccg tctccgggag ctgcatgtgt cagaggtttt caccgtcatc accgaaacgc    2580
gcgaggcagc tgcggtaaag ctcatcagcg tggtcgtgaa gcgattcaca gatgtctgcc    2640
tgttcatccg cgtccagctc gttgagtttc tccagaagcg ttaatgtctg gcttctgata    2700
aagcgggcca tgttaagggc ggttttttcc tgtttggtca ctgatgcctc cgtgtaaggg    2760
ggatttctgt tcatgggggt aatgataccg atgaaacgag agaggatgct cacgatacgg    2820
gttactgatg atgaacatgc ccggttactg gaacgttgtg agggtaaaca actggcggta    2880
tggatgcggc gggaccagag aaaaatcact cagggtcaat gccagcgctt cgttaataca    2940
gatgtaggtg ttccacaggg tagccagcag catcctgcga tgcagatccg gaacataatg    3000
gtgcagggcg ctgacttccg cgtttccaga ctttacgaaa cacggaaacc gaagaccatt    3060
catgttgttg ctcaggtcgc agacgttttg cagcagcagt cgcttcacgt tcgctcgcgt    3120
atcggtgatt cattctgcta accagtaagg caacccccgcc agcctagccg ggtcctcaac    3180
gacaggagca cgatcatgcg cacccgtggc caggacccaa cgctgcccga tgcgccgc     3240
gtgcggctgc tggagatggc ggacgcgatg gatatgttct gccaagggtt ggtttgcgca    3300
ttcacagttc tccgcaagaa ttgattggct ccaattcttg gagtggtgaa tccgttagcg    3360
aggtgccgcc ggcttccatt caggtcgagg tggcccggct ccatgcaccg cgacgcaacg    3420
cggggaggca gacaaggtat agggcggcgc ctacaatcca tgccaacccg ttccatgtgc    3480
tcgccgaggc ggcataaatc gccgtgacga tcagcggtcc agtgatcgaa gttaggctgg    3540
taagagccgc gagcgatcct tgaagctgtc cctgatggtc gtcatctacc tgcctggaca    3600
gcatggcctg caacgcgggc atcccgatgc cgccggaagc gagaagaatc ataatgggga    3660
aggccatcca gcctcgcgtc gcgaacgcca gcaagacgta gcccagcgcg tcggccgcca    3720
tgccggcgat aatggcctgc ttctcgccga aacgtttggt ggcgggacca gtgacgaagg    3780
cttgagcgag ggcgtgcaag attccgaata ccgcaagcga caggccgatc atcgtcgcgc    3840
tccagcgaaa gcggtcctcg ccgaaaatga cccagcgcgc tgccggcacc tgtcctacga    3900
gttgcatgat aaagaagaca gtcataagtg cggcgacgat agtcatgccc cgcgcccacc    3960
ggaaggagct gactggggttg aaggctctca agggcatcgg tcgacgctct cccttatgcg    4020
actcctgcat taggaagcag cccagtagta ggttgaggcc gttgagcacc gccgccgcaa    4080
ggaatggtgc atgcaaggag atggcgccca acagtccccc ggccacgggg cctgccacca    4140
tacccacgcc gaaacaagcg ctcatgagcc cgaagtggcg agcccgatct tccccatcgg    4200
tgatgtcggc gatataggcg ccagcaaccg cacctgtggc gccggtgatg ccggccacga    4260
```

```
tgcgtccggc gtagaggatt cacaggacgg gtgtggtcgc catgatcgcg tagtcgatag      4320
tggctccaag tagcgaagcg agcaggactg ggcggcggcc aaagcggtcg gacagtgctc      4380
cgagaacggg tgcgcataga aattgcatca acgcatatag cgctagcagc acgccatagt      4440
gactggcgat gctgtcggaa tggacgatat cccgcaagag gcccggcagt accggcataa      4500
ccaagcctat gcctacagca tccagggtga cggtgccgag gatgacgatg agcgcattgt      4560
tagatttcat acacggtgcc tgactgcgtt agcaatttaa ctgtgataaa ctaccgcatt      4620
aaagcttatc gatgataagc tgtcaaacat gagaa                                4655
```

<210> SEQ ID NO 10
<211> LENGTH: 4337
<212> TYPE: DNA
<213> ORGANISM: Artificial Sequence
<220> FEATURE:
<223> OTHER INFORMATION: Synthetic construct: pBR-CBST-OXA-15

<400> SEQUENCE: 10

```
ttcttgaaga cgaaagggcc tcgtgatacg cctatttta taggttaatg tcatgataat        60
aatggtttct tagacgtcag gtggcacttt tcggggaaat gtgcgcggaa cccctatttg       120 tttattttc taaatacatt caaatatgta tccgctcatg agacaataac cctgataaat       180
gcttcaataa tattgaaaaa ggaagagtca tatggcaatc cgaatcttcg cgatactttt       240
ctccattttt tctcttgcca ctttcgcgca tgcgcaagaa ggcacgctag aacgttctga       300
ctggaggaag ttttcagcg aatttcaagc caaaggcacg atagttgtgg cagacgaacg       360
ccaagcggat cgtgccatgt tggttttga tcctgtgcga tcgaagaaac gctactcgcc       420
tgcatcgaca ttcaagatac ctcatacact ttttgcactt gatgcaggcg ctgttcgtga       480
tgagttccag attttcgat gggacggcgt taacagggc tttgcaggcc acaatcaaga       540
ccaagatttg cgatcagcaa tgcggaattc tactgtttgg gtgtatgagc tatttgcaaa       600
ggaaattggt gatgacaaag ctcggcgcta tttgaagaaa atcgactatg caacgccgg       660 tccttcgaca agtaatggcg attactggat agaaggcagc cttgcaatct cggcgcagga       720
gcaaattgca tttctcagga agctctatcg taacagagctg cccttcgggg tagaacatca       780
gcgcttggtc aaggatctca tgattgtgga agccggtcgc aactggatac tgcgtgcaaa       840
gacgggctgg gaaggccgta tgggttgtg gtaggatgg gttgagtggc cgactggctc       900
cgtattcttc gcactgaata ttgatacgcc aaacagaatg gatgatcttt tcaagaggga       960
ggcaatcgtg cgggcaatcc ttcgctctat tgaagcgtta ccgcccaacc cggcagtcaa      1020
ctcggacgct gcgcgataag gatccctgtc agaccaagtt tactcatata ctttagat       1080 tgatttaaaa cttcatttt aatttaaaag gatctaggtg aagatccttt ttgataatct      1140
catgaccaaa atccttaac gtgagttttc gttccactga gcgtcagacc ccgtagaaaa      1200
gatcaaagga tcttcttgag atccttttt tctgcgcgta atctgctgct tgcaaacaaa      1260
aaaaccaccg ctaccagcgg tggtttgttt gccggatcaa gagctaccaa ctcttttcc      1320 gaaggtaact ggcttcagca gagcgcagat accaaatact gtccttctag tgtagccgta      1380
gttaggccac cacttcaaga actctgtagc accgcctaca tacctcgctc tgctaatcct      1440
gttaccagtg gctgctgcca gtggcgataa gtcgtgtctt accgggttgg actcaagacg      1500
atagttaccg gataaggcgc agcggtcggg ctgaacgggg ggttcgtgca cacagcccag      1560
cttggagcga acgacctaca ccgaactgag atacctacag cgtgagctat gagaaagcgc      1620
cacgcttccc gaagggagaa aggcggacag gtatccggta agcggcaggg tcggaacagg      1680
```

```
agagcgcacg agggagcttc caggggaaa  cgcctggtat ctttatagtc ctgtcgggtt   1740
tcgccacctc tgacttgagc gtcgattttt gtgatgctcg tcaggggggc ggagcctatg   1800
gaaaaacgcc agcaacgcgg ccttttacg  gttcctggcc ttttgctggc cttttgctca   1860
catgttcttt cctgcgttat cccctgattc tgtggataac cgtattaccg cctttgagtg   1920
agctgatacc gctcgccgca gccgaacgac cgagcgcagc gagtcagtga gcgaggaagc   1980
ggaagagcgc ctgatgcggt attttctcct tacgcatctg tgcggtattt cacaccgcat   2040
ttggtgcact ctcagtacaa tctgctctga tgccgcatag ttaagccagt atacactccg   2100
ctatcgctac gtgactgggt catggctgcg ccccgacacc cgccaacacc cgctgacgcg   2160
ccctgacggg cttgtctgct cccggcatcc gcttacagac aagctgtgac cgtctccggg   2220
agctgcatgt gtcagaggtt ttcaccgtca tcaccgaaac gcgcgaggca gctgcggtaa   2280
agctcatcag cgtggtcgtg aagcgattca cagatgtctg cctgttcatc cgcgtccagc   2340
tcgttgagtt tctccagaag cgttaatgtc tggcttctga taaagcgggc catgttaagg   2400
gcggttttt  cctgtttggt cactgatgcc tccgtgtaag ggggatttct gttcatgggg   2460
gtaatgatac cgatgaaacg agagaggatg ctcacgatac gggttactga tgatgaacat   2520
gcccggttac tggaacgttg tgagggtaaa caactggcgg tatggatgcg cgggaccag    2580
agaaaaatca ctcagggtca atgccagcgc ttcgttaata cagatgtagg tgttccacag   2640
ggtagccagc agcatcctgc gatgcagatc cggaacataa tggtgcaggg cgctgacttc   2700
cgcgtttcca gactttacga aacacggaaa ccgaagacca ttcatgttgt tgctcaggtc   2760
gcagacgttt tgcagcagca gtcgcttcac gttcgctcgc gtatcggtga ttcattctgc   2820
taaccagtaa gcaaccccg  ccagcctagc cgggtcctca acgacaggag cacgatcatg   2880
cgcacccgtg gccaggaccc aacgctgccc gagatgcgcc gcgtgcggct gctggagatg   2940
gcggacgcga tggatatgtt ctgccaaggg ttggtttgcg cattcacagt tctccgcaag   3000
aattgattgg ctccaattct tggagtggtg aatccgttag cgaggtgccg ccggcttcca   3060
ttcaggtcga ggtggcccgg ctccatgcac cgcgacgcaa cgcggggagg cagacaaggt   3120
atagggcggc gcctacaatc catgccaacc cgttccatgt gctcgccgag gcggcataaa   3180
tcgccgtgac gatcagcggt ccagtgatcg aagttaggct ggtaagagcc gcgagcgatc   3240
cttgaagctg tccctgatgg tcgtcatcta cctgcctgga cagcatggcc tgcaacgcgg   3300
gcatcccgat gccgccggaa gcgagaagaa tcataatggg gaaggccatc cagcctcgcg   3360
tcgcgaacgc cagcaagacg tagcccagcg cgtcggccgc catgccggcg ataatggcct   3420
gcttctcgcc gaaacgtttg gtggcgggac cagtgacgaa ggcttgagcg agggcgtgca   3480
agattccgaa taccgcaagc gacaggccga tcatcgtcgc gctccagcga aagcggtcct   3540
cgccgaaaat gacccagagc gctgccggca cctgtcctac gagttgcatg ataaagaaga   3600
cagtcataag tgcggcgacg atagtcatgc cccgcgccca ccggaaggag ctgactgggt   3660
tgaaggctct caagggcatc ggtcgacgct ctcccttatg cgactcctgc attaggaagc   3720
agcccagtag taggttgagg ccgttgagca ccgccgccgc aaggaatggt gcatgcaagg   3780
agatggcgcc caacagtccc ccggccacgg ggcctgccac catacccacg ccgaaacaag   3840
cgctcatgag cccgaagtgg cgagcccgat cttccccatc ggtgatgtcg gcgatatagg   3900
cgccagcaac cgcacctgtg gcgccggtga tgccggccac gatgcgtccg gcgtagagga   3960
ttcacaggac gggtgtggtc gccatgatcg cgtagtcgat agtggctcca agtagcgaag   4020
```

| | |
|---|---:|
| cgagcaggac tgggcggcgg ccaaagcggt cggacagtgc tccgagaacg ggtgcgcata | 4080 |
| gaaattgcat caacgcatat agcgctagca gcacgccata gtgactggcg atgctgtcgg | 4140 |
| aatggacgat atcccgcaag aggcccggca gtaccggcat aaccaagcct atgcctacag | 4200 |
| catccagggt gacggtgccg aggatgacga tgagcgcatt gttagatttc atacacggtg | 4260 |
| cctgactgcg ttagcaattt aactgtgata aactaccgca ttaaagctta tcgatgataa | 4320 |
| gctgtcaaac atgagaa | 4337 |

<210> SEQ ID NO 11
<211> LENGTH: 4391
<212> TYPE: DNA
<213> ORGANISM: Artificial Sequence
<220> FEATURE:
<223> OTHER INFORMATION: Synthetic construct: pBR-CBST-KPC-4

<400> SEQUENCE: 11

| | |
|---|---:|
| ttcttgaaga cgaaagggcc tcgtgatacg cctatttta taggttaatg tcatgataat | 60 |
| aatggtttct tagacgtcag gtggcacttt tcggggaaat gtgcgcggaa cccctatttg | 120 |
| tttatttttc taaatacatt caaatatgta tccgctcatg agacaataac cctgataaat | 180 |
| gcttcaataa tattgaaaaa ggaagagtca tatgtcactg tatcgccgtc tagttctgct | 240 |
| gtcttgtctc tcatggccgc tggctggctt ttctgccacc gcgctgacca acctcgtcgc | 300 |
| ggaaccattc gctaaactcg aacaggactt tggcggctcc atcggtgtgt acgcgatgga | 360 |
| taccggctca ggcgcaactg taagttaccg cgctgaggag cgcttcccac tgtgcagctc | 420 |
| attcaagggc tttcttgctg ccgctgtgct ggctcgcagc cagcagcagg ccggcttgct | 480 |
| ggacacaccc atccgttacg gcaaaaatgc gctggttcgg tggtcaccca tctcggaaaa | 540 |
| atatctgaca acaggcatga cggtggcgga gctgtccgcg gccgccgtgc aatacagtga | 600 |
| taacgccgcc gccaatttgt tgctgaagga gttgggcggc ccggccgggc tgacggcctt | 660 |
| catgcgctct atcggcgata ccacgttccg tctggaccgc tgggagctgg agctgaactc | 720 |
| cgccatccca ggcgatgcgc gcgataccta tcgccgcgc gccgtgacgg aaagcttaca | 780 |
| aaaactgaca ctgggctctg cactggctgc gccagcgg cagcagtttg ttgattggct | 840 |
| aaagggaaac acgaccggca accaccgcat ccgcgcggcg gtgccggcag actgggcagt | 900 |
| cggagacaaa accggaacct gcggagggta tggcacggca atgactatg ccgtcgtctg | 960 |
| gcccactggg cgcgcaccta ttgtgttggc cgtctacacc cgggcgccta acaaggatga | 1020 |
| caagcacagc gaggccgtca tcgccgctgc ggctagactc gcgctcgagg gattgggcgt | 1080 |
| caacgggcag taaggatccc tgtcagacca agtttactca tatatacttt agattgattt | 1140 |
| aaaacttcat ttttaattta aaaggatcta ggtgaagatc ctttttgata atctcatgac | 1200 |
| caaaatccct taacgtgagt tttcgttcca ctgagcgtca gacccccgtag aaaagatcaa | 1260 |
| aggatcttct tgagatcctt ttttctgcg cgtaatctgc tgcttgcaaa caaaaaaacc | 1320 |
| accgctacca gcggtggttt gtttgccgga tcaagagcta ccaactcttt ttccgaaggt | 1380 |
| aactggcttc agcagagcgc agataccaaa tactgtcctt ctagtgtagc cgtagttagg | 1440 |
| ccaccacttc aagaactctg tagcaccgcc tacatacctc gctctgctaa tcctgttacc | 1500 |
| agtggctgct gccagtggcg ataagtcgtg tcttaccggg ttggactcaa gacgatagtt | 1560 |
| accggataag gcgcagcggt cgggctgaac ggggggttcg tgcacacagc ccagcttgga | 1620 |
| gcgaacgacc tacaccgaac tgagatacct acagcgtgag ctatgagaaa gcgccacgct | 1680 |
| tcccgaaggg agaaaggcgg acaggtatcc ggtaagcggc agggtcggaa caggagagcg | 1740 |

```
cacgagggag cttccagggg gaaacgcctg gtatctttat agtcctgtcg ggtttcgcca    1800
cctctgactt gagcgtcgat ttttgtgatg ctcgtcaggg gggcggagcc tatggaaaaa    1860
cgccagcaac gcggccttt  tacggttcct ggccttttgc tggccttttg ctcacatgtt    1920
ctttcctgcg ttatcccctg attctgtgga taaccgtatt accgcctttg agtgagctga    1980
taccgctcgc cgcagccgaa cgaccgagcg cagcgagtca gtgagcgagg aagcggaaga    2040
gcgcctgatg cggtattttc tccttacgca tctgtgcggt atttcacacc gcatttggtg    2100
cactctcagt acaatctgct ctgatgccgc atagttaagc cagtatacac tccgctatcg    2160
ctacgtgact gggtcatggc tgcgccccga cacccgccaa cacccgctga cgcgccctga    2220
cgggcttgtc tgctcccggc atccgcttac agacaagctg tgaccgtctc cgggagctgc    2280
atgtgtcaga ggttttcacc gtcatcaccg aaacgcgcga ggcagctgcg gtaaagctca    2340
tcagcgtggt cgtgaagcga ttcacagatg tctgcctgtt catccgcgtc cagctcgttg    2400
agtttctcca gaagcgttaa tgtctggctt ctgataaagc gggccatgtt aagggcggtt    2460
ttttcctgtt tggtcactga tgcctccgtg taagggggat ttctgttcat ggggggtaatg   2520
ataccgatga aacgagagag gatgctcacg atacgggtta ctgatgatga acatgcccgg    2580
ttactggaac gttgtgaggg taaacaactg gcggtatgga tgcggcggga ccagagaaaa    2640
atcactcagg gtcaatgcca gcgcttcgtt aatacagatg taggtgttcc acagggtagc    2700
cagcagcatc ctgcgatgca gatccggaac ataatggtgc agggcgctga cttccgcgtt    2760
tccagacttt acgaaacacg gaaaccgaag accattcatg ttgttgctca ggtcgcagac    2820
gttttgcagc agcagtcgct tcacgttcgc tcgcgtatcg gtgattcatt ctgctaacca    2880
gtaaggcaac cccgccagcc tagccgggtc ctcaacgaca ggagcacgat catgcgcacc    2940
cgtggccagg acccaacgct gcccgagatg cgccgcgtgc ggctgctgga gatggcggac    3000
gcgatggata tgttctgcca agggttggtt tgcgcattca cagttctccg caagaattga    3060
ttggctccaa ttcttggagt ggtgaatccg ttagcgaggt gccgccggct tccattcagg    3120
tcgaggtggc ccggctccat gcaccgcgac gcaacgcggg gaggcagaca aggtataggg    3180
cggcgcctac aatccatgcc aacccgttcc atgtgctcgc cgaggcggca taaatcgccg    3240
tgacgatcag cggtccagtg atcgaagtta ggctggtaag agccgcgagc gatccttgaa    3300
gctgtccctg atggtcgtca tctacctgcc tggacagcat ggcctgcaac gcgggcatcc    3360
cgatgccgcc ggaagcgaga agaatcataa tggggaaggc catccagcct cgcgtcgcga    3420
acgccagcaa gacgtagccc agcgcgtcgg ccgccatgcc ggcgataatg gcctgcttct    3480
cgccgaaacg tttggtggcg ggaccagtga cgaaggcttg agcgagggcg tgcaagattc    3540
cgaataccgc aagcgacagg ccgatcatcg tcgcgctcca gcgaaagcgg tcctcgccga    3600
aaatgaccca gagcgctgcc ggcacctgtc ctacgagttg catgataaag aagacagtca    3660
taagtgcggc gacgatagtc atgccccgcg cccaccggaa ggagctgact gggttgaagg    3720
ctctcaaggg catcggtcga cgctctccct tatgcgactc ctgcattagg aagcagccca    3780
gtagtaggtt gaggccgttg agcaccgccg ccgcaaggaa tggtgcatgc aaggagatgg    3840
cgcccaacag tcccccggcc acgggccctg ccaccatacc cacgccgaaa caagcgctca    3900
tgagcccgaa gtggcgagcc cgatcttccc catcggtgat gtcggcgata taggcgccag    3960
caaccgcacc tgtggcgccg gtgatgccgg ccacgatgcg tccggcgtag aggattcaca    4020
ggacgggtgt ggtcgccatg atcgcgtagt cgatagtggc tccaagtagc gaagcgagca    4080
```

| | |
|---|---|
| ggactgggcg gcggccaaag cggtcggaca gtgctccgag aacgggtgcg catagaaatt | 4140 |
| gcatcaacgc atatagcgct agcagcacgc catagtgact ggcgatgctg tcggaatgga | 4200 |
| cgatatcccg caagaggccc ggcagtaccg gcataaccaa gcctatgcct acagcatcca | 4260 |
| gggtgacggt gccgaggatg acgatgagcg cattgttaga tttcatacac ggtgcctgac | 4320 |
| tgcgttagca atttaactgt gataaactac cgcattaaag cttatcgatg ataagctgtc | 4380 |
| aaacatgaga a | 4391 |

```
<210> SEQ ID NO 12
<211> LENGTH: 4649
<212> TYPE: DNA
<213> ORGANISM: Artificial Sequence
<220> FEATURE:
<223> OTHER INFORMATION: Synthetic construct: pBR-CBST-DHA-1

<400> SEQUENCE: 12
```

| | |
|---|---|
| ttcttgaaga cgaaagggcc tcgtgatacg cctatttttta taggttaatg tcatgataat | 60 |
| aatggtttct tagacgtcag gtggcacttt tcggggaaat gtgcgcggaa cccctatttg | 120 |
| tttattttc taaatacatt caaatatgta tccgctcatg agacaataac cctgataaat | 180 |
| gcttcaataa tattgaaaaa ggaagagtca tatgaaaaaa tcgttatctg caacactgat | 240 |
| ttccgctctg ctggcgtttt ccgccccggg gttttctgcc gctgataatg tcgcggcggt | 300 |
| ggtgacagc accattaaac cgctgatggc acagcaggat attcccggga tggcggttgc | 360 |
| cgtctccgta aagggtaagc cctattattt caattatggt tttgccgata ttcaggcaaa | 420 |
| acagccggtc actgaaaata cactatttga gctcggatct gtaagtaaaa ctttcacagg | 480 |
| tgtgctgggt gcggtttctg tggcgaaaaa agagatggcg ctgaatgatc cggcggcaaa | 540 |
| ataccagccg gagctggctc tgccgcagtg aaggggatc acattgctgg atctggctac | 600 |
| ctataccgca ggcggactgc cgttacaggt gccggatgcg gtaaaaagcc gtgcggatct | 660 |
| gctgaatttc tatcagcagt ggcagccgtc ccggaaaccg ggcgatatgc gtctgtatgc | 720 |
| aaacagcagt atcggcctgt ttggtgctct gaccgcaaac gcggcgggga tgccgtatga | 780 |
| gcagttgctg actgcacgca tcctggcacc gctgggggtta tctcacacct ttattactgt | 840 |
| gccggaaagt gcgcaaagcc agtatgcgta cggttataaa acaaaaaaac cggtccgcgt | 900 |
| gtcgccggga cagcttgatg cggaatctta cggcgtgaaa tccgcctcaa aagatatgct | 960 |
| gcgctgggcg gaaatgaata tggagccgtc acgggccggt aatgcggatc tggaaatggc | 1020 |
| aatgtatctc gcccagaccc gctactataa aaccgccgcg attaaccagg gctgggctg | 1080 |
| ggaaatgtat gactggccgc agcagaaaga tatgatcatt aacggtgtga ccaacgaggt | 1140 |
| cgcattgcag ccgcatccgg taacagacaa ccaggttcag ccgtataacc gtgcttcctg | 1200 |
| ggtgcataaa acgggcgcaa caactggttt cggcgcctat gtcgccttta ttccggaaaa | 1260 |
| acaggtggcg attgtgattc tggcgaataa aaactacccg aataccgaaa gagtcaaagc | 1320 |
| tgcacaggct atttttgagtg cactggaata aggatccctg tcagaccaag tttactcata | 1380 |
| tatactttag attgatttaa aacttcattt ttaatttaaa aggatctagg tgaagatcct | 1440 |
| ttttgataat ctcatgacca aaatccctta acgtgagttt tcgttccact gagcgtcaga | 1500 |
| ccccgtagaa aagatcaaag gatcttcttg agatcctttt tttctgcgcg taatctgctg | 1560 |
| cttgcaaaca aaaaaaccac cgctaccagc ggtggtttgt ttgccggatc aagagctacc | 1620 |
| aactcttttt ccgaaggtaa ctggcttcag cagagcgcag ataccaaata ctgtccttct | 1680 |
| agtgtagccg tagttaggcc accacttcaa gaactctgta gcaccgccta catacctcgc | 1740 |

```
tctgctaatc ctgttaccag tggctgctgc cagtggcgat aagtcgtgtc ttaccgggtt    1800
ggactcaaga cgatagttac cggataaggc gcagcggtcg ggctgaacgg ggggttcgtg    1860
cacacagccc agcttggagc gaacgaccta caccgaactg agatacctac agcgtgagct    1920
atgagaaagc gccacgcttc ccgaaggag aaaggcggac aggtatccgg taagcggcag     1980
ggtcggaaca ggagagcgca cgagggagct ccaggggga aacgcctggt atctttatag     2040
tcctgtcggg tttcgccacc tctgacttga gcgtcgattt ttgtgatgct cgtcaggggg    2100
gcggagccta tggaaaaacg ccagcaacgc ggccttttta cggttcctgg ccttttgctg    2160
gccttttgct cacatgttct ttcctgcgtt atccctgat tctgtggata accgtattac     2220
cgcctttgag tgagctgata ccgctcgccg cagccgaacg accgagcgca gcgagtcagt    2280
gagcgaggaa gcggaagagc gcctgatgcg gtattttctc cttacgcatc tgtgcggtat    2340
ttcacaccgc atttggtgca ctctcagtac aatctgctct gatgccgcat agttaagcca    2400
gtatacactc cgctatcgct acgtgactgg gtcatggctg cgccccgaca cccgccaaca    2460
cccgctgacg cgccctgacg ggcttgtctg ctcccggcat ccgcttacag acaagctgtg    2520
accgtctccg ggagctgcat gtgtcagagg ttttcaccgt catcaccgaa acgcgcgagg    2580
cagctgcggt aaagctcatc agcgtggtcg tgaagcgatt cacagatgtc tgcctgttca    2640
tccgcgtcca gctcgttgag tttctccaga agcgttaatg tctggcttct gataaagcgg    2700
gccatgttaa gggcggtttt tcctgtttg gtcactgatg cctccgtgta aggggggattt    2760 ctgttcatgg gggtaatgat accgatgaaa cgagagagga tgctcacgat acgggttact    2820
gatgatgaac atgcccggtt actggaacgt tgtgagggta acaactggc ggtatggatg     2880 cggcgggacc agagaaaaat cactcagggt caatgccagc gcttcgttaa tacagatgta    2940
ggtgttccac agggtagcca gcagcatcct gcgatgcaga tccggaacat aatggtgcag    3000
ggcgctgact ccgcgtttc cagactttac gaaacacgga aaccgaagac cattcatgtt     3060
gttgctcagg tcgcagacgt tttgcagcag cagtcgcttc acgttcgctc gcgtatcggt    3120
gattcattct gctaaccagt aaggcaaccc cgccagccta gccgggtcct caacgacagg    3180
agcacgatca tgcgcacccg tggccaggac ccaacgctgc ccgagatgcg ccgcgtgcgg    3240
ctgctggaga tggcggacgc gatggatatg ttctgccaag ggttggtttg cgcattcaca    3300
gttctccgca agaattgatt ggctccaatt cttggagtgg tgaatccgtt agcgaggtgc    3360
cgccggcttc cattcaggtc gaggtggccc ggctccatgc accgcgacgc aacgcgggga    3420
ggcagacaag gtatagggcg cgcctacaa tccatgccaa cccgttccat gtgctcgccg     3480
aggcggcata aatcgccgtg acgatcagcg gtccagtgat cgaagttagg ctggtaagag    3540
ccgcgagcga tccttgaagc tgtccctgat ggtcgtcatc tacctgcctg acagcatgg     3600 cctgcaacgc gggcatcccg atgccgccgg aagcgagaag aatcataatg gggaaggcca    3660
tccagcctcg cgtcgcgaac gccagcaaga cgtagcccag cgcgtcggcc gccatgccgg    3720
cgataatggc ctgcttctcg ccgaaacgtt tggtggcggg accagtgacg aaggcttgag    3780
cgagggcgtg caagattccg aataccgcaa gcgacaggcc gatcatcgtc gcgctccagc    3840
gaaagcggtc ctcgccgaaa atgacccaga gcgctgccgg cacctgtcct acgagttgca    3900
tgataaagaa gacagtcata agtgcggcga cgatagtcat gccccgcgcc caccggaagg    3960
agctgactgg gttgaaggct ctcaagggca tcggtcgacg ctctccctta tgcgactcct    4020
gcattaggaa gcagcccagt agtaggttga ggccgttgag caccgccgcc gcaaggaatg    4080
```

| | |
|---|---|
| gtgcatgcaa ggagatggcg cccaacagtc ccccggccac ggggcctgcc accataccca | 4140 |
| cgccgaaaca agcgctcatg agcccgaagt ggcgagcccg atcttcccca tcggtgatgt | 4200 |
| cggcgatata ggcgccagca accgcacctg tggcgccggt gatgccggcc acgatgcgtc | 4260 |
| cggcgtagag gattcacagg acgggtgtgg tcgccatgat cgcgtagtcg atagtggctc | 4320 |
| caagtagcga agcgagcagg actgggcggc ggccaaagcg gtcggacagt gctccgagaa | 4380 |
| cgggtgcgca tagaaattgc atcaacgcat atagcgctag cagcacgcca tagtgactgg | 4440 |
| cgatgctgtc ggaatggacg atatcccgca agaggcccgg cagtaccggc ataaccaagc | 4500 |
| ctatgcctac agcatccagg gtgacggtgc cgaggatgac gatgagcgca ttgttagatt | 4560 |
| tcatacacgg tgcctgactg cgttagcaat ttaactgtga taaactaccg cattaaagct | 4620 |
| tatcgatgat aagctgtcaa acatgagaa | 4649 |

<210> SEQ ID NO 13
<211> LENGTH: 4664
<212> TYPE: DNA
<213> ORGANISM: Artificial Sequence
<220> FEATURE:
<223> OTHER INFORMATION: Synthetic construct: pBR-CBST-ADC-33

<400> SEQUENCE: 13

| | |
|---|---|
| ttcttgaaga cgaaagggcc tcgtgatacg cctattttta taggttaatg tcatgataat | 60 |
| aatggttttct tagacgtcag gtggcacttt tcggggaaat gtgcgcggaa cccctatttg | 120 |
| tttatttttc taaatacatt caaatatgta tccgctcatg agacaataac cctgataaat | 180 |
| gcttcaataa tattgaaaaa ggaagagtca tatgcgattt aaaaaaattt cttgtctact | 240 |
| tttatccccg ctttttattt ttagtacctc aatttatgcg gcaatacac caaaagacca | 300 |
| agaaattaaa aaactggtag atcaaaactt taaaccgtta ttagaaaaat atgatgtgcc | 360 |
| aggtatggct gtgggtgtta ttcaaaataa taaaaagtat gaaatgtatt atggtcttca | 420 |
| atctgttcaa gataaaaaag ccgtaaatag cagtaccatt tttgagctag gttctgtcag | 480 |
| taaattattt accgcgacag caggtggata tgcaaaaaat aaaggaaaaa tctcttttga | 540 |
| cgatacgcct ggtaaatatt ggaaagaact aaaaaacaca ccgattgacc aagttaactt | 600 |
| acttcaactc gcgacgtata caagtggtaa ccttgccttg cagtttccag atgaagtaaa | 660 |
| aacagaccaa caagttttaa cttttttcaa agactggaaa cctaaaaact caatcggtga | 720 |
| atacagacaa tattcaaatc caagtattgg cctatttgga aaggttgtgg ctttgtctat | 780 |
| gaataaacct ttcgaccaag tcttagaaaa acaattttt ccggcccttg gcttaaaaca | 840 |
| tagctatgta aatgtaccta agacccagat gcaaaactat gcatttggtt ataaccaaga | 900 |
| aaatcagccg attcgagtta accgcggccc actcgatgcc gccctgcgt atggcgtcaa | 960 |
| atcgacacta cccgacatgt tgagttttat tcatgccaac cttaacccac agaaatatcc | 1020 |
| ggctgatatt caacgggcaa ttaatgaaac acatcaaggg cgctatcaag taaataccat | 1080 |
| gtatcaggca ctcggttggg aagagttttc ttatccggca acgttacaaa ctttattaga | 1140 |
| cagtaattca gaacagattg tgatgaaacc taataaagtg actgctattt caaaggaacc | 1200 |
| ttcagttaag atgtaccata aaactggctc aaccaacggt tcggaacgt atgtagtgtt | 1260 |
| tattcctaaa gaaaatattg gcttagtcat gttaaccaat aaacgtattc caaatgaaga | 1320 |
| gcgcattaag gcagcttatg ctgtgctgaa tgcaataaag aaataaggat ccctgtcaga | 1380 |
| ccaagtttac tcatatatac tttagattga tttaaaactt catttttaat ttaaaaggat | 1440 |
| ctaggtgaag atcctttttg ataatctcat gaccaaaatc ccttaacgtg agttttcgtt | 1500 |

```
ccactgagcg tcagaccccg tagaaaagat caaaggatct tcttgagatc cttttttct    1560
gcgcgtaatc tgctgcttgc aaacaaaaaa accaccgcta ccagcggtgg tttgtttgcc    1620
ggatcaagag ctaccaactc ttttccgaa ggtaactggc ttcagcagag cgcagatacc    1680
aaatactgtc cttctagtgt agccgtagtt aggccaccac ttcaagaact ctgtagcacc    1740
gcctacatac ctcgctctgc taatcctgtt accagtggct gctgccagtg gcgataagtc    1800
gtgtcttacc gggttggact caagacgata gttaccggat aaggcgcagc ggtcgggctg    1860
aacgggggt tcgtgcacac agcccagctt ggagcgaacg acctacaccg aactgagata    1920
cctacagcgt gagctatgag aaagcgccac gcttcccgaa gggagaaagg cggacaggta    1980
tccggtaagc ggcagggtcg aacaggaga gcgcacgagg gagcttccag ggggaaacgc    2040
ctggtatctt tatagtcctg tcgggtttcg ccacctctga cttgagcgtc gattttgtg    2100
atgctcgtca gggggcgga gcctatggaa aaacgccagc aacgcggcct ttttacggtt    2160
cctggccttt tgctggcctt tgctcacat gttctttcct gcgttatccc ctgattctgt    2220
ggataaccgt attaccgcct ttgagtgagc tgataccgct cgccgcagcc gaacgaccga    2280
gcgcagcgag tcagtgagcg aggaagcgga agagcgcctg atgcggtatt ttctccttac    2340
gcatctgtgc ggtatttcac accgcatttg gtgcactctc agtacaatct gctctgatgc    2400
cgcatagtta agccagtata cactccgcta tcgctacgtg actgggtcat ggctgcgccc    2460
cgacacccgc caacacccgc tgacgcgccc tgacgggctt gtctgctccc ggcatccgct    2520
tacagacaag ctgtgaccgt ctccgggagc tgcatgtgtc agaggttttc accgtcatca    2580
ccgaaacgcg cgaggcagct gcggtaaagc tcatcagcgt ggtcgtgaag cgattcacag    2640
atgtctgcct gttcatccgc gtccagctcg ttgagtttct ccagaagcgt taatgtctgg    2700
cttctgataa agcgggccat gttaagggcg ttttttcct gtttggtcac tgatgcctcc    2760
gtgtaagggg gatttctgtt catgggggta atgataccga tgaaacgaga gaggatgctc    2820
acgatacggg ttactgatga tgaacatgcc cggttactgg aacgttgtga gggtaaacaa    2880
ctggcggtat ggatgcggcg ggaccagaga aaaatcactc agggtcaatg ccagcgcttc    2940
gttaatacag atgtaggtgt tccacagggt agccagcagc atcctgcgat gcagatccgg    3000
aacataatgg tgcagggcgc tgacttccgc gttccagac tttacgaaac acggaaaccg    3060
aagaccattc atgttgttgc tcaggtcgca gacgttttgc agcagcagtc gcttcacgtt    3120
cgctcgcgta tcggtgattc attctgctaa ccagtaaggc aaccccgcca gcctagccgg    3180
gtcctcaacg acaggagcac gatcatgcgc acccgtggcc aggacccaac gctgcccgag    3240
atgcgccgcg tgcggctgct ggagatggcg gacgcgatgg atatgttctg ccaagggttg    3300
gtttgcgcat tcacagttct ccgcaagaat tgattggctc caattcttgg agtggtgaat    3360
ccgttagcga ggtgccgccg gcttccattc aggtcgaggt ggcccggctc catgcaccgc    3420
gacgcaacgc ggggaggcag acaaggtata gggcggcgcc tacaatccat gccaacccgt    3480
tccatgtgct cgccgaggcg gcataaatcg ccgtgacgat cagcggtcca gtgatcgaag    3540
ttaggctggt aagagccgcg agcgatcctt gaagctgtcc ctgatggtcg tcatctacct    3600
gcctggacag catggcctgc aacgcgggca tcccgatgcc gccggaagcg agaagaatca    3660
taatggggaa ggccatccag cctcgcgtcg cgaacgccag caagacgtag cccagcgcgt    3720
cggccgccat gccggcgata atggcctgct tctcgccgaa acgtttggtg gcgggaccag    3780
tgacgaaggc ttgagcgagg gcgtgcaaga ttccgaatac cgcaagcgac aggccgatca    3840
```

```
tcgtcgcgct ccagcgaaag cggtcctcgc cgaaaatgac ccagagcgct gccggcacct    3900
gtcctacgag ttgcatgata aagaagacag tcataagtgc ggcgacgata gtcatgcccc    3960
gcgcccaccg gaaggagctg actgggttga aggctctcaa gggcatcggt cgacgctctc    4020
ccttatgcga ctcctgcatt aggaagcagc ccagtagtag gttgaggccg ttgagcaccg    4080
ccgccgcaag gaatggtgca tgcaaggaga tggcgcccaa cagtcccccg gccacggggc    4140
ctgccaccat acccacgccg aaacaagcgc tcatgagccc gaagtggcga gcccgatctt    4200
ccccatcggt gatgtcggcg atataggcgc cagcaaccgc acctgtggcg ccggtgatgc    4260
cggccacgat gcgtccggcg tagaggattc acaggacggg tgtggtcgcc atgatcgcgt    4320
agtcgatagt ggctccaagt agcgaagcga gcaggactgg gcggcggcca aagcggtcgg    4380
acagtgctcc gagaacgggt gcgcatagaa attgcatcaa cgcatatagc gctagcagca    4440
cgccatagtg actggcgatg ctgtcggaat ggacgatatc ccgcaagagg cccggcagta    4500
ccggcataac caagcctatg cctacagcat ccagggtgac ggtgccgagg atgacgatga    4560
gcgcattgtt agatttcata cacggtgcct gactgcgtta gcaatttaac tgtgataaac    4620
taccgcatta aagcttatcg atgataagct gtcaaacatg agaa                     4664
```